United States Patent
Yaffe et al.

(10) Patent No.: US 9,023,787 B2
(45) Date of Patent: *May 5, 2015

(54) MAPKAP KINASE-2 AS A SPECIFIC TARGET FOR BLOCKING PROLIFERATION OF P53-DEFECTIVE

(71) Applicant: Massachusetts Institute of Technology, Cambridge, MA (US)

(72) Inventors: Michael B. Yaffe, West Roxbury, MA (US); Isaac A. Manke, New York, NY (US); Hans Christian Reinhardt, Cologne (DE)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/893,141

(22) Filed: May 13, 2013

(65) Prior Publication Data

US 2014/0037755 A1    Feb. 6, 2014

Related U.S. Application Data

(63) Continuation of application No. 11/789,239, filed on Apr. 24, 2007, now Pat. No. 8,440,610, and a continuation-in-part of application No. 11/273,567, filed on Nov. 14, 2005, now abandoned.

(60) Provisional application No. 60/794,451, filed on Apr. 24, 2006, provisional application No. 60/800,298, filed on May 12, 2006, provisional application No. 60/873,904, filed on Dec. 8, 2006, provisional application No. 60/627,352, filed on Nov. 12, 2004.

(51) Int. Cl.

| | | |
|---|---|---|
| *A61K 31/00* | (2006.01) | |
| *A61K 38/16* | (2006.01) | |
| *A61K 31/553* | (2006.01) | |
| *A61K 45/06* | (2006.01) | |
| *C07K 7/06* | (2006.01) | |
| *C07K 7/08* | (2006.01) | |
| *C12N 9/12* | (2006.01) | |
| *C12Q 1/48* | (2006.01) | |
| *G01N 33/573* | (2006.01) | |
| *G01N 33/574* | (2006.01) | |
| *A61K 31/7034* | (2006.01) | |
| *A61K 33/24* | (2006.01) | |
| *G06F 19/16* | (2011.01) | |
| *G06F 19/20* | (2011.01) | |
| *G06F 19/22* | (2011.01) | |

(52) U.S. Cl.
CPC .............. *A61K 31/553* (2013.01); *A61K 31/00* (2013.01); *A61K 38/16* (2013.01); *A61K 45/06* (2013.01); *C07K 7/06* (2013.01); *C07K 7/08* (2013.01); *C07K 2299/00* (2013.01); *C12N 9/1205* (2013.01); *C12Q 1/485* (2013.01); *G01N 33/573* (2013.01); *G01N 33/57407* (2013.01); *G01N 2333/4748* (2013.01); *G01N 2333/9121* (2013.01); *G01N 2500/00* (2013.01); *G01N 2500/02* (2013.01); *G06F 19/16* (2013.01); *G06F 19/20* (2013.01); *G06F 19/22* (2013.01); *A61K 31/7034* (2013.01); *A61K 33/24* (2013.01)

(58) Field of Classification Search
None
See application file for complete search history.

(56) References Cited

U.S. PATENT DOCUMENTS

| | | | |
|---|---|---|---|
| 4,244,946 | A | 1/1981 | Rivier |
| 4,305,872 | A | 12/1981 | Johnston |
| 4,316,891 | A | 2/1982 | Guillemin |
| 5,034,506 | A | 7/1991 | Summerton |
| 5,652,122 | A | 7/1997 | Frankel |
| 5,670,617 | A | 9/1997 | Frankel |
| 5,674,980 | A | 10/1997 | Frankel |
| 5,747,641 | A | 5/1998 | Frankel |
| 5,804,604 | A | 9/1998 | Frankel |
| 6,683,167 | B1 | 1/2004 | Kotlyarov |
| 8,440,610 | B2 * | 5/2013 | Yaffe et al. ................ 514/1.1 |
| 2004/0101915 | A1* | 5/2004 | Deveraux et al. ........... 435/7.23 |
| 2004/0127492 | A1 | 7/2004 | Vazquez |
| 2004/0209797 | A1 | 10/2004 | Karas |
| 2005/0003387 | A1 | 1/2005 | Aza-Blanc |
| 2005/0079172 | A1 | 4/2005 | Nasoff |
| 2005/0101623 | A1 | 5/2005 | Meyers |
| 2005/0119470 | A1 | 6/2005 | Manoharan |
| 2005/0137220 | A1 | 6/2005 | Anderson |
| 2005/0143371 | A1 | 6/2005 | Meyers |
| 2005/0181385 | A1 | 8/2005 | Linsley |
| 2005/0196808 | A1 | 9/2005 | Yaffe |
| 2005/0239731 | A1 | 10/2005 | McSwiggen |
| 2005/0245475 | A1 | 11/2005 | Khvorova |
| 2006/0052951 | A1 | 3/2006 | Yaffe |

FOREIGN PATENT DOCUMENTS

WO     2004055019     7/2004

OTHER PUBLICATIONS

Wang et al., J. of the Natl. Canc. Inst., 1996, vol. 88, pp. 956-965.*

(Continued)

*Primary Examiner* — Karlheinz R Skowronek
*Assistant Examiner* — Roy Teller
(74) *Attorney, Agent, or Firm* — Pabst Patent Group LLP

(57) ABSTRACT

The present invention relates to compounds and pharmaceutical compositions for treating cellular proliferative disorders, e.g., in patients having one or more p53-deficient cells, screening assays for identifying such compounds, and methods for treating such disorders.

14 Claims, 17 Drawing Sheets

(56) References Cited

OTHER PUBLICATIONS

Wang et al., Journal of the National Cancer Institute, 1996, vol. 88, No. 14, pp. 956-965.*
Abraham, "Cell cycle checkpoint signaling through the atm and art kinases", Genes Dev., 15:2177-96 (2001).
Abrantes, et al., "Adaptation of a surface plasmon resonance biosensor with microfluidics for use with small sample volumes and long contact times", Anal. Chem., 73:2828-35 (2001).
Agner, et al., "Differential impact of diverse anticancer chemotherapeutics on the Cdc25A-degradation checkpoint pathway", Exp. Cell Res., 302:162-69 (2005).
Altschul, et al., "Basic local alignment search tool", J. Mol. Biol. 215:403-10 (1990).
Angers, et al "Detection of beta 2-adrenergic receptor dimerization in living cells using bioluminescence resonance energy transfer (BRET)", PNAS, 97:3684-9 (2000).
Bader, et al., "A cGMP-dependent protein kinase assay for high throughput screening based on time-resolved fluorescence resonance energy transfer", J. Biomol. Screen, 6:255-64 (2001).
Barlos, et al., "Application of 2-chlorotrityl resin in solid phase synthesis of (Leu15)-gastrin I and unsulfated cholecystokinin octapeptide. Selective O-deprotection of tyrosine", Int. J. Pept. Prot. Res. 38(6):555-61 (1991).
Bartek and Lukas, Pathways governing G1/s transition and their response to DNA damage, FEBS Lett., 490:117-22 (2001).
Bartek and Lukas, "Chk1 and Chk2 kinases in checkpoint control and cancer", Cancer Cell, 3:421-29 (2003).
Barth, et al., "Combining phage display and screening of cDNA expression libraries: a new approach for identifying the target antigen of an scFv preselected by phage display", J. Mol. Biol., 301:751-7 (2000).
Ben-Levy, et al., "Identification of novel phosphorylation sited required for activation of MAPKAP kinase-2", EMBO J., 14:5920-30 (1995).
Ben-Levy, et al., "Nuclear export of the stress-activated protein kinase p38 medicated by its substrate MAPKAP kinase-2", Curr. Biol., 8:1049-57 (1998).
Berman, et al., "The protein data bank", Nuc. Acids Res., 28:235-242 (2000).
Blagosklonny, "Sequential activation and inactivation of G2 checkpoints for selective killing of p53-Deficient cells by microtubule-active drugs", Oncogene, 21:6249-54 (2002).
Block, et al., "Selective inhibition of the DNA-dependent protein kinase (DNA-PK) by the radiosensitizing agent caffeine", Nucleic Acids Res., 32:1967-72 (2004).
Brockhoff, et al., "Epidermal growth factor receptor, c-erbB2 and c-erbB3 receptor interaction, and related cell cycle kinetics of SK-BR-3 and BT474 breast carcinoma cells", Cytometry, 44:338-48 (2001).
Brummelkamp, et al., "A system for stable expression of short interfering RNAs in mammalian cells", Science 296:550-53 (2002).
Bulavin, et al., "Initiation of a G2/M checkpoint after ultraviolet radiation requires p38 kinase", Nature, 411:102-7 (2001).
Bunch and Eastman, "Enhancement of cisplation-induced cytotoxicity by 7-hydroxystaurosporine (UNC-01), a new G2-checkpoint inhibitor", Clin. Cancer Res., 2:791-97 (1996).
Busby, et al., "The radiosensitizing agent 7-hydroxystaurosporine (UNC-01) inhibits the DNA damage checkpoint kinase hChnk1", Cancer Res., 60:2108-12 (2000).
Busino, et al., "Cdc25A phosphatase: Combinatorial Phosphorylation, ubiquitylation and proteolysis", Oncogene, 23:2050-56 (2004).
Carrassa, et al., "Chk1, but not Chk2, is involved in the cellular response to DNA damaging agents", Cell Cycle, 3:1177-81 (2004).
Castedo, et al., "Cell death by mitotic catastrophe: A molecular definition", Oncogene, 23:2825-37 (2004).
Chen, et al., "The 1.7 A crystal structure of human cell cycle checkpoint kinase Chk1: Implications or Chk1 regulation", Cell, 100:681-92 (2000).
Chen, et al., "Absence of apparent phenotype in mice lacking Cdc25C protein phosphatase", Mol. Cell Biol., 21:3853-61 (2001).
Chen, et al., "Chk1 kinase negatively regulates mitotic function of Cdc25A phosphatase through 14-3-3 binding", Mol. Cell Biol., 23:7488-97 (2003).
Cheng, et al., "RNA interference and human disease", Mol. Gen. Mtab., 80:121-28 (2003).
Cheng and Lai, "Identification of mitogen-activated protein kinase-activated protein kinase-2 as a vimentin kinase activated vy okadaic acid in 9L rat brain tumor cells", J. Cell Biochem., 71:169-81 (1998).
Cheung, et al., "Feedback control of the protein kinase TAK1 by SAPK2a/p39a", EMBO J., 22:5793-5805 (2003).
Clapperton, et al., "Structure and mechanuism iof BRCA1 BRCT domain recognition of phosphorylated BACH1 with implications for cancer", Nat. Struct. Mol. Biol., 11:512-18 (2004).
Cliby, et al., "S phase and G2 arrests induced by topoisomerase I poisons are dependent on ATR kinase function", J Biol. Chem., 277:1599-1606 (2002).
Damia and Broggini, "Cell Cycle Checkpoint Proteins and Cellular Response to Treatment by Anticancer Agents," Cell Cycle 3:46-50 (2004).
Derossi, et al., "The third helix of the Antennapedia homeodomain translocates through biological membranes", J. Biol. Chem. 269:10444-10450 (1994).
Devereux, et al., "A comprehensive set of sequence analysis programs for the VAX", Nuc. Acids Res, 12: 387(1984).
Dixon and Norbury, "Therapeutic Exploitation of Checkpoint Defects in Cancer Cells Lacking p53 Function," Cell Cycle 1:362-368 (2002).
Donzelli and Draetta, "Regulating Mammalian Checkpoints through Cdc25 Inactivation," EMBO Rep. 4:671-677 (2003).
Dutertre, et al., "Phosphorylation of CDC25B by Aurora-A at the Centrosome Contributes to the G2-M Transition," J. Cell Sd. 117:2523-2531 (2004).
El-Benna, et al., "Phosphorylation of the Respiratory Burst Oxidase Subunit p470X as Determined by 2-Dimensional Phosphopeptide Mapping. Phosphorylation by Protein Kinase C, Protein Kinase A & MitogenActivated Protein Kinase," J Biol Chem, 271:6374-78 (1996).
Engel, et al., "Constitutive Activation of Mitogen-Activated Protein Kinase-Activated Protein Kinase 2 by Mutation of Phosphorylation Sites and an A-helix Motif," J. Biol. Chem. 270:27213-27221 (1995).
Engelborghs, "The analysis of time resolved protein fluorescence in multi-tryptophan proteins", Spectrochim. Acta A. Mal. Biomol. Spectrosc., 57:2255-70 (2001).
Falck, et al. "The ATM-Chk2-Cdc25A Checkpoint Pathway Guards Against Radioresistant DNA Synthesis," Nature 410:842-847(2001).
Ferbeyre, et al., "Oncogenic ras and p53 Cooperate to Induce Cellular Senescence," Mol. Cell. Biol. 22:3497-3508 (2002).
Ficarro, et al. "Phosphoproteome Analysis by Mass Spectrometry and Its Application to *Saccharomyces cerevisiae*," Nat. Biotechnol. 20:301-305 (2002).
Forrest and Gabrietli, "Cdc25B Activity Is Regulated by 14-3-3," Onocogene 20:4393-4401 (2001).
Furnari, et al., "Cdc25 Mitotic inducer Targeted by Chkl DNA Damage Checkpoint Kinase," Science 277:1495-1497 (1997).
Galaktionov, et al., "CDC25 Phosphatases as Potential Human Oncogenes," Science 269:1575-1577 (1995).
Gasparotto, et al., "Overexpression of CDC25A and CDC25B in Head and Neck Cancers," Cancer Res. 57:2366-2368(1997).
Genbank Accession No. NM 004759, Homo sapiens mitogen-activated protein kinase-activated protein kinase 2 (MAPKAPK2), transcript variant 1, mRNA, 5 pages, accessed Apr. 10, 2012, updated Apr. 1, 2012, first appeared (1993).
Genbank Accession No. NM_032960, Homo sapiens mitogen-activated protein kinase-activated protein kinase 2 (MAPKAPK2), transcript variant 2, mRNA, 5 pages, accessed Apr. 10, 2012, updated Apr. 1, 2012, first appeared (1984).
Genbank Accession No: NP_004750, MAP kinase-activated protein kinase 2 isoform 1 [Homo sapiens], 5 pages, accessed Apr. 10, 2012, updated Apr. 1, 2012, first appeared (1993).
Genbank Accession No. P49137, RecName: Full=MAP kinase-activated protein kinase 2; Short=MAPK-activated protein kinase 2;

(56) References Cited

OTHER PUBLICATIONS

Short=MAPKAP kinase 2; Short=MAPKAP-K2; Short=MAPKAPK-2; Short=MK-2; Short=MK2, 13pages, accessed Apr. 10, 2012, updated Mar. 21, 2012, first appeared (1993).
Geoghegan, et al., "Dye-pair reporter systems for protein-peptide molecular interactions", Bioconjug. Chem. 11:71-7 (2000).
Giles, et al., "14-3-3 Acts as an Intramolecular Bridge to Regulate cdc25B Localization and Activity," J. Biol. Chem., 278:28580-28587 (2003).
Goldstone, et al., "Cdc25-Dependent Activation of Cyclin a/cdk2 Is Blocked in G2 Phase Arrested Cells Independently of ATM/ATR," Oncogene 20:921-932 (2001).
Graves, et al., "Localization of Human Cdc25C Is Regulated Both by Nuclear Export and 14-3-3 Protein Binding," Onocogene 20:1839-1851 (2001).
Graves, et al., "The Chkl Protein Kinase and the Cdc25C Regulatory Pathways Are Targets of the Anticancer Agent UCN-01," J. Biol. Chem. 275:5600-5605 (2000).
Guo, et al., "Requirement for Atr in Phosphorylation of Chkl and Cell Cycle Regulation in Response to DNA Replication Blocks and UV-Damaged DNA in Xenopus Egg Extracts," Genes Dev. 14:2745-2756 (2000).
Han, et al., "Racl-MKK3-p38-MAPKAPK2 Pathway Promotes Urokinase Plasminogen Activator mRNA Stability in Invasive Breast Cancer Cells," J. Bio. Chem. 277: 48379-48385 (2002).
Hannon, "RNA interference", Nature, 418:244-251 (2002).
Hayess and Benndorf, "Effect of Protein Kinase Inhibitors on Activity of Mammalian Small Heat-Shock Protein (HSP25) Kinase," Biochem. Pharma. 53:1239-1247(1997).
Heidenreich, et al., "MAPKAP Kinase 2 Phosphorylates Serum Response Factor In Vitro and In Vivo," J. Blot Chem., 274:14434-14443 (1999).
Hirose, et al., "The p38 Mitogen-Activated Protein Kinase Pathway Links the DNA Mismatch Repair System to the G2 Checkpoint and to Resistance to Chemotherapeutic DNA-Methylating Agents," Mol. Cell. Biol. 23:8306-8315(2003).
Hirose, et al., "Cooperative Function of Chkl and p38 Pathways in Activating G2 Arrest Following Exposure to Temozolornide," J. Neurosurg. 100:1060-1065 (2004).
Ho, et al, "The Relative Contribution of CHK1 and CHK2 to Adriamycin-Induced Checkpoint," Exp. Cell Res. 304:1-15 (2005).
Hoffmann, et al "Phosphorylation and Activation of Human Cdc25-C by Cdc2" Cyclin B and Its Involvement in the Self-Amplification of MPF at Mitosis, EMBO J. 12:53-63 (1993).
Huang, et al., "LSP1 Is the Major Substrate for Mitogen-Activated Protein Kinase 2 in Human Neutrophils," J. Bid. Chem. 272:17-19(1997).
Hutvagner and Zamore, "RNAi: nature abhors a double-strand.", Curr. Opin. Genet. Devel. 12:225-32 (2002).
Ignatovich, et al., "Complexes of Plasmid DNA with Basic Domain 47-57 of the HIV-1 Tat Protein Are Transferred to Mammalian Cells by Endocytosis-mediated Pathways," J. Blo. Chem, 278: 42625-42636 (2003).
Jackman, et al., "Active Cyclin B1-Cdkl First Appears on Centrosomes in Prophase," Nat. Cell Biol. 5:143-148 (2003).
Jackson, et al., "An Indolocarbazole Inhibitor of Human Checkpoint Kinase (Chkl) Abrogates Cell Cycle Arrest Caused by DNA Damage," Cancer Res. 60:566-572 (2000).
Jin, et al., $SCF^2$-TRCP Links Chkl Signaling to Degradation of the Cdc25A Protein Phosphatase, Genes Dev. 17:3062-3074(2003).
Judkins, et al., "A Versatile Synthesis of Amidines from Nitriles Via Amidoximes", Synthetic Communications, 26(23):4351-67 (1996).
Kastan and Lin, "The Many Substrates and Functions of ATM," Nat. Rev. Mat Cell Blol. 1:179-186 (2000).
Kastan and Bartek, "Cell-Cycle Checkpoints and Cancer," Nature 432:316-323 (2004).
Kawabe, "02 Checkpoint Abrogators as Anticancer Drugs," Mol. Cancer Ther. 3:513-519 (2004).
Kotlyarov, et al, MAPKAP Kinase 2 Is Essential for LPS-Induced TNF-Alpha Biosynthesis, Nat. Cell Biol. 1:94-97 (1999).
Kotlyarov, et al., "Distinct Cellular Functions of MK2," Mol. Cell. Biol. 22:4827-35 (2002).
Kumagai, et al. "14-3-3 Proteins Act as Negative Regulators of the Mitotic Inducer Cdc25 in Xenopus Egg Extracts," Mol. Biol. Cell 9:345-354 (1998).
Kumagai and Dunphy, "Binding of 14-3-3 Proteins and Nuclear Export Control the Intracellular Localization of the Mitotic Inducer Cdc25," Genes Dev. 13:1067-1072 (1999).
Landry, et al., "Human HSP27 Is Phosphorylated at Serines 78 and 82 by Heat Shock and Mitogen-Activated Kinases That Recognize the Same Amino Acid Motif as S6 Kinase II," J. Biol. Chem. 267:794-803(1992).
Lee, et al., "Expression of small interfering RNAs targeted against HIV-1 rev transcripts in human cells", Nature Biotechnol., 20:500-05 (2002).
Lin, et al., "Inhibition of nuclear translocation of transcription factor NF-kappa B by a synthetic peptide containing a cell membrane-permeable motif and nuclear localization sequence", J. Biol. Chem., 270:14255-14258, (1995).
Liu, et al., "Chkl Is an Essential Kinase That Is Regulated by Atr and Required for the G2/M DNA Damage Checkpoint," Gene Dev. 14:1448-1459(2000).
Luo et al., "Blocking CHK1 Expression Induces Apoptosis and Abrogates the G2 Checkpoint Mechanism," Neoplasia 3:411-419(2001).
Mack, et al., "Enhancement of Radiation Cytotoxicity by UCN-01 in Non-Small Cell Lung Carcinoma Cells," Radiat. Res. 162:623-634 (2004).
Maerki, et al., "Total solid-phase synthesis of porcine gut gastrin releasing peptide (GRP), a mammalian bombesin", J.Am. Chem. Soc., 103(11):3178-85 (1981).
Mailand, et al., "Rapid Destruction of Human Cdc25A in Response to DNA Damage," Science 288:1425-1429(2000).
Mailand, et al., "Regulation of G2/M Events by Cdc25A through Phosphorylation-Dependent Modulation of Its Stability," EMBO J. 21:5911-5920 (2002).
Manke, et al. "MAPKAP Kinase-2 Is a Cell Cycle Checkpoint Kinase That Regulates the G2/M Transition and S Phase Progression in Response to UV Irradiation," Mol. Cell 17:37-48(2005).
McLaughlin, et al., "Identification of Mitogen-Activated Protein (MAP) Kinase-Activated Protein Kinase-3, a Novel Substrate of CSBP p38 MAP Kinase," J. Biol. Chem. 271:8488-8492 (1996).
Merrifield, "Solid Phase Peptide Synthesis. I. The Synthesis of a Tetrapeptide", J. Am. Chem. Soc., 85(14):2149-54 (1963).
Mikhailov, et al., "Topoisomerase II and Histone Deacetylase Inhibitors Delay the G21M Transition by Triggering the p38 MAPK Checkpoint Pathway," J. Cell Biol. 166:517-526(2004).
Miyagishi and Taira, "U6 promoter-driven siRNAs with four uridine 3' overhangs efficiently suppress targeted gene expression in mammalian cells", Nat. Biotechnol., 20:497-500 (2002).
Nelson and Krone, "Advances in surface plasmon resonance biomolecular interaction analysis mass spectrometry (BIA/MS).",J. Mol. Recognit., 12:77-93 (1999).
Nicholls, et al., "Grasp Graphical Representation and Analysis of Surface Properties," Biophys. J. 64:A166 (1993).
Nielsen, et al.,"Sequence-selective recognition of DNSA by strand displacement with a thymine-substituted polyamide", Science, 254 (5037):1497-1500 (1991).
Nilsson and Hoffmann, "Cell Cycle Regulation by the Cdc25 Phosphatase Family," Prog. Cell Cycle Res. 4:107-114 (2000).
Nishikawa, et al., "Determination of the Specific Substrate Sequence Motifs of Protein Kinase C Isozymes," J. Biol. Chem. 272:952-960 (1997).
O\Driscoll, et al., "A Splicing Mutation Affecting Expression of Ataxia-Telangiectasia and Rad3-Related Protein (ATR) Results in Seckel Syndrome," Nat. Gene!. 33:497-501 (2003).
Obata, et al., "MAP Kinase Pathways Activated by Stress: The p38 MAPK Pathway," Crlf. Care Med. 28:N67-N77 (2000).
O\Neill, et al., "Determination of Substrate Motifs for Human Chkl and hCdsl/Chk2 by the Oriented Peptide Library Approach" J. Biol. Chem. 277:16102-16115 (2002).
Paddison, et al., "Short hairpin RNAs (shRNAs) induce sequence-specific silencing in mammalian cells", Genes & Devel., 16:948-58 (2002).

(56) References Cited

OTHER PUBLICATIONS

Paul, et al., "Effective expression of small interfering RNA in human cells", Nature Biotechnol., 20:505-08 (2002).

Peng, et al, "Mitotic and G2 Checkpoint Control: Regulation of 14-3-3 Protein Binding by Phosphoration of Cdc25C on Serine-216," Science 277:1501-1505 (997).

Pommier, "Eukaryotic DNA Topoisomerase I: Genome Gatekeeper and Its Intruders, Camptothecins," Semin. Oncol. 23:3-10(1996).

Raingeaud, et al. "Pro-Inflammatory Cytokines and Environmental Stress Cause p38 Mitogen-Activated Protein Kinase Activation by Dual Phosphorylation on Tyrosine and Threonine," J. Biol. Chem, 270:7420-7426 (1995).

Reynolds, et al., "Rational siRNA design for RNA interference", Nat. Biotechnol., 22:326-330 (2004).

Rich and Mizka, "Biacore J: a new platform for routine biomolecular interaction analysis", J. Mol. Recognit., 14:223-8 (2001).

Roth, et al., "Gene therapy clinical trials for cancer: replacement of tumor suppressor gene p53", Gene and Cell Therapy: Therapeutic Mechanisms and Strategies, second edition, chapter 38:743-52 (2004).

Rouse, et al, "A Novel Kinase Cascade Triggered by Stress and Heat Shock That Stimulates MAPKAP Kinase-2 and Phosphorylation of the Small Heat Shock Proteins," Cell 78:1027-1037 (1994).

Rouse and Jackson, "Interfaces Between the Detection, Signaling, and Repair of DNA Damage," Science 297:547-551 (2002).

Roux and Blenis, "ERK and p38 MAPK-Activated Protein Kinases: A Family of Protein Kinases with Diverse Biological Functions," Microbial. MoL Biol. Rev. 68:320-344 (2004).

Rubinson, et al., "A Lentivirus-Based System to Functionally Silence Genes in Primary Mammalian Cells, Stem Cells and Transgenic Mice by RNA Interference," Nat. Genet. 33:401-406 (2003).

Saalik, et al., "Protein Cargo Delivery Properties of Cell-Penetrating Peptides: A Comparative Study," Bioconj. Chem. 15:1246-1253 (2004).

Saklatvala, et al., "The p38 Map kinase pathway as a therapeutic target in inflammatory disease," Cuff. Op. Pharm. 4: 372-377 (2004).

Sarkaria, et al., "Inhibition of ATM and ATR Kinase Activities by the Radiosensitizing Agent, Caffeine," Cancer Res.59:4375-4382 (1999).

Schmidt, Negotiating RNAi patent thicket, Nat. Biotech., 25:273-5 (2007).

Shao, et al., "Abrogation of an S-Phase Checkpoint and Potentiation of Camptothecin Cytotoxicity by 7- Hydroxystaurosporine (UCN-01) in Human Cancer Cell Lines, Possibly Influenced by p53 Function," Cancer Res.57:4029-4035 (1997).

Shao, et al., "Abrogation of Chkl-Mediated S/G2 Checkpoint by UCN-01 Enhances Ara-C-Induced Cytotoxicity in Human Colon Cancer Cells," Acta Pharmacol. Sin. 25:756-762 (2004).

Sharp, "RNA interference 2001", Genes &Devel., 15:485-90 (2001).

She, et al, "Role of Map Kinases in UVB-Induced Phosphorylation of p53 at Serine 20," Oncogene 21:1580-1589 (2002).

Shiloh, "ATM and Related Protein Kinases: Safeguarding Genome Integrity," Nat. Rev. Cancer 3:155-168(2003).

Simons, et al., "Inversin, the Gene Product Mutated in Nephronophthisis Type II, Functions as a Molecular Switch Between Wnt Signaling Pathways," Nat.Genet 37:537-43 (2005).

Song, et al., "Detection of multivalent interactions through two-tiered energy transfer", Anal. Biochem. 291:133-41 (2001).

Songyang and Cantley, "The Use of Peptide Library for the Determination of Kinase Peptide Substrates," Methods Mol. Biol. 87:87-98(1998).

Sørensen, et al., "Chkl Regulates the S Phase Checkpoint by Coupling the Physiological Turnover and Ionizing Radiation-Induced Accelerated Proteolysis of Cdc25A," Cancer Cell 3:247-258 (2003).

Spiga, et al., "Peptide-protein interactions studied by surface plasmon and nuclear magnetic resonances", FEBS Lett., 511:33-35 (2002).

Sportsman, et al., "Fluorescence Polarization Assays in Signal Transduction Discovery," Comb. Chem. HighThroughput Screening 6:195-200 (2003).

Stokes and Michael, "DNA Damage-Induced Replication Arrest in Xenopus Egg Extracts," J. Cell Biol. 163:245-255 (2003).

Stokoe, et al., "MAPKAP Kinase-2; A Novel Protein Kinase Activated by Mitogen-Activated Protein Kinase," EMBO J. 11:3985-3994 (1992).

Stokoe, et al., "The Substrate Specificity and Structure of Mitogen-Activated Protein (MAP) Kinase-Activated Protein Kinase-2," B/oche,\n. J. 296:843-849 (1993).

Sui, et al., "A DNA vector-based RNAi technology to suppress gene expression in mammalian cells", PNAS, 99:5515-20 (2002).

Syljuasen, et al., "Inhibition of Human Chkl Causes Increased Initiation of DNA Replication, Phosphorylation of ATR Targets, and DNA Breakage," Mol. Cell, Biol. 25:3553-3562 (2005).

Takai, et al., "Aberrant Cell Cycle Checkpoint Function and Early Embryonic Death in Chkl" Mice, Genes Dev. 14:1439-1447 (2000).

Tanoue, et al., "A Conserved Docking Motif in MAP Kinases Common to Substrates, Activators and Regulators," Nat. Cell Biol. 2:110-116 (2000).

Tanoue and Nishida, "Molecular Recognitions in the MAP Kinase Cascades," Cell. Signal. 15:455-462 (2003).

Theard, et al., "Etoposide and Adriamycin but not Genistein can Activate the Checkpoint Kinase Chk2 Independently of ATM/ATR," Biochem. Biophys. Res. Commun. 289:1199-1204(2001).

Tsao, et al., "The Involvement of Active DNA Synthesis in Camptothecin-Induced G2 Arrest: Altered Regulation of p34cdc21Cyclin B," Cancer Res. 52:1823-1829 (1992).

Tse and Schwartz, "Potentiation of Cytotoxicity of Topoisomerase I Poison by Concurrent and Sequential Treatment with the Checkpoint Inhibitor UCN-01 Involves Disparate Mechanisms Resulting in Either p53-Independent Clonogenic Suppression or p53-Dependent Mitotic Catastrophe," Cancer Res. 64:6635-6644 (2004).

Tuschl, "RNA interference and small interfering RNAs", Chembiochem, 2:239-245 (2001).

Vale, et al., "Characterization of a 41-residue ovine hypothalamic peptide that stimulates secretion of corticotropin and beta-endorphin", Science ,213:1394-97 (1984).

van Vugt, et al., "Polo-Like Kinase-1 Controls Recovery from a G2 DNA Damage-induced Arrest in MammalianCells,"M0L Cell 15:799-811(2004).

Wang and Ron, "Stress-induced Phosphorylation and Activation of the Transcnption Factor Chop (GADD153)by p38 MAP Kinase," Science 272:1347-1349(1996).

Wang, et al., "UCN-01: A Potent Abrogator of G2 Checkpoint Function in Cancer Cells with Disrupted p53," J. NatL Cancer Inst. 88:956-965 (1996).

Werz, et al., "Arachidonic Acid Promotes Phosphorylation of 5-Lipoxygenase at Ser-271 by MAPK-Activated Protein Kinase 2 (MK2)," J. Biol. Chem. 277:14793-14800(2002).

Xiao, et al., "Chkl Mediates S and G2 Arrests through Cdc25A Degradation in Response to DNA-Damaging Agents," J. Biol. Chem. 278:21767-21773(2003).

Xu, et al., "A bioluminescence resonance energy transfer (BRET) system: application to interacting circadian clock proteins", PNAS, 96:151-6 (1999).

Yaffe, et al., "The Structural Basis for 14-3-3:Phosphopeptide Binding Specificity," Cell 91:961-971(1997).

Yaffe, at al., "A Motif-Based Profile Scanning Approach for Genome-Wide Prediction of Signaling Pathways," Nat. Biotechnol. 19:348-353 (2001).

Yang, et al. "Targeting of p38 Mitogen-Activated Protein Kinases to MEF2 Transcription Factors," Mol. Cell. Blot 19:4028-4038(1999).

Yu, et al., "RNA interference by expression of short-interfering RNAs and hairpin RNAs in mammalian cells", PNAS, 99:6047-52 (2002).

Zhao, et al., "Disruption of the Checkpoint Kinase 1/Cell Division Cycle 25A Pathway Abrogates Ionizing Radiation Induced Sand 02 Checkpoints," Proc. NafL Acad. ScL USA 99:14795-14800 (2002).

(56) References Cited

OTHER PUBLICATIONS

Zhao and Piwnica-Worms, "ATR-Mediated Checkpoint Pathways Regulate Phosphorylation and Activation of Human Chkl," Mol. Cell. Bial. 21:4129-4139 (2001).

Zhao, et al. "Structural Basis for Chkl Inhibition by UCN-01," J. Blot Chem. 277:46609-46615 (2002b).

Zhou and Elledge, "The DNA Damage Response: Putting Checkpoints in Perspective," Nature 408:433-439 (2000).

Zhou and Bartek, "Targeting the Checkpoint Kinases: Chemosensitization versus Chernoprotection," Nat. Rev. Cancer 4:1-10 (2004).

Zunino and Capranico, "DNA Topoisomerase II as the Primary Target of Anti-Tumor Tumor Anthracyclines," Anticancer Drug Des. 5:307-317 (1990).

International Search Report issued in PCT/USO5/41294 (Jun. 20, 2006).

\* cited by examiner p38a MAP Kinase Phosphorylation Motif

| | -3 | -2 | -1 | S | P | +2 |
|---|---|---|---|---|---|---|
| SP library | M(1.6) F(1.5) Q(1.5) N(1.4) | P(2.1) M(1.7) L(1.5) V(1.5) I(1.5) | M(1.9) L(1.6) Q(1.5) | ↓ | ↓ | P(1.7) V(1.4) I(1.3) |

| | -3 | P | -1 | S | P | +2 |
|---|---|---|---|---|---|---|
| PxSP library | G(2.1) I(1.5) V(1.5) Y(1.4) | ↓ | Q(1.9) M(1.8) G(1.7) P(1.4) S(1.3) T(1.3) | ↓ | ↓ | I(1.8) W(1.7) Y(1.7) T(1.6) V(1.6) |

Comparison of p38 MAP Kinase Substrates

| Substrate | -3 | -2 | -1 | S/T | P | +2 |
|---|---|---|---|---|---|---|
| 3PK1(T313) | V | P | Q | | | L |
| 3PK1(T201) | A | L | Q | | | C |
| MAPKAP2(T334) | V | P | Q | | | L |
| MAPKAP2(S272) | L | A | I | | | G |
| MAPKAP2(T222) | S | L | T | | | C |
| MAPKAP2(T25) | Q | P | P | | | A |
| GADD153(S78) | T | S | Q | | | R |
| GADD153(S81) | S | P | R | | | D |
| MEF2A(T312) | P | L | A | | | V |
| MEF2A(T319) | S | V | T | | | S |
| ATF2(T51) | A | D | Q | | | T |
| ATF2(T53) | Q | T | P | | | T |
| p47phox(S345) | G | P | Q | ↓ | ↓ | G |
| p47phox(S348) | S | P | G | | | L |

*FIG. 1A*

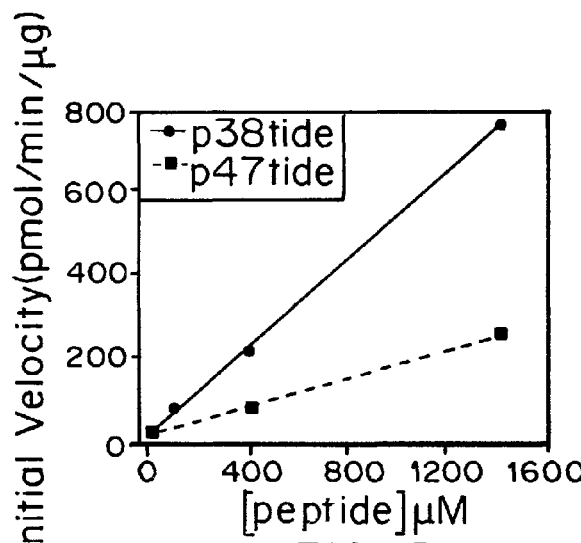
FIG. 1B
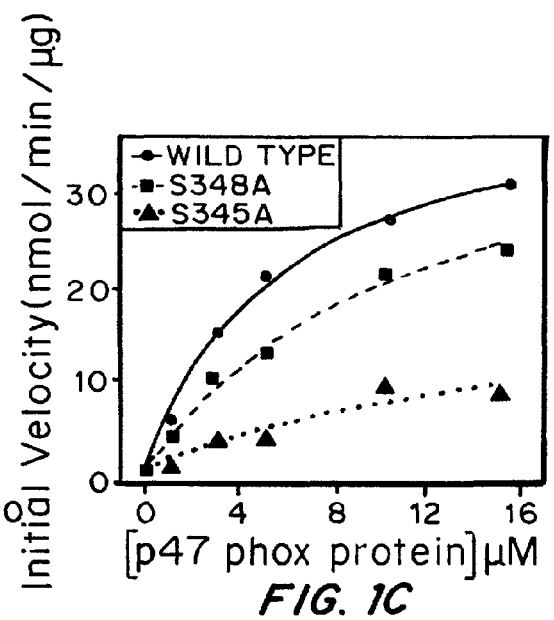
FIG. 1C
| p47phox | $K_m$(uM) | $V_{max}$(nmol/min/ug) | $V_{max}/K_m$ |
| --- | --- | --- | --- |
| Wild Type | 6.0±1.8 | 36.6±2.5 | 6.1±2.2 |
| S348A | 8.3±2 | 36.8±0.3 | 4.4±1.1 |
| S345A | 10.7±0.7 | 17.3±4.4 | 1.6±0.5 |
FIG. 1D

| MAPKAP Kinase-2 Phosphorylation Motif | | | | | | | |
|---|---|---|---|---|---|---|---|
| | -5 | -4 | R | -2 | -1 | S | +1 |
| RxxS library | L(2.5) | Q(1.3) | | Q(2.6) | L(1.6) | | I(1.8) |
| | F(1.9) | A(1.2) | | M(1.3) | N(1.3) | | V(1.7) |
| | I(1.6) | M(1.2) | | | | | F(1.4) |
| | V(1.3) | | ↓ | | | | L(1.3) ↓ |

| Comparison of MK2 Kinase Substrates | | | | | | | |
|---|---|---|---|---|---|---|---|
| Substrate | -5 | -4 | R | -2 | -1 | S | +1 |
| HSP-27(82) | L | S | | Q | L | | S |
| 5-LO(271) | L | E | | Q | L | | L |
| LSP1(204) | I | D | | T | E | | L |
| LSP1(252) | L | A | | Q | A | | I |
| SRF(103) | L | K | | T | L | | E |
| GS(7) | L | N | | S | L | | V |
| TH(19) | F | R | | A | V | | E |
| CDC25B(309) | L | F | | S | P | | M |
| CDC25C(216) | L | Y | ↓ | S | P | | M ↓ |

FIG. 2A

| Optimal MK2tide | | | | | | | | | | | |
|---|---|---|---|---|---|---|---|---|---|---|---|
| | | | -5 | -4 | -3 | -2 | -1 | 0 | +1 | Motif Position | |
| 1 | 2 | 3 | 4 | 5 | 6 | 7 | 8 | 9 | 10 | 11 | 12 |
| Ala | His | Leu | Gln | Arg | Gln | Leu | Ser | Ile | Ala | His | His |

| Peptide | $Km_{\mu M}$ | $V_{max}$ (pmol/min/µg) | $V_{max}/Km$ |
|---|---|---|---|
| MK2tide | 31 | 1098 | 35 |
| L3Atide | 29 | 463 | 16 |
| Q4Atide | 41 | 1209 | 29 |
| R5Atide | 310 | 282 | <1 |
| Q6Atide | 51 | 1058 | 21 |
| L7Atide | 35 | 955 | 27 |
| I9Atide | 43 | 627 | 15 |

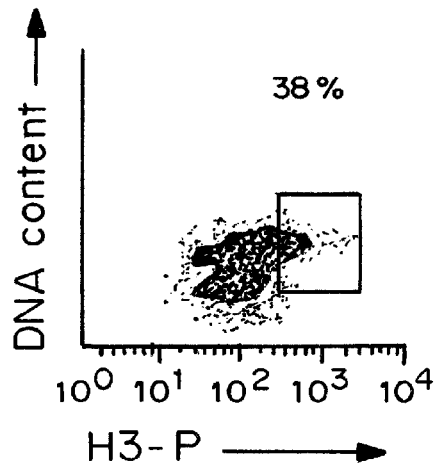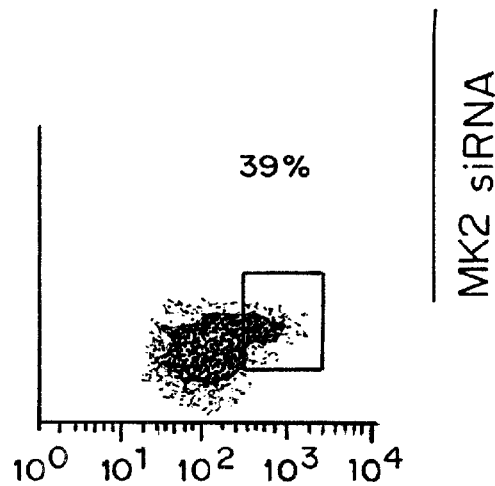
FIG. 3F        FIG. 3H
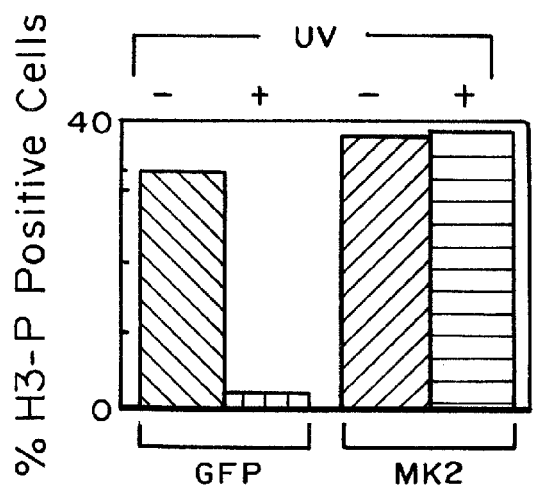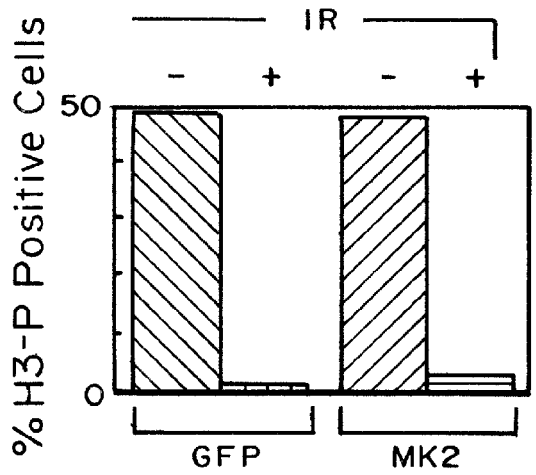
FIG. 3I        FIG. 3J

FIG. 6
|  | Control Fibroblasts | A-T Fibroblasts | Seckel Fibroblasts |
|---|---|---|---|
| Cisplatin | + | + | − |
| Doxorubicin | + | − | − |
| Camptothecin | + | + | − |
| UV | + | + | + |
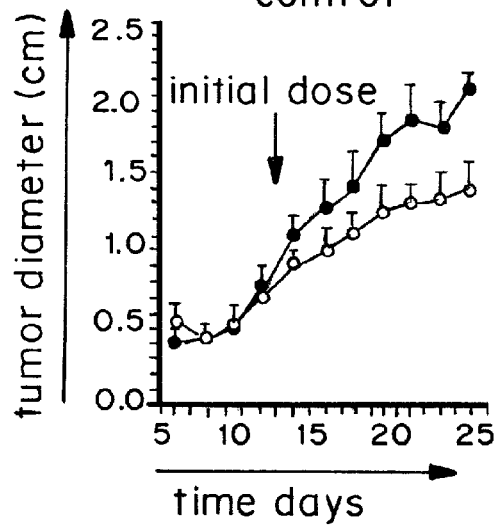
FIG. 7A control
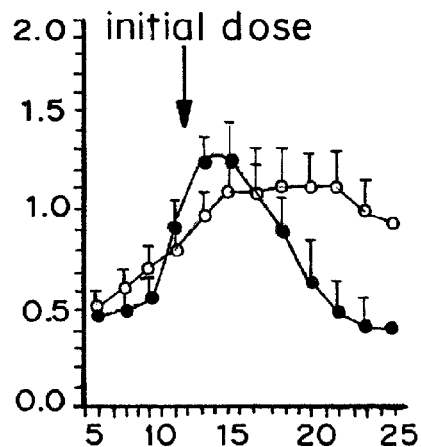
FIG. 7C cisplatin
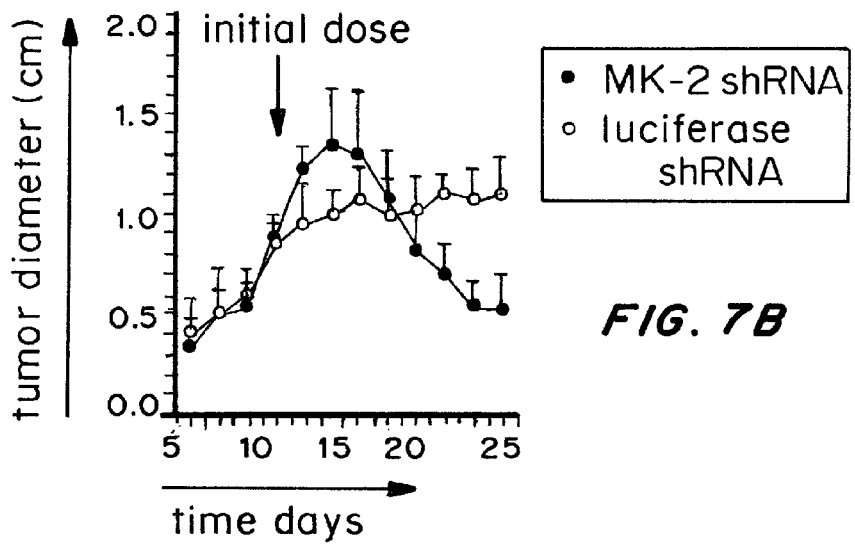
FIG. 7B
● MK-2 shRNA
○ luciferase shRNA

MAPKAP KINASE-2 AS A SPECIFIC TARGET FOR BLOCKING PROLIFERATION OF P53-DEFECTIVE

CROSS-REFERENCE TO RELATED APPLICATIONS

This application is a continuation-in-part of U.S. application Ser. No. 11/273,567, filed Nov. 14, 2005, which claims benefit of U.S. Provisional Application No. 60/627,352, filed Nov. 12, 2004, each of which is hereby incorporated by reference.

This application also claims benefit of U.S. Provisional Application Nos. 60/794,451, filed Apr. 24, 2006; 60/800,298, filed May 12, 2006; and 60/873,904, filed Dec. 8, 2006, each of which is hereby incorporated by reference.

STATEMENT AS TO FEDERALLY SPONSORED RESEARCH

The present research was supported by grants from the National Institutes of Health (grant numbers GM60594 and CA112967) and from the National Institute of Environmental Health Sciences (grant number ES015339). The U.S. government has certain rights to this invention.

REFERENCE TO SEQUENCE LISTING

The Sequence Listing Submitted Oct. 17, 2013 as a text filed named "MIT_12175_CIP_CON_ST25.txt," created on Jul. 16, 2013, and having a size of 23,787 bytes is hereby incorporated by reference pursuant to 37 C.F.R. §1.52(e)(5).

BACKGROUND OF THE INVENTION

The maintenance of genomic integrity is essential for the health of multi-cellular organisms. DNA damage checkpoints constitute a mechanism where cell division is delayed to allow repair of damaged DNA, or if the extent of DNA damage is beyond repair, induce apoptosis. The three major DNA damage-responsive cell cycle checkpoints are the $G_1/S$ checkpoint, intra S-phase checkpoint, and the $G_2/M$ checkpoint.

In response to DNA damage, eukaryotic cells activate a complex signaling network to arrest the cell cycle and facilitate DNA repair. This signaling network has traditionally been divided into two major protein kinase pathways, one mediated by Ataxia-Telangiectasia mutated (ATM) through Chk2, and the other mediated by Ataxia-Telangiectasia and Rad-3 related (ATR) through Chk1. Some cross-talk exists between the ATM/Chk2 and ATR/Chk1 kinase pathways, particularly when signaling through one pathway is partially or totally deficient. Normally, however the pathways show only partial functional overlap in response to particular forms of DNA damage. The ATM/Chk2 pathway responds primarily to DNA double strand breaks (DSBs), while the ATR/Chk1 pathway is activated by bulky DNA lesions, and following replication fork collapse during S-phase. The tumor suppressor protein p53 is a major downstream effector of these DNA damage kinase pathways. In normal cells, p53-dependent signaling results in $G_1$ arrest, mainly mediated by transcriptional upregulation of p21. In addition, p21 also appears to play a role in sustaining the $G_2$ checkpoint after γ-irradiation. If the DNA damage is extensive, however, then p53-dependent pathways target the damaged cell for apoptotic cell death through both the intrinsic and extrinsic pathways. Most tumor cells show specific disruptions in the p53 pathway, leading to selective loss of the $G_1$ checkpoint. These cells are then entirely dependent on intra-S and $G_2/M$ checkpoints to maintain their genomic integrity in response to DNA damage.

In contrast to the DNA damage-specific activation of Chk1 and Chk2, the p38MAPK pathway is a general stress-activated kinase pathway that responds to various cellular stimuli, including cytokines, hyperosmolarity, and UV irradiation. Activity of p38MAPK is important for $G_2/M$ checkpoint function in immortalized fibroblasts and HeLa cells following UV exposure. Furthermore, MAPKAP Kinase-2 (MK2) is the critical downstream effector kinase of p38MAPK required for UV-induced cell cycle checkpoints in U2OS cells.

Whether the observed activation of p38 MAPK/MK2 is a direct result of UV-induced DNA lesions, or results instead from other non-genotoxic effects of UV radiation has been unclear. Similarly, whether the p38MAPK/MK2 pathway is an important part of a general cellular response to genotoxic stress has been unclear. There exists a need to better understand this checkpoint and to develop methods and therapies for disease treatment based on this improved understanding.

SUMMARY OF THE INVENTION

We now report that MAPKAP kinase-2 is specifically activated in response to DNA damage caused by chemotherapeutic agents in an ATR and/or ATM-dependent manner, and that MAPKAP kinase-2 is critical for the activation of $G_1$, S-phase and $G_2/M$ checkpoints after exposure to these drugs. Downregulation of MAPKAP kinase-2 using RNA interference profoundly increases the anti-proliferative and cytotoxic effects of cisplatin and doxorubicin on tumor cells in vitro, and in a murine tumor model in vivo. MAPKAP kinase-2 depletion is especially effective in increasing the chemosensitivity of p53-deficient cells, suggesting that compounds that target MAPKAP kinase-2 can be used as specific therapeutics that can sensitize p53-deficient tumor cells without sensitizing normal cells. At the systems level, in response to DNA damage, Chk1 and MAPKAP kinase-2 appear to function in parallel independent pathways that converge to phosphorylate similar molecular targets, such that checkpoint abrogation following MAPKAP kinase-2 depletion can be rescued by overexpression of Chk1.

Based on these results, we have invented novel methods of treating cellular proliferative disorders by inhibiting MAPKAP kinase-2 expression. We have also discovered MAPKAP kinase-2 inhibitors, pharmaceutical compounds containing such inhibitors that are useful for treating cellular proliferative disorders, and screening methods for identifying additional inhibitors. The methods and compounds of the invention may be used, for example, to treat cancer or to aid in the development of other anti-cancer therapies.

Accordingly, in one aspect, the invention features a method for treating a cellular proliferative disorder in a patient that includes the steps of: (a) determining whether the patient has a p53-deficient cell; and (b) if the patient has a p53-deficient cell, administering to the patient a compound, e.g., UCN-01, that is capable of inhibiting an activity of a MAPKAP kinase-2 polypeptide. Any method can be used to determine whether the patient has a p53-deficient cell, e.g., an antibody assay of a cell sample, e.g., from a tumor biopsy. The MAPKAP kinase-2 inhibition can be either specific or non-specific. The activity being inhibited may include, for example, MAPKAP kinase-2 polypeptide expression or substrate-binding. The method may also include the step of administering an additional treatment to the patient, such as a chemotherapeutic agent or radiation therapy, such that the compound and the chemotherapeutic agent or the radiation therapy are administered in amounts sufficient to treat the patient's cellular proliferative disorder. The additional treatment may be administered simultaneously or nonsimultaneously, e.g., up to twenty-eight days apart, in relation to the administration of the inhibitory compound. Any chemotherapeutic agent or radiation therapy known in the art may be useful in the methods of the invention. Exemplary chemotherapeutic agents are antimicrotubule drugs, e.g., nocodazole; compounds that create double-strand DNA breakage, e.g., doxorubicin and daunorubicin; compounds that induce single-strand DNA breaks, e.g., camptothecin; and cross-linking agents, e.g., cisplatin. Exemplary cellular proliferative disorders include neoplasms, e.g., any known form of cancer. In one embodiment, a solid tumor may be treated by injecting a MAPKAP kinase-2 inhibitor, alone or in combination with an additional therapeutic agent, directly into the tumor or by systemic administration. If given as a monotherapy, the compound is administered in an amount sufficient to treat the patient's cellular proliferative disorder; alternatively, in the case of combination therapy, the combination of compounds is collectively administered in an amount sufficient to treat the patient's cellular proliferative disorder.

An inhibitory compound used in the foregoing method may include a covalently-linked moiety capable of translocating across a biological membrane, such as a penetratin or TAT peptide. Alternatively, such a compound may be administered in the form of a prodrug. Suitable compounds include small molecule inhibitors of MAPKAP kinase-2 biological activity, RNA molecules useful in RNA interference therapy, RNA molecules useful in antisense therapy, and peptides capable of inhibiting a MAPKAP kinase-2 polypeptide. For example, an RNA molecule useful in the methods of the invention includes a double-stranded small interfering nucleic acid (siNA) molecule that is capable of directing cleavage of a MAPKAP kinase-2 RNA via RNA interference, wherein each strand of the siNA molecule is about 18 to 23 nucleotides in length, and one strand of the siNA molecule includes a nucleotide sequence that is substantially identical to the sequence of the MAPKAP kinase-2 RNA. In one embodiment, the siNA molecule includes RNA, the sequence of such RNA including, for example, any one of SEQ ID NOs: 29-32. Small hairpin nucleic acid (shNA) molecules may also be used in the methods of the invention. Alternatively, antisense therapy may be performed by administering a nucleobase oligomer, wherein the sequence of the oligomer is complementary to at least 10 consecutive residues of a nucleotide sequence encoding a MAPKAP kinase-2 polypeptide. Therapy may also be performed by utilizing a compound that includes a peptide or peptidomimetic, e.g., containing the amino acid sequence [L/F/I]XR[Q/S/T]L[S]L[S/T][Hydrophobic] (SEQ ID NO: 17), wherein X represents any amino acid and the peptide or peptidomimetic includes no more than 50 amino acids. Hydrophobic amino acids are selected from the group consisting of alanine, cysteine, isoleucine, leucine, methionine, phenylalanine, proline, tryptophan, tyrosine, and valine. In one embodiment, the peptide or peptidomimetic includes the amino acid sequence LQRQLSI (SEQ ID NO: 16).

In one aspect of the invention, administering a compound that is capable of inhibiting an activity of a MAPKAP kinase-2 polypeptide for treating a cellular proliferative disorder in a patient sensitizes p53-deficient cells to chemotherapeutic challenge. This can result in increased likelihood of death of aberrantly proliferating cells in a patient, in comparison to p53-deficient cells in a patient not receiving a MAPKAP kinase-2 inhibitor. The chemotherapeutics can be administered subsequently or concomitantly to administration of a MAPKAP kinase-2 inhibitor. An exemplary chemotherapeutic used in this regimen is UCN-01. Increased chemosensitivity of p53-deficient cells to a MAPKAP kinase-2 treatment may alter a DNA damage-responsive cell cycle checkpoint, in comparison to control p-53 deficient cells in a control patient not receiving the described therapy. Alteration of a DNA damage-responsive cell cycle checkpoint may occur at $G_1$/S phase arrest, where Cdc25a degradation impaired. Alteration of a DNA damage-responsive cell cycle checkpoint may occur at $G_2$/M phase arrest, where, the interaction between Cdc25b and a 14-3-3 protein is reduced. The above-mentioned alterations of cell cycle checkpoints may increase the likelihood of cell death, including cell death by apoptosis.

The invention further features kits that include: (a) a means of detecting the level of p53 polypeptide expression or activity in a cellular sample, e.g., by using an anti-p53 antibody; and (b) a compound that is capable of inhibiting an activity of a MAPKAP kinase-2 polypeptide, e.g., UCN-01. In some instances, the kit can also contain one or more chemotherapeutic agents.

The invention additionally features a method for treating a cellular proliferative disorder in a patient including administering to the patient a compound that is capable of inhibiting an activity of a MAPKAP kinase-2 polypeptide. In some instances, the cellular proliferative disorder includes the presence of one or more p53-deficient cells, e.g., tumor cells, in the patient. Administration of a MAPKAP kinase-2 polypeptide together with a chemotherapeutic compound has the desired effect of reducing tumor size. Administration of the described therapy can be, e.g., by direct injection into the tumor.

The invention further features a method for identifying a compound that may be an inhibitor of substrate binding to a MAPKAP kinase-2 polypeptide, the method including the steps of: contacting the MAPKAP kinase-2 polypeptide and a compound capable of binding the MAPKAP kinase-2 polypeptide under conditions allowing the formation of a complex between the compound and the MAPKAP kinase-2 polypeptide; contacting the complex with a candidate compound; and measuring the displacement of the compound capable of binding the MAPKAP kinase-2 polypeptide from the MAPKAP kinase-2 polypeptide. The displacement of the compound capable of binding identifies the candidate compound as a compound that may be an inhibitor of substrate binding to a MAPKAP kinase-2 polypeptide. In one embodiment, the compound capable of binding the MAPKAP kinase-2 polypeptide includes a peptide or peptidomimetic, e.g., containing the amino acid sequence [L/F/I]XR[Q/S/T] L[S/T][Hydrophobic] (SEQ ID NO: 17), wherein the peptide or peptidomimetic includes no more than 50 amino acids. For example, the peptide or peptidomimetic may include the amino acid sequence LQRQLSI (SEQ ID NO: 16). In the foregoing method, a substrate-binding fragment of a MAPKAP kinase-2 polypeptide may be utilized in place of a full-length MAPKAP kinase-2 polypeptide.

Variations of the foregoing aspect are also possible in the methods of the invention. The MAPKAP kinase-2 polypeptide, or substrate-binding fragment thereof, and compound capable of binding the polypeptide may be contacted in the presence of a candidate compound, and any means of measuring the binding of the MAPKAP kinase-2 polypeptide and the compound capable of binding may be used in the methods of the invention. In general, if the amount of binding of the MAPKAP kinase-2 polypeptide and the compound capable of binding is decreased in the presence of the candidate compound in comparison to the amount of binding measured in the absence of the candidate compound, then the candidate compound is determined to be an inhibitor of substrate binding using the methods of the invention.

In another aspect, the invention features a method for identifying a compound that may be an inhibitor of substrate binding to a MAPKAP kinase-2 polypeptide or substrate-binding fragment thereof, the method including the steps of: providing a three-dimensional model of the MAPKAP kinase-2 polypeptide having at least one atomic coordinate, or surrogate thereof, from Table 1 for at least three of the residues Ile74, Glu145, Lys188, Glu190, Phe210, Cys224, Tyr225, Thr226, Pro227, Tyr228, Tyr229, and Asp345, or atomic coordinates that have a root mean square deviation of the coordinates of less than 3 Å; and producing a structure for a candidate compound, the structure defining a molecule having sufficient surface complementary to the MAPKAP kinase-2 polypeptide to bind the MAPKAP kinase-2 polypeptide in an aqueous solution.

The invention further features a compound that includes a peptide or peptidomimetic, e.g., containing the amino acid sequence [L/F/I]XR[Q/S/T]L[S/T][Hydrophobic] (SEQ ID NO: 17), wherein the peptide or peptidomimetic includes no more than 50 amino acids. In one embodiment, the peptide or peptidomimetic includes the amino acid sequence LQRQLSI (SEQ ID NO: 16). An inhibitory compound of the invention may include a covalently-linked moiety capable of translocating across a biological membrane, such as a penetratin or TAT peptide. Alternatively, such a compound may be administered in the form of a prodrug.

In another aspect, the invention features a pharmaceutical composition for treating a cellular proliferative disorder in a patient, the composition including: a compound that is capable of inhibiting an activity of a MAPKAP kinase-2 polypeptide; and a chemotherapeutic agent, wherein the composition is formulated in an amount sufficient to treat the cellular proliferative disorder. Any chemotherapeutic agent known in the art may be useful in the compositions of the invention. An inhibitory compound useful in the pharmaceutical composition may include a covalently-linked moiety capable of translocating across a biological membrane, such as a penetratin or TAT peptide. Alternatively, such a compound may be administered in the form of a prodrug. Any compounds described in any of the foregoing aspects, including small molecule inhibitors, compounds containing siNA molecules, antisense RNA molecules, or peptides, may be useful in the pharmaceutical compositions of the invention.

In any of the foregoing aspects of the invention, it is desirable that the inhibitory compounds be specific inhibitors of MAPKAP kinase-2, e.g., compounds that inhibit a MAPKAP kinase-2 polypeptide without also substantially inhibiting related kinases such as Chk1, Chk2, and p38 SAPK, although compounds that inhibit a MAPKAP kinase-2 polypeptide in a less selective or non-selective manner are also useful in the methods of the invention.

As used throughout this specification and the appended claims, the following terms have the meanings specified.

By an "amino acid fragment" is meant an amino acid residue that has been incorporated into a peptide chain via its alpha carboxyl, its alpha nitrogen, or both. A terminal amino acid is any natural or unnatural amino acid residue at the amino-terminus or the carboxy-terminus. An internal amino acid is any natural or unnatural amino acid residue that is not a terminal amino acid.

By "analog" is meant a molecule that is not identical but has analogous features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "antisense," as used herein in reference to nucleic acids, is meant a nucleic acid sequence, regardless of length, that is complementary to the coding strand of a gene.

By "atomic coordinates" is meant those three-dimensional coordinates of the atoms in a crystalline material derived from mathematical equations related to the patterns obtained on diffraction of x-rays by the atoms (x-ray scattering centers) of the crystalline material. The diffraction data are used to calculate an electron density map of the unit cell of the crystal. These electron density maps are used to establish the positions of the individual atoms within the unit cell of the crystal. Atomic coordinates can be transformed, as is known to those skilled in the art, to different coordinate systems (i.e., surrogate systems) without affecting the relative positions of the atoms.

By "binding to" a molecule is meant having a physicochemical affinity for that molecule. Binding may be measured by any of the methods of the invention, e.g., using an in vitro translation binding assay.

By "biological activity" of a polypeptide or other compound is meant having structural, regulatory, or biochemical functions of a naturally occurring molecule. For example, one biological activity of a MAPKAP kinase-2 polypeptide is substrate binding, e.g., peptide binding, which may be measured using in vivo or in vitro binding assays.

By "caged compound" is meant a biologically active molecule coupled to a cleavable moiety such that the resulting coupled compound lacks biological activity as long as the moiety remains attached. Such a moiety prevents bioaction by sterically shielding one or more chemical groups of the molecule. The moiety may be removed by any means, including enzymatic, chemical, or photolytic; removal of the moiety results in restoration of the molecule's biological activity.

By "candidate compound" is meant any nucleic acid molecule, polypeptide, or other small molecule that is assayed for its ability to alter gene or protein expression levels, or the biological activity of a gene or protein by employing one of the assay methods described herein. Candidate compounds include, for example, peptides, polypeptides, synthesized organic molecules, naturally occurring organic molecules, nucleic acid molecules, and components thereof.

By "cellular proliferative disorder" is meant any pathological condition in which there is an abnormal increase or decrease in cell proliferation. Exemplary cellular proliferative disorders include cancer or neoplasms, inflammatory diseases, or hyperplasias (e.g., some forms of hypertension, prostatic hyperplasia).

By "chemotherapeutic agent" is meant one or more chemical agents used in the treatment or control of proliferative diseases, including cancer. Chemotherapeutic agents include cytotoxic and cytostatic agents.

By "complex" is meant a chemical association of two or more molecules. Complexes may include a network of weak electrostatic bonds that maintain the association of the molecules. Other types of interactions, such as covalent, ionic, hydrogen bond, hydrophobic, or van der Waals interactions, may be present instead of or in addition to electrostatic bonds between members of a complex.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model. Examples of techniques useful in the above evaluations include: quantum mechanics, molecular mechanics, molecular dynamics, Monte Carlo sampling, systematic searches and distance geometry methods. Further descriptions of computer modeling programs are provided elsewhere herein.

By "detectably-labeled" is meant any means for marking and identifying the presence of a molecule, e.g., a peptide or a peptidomimetic small molecule that interacts with a MAPKAP kinase-2 domain. Methods for detectably-labeling a molecule are well known in the art and include, without limitation, radionuclides (e.g., with an isotope such as $^{32}P$, $^{33}P$, $^{125}I$, or $^{35}S$), nonradioactive labeling (e.g., chemiluminescent labeling or fluorescein labeling), and epitope tags.

If required, molecules can be differentially labeled using markers that can distinguish the presence of multiply distinct molecules. For example, a peptide that interacts with a MAPKAP kinase-2 domain can be labeled with fluorescein and a MAPKAP kinase-2 domain can be labeled with Texas Red. The presence of the peptide can be monitored simultaneously with the presence of the MAPKAP kinase-2 domain.

By "fragment" is meant a portion of a polypeptide or nucleic acid having a region that is substantially identical to a portion of a reference protein or nucleic acid and retains at least 50%, 75%, 80%, 90%, 95%, or even 99% of at least one biological activity of the reference protein or nucleic acid.

By "hydrophobic" in the context of amino acids is meant any of the following amino acids: alanine, cysteine, isoleucine, leucine, methionine, phenylalanine, proline, tryptophan, tyrosine, or valine.

By "inhibit an activity of a MAPKAP kinase-2 polypeptide" is meant to reduce one or more biological activities of MAPKAP kinase-2 polypeptide. Desirably, the inhibition is a decrease of at least 10%, 20%, 30%, 40%, 50%, 60%, 70%, 80%, 90% or 95% in biological activity, relative to a control activity, for example the expression or substrate-binding capability of a naturally occurring MAPKAP kinase-2 polypeptide. An example of a compound that inhibits a MAPKAP kinase-2 polypeptide is UCN-01.

By "MAPKAP kinase-2 biological activity" is meant any activity known to be caused in vivo or in vitro by a MAPKAP kinase-2 polypeptide. For example, such activity could be caused by at least one of the following: function in a DNA damage response pathway, cell cycle control, transcriptional regulation, chromatin remodeling, or substrate binding. In one assay for MAPKAP kinase-2 biological activity, the ability of MAPKAP kinase-2, or a fragment or mutant thereof comprising a substrate-binding domain, to bind a substrate is measured.

By "MAPKAP kinase-2 nucleic acid" is meant a nucleic acid that encodes all or a portion of a MAPKAP kinase-2 polypeptide or is substantially identical to all or a portion of the nucleic acid sequence of Genbank Accession Nos. NM_004759 (SEQ ID NO: 1) or NM_032960 (SEQ ID NO: 2), or analog thereof.

By "MAPKAP kinase-2 polypeptide" and "MK2" are used interchangeably herein, and denote a polypeptide substantially identical to all or a portion of the polypeptide sequence of Genbank Accession Nos. NP_004750 (SEQ ID NO: 3) or P49137 (SEQ ID NO: 4), or analog thereof, and having MAPKAP kinase-2 biological activity.

By "neoplasia" or "neoplasm" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred nucleic acids may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—

CH$_2$ backbones (where phosphodiester is O—P—O—CH$_2$). Also preferred are oligonucleotides having morpholino backbone structures (Summerton, J. E. and Weller, D. D., U.S. Pat. No. 5,034,506). In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone (P. E. Nielsen et al. Science 199: 254, 1997). Other preferred oligonucleotides may contain alkyl and halogen-substituted sugar moieties comprising one of the following at the 2' position: OH, SH, SCH$_3$, F, OCN, O(CH$_2$)$_n$NH$_2$ or O(CH$_2$)$_n$CH$_3$, where n is from 1 to about 10; C$_1$ to C$_{10}$ lower alkyl, substituted lower alkyl, alkaryl or aralkyl; Cl; Br; CN; CF$_3$; OCF$_3$; O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group.

Other preferred embodiments may include at least one modified base form. Some specific examples of such modified bases include 2-(amino)adenine, 2-(methylamino)adenine, 2-(imidazolylalkyl)adenine, 2-(aminoalklyamino)adenine, or other heterosubstituted alkyladenines.

By "p53-deficient cell" is meant a cell expressing substantially less p53 polypeptide, or exhibiting substantially less p53 polypeptide activity, e.g., 10%, 20%, 30%, 40%, 50%, 60%, 70%, 80%, 90%, 95%, 98%, 99%, or even 100% less p53 expression or activity, than a corresponding wild-type cell. For example, p53-deficient cells, e.g., tumor cells, are present in some neoplastic disorders. p53-deficient cells include cells with one or more p53 gene mutations, e.g., point mutations or null mutations, that reduce or eliminate expression or activity.

By a "peptidomimetic" is meant a compound that is capable of mimicking or antagonizing the biological actions of a natural parent peptide. A peptidomimetic may include non-peptidic structural elements, unnatural peptides, synthesized organic molecules, naturally occurring organic molecules, nucleic acid molecules, and components thereof. Identification of a peptidomimetic can be accomplished by screening methods incorporating a binding pair and identifying compounds that displace the binding pair. Alternatively, a peptidomimetic can be designed in silico, by molecular modeling of a known protein-protein interaction, for example, the interaction of a peptide of the invention and a MAPKAP kinase-2 domain. In one embodiment, the peptidomimetic will displace one member of a binding pair by occupying the same binding interface. It is desirable that the peptidomimetic have a higher binding affinity to the binding interface.

By "pharmaceutically acceptable excipient" is meant a carrier that is physiologically acceptable to the subject to which it is administered and that preserves the therapeutic properties of the compound with which it is administered. One exemplary pharmaceutically acceptable excipient is physiological saline. Other physiologically acceptable excipients and their formulations are known to one skilled in the art and described, for example, in "Remington: The Science and Practice of Pharmacy," (20th ed., ed. A. R. Gennaro, 2000, Lippincott Williams & Wilkins).

By "phosphopeptide" is meant a peptide in which one or more phosphate moieties are covalently linked to serine, threonine, tyrosine, aspartic acid, histidine amino acid residues, or amino acid analogs. A peptide can be phosphorylated to the extent of the number of serine, threonine, tyrosine, or histidine amino acid residues that is present. A phosphopeptide may be phosphorylated at four independent Ser/Thr/Tyr residues, at three independent Ser/Thr/Tyr residues, or at two independent Ser/Thr/Tyr residues. Desirably, a phosphopeptide is phosphorylated at one Ser/Thr/Tyr residue regardless of the presence of multiple Ser, Thr, or Tyr residues.

Typically, a phosphopeptide is produced by expression in a prokaryotic or eukaryotic cell under appropriate conditions or in translation extracts where the peptide is subsequently isolated, and phosphorylated using an appropriate kinase. Alternatively, a phosphopeptide may be synthesized by standard chemical methods, for example, using N-α-FMOC-protected amino acids (including appropriate phosphoamino acids). In a desired embodiment, the use of non-hydrolysable phosphate analogs can be incorporated to produce non-hydrolysable phosphopeptides (Jenkins et al., J. Am. Chem. Soc., 124:6584-6593, 2002; herein incorporated by reference). Such methods of protein synthesis are commonly used and practiced by standard methods in molecular biology and protein biochemistry (Ausubel et al., Current Protocols in Molecular Biology, John Wiley & Sons, New York, N.Y., 1994, J. Sambrook and D. Russel, Molecular Cloning: A Laboratory Manual, 3$^{rd}$ Edition, Cold Spring Harbor Laboratory Press, Woodbury N.Y., 2000). In one embodiment, a phosphopeptide is generally not longer than 100 amino acid residues in length. Shorter phosphopeptides, e.g., less than 50, 25, 20, or 15 residues, are also possible. Phosphopeptides may be as short as 2, 3, 4, 5, 6, 7, 8, 9, or 10 amino acid to residues long.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

As used herein, a natural amino acid is a natural α-amino acid having the L-configuration, such as those normally occurring in natural proteins. Unnatural amino acid refers to an amino acid, which normally does not occur in proteins, e.g., an epimer of a natural α-amino acid having the L configuration, that is to say an amino acid having the unnatural D-configuration; or a (D,L)-isomeric mixture thereof; or a homologue of such an amino acid, for example, a β-amino acid, an α,α-disubstituted amino acid, or an α-amino acid wherein the amino acid side chain has been shortened by one or two methylene groups or lengthened to up to 10 carbon atoms, such as an α-amino alkanoic acid with 5 up to and including 10 carbon atoms in a linear chain, an unsubstituted or substituted aromatic (α-aryl or α-aryl lower alkyl), for example, a substituted phenylalanine or phenylglycine. Other amino acids that may also be incorporated into a polypeptide include ornithine (O or Orn) and hydroxyproline (Hyp).

Polypeptides or derivatives thereof may be fused or attached to another protein or peptide, for example, as a Glutathione-S-Transferase (GST) fusion polypeptide. Other commonly employed fusion polypeptides include, but are not limited to, maltose-binding protein, *Staphylococcus aureus* protein A, Flag-Tag, HA-tag, green fluorescent proteins (e.g., eGFP, eYFP, eCFP, GFP, YFP, CFP), red fluorescent protein, polyhistidine (6×His), and cellulose-binding protein.

By "prodrug" is meant a compound that is modified in vivo, resulting in formation of a biologically active drug compound, for example by hydrolysis in blood. A thorough discussion of prodrug modifications is provided in T. Higuchi and V. Stella, Pro-drugs as Novel Delivery Systems, Vol. 14 of the A. C. S. Symposium Series, Edward B. Roche, ed., Bioreversible Carriers in Drug Design, American Pharmaceutical Association and Pergamon Press, 1987, and Judkins et al., Synthetic Communications 26 (23):4351-4367, 1996, each of which is incorporated herein by reference.

By "purified" is meant separated from other components that naturally accompany it. Typically, a factor is substantially pure when it is at least 50%, by weight, free from proteins, antibodies, and naturally-occurring organic molecules with which it is naturally associated. The factor may be at least 75%, 90%, or even 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques such as those described by Coligan et al. (Current Protocols in Protein Science, John Wiley & Sons, New York, 2000). The factor is desirably at least 2, 5, or 10 times as pure as the starting material, as measured using polyacrylamide gel electrophoresis or column chromatography (including HPLC) analysis (Coligan et al., supra). Exemplary methods of purification include (i) salting-out, i.e., $(NH_4)_2SO_4$ precipitation; (ii) conventional chromatography, e.g., ion exchange, size exclusion, hydrophobic interaction, or reverse-phase; (iii) affinity chromatography, e.g., immunoaffinity, active site affinity, dye affinity, or immobilized-metal affinity; and (iv) preparative electrophoresis, e.g., isoelectric focusing or native PAGE.

By "RNA interference" (RNAi) is meant a phenomenon where double-stranded RNA homologous to a target mRNA leads to degradation of the targeted mRNA. More broadly defined as degradation of target mRNAs by homologous siRNAs.

By "sensitivity" or "sensitivity to an agent" is meant an increased likelihood of cell death in response to genotoxic stress. An exemplary means of sensitivity occurs when a patient having p53-deficient tumor cell is administered a composition including MAPKAP kinase-2 polypeptide inhibitor and a chemotherapeutic agent, resulting in reduction of tumor size. A reduction in tumor size in the described patient receiving the described therapy is determined in comparison to a control p53-deficient tumor cell in a to control patient not receiving the described therapy. Desirably, tumors are reduced is size by 10%, 20%, 30%, 40%, 50%, 60%, 70%, 80%, 90% or 95% in comparison to the described control.

By "siNA" is meant small interfering nucleic acids. One exemplary siNA is composed of ribonucleic acid (siRNA). siRNAs can be 21-25 nt RNAs derived from processing of linear double-stranded RNA. siRNAs assemble in complexes termed RISC (RNA-induced silencing complex) and target homologous RNA sequences for endonucleolytic cleavage. Synthetic siRNAs also recruit RISCs and are capable of cleaving homologous RNA sequences By "specifically inhibit an activity of a MAPKAP kinase-2 polypeptide" is meant to reduce one or more biological activities of MAPKAP kinase-2 polypeptide, without substantially inhibiting related kinases, e.g., Chk1, Chk2, and p38 SAPK. Desirably, the specific inhibition is a decrease of at least 10%, 20%, 30%, 40%, 50%, 60%, 70%, 80%, 90% or 95% in biological activity, relative to a control activity, for example the expression or substrate-binding capability of a naturally occurring MAPKAP kinase-2 polypeptide. An exemplary means of specific inhibition occurs through use of RNA interference. An example of a compound that inhibits a MAPKAP kinase-2 polypeptide, but does not do so specifically, is UCN-01.

By "substantially identical" is meant a polypeptide or nucleic acid exhibiting at least 75%, 85%, 90%, 95%, or even 99% identity to a reference amino acid or nucleic acid sequence. For polypeptides, the length of comparison sequences will generally be at least 35 amino acids, 45 amino acids, 55 amino acids, or even 70 amino acids. For nucleic acids, the length of comparison sequences will generally be at least 60 nucleotides, 90 nucleotides, or even 120 nucleotides.

Sequence identity is typically measured using publicly available computer programs. Computer program methods to determine identity between two sequences include, but are not limited to, the GCG program package (Devereux et al., Nucleic Acids Research 12: 387, 1984), BLASTP, BLASTN, and FASTA (Altschul et al., J. Mol. Biol. 215:403 (1990). The well-known Smith Waterman algorithm may also be used to determine identity. The BLAST program is publicly available from NCBI and other sources (e.g., BLAST Manual, Altschul et al., NCBI NLM NIH, Bethesda, Md. 20894). These software programs match similar sequences by assigning degrees of homology to various substitutions, deletions, and other modifications. Conservative substitutions for amino acid comparisons typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "substantially inhibit" is meant to reduce one or more activities of the molecule being inhibited by at least 50%, 60%, 70%, 80%, 90%, 95%, or even 98% compared to a control activity value.

By "substrate-binding fragment" in reference to a MAPKAP kinase-2 polypeptide is meant a portion of the polypeptide that is capable of binding a peptide or peptidomimetic substrate. For example, fragments of MAPKAP kinase-2 polypeptide that include the region Phe46-Asp345 (with reference to SEQ ID NO: 3) are substrate-binding fragments.

By "surrogate," in the context of atomic coordinates, is meant any modification (e.g., mathematical modification or scaling) of the coordinates that preserves the relative relationships among the coordinates.

By "three-dimensional model" is meant a three-dimensional representation of a molecule's structure. Computer modeling may be used to generate such a model in conjunction with structural data. These data could include x-ray crystallographic data, nuclear magnetic resonance data, electron microscopy data, or any other source of experimental or theoretical data useful for generating a model of a molecule or complex of molecules.

By "treating" a disease, disorder, or condition is meant preventing or delaying an initial or subsequent occurrence of a disease, disorder, or condition; increasing the disease-free survival time between the disappearance of a condition and its reoccurrence; stabilizing or reducing an adverse symptom associated with a condition; or inhibiting, slowing, or stabilizing the progression of a condition. Desirably, at least 20, 40, 60, 80, 90, or 95% of the treated subjects have a complete remission in which all evidence of the disease disappears. In another desirable embodiment, the length of time a patient survives after being diagnosed with a condition and treated with a compound of the invention is at least 20, 40, 60, 80, 100, 200, or even 500% greater than (i) the average amount of time an untreated patient survives or (ii) the average amount of time a patient treated with another therapy survives.

By "unnatural amino acid" is meant an organic compound that has a structure similar to a natural amino acid, where it mimics the structure and reactivity of a natural amino acid. The unnatural amino acid as defined herein generally increases or enhances the properties of a peptide (e.g., selectivity, stability, binding affinity) when the unnatural amino acid is either substituted for a natural amino acid or incorporated into a peptide. Unnatural amino acids and peptides including such amino acids are described, e.g., in U.S. Pat. Nos. 6,566,330 and 6,555,522.

Other features and advantages of the invention will be apparent from the following description of the desirable embodiments thereof, and from the claims.

BRIEF DESCRIPTION OF THE DRAWINGS

FIGS. 1A-1D depict the substrate specificity and kinetic analysis of substrate phosphorylation by p38α SAPK. FIG. 1A is a table showing p38 substrate specificity determined using oriented peptide library screening. Residues displaying the highest selectivity are shown; those with selection values >1.7 in bold. Abbreviations: MEF2A, Myocyte Enhancer Factor 2; ATF2, Activating Transcription Factor 2; 3PK1, MAP Kinase-activated Protein Kinase-3. FIG. 1B is a graph showing the kinetics of in vitro phosphorylation of an optimal p38 peptide (p38tide) and a peptide from p47phox (p47tide) by p38α kinase. FIG. 1C is a graph showing the kinetics of in vitro phosphorylation of wild-type GST-p47phox, the Ser345→Ala mutant, and the Ser348→Ala mutant. Typical data from n=3 experiments is shown. FIG. 1D is a table of kinetic parameters for the reactions shown in FIG. 1C.

FIGS. 2A-2C depict the substrate specificity and kinetic analysis of substrate phosphorylation by MAPKAP kinase-2. FIG. 2A is a table showing MAPKAP kinase-2 substrate specificity determined by oriented peptide library screening. Abbreviations: HSP27, Heat Shock protein 27; 5-LO, 5-Lipoxygenase; LSP1, lymphocyte-specific protein; SRF, Serum Response Factor; GS, Glycogen Synthase; TH, Tyrosine Hydroxylase. FIG. 2B is a graph showing the kinetics of in vitro phosphorylation of the optimal MAPKAP kinase-2 peptide (MK2tide) by MAPKAP kinase-2. FIG. 2C is a table of kinetic parameters for MAPKAP kinase-2 phosphorylation of wild-type and mutant MK2tides.

FIGS. 3A-3J show that MAPKAP kinase-2 is required for $G_2/M$ arrest following DNA damage. FIG. 3A is a graph depicting a FACS analysis of GFP siRNA-treated non-irradiated U2OS cells placed in 50 ng/ml nocodazole-containing media for 16 hours. Cells were analyzed for DNA content by PI staining. FIG. 3B is a graph depicting a FACS analysis of GFP siRNA-treated non-irradiated U2OS cells placed in 50 ng/ml nocodazole-containing media for 16 hours. Cells were analyzed for phospho-histone H3 staining as a marker of mitotic entry. FIG. 3C is a graph depicting a FACS analysis of GFP siRNA-treated irradiated U2OS cells placed in 50 ng/ml nocodazole-containing media for an additional 16 hours. Cells were analyzed for DNA content by PI staining. FIG. 3D is a graph depicting a FACS analysis of GFP siRNA-treated irradiated U2OS cells placed in 50 ng/ml nocodazole-containing media for an additional 16 hours. Cells were analyzed for phospho-histone H3 staining as a marker of mitotic entry. FIG. 3E is a graph depicting a FACS analysis of MAPKAP kinase-2 siRNA-treated non-irradiated U2OS cells placed in 50 ng/ml nocodazole-containing media for 16 hours. Cells were analyzed for DNA content by PI staining. FIG. 3F is a graph depicting a FACS analysis of MAPKAP kinase-2 siRNA-treated non-irradiated U2OS cells placed in 50 ng/ml nocodazole-containing media for 16 hours. Cells were analyzed for phospho-histone H3 staining as a marker of mitotic entry. FIG. 3G is a graph depicting a FACS analysis of MAP-KAP kinase-2 siRNA-treated irradiated U2OS cells placed in 50 ng/ml nocodazole-containing media for 16 hours. Cells were analyzed for DNA content by PI staining. FIG. 3H is a graph depicting a FACS analysis of MAPKAP kinase-2 siRNA-treated irradiated U2OS cells placed in 50 ng/ml nocodazole-containing media for 16 hours. Cells were analyzed for phospho-histone H3 staining as a marker of mitotic entry. FIG. 3I is a graph depicting the results of an experiment in which GFP siRNA- or MAPKAP kinase-2-siRNA treated U2OS cells were either mock treated or exposed to 20 J/m$^2$ of UV-C irradiation, and analyzed as described for FIGS. 3A-3H. Representative results of each experiment are shown. FIG. 3J is a graph depicting the results of an experiment in which GFP siRNA- or MAPKAP kinase-2-siRNA treated U2OS cells were either mock treated or exposed to 10 Gy of ionizing radiation, and analyzed as described for FIGS. 3A-3H. Representative results of each experiment are shown.

In FIG. 4A, GFP siRNA- or MAPKAP kinase-2-siRNA-treated U2OS cells were mock treated or UV-irradiated and allowed to recover for 30 min. BrdU was added and cells were fixed and analyzed by FACS for DNA content and BrdU incorporation twelve hours later. FIG. 4B is a graph showing the percentage of cells in FIG. 4A showing BrdU incorporation at two and twelve hours following BrdU addition. In FIG. 4C, GFP siRNA- or MAPKAP kinase-2-siRNA-treated U2OS cells were either mock treated or UV-irradiated, allowed to recover for 30 min, then pulse-labeled with BrdU for 30 minutes. At the indicated times after irradiation the distribution of DNA content was analyzed in the BrdU-positive population. FIG. 4D is a graph showing the results of quantitative colony forming assays performed by plating cells at a density of ~100 cells per 35 mm$^2$ dish. Cells were either mock treated or irradiated at the indicated UV C dose, and assays were performed in triplicate for each condition.

FIG. 6 is a summary of the requirement for ATM and/or ATR for the activation of MK2.

FIGS. 7A-7D show that MAPKAP kinase-2 depletion enhances regression of established tumors after DNA damaging chemotherapy in a murine model. In FIGS. 7A-7C, following subcutaneous injection of 10$^6$ MAPKAP kinase-2 siRNA or control (Luciferase) siRNA treated cells into the flanks of NCR nude outbred mice, tumor growth was measured every two days. In FIGS. 7A-7C, the arrow indicates the start of intraperitoneal administration of DMSO, cisplatin, or doxorubicin on day twelve. In the absence of DNA damaging chemotherapy, the MAPKAP kinase-2 depleted tumors were statistically significantly larger than the control tumors at each time point beginning on day thirteen (Student's t-test, 2-tailed, p<0.02). In contrast, after cisplatin or doxorubicin treatment the MAPKAP kinase-2 depleted tumors were statistically smaller than the control tumors beginning on days twenty-one and twenty-three, respectively (p<0.02). Lower panels are close-up views of the excised tumors. FIG. 7D is a graph showing an analysis of tumor weight at the twenty-six-day endpoint.

DETAILED DESCRIPTION OF THE INVENTION

Figures 2B, 2C:
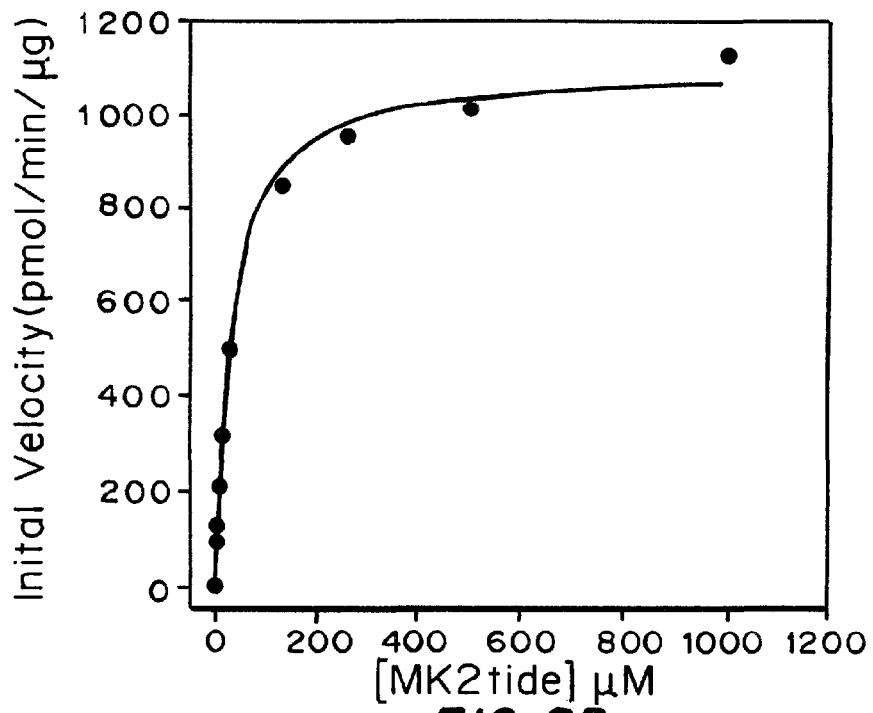

The invention features methods and compounds that are useful in treating cellular proliferative disorders. The methods of treatment feature administration of a compound that is capable of inhibiting an activity of a MAPKAP kinase-2 polypeptide, or a substrate-binding fragment thereof. Such compounds include, without limitation, compounds that contain peptides, peptidomimetics, or nucleic acid molecules. The invention further features screening assays for identifying MAPKAP kinase-2 inhibitors. In addition, the invention includes pharmaceutical compositions and compounds, e.g., peptides and peptidomimetics, that target the substrate-binding site of MAPKAP kinase-2, thereby inhibiting it.

It was recently shown that, in addition to the ATR-Chk1 pathway, the p38 SAPK pathway is also required for full activation of the DNA damage response following UV irradiation. We now demonstrate that MAPKAP kinase-2, a direct downstream target of p38 SAPK, is directly responsible for phosphorylating Cdc25B and C and maintaining the $G_1$, S, and $G_2/M$ checkpoints in response to UV-induced DNA damage. Thus, MAPKAP kinase-2 constitutes a third checkpoint kinase, in addition to Chk1 and Chk2, involved in coordinating the DNA damage response of higher eukaryotic cells.

A number of important questions regarding this third DNA damage response pathway have not been previously answered. Is p38 MAPK/MAPKAP kinase-2 activation after DNA damage dependent on ATR or ATM? Is p38 MAPK/MAPKAP kinase-2 cascade important for DNA damage checkpoints in response to other types of genotoxic stress besides UV? How are signals from the Chk1 pathway and the MAPKAP kinase-2 pathway integrated together at the systems level? We were particularly interested in investigating whether MAPKAP kinase-2/Chk3 participates in the genotoxic stress response of cells exposed to conventional anti-cancer chemotherapeutic agents. A demonstration that MAPKAP kinase-2 has an important role in preventing cells with chemotherapy induced DNA damage from progressing through the cell cycle would implicate MAPKAP kinase-2 as a clinically important target for anti-cancer drug design.

Defining the Optimal Phosphorylation Motif for p38 SAPK

To identify substrates and targets of the p38 SAPK signaling pathway involved in DNA damage responses, we determined the optimal substrate phosphorylation motif for p38α SAPK using oriented peptide library screening. Efficient peptide phosphorylation by p38 SAPK required a fixed Pro residue in the Ser+1 position, consistent with the known identification of p38 SAPK as a Pro-directed MAP kinase. Screening performed with a library containing the degenerate sequence XXXXSPXXXX (SEQ ID NO: 8) (X denotes all amino acids except Cys, Ser, Thr, and Tyr) displayed strongest selection for Pro in the Ser-2 position with weaker selection for other aliphatic residues (FIG. 1A). Additional selection was also observed at the Ser-3, Ser-1, and Ser+2 positions.

To further refine the optimal phosphorylation motif, a secondary screen was performed based on results from the initial screen by using a library with Pro fixed in both the Ser-2 and Ser+1 positions, and Ser, Thr, and Tyr included in the X positions. This revealed selection for Gln, Met, and Gly in the Ser-1 position, along with slightly weaker selection for Pro, Ser and Thr (FIG. 1A). Gly was the preferred residue in the Ser-3 position, along with Ile, Val, and Tyr. Hydrophobic residues, particularly aromatic and β-branched amino acids, were selected at the Ser+2 position. The resulting optimal motif for p38α SAPK determined by oriented peptide library screening closely matches the sequence of mapped p38 MAPK phosphorylation sites on most, though not all, known substrates (FIG. 1A).

A peptide containing the optimal p38 SAPK consensus phosphorylation motif GPQSPI (SEQ ID NO: 9), "p38tide," was synthesized for kinetic analysis. This peptide was readily phosphorylated by p38 SAPK in vitro; however, it failed to display saturable Michaelis-Menton-type kinetics (FIG. 1B). Instead, the initial velocity increased linearly with increasing p38tide concentration up to 1400 µM. This finding suggests that additional interactions besides an optimal phosphorylation motif are likely to be involved in optimizing p38 SAPK-substrate binding, such as MAP kinase docking sites.

To search for potential p38 SAPK substrates, particularly those relevant to DNA damage signaling, the Swiss-Prot database was queried with the p38 SAPK consensus phosphorylation motif using Scansite. Other than GADD153, a known p38 SAPK substrate, we were unable to identify any DNA damage response proteins in the top 250 hits. Database searching did, however, reveal two tandem near-optimal p38 SAPK phosphorylation sites (Ser345 and Ser348) in p47phox, a cytosolic component of the NADPH oxidase enzyme. A peptide containing this sequence, PGPQSPGSPL (SEQ ID NO: 10), "p47tide," was strongly phosphorylated by p38 SAPK, but like p38tide, the isolated peptide displayed linear non-saturable kinetics (FIG. 1B).

Wild-type and mutant versions of GST-tagged full-length p47phox protein, rather than isolated peptides, were then used as substrates for in vitro phosphorylation reactions. The wild-type full-length p47phox protein was rapidly phosphorylated by p38α SAPK (FIG. 1C). Mutation of Ser345→Ala had a more pronounced effect on p47phox phosphorylation than mutation of Ser348→Ala, in excellent agreement with the observation that the Ser345 site is a better match for the optimal p38 SAPK consensus motif than the Ser348 site. Simultaneous mutation of both Ser345 and Ser348 to Ala eliminated phosphorylation of p47phox by p38 SAPK altogether. Kinetic analysis revealed classical Michaelis-Menton behavior for p38 SAPK phosphorylation of the wild-type p47phox with a $K_m$ of 6.0 µM and a $V_{max}$ of 36.6 nmol/min/µg. Mutation of Ser345 to Ala both increased the $K_m$ and reduced the $V_{max}$, while mutation of Ser348 to Ala primarily increased the $K_m$ (FIG. 1D).

These data from isolated peptides and intact proteins argue that efficient substrate phosphorylation by p38 SAPK requires sequences with reasonable matches to the optimal substrate motif determined by oriented peptide library screening, and that additional interactions involving MAPK docking sites are likely to be critical for strong kinase-substrate interactions. Several docking motifs have been identified for p38 SAPK, particularly a short cluster of positively charged amino acid residues often flanked by hydrophobic amino acids. Two sequences corresponding to this type of docking motif are present near the p38SAPK phosphorylation sites in p47 phox, IHQRSRKRLSQ (SEQ ID NO: 11) and VRFLQQRRRQA (SEQ ID NO: 12). Mutation of RRR to LLL in the latter motif decreased the rate of p38α SAPK phosphorylation of p47phox by over 70%.

Bulavin et al. (Nature, 411:102-107, 2001) implicated p38 SAPK in the DNA damage response pathway and reported that p38 SAPK was directly responsible for generating a 14-3-3-binding site on Cdc25B (Ser323 in Cdc25B2; Ser309 in Cdc25B1) in response to UV-C-induced DNA damage. Like p47phox, Cdc25B contains a potential p38 SAPK docking motif, PVQNKRRRSV (SEQ ID NO: 13); however, the sequence flanking Ser323, LXRSPSMP (SEQ ID NO: 14), lacks a Pro in the Ser+1 position and does not resemble the optimal p38 SAPK motif shown in FIG. 1A. Recombinant p38 SAPK readily phosphorylated bacterially produced Cdc25B in vitro. However, this phosphorylation did not induce 14-3-3-binding, and a Ser323→Ala mutant form of Cdc25B was phosphorylated by p38 SAPK equivalently to the wild-type Cdc25B protein. These data argue that, while Cdc25B may be a p38 SAPK substrate, this phosphorylation event is not responsible for the 14-3-3-binding event that results in a $G_2$/M checkpoint.

Defining the Optimal Phosphorylation Motif for MAPKAP Kinase-2

A number of Ser/Thr kinases are activated downstream of p38 SAPK, including MAPKAP Kinases-2 and -3, MNK1 and MNK2, MSK1 and MSK2, and PRAK. In response to UV-B-induced DNA damage, She et al. (Oncogene, 21:1580-1589, 2002) reported that MAPKAP kinase-2 could phosphorylate p53 on Ser20, the same site that is phosphorylated by two well-established checkpoint kinases, Chk1 and Chk2. Both Chk1 and Chk2 can also phosphorylate Cdc25 family members to create 14-3-3 binding sites, suggesting that MAPKAP kinase-2 might share a similar motif. The optimal substrate phosphorylation motif for MAPKAP kinase-2 was therefore investigated using oriented peptide library screening.

Efficient peptide phosphorylation by MAPKAP kinase-2 was only observed with a library containing a fixed Arg in the Ser-3 position (XXXXRXXSXXXX (SEQ ID NO: 15), where X denotes all amino acids except Cys, Ser, Thr, or Tyr). A critical step in determining protein kinase phosphorylation motifs by peptide library screening involves purification of the phosphorylated peptides from the non-phosphorylated peptide background. In the case of MAPKAP kinase-2, this was dramatically improved by conversion of all Glu and Asp residues to their methyl esters prior to metal-affinity chromatography and sequencing. This resulting motif revealed clear amino acid selection at almost all degenerate positions (FIG. 2A). MAPKAP kinase-2 displayed strong selection for the hydrophobic residues Leu, Phe, Ile, and Val in the Ser-5 position and the Ser+1 position. Strong selection was also observed for Gln in the Ser-2 position, and modest selection for Leu in the Ser-1 position. The motif determined for MAPKAP kinase-2 using oriented peptide library screening is in remarkably good agreement with the sequence of mapped MAPKAP kinase-2 phosphorylation sites on known substrates (FIG. 2A, bottom), which primarily contain Leu, Ile or Phe in the Ser-5 position; Arg in the Ser-3 position; Gln, Ser, or Thr in the Ser-2 position; Leu, Val or Pro in the Ser-1 position; and hydrophobic residues along with Glu in the Ser+1 position. The preference for polar residues Ser and Thr in addition to Gln in the Ser-2 position in known MAPKAP kinase-2 substrates would not have been detected by oriented peptide library screening, since Ser and Thr were not present in the library.

To verify the peptide library screening results, individual peptides (MK2tides) containing the optimal MAPKAP kinase-2 consensus motif LQRQLSI (SEQ ID NO: 16), or mutant versions with Ala substituted at each position in the motif, were synthesized and used for kinetic analysis (FIGS. 2B and 2C). The optimal MK2tide displayed a $K_m$ value two-fold lower than the best MAPKAP kinase-2 peptide substrate known to date, a sequence derived from HSP27. Substitution of Ala at each position in the motif affected $K_m$ and $V_{max}$ differently, with some positions showing primarily a $K_{max}$ effect (i.e., Arg in the Ser-3 position), while others revealed a primary effect on $V_{max}$ (i.e., Leu in the Ser-5 position) (FIG. 2C). The rank order of importance of key residues is Arg-3>Leu-5 Ile+1>Gln−3. The optimal MK2tide had neither the lowest $K_m$ nor the highest $V_{max}$, but rather had the highest $V_{max}/K_m$ ratio, consistent with the fact that the peptide library screening approach selects substrates on the basis of optimal $V_{max}/K_m$, rather than low $K_m$ or high $V_{max}$ alone. Combining the data from oriented peptide library screening, known substrate sequences, and our kinetic studies, the optimal MAPKAP kinase-2 phosphorylation motif is [L/F/I]XR[Q/S/T]L[S/T][Hydrophobic] (SEQ ID NO: 17).

The optimal MAPKAP kinase-2 substrate motif is an excellent match for the known Ser323 phosphorylation/14-3-3 binding motif in Cdc25B, as well as the Ser216 phosphorylation/14-3-3-binding site in Cdc25C (FIG. 2A). Initial experiments focused on Cdc25B, since, unlike Cdc25C, Cdc25B can be produced in modest quantities in bacteria, and the Ser323 site in Cdc25B had been previously reported to be a direct p38 SAPK site. Incubation of recombinant Cdc25B with purified MAPKAP kinase-2 resulted in significant Cdc25B phosphorylation and strong binding of the phosphorylated protein to 14-3-3. Mutation of Ser323→Ala substantially reduced the ability of MAPKAP kinase-2 to phosphorylate Cdc25B, and completely eliminated the ability of Cdc25B to bind to 14-3-3. These in vitro results strongly suggest that MAPKAP kinase-2 is the critical Cdc25/14-3-3 checkpoint kinase downstream of DNA damage signals relayed by the p38 SAPK pathway.

MAPKAP Kinase-2 is Critical for the $G_2$/M Checkpoint Following UV-Induced DNA Damage The importance of MAPKAP kinase-2 in DNA damage checkpoint function was investigated in U2OS cells. Activation of MAPKAP kinase-2 in response to UV-C irradiation-induced DNA damage was monitored by its reduced mobility on SDS-PAGE gels, and by immunoblotting using a phospho-specific antibody against pThr344, a site phosphorylated by p38 and required for MAPKAP kinase-2 activation. MAPKAP kinase-2 was activated within one hour of irradiation, and remained activated for the to eight hour duration of the experiment. The kinetics of MAPKAP kinase-2 activation paralleled the ability of Cdc25B from these cells to bind to 14-3-3. Based on these data, a two hour time point was chosen for use in further studies.

RNA interference was used to confirm a direct role for endogenous MAPKAP kinase-2 in the UV-induced DNA damage response. Treatment of U2OS cells with MAPKAP kinase-2-specific siRNA oligonucleotides, but not with control GFP siRNA oligonucleotides, resulted in a substantial reduction of MAPKAP kinase-2 to nearly undetectable levels by forty-eight hours after transfection. No reduction in the levels or UV-C-induced activation of p38 SAPK, Chk1 or Chk2 was observed in these cells. Despite the presence of these other active kinases, siRNA-mediated knockdown of MAPKAP kinase-2 caused a loss of both Cdc25B- and Cdc25C-binding to 14-3-3 after UV-C exposure.

Figure 3A:
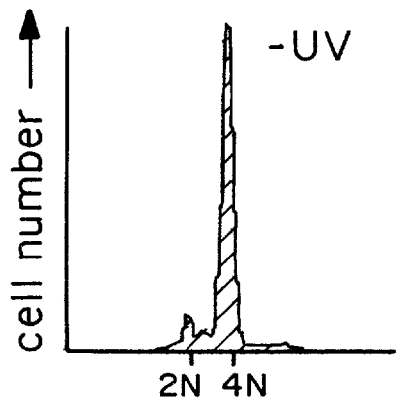
Figure 3C:
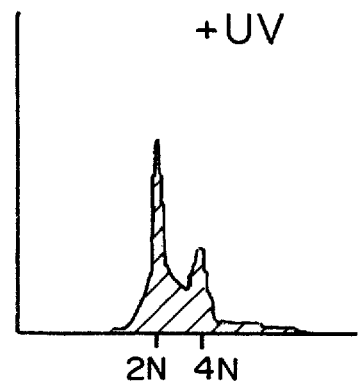
Figure 3B:
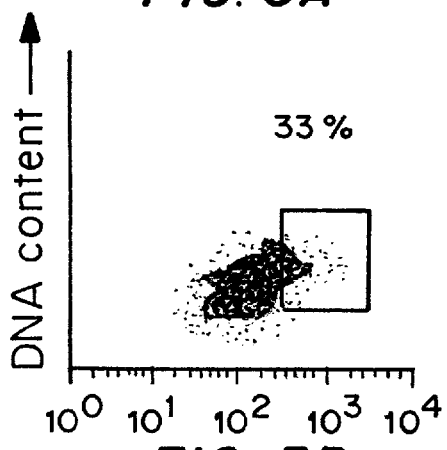
Figure 3D:
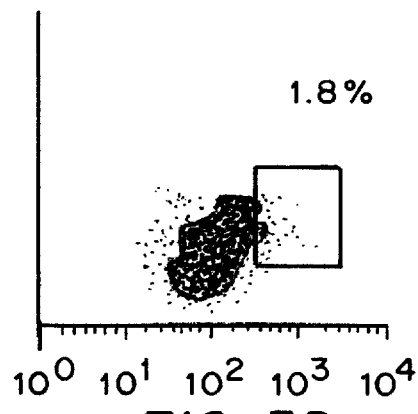

We studied cell cycle progression in the control GFP and MAPKAP kinase-2 knockdown cells following UV-C-irradiation using FACS (FIGS. 3A-3J). In these experiments, cells were irradiated with 20 J/m² of UV-C radiation, allowed to recover for two hours, then placed in nocodazole-containing media for an additional sixteen hours to cause any cells progressing through the cell cycle to arrest in mitosis, where they can stained for the mitotic marker phosho-histone H3. Under these conditions, un-irradiated cultures of asynchronous GFP siRNA-transfected cells accumulated in a 4N-DNA-containing peak, with prominent levels of phospho-histone H3 staining (FIGS. 3A and 3B), consistent with a nocodazole-mediated M-phase arrest. In response to UV-irradiation, control cells displayed a prominent $G_1$, S, and $G_2$ distribution, with near-complete loss of phosphohistone H3 staining, indicating intact $G_1$, S, and $G_2$ checkpoints (FIGS. 3C and 3D).

Figure 3E:
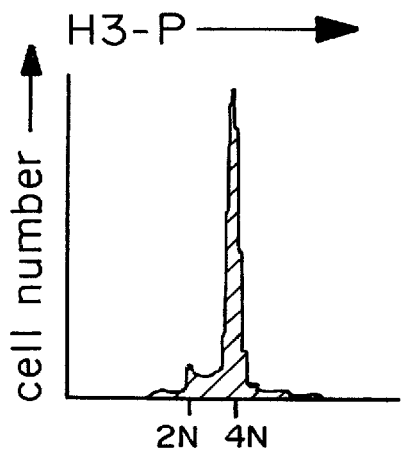
Figure 3G:
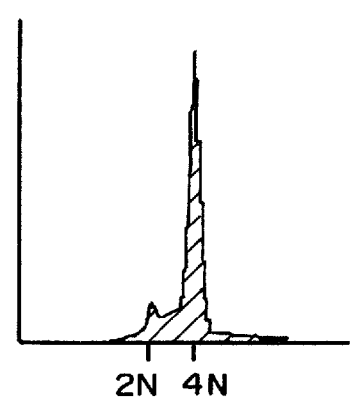

The behavior of the MAPKAP kinase-2 siRNA transfected cells was dramatically different. In the absence of UV irradiation, MAPKAP kinase-2 siRNA transfected cells, like control GFP siRNA-transfected cells, accumulate in a 4N DNA-containing peak with high levels of phospho-histone H3 staining (FIGS. 3E and 3F). Following UV-induced DNA damage, however, the MAPKAP kinase-2 knockdown cells failed to arrest cell cycle progression. Instead, these cells proceeded to enter mitosis to the same extent as unirradiated cells, as shown by a comparable 4N-DNA peak and similar levels of phoshohistone H3 staining as those observed in un-irradiated cells (FIGS. 3G and 3H). Together with the Cdc25B/C:14-3-3 results, these FACS data demonstrate that MAPKAP kinase-2 is critical for the UV-induced $G_2$/M checkpoint in response to UV-irradiation. In contrast to the UV response, summarized in FIG. 3I, the $G_2$/M checkpoint response to ionizing radiation in MAPKAP kinase-2 knockdown cells is intact (FIG. 3J).

Figure 4A:
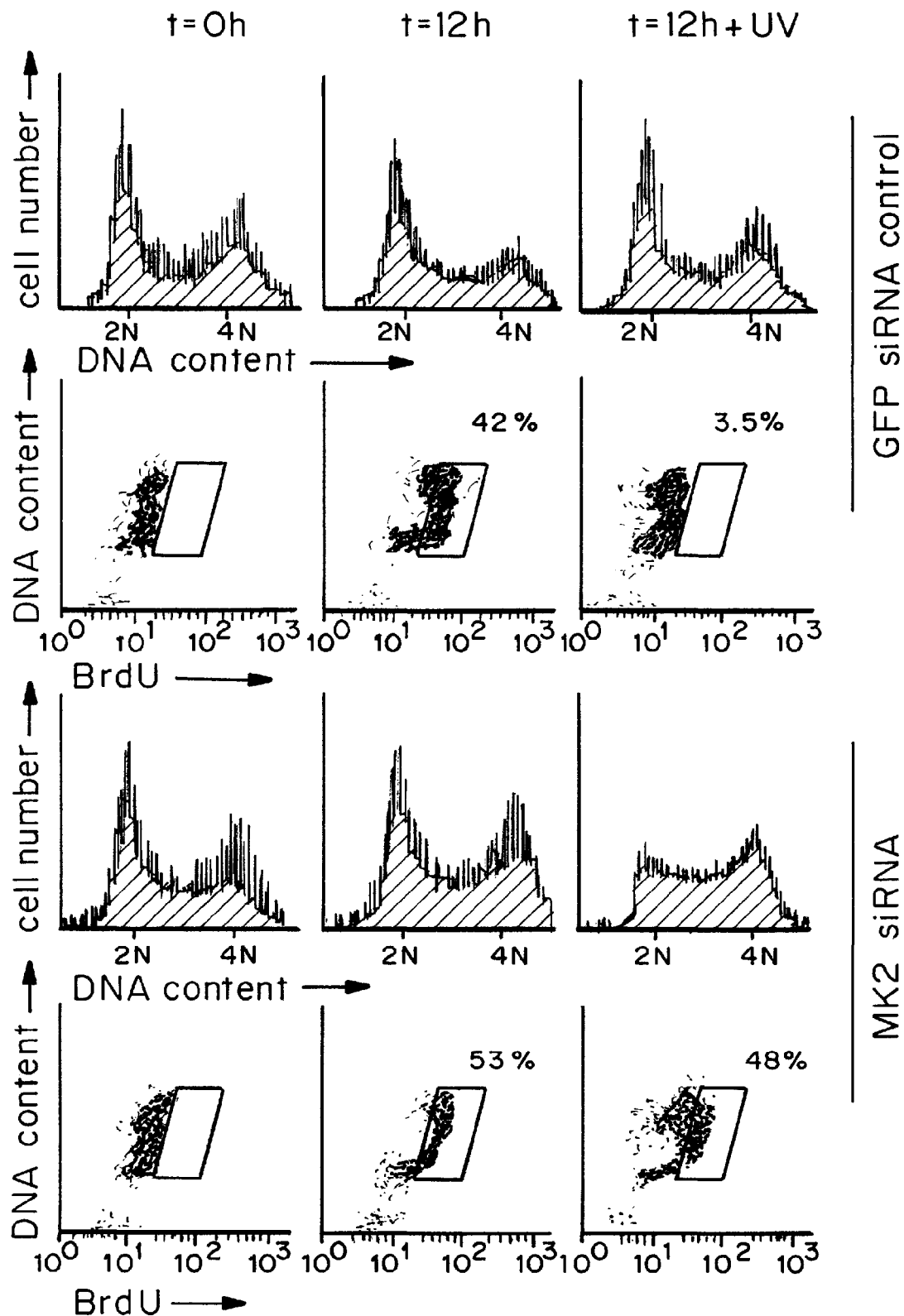
FIGS. 4A-4D show that MAPKAP kinase-2 is required for S-phase arrest and cell survival following DNA damage.
Figure 4B:
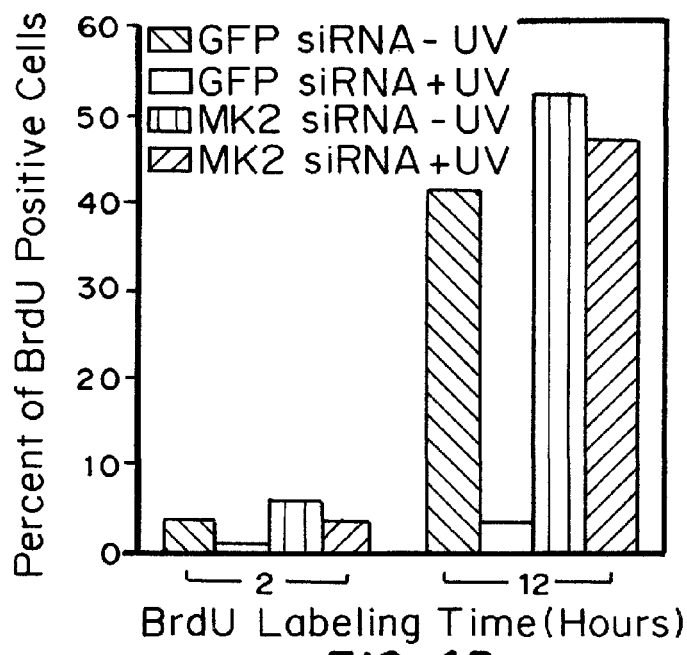

MAPKAP Kinase-2 is Critical for the S-Phase Checkpoint and $G_1$ Arrest Following UV-Induced DNA Damage The MAPKAP kinase-2 knockdown cells in FIGS. 3A-3J also showed a loss of the $G_1$ and S-phase checkpoints following DNA damage, since UV-irradiation of asynchronous cultures resulted in accumulation of the cells in a 4N DNA-containing peak when the cells were transferred to nocodazole-containing medium. To investigate the direct role of MAPKAP kinase-2 in S-phase checkpoint function, control or MAPKAP kinase-2 knockdown U2OS cells were UV-irradiated, allowed to recover for 30 min, and then labeled with BrdU for various times. In the absence of irradiation, 42% of the control siRNA-transfected cells showed substantial BrdU incorporation after twelve hours, compared with 53% of the MAPKAP kinase-2-siRNA transfected cells (FIGS. 4A and 4B). When the cells were irradiated with 20 J/m² of UV light prior to BrdU labeling, only 3.5% of the control siRNA transfected cells showed BrdU incorporation at twelve hours. In marked contrast, 48% of the MAPKAP kinase-2-knockdown cells continued to incorporate substantial amounts of BrdU. A similar difference in BrdU uptake between control siRNA-treated cells and MAPKAP kinase-2-knockdown cells was also seen at shorter times after irradiation (FIG. 4B).

Examination of the FACS profiles twelve hours following UV-irradiation revealed a dramatic decrease in the $G_1$ population in the MAPKAP kinase-2-knockdown cells compared with the control GFP siRNA-transduced cells (FIG. 4A, rightmost upper and lower FACS profiles). This loss of the $G_1$ peak, together with the increased percentage of cells showing BrdU incorporation at twelve hours versus two hours of labeling, implies that endogenous MAPKAP kinase-2 plays important roles in both the inhibition of DNA synthesis following damage (S-phase checkpoint function), and in the damage-induced arrest of cells in $G_1$ prior to S-phase entry ($G_1$/S checkpoint function). Loss of the $G_1$/S and S-phase checkpoints in MAPKAP kinase-2 knockdown cells was associated with higher levels of Cdc25A, decreased levels of p53, and reduced phosphorylation of p53 on Ser20 following UV-irradiation compared with control siRNA-treated cells.

Figure 4C:
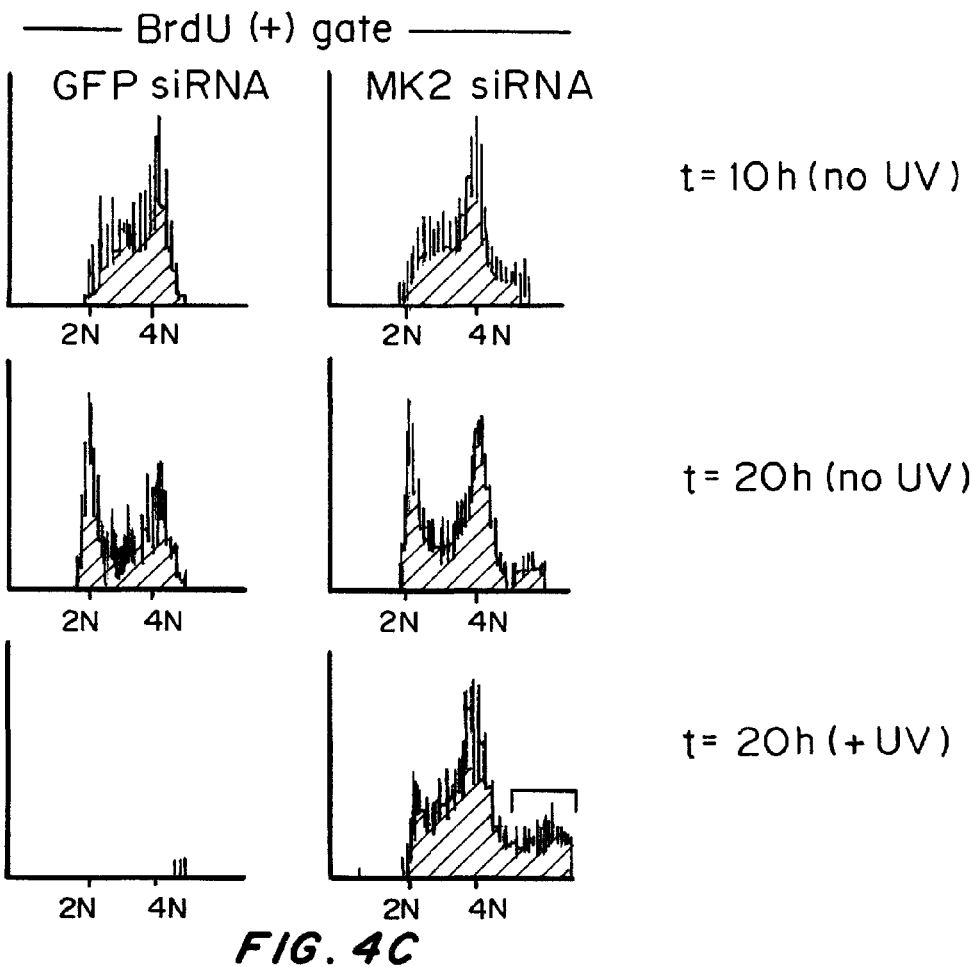

The fate of S-phase control or MAPKAP kinase-2 siRNA-treated cells in response to UV-C-induced DNA damage was examined by using FACS. In this experiment, asynchronous cells were mock-treated or irradiated with 20 J/m² of UV-C radiation and then pulse-labeled with BrdU. The cells showing BrdU uptake were subsequently analyzed ten and twenty hours later (FIG. 4C). In both non-irradiated control and MAPKAP kinase-2 knockdown cells, the BrdU pulse-labeled population showed a late S and $G_2$/M distribution at ten hours, and a re-appearance of a $G_1$ peak at twenty hours, indicating full transit through the cell cycle. In response to UV-C irradiation, control siRNA-treated cells failed to show significant BrdU uptake upon which to gate for FACS analysis (FIG. 4C, lower left panel). In contrast, the large population of MAPKAP kinase-2 siRNA treated cells, which had lost the S-phase checkpoint and incorporated BrdU, went on to display a greatly reduced $G_1$ peak at twenty hours, with many cells showing DNA staining >4N (FIG. 4C, bracket in lower right panel), consistent with mitotic death and exit from the cell cycle.

Figure 4D:
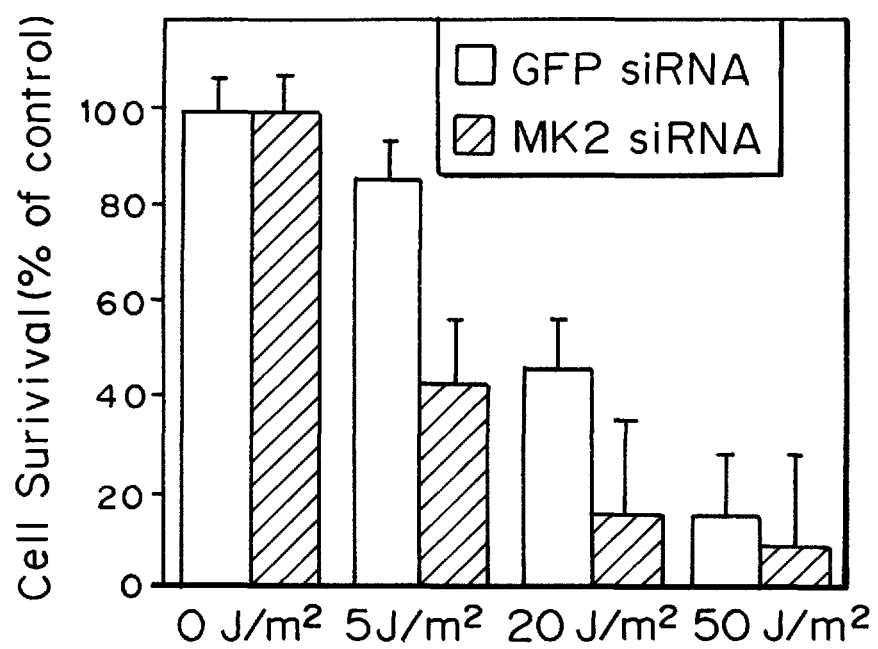

MAPKAP Kinase-2 Depleted Cells are More Sensitive to DNA Damage-Induced Cell Death The experiments in FIGS. 3A-3J and 4A-4C indicate that MAPKAP kinase-2 is involved in each of the cell cycle checkpoints triggered by UV-induced DNA damage. To determine the effect of MAPKAP kinase-2 depletion on cell survival, we transfected cells with control siRNA or MAPKAP kinase-2 siRNA for forty-eight hours, trypsinized, replated, and analyzed for colony formation in response to various doses of UV-C irradiation twelve hours after re-plating. As shown in FIG. 4D, MAPKAP kinase-2 knockdown cells displayed a significant reduction in colony formation when compared to control-treated cells at all doses of UV-C irradiation examined. This difference in survival after UV-C exposure was most pronounced at low to moderate UV doses.

A Structural Model for MAPKAP Kinase-2 Substrate Selectivity.

The optimal phosphorylation motif determined for MAPKAP kinase-2 is strikingly similar to that determined for two other checkpoint kinases, Chk1 and Chk2. All three of these CAMK superfamily members—MAPKAP kinase-2, -Chk1, and Chk2—strongly select for aliphatic residues in the Ser-5 position, Arg in the Ser-3 position, and aromatic/aliphatic residues in the Ser+1 position, along with additional less stringent selection for particular amino acids in other positions. In contrast, members of the AGC kinase superfamily, such as Akt/PKB and conventional protein kinase C superfamily members, preferentially phosphorylate sequences containing Arg residues in both the Ser-5 and Ser-3 positions, and play important roles in anti-apoptotic signaling and other signaling events unique to differentiated cell function, rather than critical roles in cell cycle control.

To investigate the structural basis for substrate motif selection, we performed molecular modeling studies of activated MAPKAP kinase-2, using the published MAPKAP kinase-2:ADP co-crystal structure (Underwood et al., Structure, 11:627-636, 2003) as a base model. The optimal substrate peptide LQRQLSIA (SEQ ID NO: 6) was modeled into the kinase active site in an extended conformation, and the kinase:substrate complex compared with the structures of Akt/PKB:AMP-PNP:GSK3-peptide ternary complex (Yang et al., Nat. Struct. Biol., 9:940-944, 2002) and the Chk1 crystal structure containing a modeled Cdc25C peptide (Chen et al., Cell, 100:681-692, 2000). Strong selection for Arg in the Ser-3 position for MAPKAP kinase-2, Akt/PKB and Chk1 is rationalized by the presence of a conserved glutamate residue at a similar location in all three kinases (Glu145 in MAPKAP kinase-2, Glu236 in Akt/PKB and Glu91 in Chk1), to which in Akt/PKB forms a bidentate salt bridge with the Ser-3 arginine guanidino group on GSK3-peptide. Similarly, selection for a hydrophobic residue at the Ser+1 position is explained by a hydrophobic pocket that is conserved at this position in all three kinases. The pocket is lined by Phe310, Pro314, Leu317 and Phe359 in Akt/PKB and by Met167, Leu171, Val174, Leu178 and Leu179 in Chk1. The corresponding Ser+1 pocket in MAPKAP kinase-2 is lined by Pro223, Pro227, Val234 and Leu235. Within this region, Gly312 in Akt/PKB and Gly169 in Chk1 are replaced by Tyr225 in MAPKAP kinase-2, which may reduce the depth of the MAPKAP kinase-2 hydrophobic pocket and explain selection for branched chain aliphatic residues in this position compared with Phe selection by Akt/PKB and Chk1.

The marked contrast between Arg selection at the Ser-5 position in Akt/PKB with the corresponding selection for hydrophobic residues at this position by MAPKAP kinase-2 and Chk1 is accounted for by the presence of Glu342 in Akt/PKB at the base of the Ser-5 pocket. This residue is not conserved in MAPKAP kinase-2 and Chk1, and is instead substituted by Ile255 in MAPKAP kinase-2 and by Ala200 in Chk1. Additional residues, notably Phe147, Pro189, Pro261 and Leu342 in MAPKAP kinase-2, and similarly Phe93, Ile96, Pro98, Pro133 and Leu206 in Chk1, contribute a significant hydrophobic character to this region.

MAPKAP Kinase-2 is Required for the $G_2$/M Checkpoint Following Doxorubicin Treatment.

Treatment of U2OS cells with doxorubicin generates DNA double strand breaks, and induced a prominent $G_2$/M arrest between eighteen and thirty hours following treatment. In addition to this large $G_2$/M population, a minor accumulation of cells in G and S phase was also observed. To investigate whether MAPKAP kinase-2 activation was involved in the checkpoint response, RNA interference was used to generate U2OS cells in which MAPKAP kinase-2 protein levels were stably repressed. Introduction of MAPKAP kinase-2 specific shRNA, but not luciferase shRNA, resulted in a robust knockdown of MAPKAP kinase-2 protein when the entire population of transfected cells was analyzed.

Asynchronous MAPKAP kinase-2 or luciferase shRNA knockdown cells were mock treated or exposed to doxorubicin for thirty hours, and cell cycle progression was monitored by FACS. In one set of experiments, the spindle poison nocodazole was added to the media three hours after addition of doxorubicin, to cause any cells progressing through the cell cycle to arrest in mitosis. DNA content was monitored by PI staining; phospho-histone-H3 staining was used as an indicator of mitotic entry. Treatment of control luciferase shRNA knockdown cells with doxorubicin led to the accumulation of cells with 4N DNA content, and a lack of phospho-histone-H3 staining in either the absence or presence of nocodazole. The cells expressing the luciferase shRNAs behaved identically to the untransfected doxorubicin-treated control U2OS cell population, with the prominent 4N DNA component and the absence of phospho-histone-H3 staining indicative of an intact $G_2$/M checkpoint. In marked contrast, MAPKAP kinase-2-depleted cells treated with doxorubicin displayed a cell cycle profile essentially identical to that of untreated cells. Addition of nocodazole following doxorubicin treatment to the MAPKAP kinase-2 depleted cells caused them to accumulate in a 4N DNA containing peak, with 36.3% of the cells staining positively for phospho-histone H3, a value similar to that of untreated U2OS cells blocked in mitosis with nocodazole (42%). Identical results were obtained using a second unrelated RNAi sequence against MAPKAP kinase-2, indicating that these results did not arise from RNAi off-target effects. MAPKAP kinase-2 depletion did not alter total Chk1 levels or reduce Chk1 activation following DNA damage. These findings demonstrate that loss of MAPKAP kinase-2 prevents cells from establishing a functional $G_2$/M checkpoint following doxorubicin-induced DNA damage, despite the presence of activated Chk1.

MAPKAP Kinase-2 Induces Binding of Cdc25B to 14-3-3 in Response to Topoisomerase Inhibitor-Induced DNA Damage.

Two Cdc25 family members, Cdc25B and C, play important roles in initiating and maintaining mitotic entry in normal cells, and are prominent targets of the $G_2$/M checkpoint. Cdc25B is believed to function by activating Cdk1/Cyclin B at the centrosome in late $G_2$ as an initiator of early mitotic events, while Cdc25C functions to further amplify Cdk1/CyclinB activity within a nuclear autoamplification loop once mitosis has begun. In response to γ- or UV-radiation-induced DNA damage, checkpoint kinases phosphorylate Cdc25B and C on Ser323 and Ser216, respectively, to induce their binding to 14-3-3 proteins, which, along with a modest reduction in their catalytic activity, sequesters them in the cytoplasm away from their nuclear cyclin/Cdk substrates. Recent studies suggest that Cdc25B plays a particularly crucial role in initiating and maintaining normal cell cycle $G_2$/M checkpoint responses, since reactivation of Cdc25B is critical for DNA-damaged cells to re-enter the cell cycle. We have shown-above that MAPKAP kinase-2 is capable of directly phosphorylating Cdc25B on Ser323 to generate the 14-3-3 binding site. We therefore investigated whether MAPKAP kinase-2 signaling was required for association of Cdc25B with 14-3-3 in response to DNA damage by chemotherapeutic drugs. Control luciferase and MAPKAP kinase-2 knockdown cells were either mock treated or incubated with cisplatin, camptothecin, or doxorubicin. Cell lysates were prepared eight hours later and incubated with recombinant GST-14-3-3β/ζ. Binding of endogenous Cdc25B to 14-3-3 was detected by immunoblotting. Both doxorubicin and camptothecin treatment, but not cisplatin exposure, resulted in the generation of stable 14-3-3-binding sites on Cdc25B in the luciferase shRNA control cells. No 14-3-3 binding of Cdc25B, however, was detected in lysates from the MAPKAP kinase-2 depleted cells. This result is in good agreement with the cell cycle studies, which showed loss of the $G_2$/M checkpoint in MAPKAP kinase-2 depleted cells after treatment with the topoisomerase inhibitor doxorubicin. These data indicate that loss of the chemotherapy-induced $G_2$/M checkpoint in MAPKAP kinase-2 depleted cells likely arises, at least in part, from loss of Cdc25B binding to 14-3-3 proteins.

MAPKAP Kinase-2 is Required for $G_1$/S Checkpoint Arrest Following Cisplatin Treatment.

In contrast to the $G_2$/M checkpoint response observed in doxorubicin-treated cells, treatment with the DNA intrastrand cross-linker cisplatin caused U2OS cells to predominantly accumulate in the $G_1$ and S phases of the cell cycle over the subsequent thirty hours-. RNA interference was used to investigate the role of MAPKAP kinase-2 in this process. Control luciferase knockdown cells showed an identical accumulation in $G_1$ and S after cisplatin exposure as that seen in U2OS cells lacking shRNA. Addition of nocodazole to the luciferase knockdown cells three hours following cisplatin treatment did not reveal the appearance of any mitotic cells over the ensuing twenty-seven hours, as monitored by phospho-histone H3 staining, indicating a functionally intact $G_1$/S checkpoint. Depletion of MAPKAP kinase-2 prior to cisplatin exposure resulted in a dramatically different result. Further, MAPKAP kinase-2 depleted cells showed a cell cycle profile after cisplatin treatment that was similar to that of untreated cells other than a very slight increase in the total number of cells in S-phase. Strikingly, when nocodazole was added three hours following cisplatin addition, the MAPKAP kinase-2 depleted cells accumulated in a 4N DNA containing peak with ~42% of the cells staining strongly for phosphohistone H3. Identical results were obtained in cells treated with a second unrelated siRNA sequence against MAPKAP kinase-2. MAPKAP kinase-2 depletion did not impair activation of Chk1 after cisplatin exposure. These data imply that MAPKAP kinase-2 is essential for the cisplatin induced $G_1$/S arrest and that loss of MAPKAP kinase-2 enables U2OS cells to override the cisplatin-induced $G_1$/S checkpoints, despite the presence of activated Chk1, and proceed into mitosis.

MAPKAP kinase-2 is required for Cdc25A degradation in response to cisplatin-induced DNA damage.

In contrast to the 14-3-3-mediated sequestration of Cdc25B and C involved in the $G_2$/M checkpoint response, the $G_1$ and S phase checkpoints are largely controlled by the phosphorylation-dependent degradation of another Cdc25 isoform, Cdc25A. Based on our observation that depletion of MAPKAP kinase-2 resulted in loss of the $G_1$/S checkpoint response, we investigated whether MAPKAP kinase-2 was required for the degradation of Cdc25A following cisplatin-induced DNA damage. Luciferase shRNA control cells and MAPKAP kinase-2 depleted cells were treated with cisplatin, and cell lysates immunoblotted for Cdc25A at eight and twelve hours following treatment. Cdc25A levels decreased dramatically in the control luciferase knockdown cells after treatment with cisplatin. In contrast, in the MAPKAP kinase-2 depleted cells, the level of Cdc25A following cisplatin exposure was only minimally reduced, and remained comparable to that seen in undamaged cells. These data indicate that in the absence of MAPKAP kinase-2, U2OS cells are defective in targeting Cdc25A for degradation in response to cisplatin induced DNA damage. This inability of MAPKAP kinase-2 depleted cells to degrade Cdc25A likely explains the failure of MAPKAP kinase-2 depleted cells to establish a sustained $G_1$/S checkpoint following cisplatin exposure.

The degradation of Cdc25A in response to DNA damage involves the direct phosphorylation of Cdc25A by checkpoint kinases. In response to UV and γ-irradiation, for example, Chk1 phosphorylates Cdc25A at multiple sites facilitating its subsequent ubiquitin-mediated destruction by the proteosome. Chk1, however, is activated normally in the MAPKAP kinase-2 depleted cells after cisplatin treatment. Other kinases besides Chk1, such as Chk2, have been recently reported to be able to phosphorylate Cdc25A on at least some of the same sites as Chk1 under certain conditions. Furthermore, we have shown that the optimal amino acid sequence motif on peptides and proteins phosphorylated by MAPKAP kinase-2 is nearly identical to the optimal sequence motif phosphorylated by Chk1 and Chk2. We therefore investigated whether Cdc25A could be a direct MAPKAP kinase-2 substrate. Recombinant Cdc25A was incubated with purified MAPKAP kinase-2 or Chk1 in vitro in the presence of 32P-γ-ATP, and phosphorylation monitored by SDS-PAGE/autoradiography. MAPKAP kinase-2 phosphorylated Cdc25A in vitro as efficiently as Chk1. Together, these findings suggest that degradation of Cdc25A in response to cisplatin treatment either requires direct phosphorylation of Cdc25A by MAPKAP kinase-2, or that MAPKAP kinase-2 activity is required to target Chk1 to Cdc25A in vivo.

Down-Regulation of MAPKAP Kinase-2 Increases the Sensitivity of Tumor Cells to Chemotherapy.

The data previously discussed indicate that MAPKAP kinase-2 is critical for cisplatin- and doxorubicin-triggered $G_1$/S and $G_2$/M arrest. These checkpoint defects in MAPKAP kinase-2 depleted cells might render them more sensitive to the antiproliferative and cytotoxic effects of chemotherapy.

To investigate this, control or MAPKAP kinase-2 knockdown U2OS cells were mock treated or incubated with increasing doses of cisplatin or doxorubicin for eight hours, washed, trypsinized and replated, and assayed for colony formation eight days later. When compared to the control shRNA-treated cells, MAPKAP kinase-2 depleted cells displayed a dramatically increased sensitivity to both cisplatin and doxorubicin treatment, particularly at relatively low drug doses. For example, luciferase shRNA cells treated with either 10 µM cisplatin or 1 µM doxorubicin formed ~40% of the number of colonies as those formed by untreated cells, while in MAPKAP kinase-2-depleted cells, these same cisplatin and doxorubicin treatments reduced the number of colonies to only 4% and 2%, respectively, of those seen in the untreated cells.

To establish whether the absence of MAPKAP kinase-2 could also enhance the anti-tumorigenic effect of cisplatin or doxorubicin in vivo, we introduced control or MAPKAP kinase-2 siRNAs into H-Ras-V12 transformed p53$^{-/-}$ MEFs, treated them with either vehicle alone, 1 µM cisplatin or 0.1 µM doxorubicin, and then implanted them into nude mice. Each animal received two injections of MAPKAP kinase-2 siRNA-transfected cells (left flank), and two injections of control siRNA transfected cells (right flank), and tumor formation was assessed at fifteen days. In the absence of treatment with DNA damaging agents, all four injections resulted in formation of solid fibrous tumors after fifteen days. In general, the size of the tumors resulting from injection of MAPKAP kinase-2 depleted cells was larger than that from control siRNA-transfected cells. Pre-treatment of the control siRNA transfected cells with either cisplatin or doxorubicin prior to implantation did not prevent tumor formation. The resulting tumors, however, were reduced to ~35% of the size and weight of the tumors formed by untreated cells. Depletion of MAPKAP kinase-2 prior to treatment with either cisplatin or doxorubicin completely eliminated the formation of tumors, indicating that the enhanced sensitivity of these cells to chemotherapeutic drugs seen in culture was maintained even when the cells were grown within a normal tissue microenvironment.

Taken together with the loss of $G_1/S$ and $G_2/M$ checkpoints observed by FACS analysis, and the mis-regulation of the mitotic phosphatases Cdc25A and B, these data provide strong evidence that down-regulation of MAPKAP kinase-2 activity results in enhanced sensitivity of cells to genotoxic stress in vitro and in vivo. These findings have potential therapeutic implications, since they suggest that targeting of MAPKAP kinase-2 with small molecule inhibitors should result in an enhanced sensitivity of tumor cells to conventional chemotherapeutic agents.

MAPKAP Kinase-2 and Chk1 are Activated Independently.

The activation of MAPKAP kinase-2 by cisplatin, camptothecin, doxorubicin, and UV irradiation that we observed is strikingly similar to the activation profile reported for Chk1. Similarly, the impaired $G_1/S$ and $G_2/M$ checkpoints seen after these DNA damaging stimuli in MAPKAP kinase-2 knockdown cells bears some resemblance to what has been reported for Chk1-deficient cells. These phenotypic similarities prompted us to further investigate whether the activation of Chk1 and MAPKAP kinase-2 was interdependent. As previously discussed, activation of Chk1 in response to cisplatin and doxorubicin was unimpaired in MAPKAP kinase-2 depleted cells. We therefore investigated the opposite possibility—whether the activation of MAPKAP kinase-2 after DNA damage was dependent on Chk1. U2OS cells were depleted of Chk1 using siRNA, exposed to cisplatin and doxorubicin, and analyzed for activation of MAPKAP kinase-2. Phosphorylation/activation of MAPKAP kinase-2 occurred normally after treatment with these DNA damaging agents, regardless of the presence or absence of Chk1. Thus, activation of MAPKAP kinase-2 and Chk1 after genotoxic stress appears to occur independently of each other.

The MAPKAP Kinase-2 DNA Damage Checkpoint Phenotype can be Synthetically Rescued by Chk1 Overexpression.

The observation that Chk1 and MAPKAP kinase-2 phosphorylate the same optimal sequence motif, target a set of overlapping substrates, and are activated independently of each other, prompted us to perform a genetic experiment to investigate whether loss of MAPKAP kinase-2 could be rescued by overexpression of Chk1 in mammalian cells. In these experiments, luciferase- or MAPKAP kinase-2 shRNA-expressing cells were transiently transfected with a mammalian Chk1 expression construct, or with an empty vector control. Cells were exposed to cisplatin, doxorubicin, or UV radiation thirty hours following transfection, harvested after an additional thirty hours, and cell cycle progression analyzed by FACS. In one set of experiments, nocodazole was added to the media three hours following addition of chemotherapy or UV, to cause any cells progressing through the cell cycle to arrest in mitosis.

Consistent with what we observed previously, luciferase shRNA control cells transfected with the empty vector DNA executed a $G_1/S$ arrest following exposure to cisplatin and UV irradiation, and displayed a prominent $G_2$ arrest in response to doxorubicin. These cell cycle profiles were unchanged when the luciferase shRNA cells were transfected with Chk1. MAPKAP kinase-2 depleted cells transfected with empty vector DNA broke through both checkpoints and accumulated in mitosis when nocodazole was added to the media. Overexpression of Chk1 in the MAPKAP kinase-2 depleted cells, however, completely restored their ability to establish functional checkpoints following genotoxic stress. The cells now arrested in $G_1/S$ in response to cisplatin and UV irradiation, and in $G_2$ following doxorubicin. Addition of nocodazole to the growth media of these MAPKAP kinase-2 depleted Chk1 over-expressing cells did not increase the number of phosphohistone H3 positive cells. Thus, overexpression of Chk1 prevented MAPKAP kinase-2 depleted cells from progressing through the cell cycle after genotoxic stress.

We investigated whether the synthetic rescue of $G_1/S$ and $G_2/M$ checkpoints by Chk1 in MAPKAP kinase-2 depleted cells was also sufficient to reduce their susceptibility to chemotherapeutic treatment. Luciferase and MAPKAP kinase-2 knockdown cells transfected with Chk1 or vector alone were mock treated or incubated with increasing doses of cisplatin and doxorubicin for eight hours, or irradiated with 20 J/m² of UV light. Cells were washed, trypsinized, replated and assayed for colony formation after eight days as described previously. Further, MAPKAP kinase-2 depleted cells, transfected with the empty control vector, showed enhanced sensitivity to the anti-proliferative effects of cisplatin, doxorubicin and UV. Overexpression of Chk1 in these MAPKAP kinase-2 depleted cells restored their clonogenic survival to levels that were indistinguishable from those seen with control cells containing wild-type levels of MAPKAP kinase-2.

UCN-01 is a Potent Inhibitor of Both Chk1 and MAPKAP Kinase-2.

Figure 8:
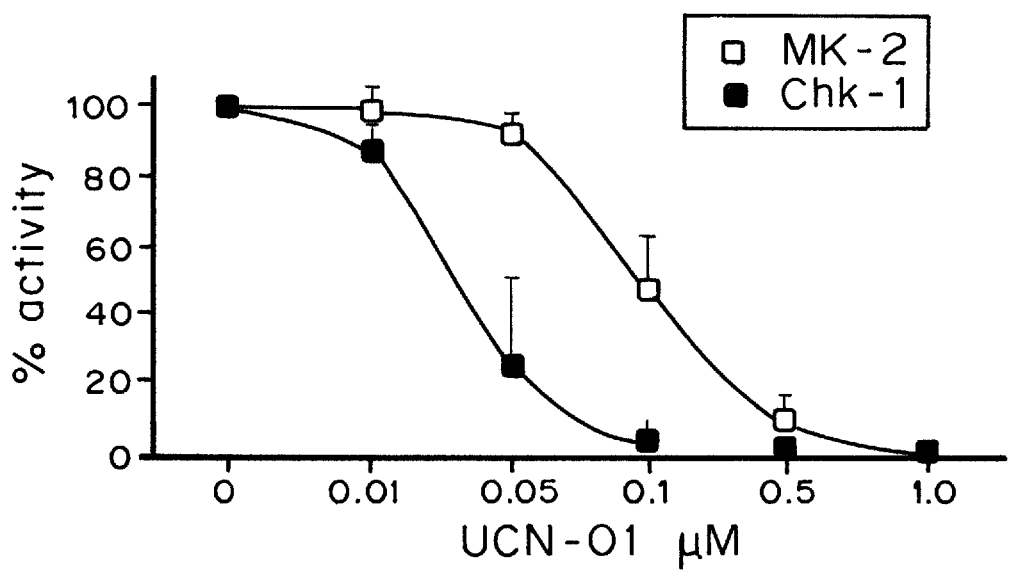
FIG. 8 shows in vitro kinase assays performed in the presence of increasing doses of UCN-01 with Chk1 and MAPKAP kinase-2 using the MK-2tide as a substrate.

The staurosporine derivative 7-hydroxystaurosporin/UCN-01 inhibits Chk1 with an $IC_{50}$ that is ~1000 fold lower than that for Chk2, and hence has been used experimentally as a Chk1-specific inhibitor. Strong circumstantial evidence, however, suggests that UCN-01 inhibits other kinases involved in cell cycle control at similar concentrations as those used for Chk1 inhibition studies. For example, Chk1-depleted cells maintain phosphorylation of Cdc25C on Ser-216 both during asynchronous growth and following γ-irradiation. Phosphorylation at this site is lost when cells are treated with low doses of UCN-01 (~300 nM), indicating that UCN-01 inhibitable kinase(s) other than Chk1 participate in Cdc25C phosphorylation. Based on our finding that MAPKAP kinase-2 is a critical checkpoint regulator, we investigated whether UCN-01 inhibited MAPKAP kinase-2 at doses typically used in Chk1 inhibition experiments. In vitro kinase assays were performed with Chk1 and MAPKAP kinase-2 using an optimal peptide substrate with the core consensus sequence LQRQLSI (SEQ ID NO: 16), similar to the 14-3-3 binding sequence in Cdc25B and C, in the presence of various concentrations of UCN-01. As shown in FIG. 8, UCN-01 potently inhibited both kinases, with an $IC_{50}$ value of ~35 nM for Chk1 and ~95 nM for MAPKAP kinase-2. The $IC_{50}$ value we measured for Chk1 is in good agreement with previously published data. Importantly, the $IC_{50}$ value we measured for MAPKAP kinase-2 is significantly below the concentrations of UCN-01 that are used in "Chk1-specific" checkpoint abrogation assays, suggesting that under the conditions used in those studies, both Chk1 and MAPKAP kinase-2 were being inhibited.

To examine the structural basis for UCN-01 inhibition of MAPKAP kinase-2, the structure of the MAPKAP kinase-2:UCN-01 complex was modeled using coordinates from the published MAPKAP kinase-2:staurosporine structure, and compared the results with the co-crystal structure of Chk1:UCN-01. The 7-hydroxy moiety of UCN-01 can be easily accommodated into the MAPKAP kinase-2:staurosporine structure, where its closest neighboring residues would be Val118 (2.8 Å to Cγ2), Leu 141 (3.2 Å to Cδ1), and Thr206 (3.6 Å to Cγ2). This lack of steric hindrance, and the overall similarity of the modeled MAPKAP kinase-2:UCN-01 structure to the Chk1:UCN-01 structure, provides a structural rationale for the tight binding observed biochemically.

To verify that MAPKAP kinase-2 is a direct target of UCN-01 in cells, we measured the phosphorylation of the MAPKAP kinase-2-specific substrate hsp-27 after heat shock, a stimulus that activates the p38 MAPK/MAPKAP kinase-2 pathway. Control luciferase shRNA expressing or MAPKAP kinase-2 shRNA expressing U2OS cells were incubated at 42° C. or 37° C. for two hours in the presence or absence of 250 nM UCN-01, and phosphorylation of hsp-27 monitored by immunoblotting with an antibody against pSer82, a well established MAPKAP kinase-2 phosphorylation site. The hsp-27 was phosphorylated when the control luciferase shRNA cells were placed at 42° C. This phosphorylation was completely abrogated by treatment with UCN-01. No phosphorylation was observed in MAPKAP kinase-2 knockdown cells placed at 42° C. regardless of the presence or absence of UCN-01. Likewise, no signal was observed in both the control and MAPKAP kinase-2 knockdown cells that were maintained at 37° C., with or without UCN-01 treatment. Furthermore, heat shock was equally effective in promoting the phosphorylation of hsp-27 on Ser-82, and UCN-01 was equally effective in blocking Ser-82 phosphorylation in cells that were depleted of Chk1. Thus, UCN-01 inhibition of MAPKAP kinase-2 in vivo is independent of Chk1 function. These findings provide strong evidence that UCN-01 is a direct inhibitor of MAPKAP kinase-2 within cells, and suggest that the clinical efficacy of UCN-01 in cancer treatment likely arises from the simultaneous inhibition of two parallel but non-redundant checkpoint pathways involving Chk1 and MAPKAP kinase-2.

Since disruption of the MAPKAP kinase-2 signaling pathway enhances chemotherapeutic responses even in the presence of a functional Chk1 response, and since MAPKAP kinase-2 knock-out mice are viable, in contrast to Chk1 knock-out mice, our results suggest that a MAPKAP kinase-2 specific inhibitor might provide significant clinical benefit with fewer undesirable side-effects. In either case, our current data strongly support the development of clinical MAPKAP kinase-2 inhibitors as viable anti-cancer agents. Given the dependence of p53-defective cells on intra-S and $G_2$/M checkpoint pathways, targeting MAPKAP kinase-2 may be a particularly efficacious approach to treating these types of human cancers. Thus, therapeutic treatments that interfere with MAPKAP kinase-2 function would be expected to preferentially sensitize p53-deficient cells to treatment with DNA-damaging chemotherapeutic drugs without similarly sensitizing wild-type cells. Disorders, e.g., neoplastic disorders, that include p53-deficient cells could be treated effectively and specifically using therapy that combines administration of a MAPKAP kinase-2-interfering compound, e.g., UCN-01, and one or more chemotherapeutic agents, preferably at substantially lower levels than would otherwise be necessary to treat the disorder, thereby largely sparing normal cells from the deleterious effects of chemotherapy.

Model for the Role of MAPKAP Kinase-2

Our data show that a crucial role of p38 SAPK in response to UV-induced DNA damage is the phosphorylation and activation of MAPKAP kinase-2, leading to MAPKAP kinase-2-directed phosphorylation of Cdc25 family members to induce 14-3-3-binding and subsequent cell cycle arrest. In this way, MAPKAP kinase-2 performs similar functions after UV-C induced DNA damage as those performed by Chk1 and Chk2 after exposure of cells to ionizing radiation.

Figure 5:
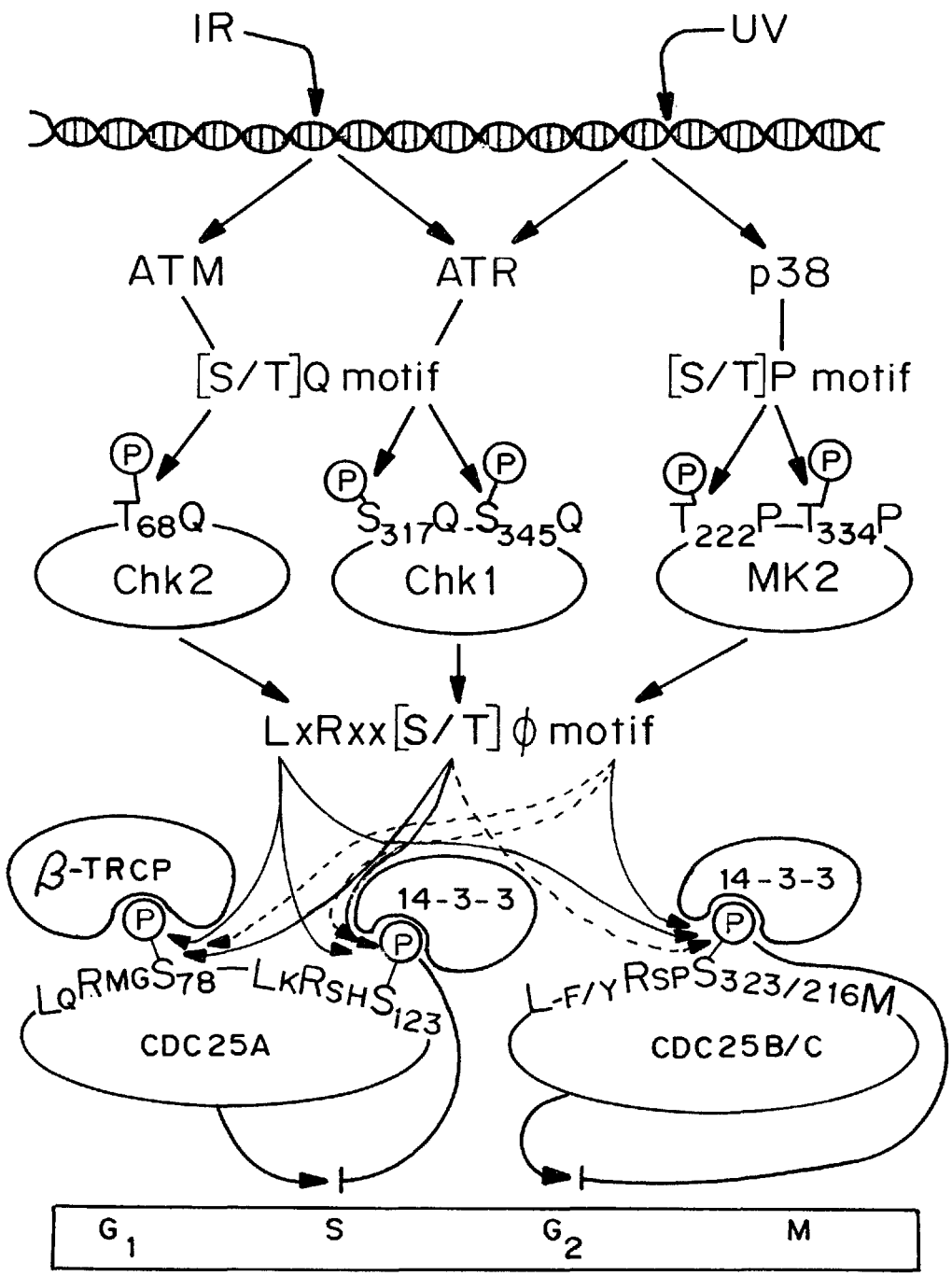
FIG. 5 is a representation of a unified model of the kinase-dependent DNA damage checkpoint. In this model, parallel pathways in the DNA damage checkpoint signal transduction network converge on common substrates by signaling to downstream kinases with similar phosphorylation motif specificities. φ indicates hydrophobic residues. The dashed line from Chk1 to Cdc25B/C indicates that this phosphorylation event remains controversial in response to ionizing radiation.

MAPKAP kinase-2 undergoes initial activation in the nucleus with subsequent export of the active kinase to the cytoplasm. Thus, MAPKAP kinase-2 is well-positioned to function as both a nuclear initiator of Cdc25B/C phosphorylation in response to DNA damage, and as a maintenance kinase that keeps Cdc25B/C inhibited in the cytoplasm. A unified model for kinase-dependent DNA damage checkpoints is presented in FIG. 5. In response to ionizing radiation, ATM activation of Chk2 and ATR activation of Chk1 leads to phosphorylation of Cdc25 family members on related sequences corresponding to the checkpoint kinase core "motif" LXRXX[S/T][Hydrophobic] (SEQ ID NO: 18). Similarly, in response to UV-induced DNA damage, ATR activates Chk1 and p38 SAPK activates MAPKAP kinase-2, leading to phosphorylation of the same core motif on Cdc25 family members. The major role of Chk1 appears to involve phosphorylation of Cdc25A after IR, whereas Chk2 appears to phosphorylate all three Cdc25 family members. In the absence of Chk2, Chk1 appears to be able to subsume at least part of this function. Our data now indicate that MAPKAP kinase-2 is the primary effector kinase that targets Cdc25B/C after UV-C exposure. MAPKAP kinase-2 may also be involved in Cdc25A phosphorylation, since we observed that the $G_1$ and S-phase checkpoints were eliminated in the MAPKAP kinase-2 knockdown cells.

Figure 9:
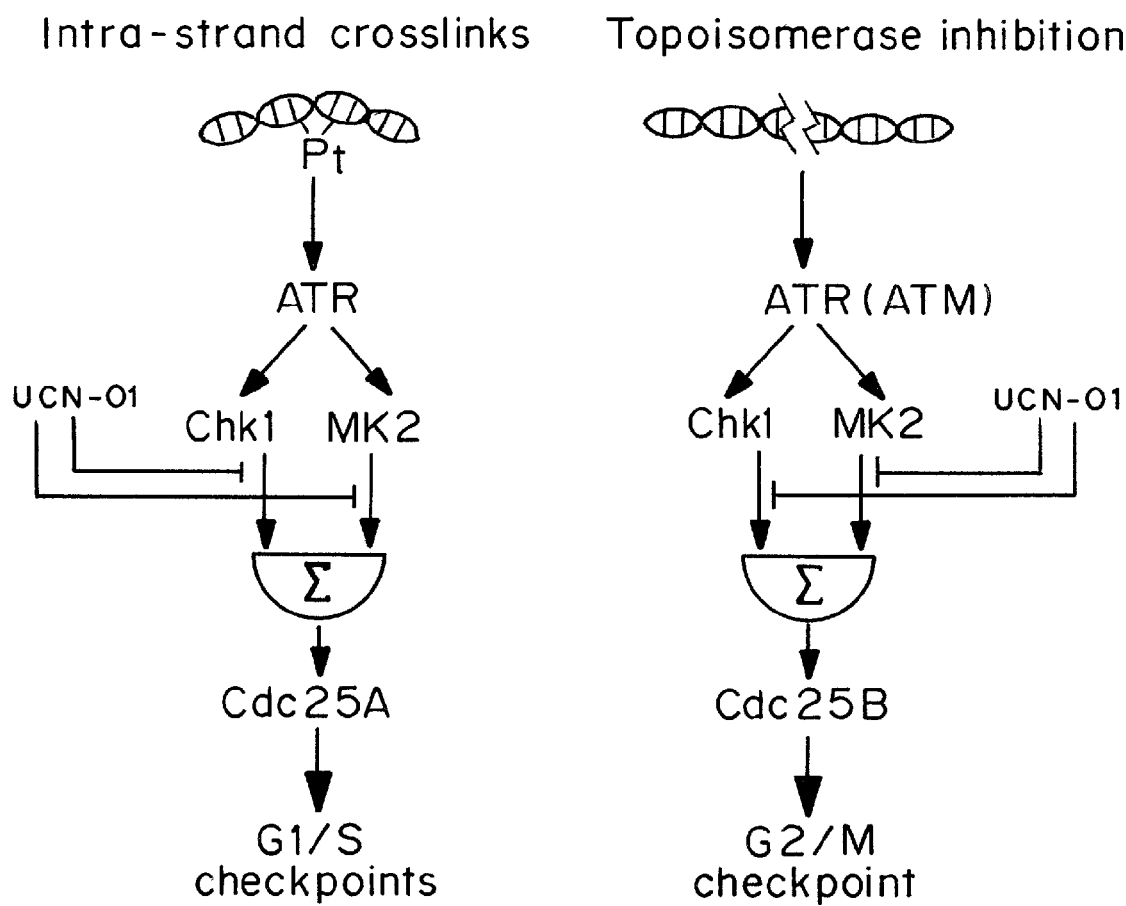
FIG. 9 is a representation of a model for MAPKAP kinase-2 checkpoint signaling in response to DNA damaging chemotherapy. Checkpoint function in response to DNA damaging agents normally requires the combined action of both the Chk1 and MAPKAP kinase-2 pathways, and both pathways are simultaneously inhibited by the indolocarbazole drug UCN-01.

The results presented here indicate that the activities of both Chk1 and MAPKAP kinase-2 are required for $G_1$/S and $G_2$/M cell cycle arrest in response to DNA damaging chemotherapy and UV-irradiation (FIG. 9). At a systems level, these observations suggest that the normal DNA damage checkpoint response involves the unified actions of a dedicated DNA damage response pathway (i.e., Chk1) and a potentially more global stress response pathway (MAPKAP kinase-2). Individual kinase activities emerging from each of these pathways appear to be titered to levels that, in combination, are just adequate to arrest the cell cycle after damage, presumably facilitating rapid checkpoint release once the DNA damage has been repaired. In agreement with this hypothesis, overexpression of Chk1 rescued both the $G_2/M$ and $G_1/S$ cell cycle checkpoint defects observed in MAPKAP kinase-2 depleted cells.

Experimental Procedures

Chemicals, Antibodies, and Drugs.

UCN-01 was the kind gift of R. Schultz, Drug Synthesis and Chemistry Branch, Developmental Therapeutics Program, Division of Cancer Treatment and Diagnosis, National Cancer Institute (Bethesda, Md.). Cisplatin, doxorubicin and camptothecin, puromycin, and glutathione beads were purchased from Sigma-Aldrich. Propidium iodide was purchased from Calbiochem. Antibodies against total and phosphorylated forms of MAPKAP kinase-2, p38 MAPK, Chk1, Chk2, ATM/ATR substrate, hsp-27, and p53 (pS20) were purchased from Cell Signaling Technology (Beverly, Mass.). Antibodies against β-actin and 5-bromo-2-deoxyuridine (BrdU) were purchased from Sigma-Aldrich; an anti-Cdc25A antibody (MS-640-P1, cocktail) was from NeoMarker (Fremont, Calif.); an anti-Cdc25B antibody was from Transduction Labs, an anti-GST antibody was from Amersham/GE Healthcare, and an anti-phospho histone H3 antibody was from Upstate. Active MAPKAP kinase-2 was purchased from Upstate. Propidium Iodide (PI) was purchased from Calbiochem, amylose beads were purchased from New England Biolabs, Ni-NTA agarose were purchased from QIAGEN, and glutathione beads and BrdU were purchased from Sigma-Aldrich.

Cell Culture.

U2OS cells, HeLa cells, U87MG cells and H-Ras-V12 transformed $p53^{-/-}$ MEFs were cultured in DMEM supplemented with 10% FCS and penicillin/streptomycin at 37° C. in a humidified incubator supplied with 5% CO2. GM05849 A-T fibroblasts and the corresponding control GM00637 fibroblasts, and GM18366 ATR-defective Seckel syndrome fibroblasts and the corresponding control GM00023 fibroblasts were obtained from the Coriell cell repository and were cultured in MEM supplemented with Eagle's salts, 10% FCS, and penicillin/streptomycin.

Purification of Recombinant Proteins.

Constructs encoding GST- and MBP-fusion proteins were transformed into DH5α or BL21 (DE3) strains of E. coli and recombinant proteins obtained by inducing late log-phase cells with 0.4 mM IPTG at 37° C. for three to five hours. Cells were lysed by sonication in lysis buffer containing 50 mM Tris-HCl, pH 7.5, 250 mM NaCl, 1 mM DTT, 8 μg/mL pepstatin, 8 μg/mL aprotinin, and 8 μg/mL leupeptin. Fusion proteins were purified from cell lysates by using amylose or glutathione beads. Following extensive washing with PBS containing 0.5% NP-40 and a final wash with PBS, fusion proteins were eluted from the beads with HEPES, pH 7.2, containing 40 mM maltose or 20 mM glutathione, followed by exchange into PBS using duplicate Sephadex G-25 columns (NAP-10 columns, Pharmacia). Protein concentrations were determined using the bicinchoninic acid assay (Pierce) as recommended by the manufacturer, using BSA as the standard. Full-length Chk1-GST or full-length Chk2-His6 in pFASTBAC was expressed in Sf9 insect cells. Chk1-expressing cells were lysed in buffer containing 50 mM Tris-HCl, pH 7.5, 250 mM NaCl, 1 mM DTT, 1.0% NP-40, 8 μg/mL pepstatin, 8 μg/mL aprotinin, 8 μg/mL leupeptin, 2 mM Na3VO4, 10 mM NaF, and 1 μM microcystin, and Chk1 was purified using glutathione beads. Chk1 was eluted from the beads with 10 mM glutathione in 50 mM Tris-HCl, pH 8.0, and dialyzed into kinase buffer. Chk2 expressing cells were lysed in buffer containing 50 mM Tris-HCl, pH 7.5, 250 mM NaCl, 1 mM DTT, 1.0% NP-40, 8 μg/mL pepstatin, 8 μg/mL aprotinin, 8 μg/mL leupeptin, 2 mM $Na_3VO_4$, 10 mM NaF, and 1 μM microcystin, and Chk2 was purified using Ni-NTA agrose beads. After washing extensively with lysis buffer containing 40 mM imidazole, Chk2 was eluted from the beads with 100 mM imidazole in 50 mM Tris-HCl, pH 8.0, and dialyzed into kinase buffer.

Point mutations were generated using the Stratagene Quick Change Mutagenesis Kit and confirmed by sequencing the entire coding regions.

Kinase Motif Screening with Oriented Peptide Libraries and In Vitro Kinase Assays.

Using the methods of the invention, one skilled in the art would be able to utilize a peptide library screen to identify peptides that bind to a p38 SAPK polypeptide, to MAPKAP kinase-2 polypeptide, or other biologically relevant target. Peptides identified in such a screen, or related compounds, would have potential therapeutic benefit due to their ability to inhibit the biological activity of, e.g., a MAPKAP kinase-2 polypeptide.

Combinatorial peptide library screening was performed using recombinant purified p38α SAPK, MK2, Chk1 and Chk2 as previously described (Songyang and Cantley, Methods Mol. Biol., 87:87-98, 1998) with minor modifications. Briefly, 5.0 μg of recombinant p38α SAPK, 3.0 μg MK2, 2.0 μg Chk1 and 2.0 μg Chk2 were incubated with 1 mg of each peptide library in 300 μl reaction volumes containing 20 mM HEPES, pH 7.5, 10 mM $MgCl_2$, 3 mM 2-mercaptoethanol, and 100 μM ATP containing 2.5 μCi of 32P-γ-ATP for 120 min at 30° C. Under these conditions, approximately 1% of the peptide mixture was phosphorylated. The reaction mixture was diluted by addition of 300 μl of 30% acetic acid, and the phosphorylated peptides separated from unincorporated 32P-γ-ATP by DEAE column chromatography (1 ml bed volume) using isocratic elution with 30% acetic acid. The peptide mixture (both phosphorylated and unphosphorylated, but free of ATP) eluted within the first 1 ml following the 600 μl void volume of the column. Samples were dried in a Speed-Vac apparatus.

For the p38α SAPK peptide library experiments, the sample was resuspended in 200 μl of 50 mM MES, pH 5.5, containing 1 M NaCl. Separation of phosphorylated from non-phosphorylated peptides was achieved by IMAC using ferric-iminodiacetic acid beads. A 0.5 ml iminodiacetic acid column was charged with 2.5 ml of 20 mM $FeCl_3$ and extensively washed with $H_2O$, then with 3 ml of 500 mM $NH_4HCO_3$, pH 8.0, 3 ml of $H_2O$, and 3 ml of 50 mM MES (pH 5.5)/1 M NaCl. The peptide mixture was applied and the column was developed with 3 ml 50 mM MES, pH 5.5, 1 M NaCl, followed by 4 ml of $H_2O$ to remove nonphosphorylated peptides. Phosphorylated peptides were then eluted with 2 ml of 500 mM $NH_4HCO_3$, pH 8.0, and dried in a Speed-Vac apparatus, and resuspended in 80 μl H2O.

Peptide library screens using basophilic kinase-directed libraries are complicated by a high background of non-phosphorylated Asp/Glu-rich peptides that co-purified with the phosphorylated peptides during the immobilized metal affinity chromatography (IMAC) step prior to peptide sequencing, greatly complicating the analysis. To overcome this problem, we developed a new approach in which peptide libraries are first phosphorylated by the kinase of interest, and then treated with methanolic HCl to convert Asp and Glu residues to their uncharged methyl esters. Using this approach, the background of nonphosphorylated peptides that adhere to the IMAC column was reduced to insignificant levels. Furthermore, the Asp and Glu methyl esters were converted back to their free acids during the sequencing reaction, allowing selection for these residues, if present in the phosphorylation motif, to be accurately measured.

For the MAPKAP kinase-2, Chk1, and Chk2 peptide library experiments, 40 µl of thionyl chloride was added dropwise in a hood to 1 ml of dry methanol. This solution was then used to dissolve each of the dried peptide libraries, followed by stirring at room temperature for one hour. The peptide library was dried down overnight and resuspended in 100 µl of a 1:1:1 mixture of methanol/acetonitrile/water. A 0.5 ml iminodiacetic acid column was charged with 2.5 ml of 20 mM FeCl$_3$ and extensively washed with H$_2$O, then with 3 ml of 500 mM NH$_4$HCO$_3$ (pH 8.0), 3 ml of H$_2$O, and 3 ml of 50 mM MES, pH 5.5, 1 M NaCl. The peptide mixture was applied and the column was developed with 4 ml of H$_2$O followed by 3 ml NH$_4$HCO$_3$, pH 8.0, to remove non-phosphorylated peptides. Phosphorylated peptides were eluted with 2 ml of 500 mM NH$_4$HCO$_3$, pH 11.0, dried in a Speed-Vac apparatus, and resuspended in 40-80 µl H$_2$O.

Following IMAC purification, libraries (0.5-1.5 nmoles) were subjected to automated Edman sequencing using an Applied Biosystems model 477A peptide sequencer. Data analysis was performed by normalizing the abundance (mol-%) of each amino acid in the phosphorylated peptide mixture to that present in the starting libraries. The sums of the final preference ratios were normalized to the total number of amino acids in the degenerate positions within the peptide libraries so that a particular amino acid would have a preference value of 1 in the absence of selectivity at a particular position. The degenerate peptide libraries used for in vitro kinase screening with p38 MAP kinase, MK2, Chk1, and Chk2 consisted of the sequences GAXXXXSPXXXXAKKK [SP library] (SEQ ID NO: 19), where X denotes all amino acids except Cys, Ser, Thr, and Tyr; GAXXXXPX-SPXXXXXAKKK [PxSP library](SEQ ID NO: 20), where X denotes all amino acids except Cys; or GAXXXXRXX-SXXXXAKKK [RxxS library] (SEQ ID NO: 21), where X denotes all amino acids except Cys, Ser, Thr and Tyr. In all libraries, S denotes Ser, P denotes Pro, and R denotes Arg.

Kinase reactions were performed in 30 µl of kinase reaction buffer (20 mM HEPES, pH 7.5, 10 mM MgCl$_2$, 3 mM 2-mercaptoethanol, 100 µg/ml BSA, 50 µM ATP, 10 µCi 32P-γ-ATP) containing 2.0 µg of recombinant p47 or Cdc25B substrate protein or the specified amount of peptide and 0.10 µg of recombinant p38α SAPK or 0.03 µg of recombinant MAPKAP kinase-2 at 30° C. for the indicated time. The sequences of the p38 optimal peptide and the p47phox peptide were KKAZGPQGPQSPIE (SEQ ID NO: 22) and KKA-ZGPQSPGSPLE (SEQ ID NO: 23), respectively. For 14-3-3 pulldowns of Cdc25 following in vitro phosphorylation by p38 or MAPKAP kinase-2, 2.0 kg of Cdc25B was incubated with 10-fold excess 14-3-3-MBP and analyzed by autoradiography. For kinetic measurements, the reactions were terminated by the addition of an equal volume of 0.5 percent phosphoric acid, and 5 µl was spotted onto p81 paper. The p81 paper was washed 5× in 0.5 percent phosphoric acid and added to scintillation fluid for scintillation counting. For in vitro phosphorylation reactions, the reactions were terminated by the addition of an equal volume of sample buffer followed by heating at 95° C. for 3 min. Samples were analyzed by SDS-PAGE followed by transfer to nitrocellulose for autoradiography and immunoblotting. The rate of p38α phosphorylation of isolated peptides and full-length p47phox proteins was determined by scintillation counting using peptide concentrations of 100, 400, and 1400 M, and protein concentrations of 1, 5, 10 and 15 M, with time points taken at five, ten, and twenty minutes. MAPKAP kinase-2 phosphorylation of MK2tides was performed using peptide concentrations of 5, 10, 20, 40, 80, 160, 320, 500, and 1000 M, with time points taken at three, six, nine, and twelve minutes. From these enzymatic studies, $K_m$, $V_{max}$ and $V_{max}/K_m$ values were then ascertained. All kinetic experiments were performed a minimum of three times. For each experimental condition in the determination of the $K_m$ and $V_{max}$ values, we verified that the reaction rates were linear with respect to time for all substrate concentrations and that less than 10% substrate was phosphorylated.

In vitro kinase assays for UCN-01 IC$_{50}$ determination were performed in 30 µl reactions containing 20 mM HEPES (pH 7.5), 10 mM MgCl2, 3 mM 2-mercaptoethanol, 100 µg/ml BSA, 50 mM ATP, 10 µCi 32P-γ-ATP, and 50 µM. MK2-tide substrate for twenty minutes at 30° C. Chk1 was used at a concentration of 0.3 M; MAPKAP kinase-2 was used at a concentration of 0.1 µM. Reactions were terminated by adding an equal volume of 0.5% phosphoric acid to the reaction and 5 µl was spotted onto P81 paper. After washing 5× in 0.5% phosphoric acid, sample were subjected to scintillation counting. Cdc25A phosphorylation studies were performed using GST-Cdc25A immunoprecipitated from HEK293T cells transfected with pCMV GST-Cdc25A, a generous gift from Dr. W. Harper (Harvard Medical School). In brief, HEK293T cells were transfected with pCMV GST-Cdc25A construct using the calcium phosphate method described earlier. Cells were harvested thirty-six hours later, lysed in a buffer containing 50 mM Tris-HCl, pH 7.8, 150 mM NaCl, 1.0% NP-40, 5 mM EDTA, 2 mM DTT, 8 µg/ml pepstatin, 8 µg/ml aprotinin, 8 µg/ml leupeptin, 2 mM Na3VO4, 10 mM NaF, and 1 µM microcystin and cleared by centrifugation. Supernatants were precleared with protein G beads for one hour. GST-Cdc25A was precipitated with 50 µl GSH beads (Sigma-Aldrich). Beads were washed five times in kinase buffer and used in kinase reactions. Kinase reactions were performed in 50l of kinase reaction buffer using 0.3 µM Chk1 and 0.1 µM MAPKAP kinase-2. Reactions were performed at 30° C. for twenty minutes and terminated by addition of 50 µl 2× sample buffer. Samples were heated at 95° C. for three minutes, separated on a 12.5% SDS-PAGE, and visualized using a phosphor imager (Molecular Dynamics).

14-3-3 Pull-Down Assays, Immunoblotting, and Immunofluorescence.

U2OS cells were lysed in lysis buffer: 50 mM Tris/HCl, pH7.8, 150 mM NaCl, 1.0% NP-40, 5 mM EDTA, 2 mM DTT, 8 µg/ml pepstatin, 8 µg/ml aprotinin, 8 µg/ml leupeptin, 2 mM Na$_3$VO$_4$, 10 mM NaF, 1 µM microcystin for twenty minutes at 4° C. Clarified lysates (0.5-2 mg protein) were incubated with 20 µL glutathione beads or amylose beads containing 10-20 µg 14-3-3-GST or 14-3-3-MBP, respectively, for 120 minutes at 4° C. Following washing, lysates and bead-bound proteins were analysed by SDS-PAGE, followed by transfer to PVDF membranes and immunoblotted with the indicated antibodies. For immunofluorescence experiments, U2OS cells were seeded onto 18 mm$^2$ coverslips, irradiated or mock-treated, fixed, extracted, and immunostained as described previously (Clapperton et al., Nat. Struct. Mol. Biol., 11:512-518, 2004).

FACS Analysis.

UV irradiation was performed at 254 nm (UV-C) using a Stratalinker 2400 (Stratagene). U2OS cells were fixed in 70% ethanol overnight at −20° C., permeabilized with PBS containing 0.2% Triton X-100 for twenty minutes at 4° C., blocked with 2% FBS in PBS, and incubated with 1 µg of anti-phospho-histone H3 per 10$^6$ cells for sixty minutes on ice. Following washing, cells were incubated with FITC-conjugated goat anti-rabbit antibody (diluted 1:500) for thirty minutes on ice, washed, and resuspended in PBS containing 50 μg/ml PI for twenty minutes immediately prior to FACS analysis. Analysis was performed using a Becton Dickinson FACS machine with CellQuest software.

For BrdU incorporation experiments, cells were incubated with 30 M BrdU for the indicated times, then fixed and permeabilized as above. Cells were denatured in 2N HCl for twenty minutes at room temperature, neutralized with 0.1M Na$_2$B$_4$O$_7$ (pH 8.5), blocked with 2% FBS in PBS, and incubated with a murine anti-BrdU antibody for sixty minutes on ice. Following washing, cells were incubated with FITC-conjugated goat anti-mouse antibodies and PI as above. Analysis was performed using a Becton Dickinson FACS machine with CellQuest software.

Clonogenic Survival Assay.

Cells were either mock-treated or treated with increasing doses of doxorubicin or cisplatin. After eight hours of treatment, cells were washed three times with growth media and three times with PBS, trypsinized and replated at a concentration of 5000 cells/10 cm$^2$ dish. After eight days, cells were fixed and stained with 0.1% crystal violet (Sigma-Aldrich). Colonies consisting of >50 cells were counted, and surviving fractions were determined by normalization against untreated cells. Experiments were performed in triplicate and are plotted as mean values with standard deviations indicated by the error bars.

Murine Tumor Models.

H-Ras-V 12-transformed p53$^{-/-}$ MEFs were used for in vivo tumor formation assays. Cells were transfected with siRNA oligonucleotides against GFP or murine MAPKAP kinase-2 for forty-eight hours, then mock treated or incubated with 0.1 μM doxorubicin or 1 μM cisplatin for eight hours, washed three times in growth media, three times in PBS, trypsinized, and resuspended at a concentration of 10$^7$ cells/ml in PBS. 10$^6$ cells were subcutaneously injected into the flanks of nude mice (Ncr nu/nu, Taconic).

For tumor regression assays, H-Ras-V12 transformed p53$^{-/-}$ MEFs were stably transfected with a lentiviral transfer vector encoding for shRNA targeting either MAPKAP kinase-2 or luciferase. 10$^6$ cells were injected into the flanks of nude mice as above, and tumors were allowed to form for twelve days. Mice were then treated with either cisplatin (2 mg/kg, intraperitoneal administration 3× per week) or doxorubicin (4 mg/kg, intraperitoneal administration 3× per week), monitored for a total of twenty-six days, and then sacrificed. Tumor diameter was measured periodically during growth and tumors were weighed at the endpoint. Experiments were performed in quadruplicate, and data plotted as sample means with error bars showing standard deviation.

Structural Modeling.

Activated MAPKAP kinase-2 (phosphorylated on Thr 222) to was modeled using the crystal structure of the ADP complex (Underwood et al., Structure, 11:627-636, 2003) with the activation loop (residues 213 to 241) deleted and rebuilt using the corresponding region (residues 299 to 328) from the structure of activated Akt/PKB in complex with AMP-PNP and GSK3-peptide (Yang et al., Nat. Struct. Biol., 9:940-944, 2002) as a template. A substrate peptide, GRPRTTSFAE (SEQ ID NO: 5), was modeled in the active site. An optimal peptide, LQRQLSIA (SEQ ID NO: 6), was modeled in the active site based on the GSK3-peptide. Coordinates for the activated MAPKAP kinase-2/peptide complex are listed in Table 1 in standard Protein Data Bank (PDB) format (details about the Protein Data Bank and the associated format for coordinates may be found in Berman et al., Nuc. Acids Res., 28:235-242, 2000). Table 2 lists pairs of atoms in the complex that form the closest protein-peptide contacts and that are useful for designing or identifying additional molecules that bind in the active site. A substrate peptide, LYRSPSMPL (residues 211-219 of human Cdc25C) (SEQ ID NO: 7) in the Chk1 active site was similarly modeled using the GSK3-peptide as a template and manually adjusted to resemble the published model (Chen et al., Cell, 100:681-692, 2000). Structures were superimposed using ALIGN and SUPERIMPOSE. Manual adjustments of the models were made using XFIT from the XtalView suite.

The structure of MAPKAP kinase-2 bound to UCN-01 was modeled using PyMOL with the structure of MAPKAP kinase-2 bound to staurosporine (PDB ID 1NXK) as a base model.

TABLE 1

Coordinates of the activated MAPKAP kinase-2/peptide complex

| ATOM | 1 | N | PHE | A | 46 | 214.820 | 109.707 | 179.069 | 1.00 | 118.35 | N |
|---|---|---|---|---|---|---|---|---|---|---|---|
| ATOM | 2 | CA | PHE | A | 46 | 214.336 | 108.388 | 178.678 | 1.00 | 109.39 | C |
| ATOM | 3 | C | PHE | A | 46 | 215.483 | 107.382 | 178.556 | 1.00 | 92.52 | C |
| ATOM | 4 | O | PHE | A | 46 | 216.008 | 107.116 | 177.483 | 1.00 | 93.11 | O |
| ATOM | 5 | CB | PHE | A | 46 | 213.617 | 108.523 | 177.335 | 1.00 | 106.31 | C |
| ATOM | 6 | CG | PHE | A | 46 | 212.712 | 107.345 | 177.122 | 1.00 | 100.53 | C |
| ATOM | 7 | CD1 | PHE | A | 46 | 213.246 | 106.138 | 176.688 | 1.00 | 94.28 | C |
| ATOM | 8 | CD2 | PHE | A | 46 | 211.347 | 107.468 | 177.345 | 1.00 | 81.06 | C |
| ATOM | 9 | CE1 | PHE | A | 46 | 212.408 | 105.049 | 176.480 | 1.00 | 71.80 | C |
| ATOM | 10 | CE2 | PHE | A | 46 | 210.515 | 106.370 | 177.135 | 1.00 | 83.85 | C |
| ATOM | 11 | CZ | PHE | A | 46 | 211.041 | 105.159 | 176.704 | 1.00 | 54.26 | C |
| ATOM | 12 | N | HIS | A | 47 | 215.896 | 106.847 | 179.719 | 1.00 | 99.95 | N |
| ATOM | 13 | CA | HIS | A | 47 | 216.976 | 105.867 | 179.715 | 1.00 | 110.68 | C |
| ATOM | 14 | C | HIS | A | 47 | 216.467 | 104.473 | 179.342 | 1.00 | 99.74 | C |
| ATOM | 15 | O | HIS | A | 47 | 215.591 | 103.903 | 179.979 | 1.00 | 108.34 | O |
| ATOM | 16 | CB | HIS | A | 47 | 217.598 | 105.835 | 181.111 | 1.00 | 128.34 | C |
| ATOM | 17 | CG | HIS | A | 47 | 217.973 | 107.234 | 181.527 | 1.00 | 172.75 | C |
| ATOM | 18 | ND1 | HIS | A | 47 | 219.157 | 107.813 | 181.211 | 1.00 | 209.78 | N |
| ATOM | 19 | CD2 | HIS | A | 47 | 217.216 | 108.147 | 182.270 | 1.00 | 195.55 | C |
| ATOM | 20 | CE1 | HIS | A | 47 | 219.113 | 109.047 | 181.749 | 1.00 | 214.52 | C |
| ATOM | 21 | NE2 | HIS | A | 47 | 217.963 | 109.275 | 182.389 | 1.00 | 216.85 | N |
| ATOM | 22 | N | VAL | A | 48 | 217.023 | 103.942 | 178.238 | 1.00 | 93.29 | N |
| ATOM | 23 | CA | VAL | A | 48 | 216.620 | 102.613 | 177.798 | 1.00 | 69.76 | C |
| ATOM | 24 | C | VAL | A | 48 | 217.795 | 101.841 | 177.194 | 1.00 | 72.39 | C |
| ATOM | 25 | O | VAL | A | 48 | 218.595 | 102.370 | 176.434 | 1.00 | 67.87 | O |
| ATOM | 26 | CB | VAL | A | 48 | 215.510 | 102.770 | 176.757 | 1.00 | 60.38 | C |

TABLE 1-continued

Coordinates of the activated MAPKAP kinase-2/peptide complex

| ATOM | 27 | CG1 | VAL | A | 48 | 215.345 | 101.470 | 175.973 | 1.00 | 76.52 | C |
|---|---|---|---|---|---|---|---|---|---|---|---|
| ATOM | 28 | CG2 | VAL | A | 48 | 214.200 | 103.110 | 177.443 | 1.00 | 87.98 | C |
| ATOM | 29 | N | LYS | A | 49 | 217.962 | 100.570 | 177.519 | 1.00 | 63.04 | N |
| ATOM | 30 | CA | LYS | A | 49 | 219.047 | 99.811 | 176.921 | 1.00 | 61.31 | C |
| ATOM | 31 | C | LYS | A | 49 | 218.424 | 98.945 | 175.833 | 1.00 | 56.33 | C |
| ATOM | 32 | O | LYS | A | 49 | 217.205 | 98.904 | 175.688 | 1.00 | 61.95 | O |
| ATOM | 33 | CB | LYS | A | 49 | 219.741 | 98.923 | 177.947 | 1.00 | 46.86 | C |
| ATOM | 34 | CG | LYS | A | 49 | 220.349 | 99.673 | 179.103 | 1.00 | 52.81 | C |
| ATOM | 35 | CD | LYS | A | 49 | 221.201 | 100.796 | 178.607 | 1.00 | 52.94 | C |
| ATOM | 36 | CE | LYS | A | 49 | 222.255 | 101.150 | 179.627 | 1.00 | 106.42 | C |
| ATOM | 37 | NZ | LYS | A | 49 | 223.200 | 102.166 | 179.091 | 1.00 | 117.49 | N |
| ATOM | 38 | N | SER | A | 50 | 219.258 | 98.248 | 175.073 | 1.00 | 67.67 | N |
| ATOM | 39 | CA | SER | A | 50 | 218.768 | 97.403 | 173.994 | 1.00 | 61.19 | C |
| ATOM | 40 | C | SER | A | 50 | 218.240 | 96.087 | 174.484 | 1.00 | 62.93 | C |
| ATOM | 41 | O | SER | A | 50 | 218.661 | 95.592 | 175.528 | 1.00 | 78.88 | O |
| ATOM | 42 | CB | SER | A | 50 | 219.875 | 97.119 | 172.994 | 1.00 | 59.19 | C |
| ATOM | 43 | OG | SER | A | 50 | 220.167 | 98.279 | 172.248 | 1.00 | 125.35 | O |
| ATOM | 44 | N | GLY | A | 51 | 217.318 | 95.516 | 173.718 | 1.00 | 62.13 | N |
| ATOM | 45 | CA | GLY | A | 51 | 216.773 | 94.223 | 174.070 | 1.00 | 45.10 | C |
| ATOM | 46 | C | GLY | A | 51 | 217.728 | 93.155 | 173.571 | 1.00 | 32.66 | C |
| ATOM | 47 | O | GLY | A | 51 | 218.558 | 93.420 | 172.709 | 1.00 | 72.20 | O |
| ATOM | 48 | N | LEU | A | 52 | 217.634 | 91.951 | 174.114 | 1.00 | 65.04 | N |
| ATOM | 49 | CA | LEU | A | 52 | 218.509 | 90.868 | 173.671 | 1.00 | 48.78 | C |
| ATOM | 50 | C | LEU | A | 52 | 218.154 | 90.388 | 172.252 | 1.00 | 54.66 | C |
| ATOM | 51 | O | LEU | A | 52 | 216.986 | 90.340 | 171.866 | 1.00 | 70.19 | O |
| ATOM | 52 | CB | LEU | A | 52 | 218.420 | 89.677 | 174.635 | 1.00 | 67.84 | C |
| ATOM | 53 | CG | LEU | A | 52 | 219.214 | 88.431 | 174.227 | 1.00 | 72.80 | C |
| ATOM | 54 | CD1 | LEU | A | 52 | 220.719 | 88.700 | 174.309 | 1.00 | 57.35 | C |
| ATOM | 55 | CD2 | LEU | A | 52 | 218.844 | 87.283 | 175.128 | 1.00 | 66.63 | C |
| ATOM | 56 | N | GLN | A | 53 | 219.170 | 90.031 | 171.477 | 1.00 | 68.12 | N |
| ATOM | 57 | CA | GLN | A | 53 | 218.958 | 89.546 | 170.125 | 1.00 | 54.88 | C |
| ATOM | 58 | C | GLN | A | 53 | 219.752 | 88.291 | 169.858 | 1.00 | 40.76 | C |
| ATOM | 59 | O | GLN | A | 53 | 220.978 | 88.278 | 169.936 | 1.00 | 66.36 | O |
| ATOM | 60 | CB | GLN | A | 53 | 219.372 | 90.588 | 169.115 | 1.00 | 47.08 | C |
| ATOM | 61 | CG | GLN | A | 53 | 219.428 | 90.042 | 167.731 | 1.00 | 60.85 | C |
| ATOM | 62 | CD | GLN | A | 53 | 220.160 | 90.974 | 166.832 | 1.00 | 80.61 | C |
| ATOM | 63 | OE1 | GLN | A | 53 | 220.236 | 90.753 | 165.627 | 1.00 | 99.15 | O |
| ATOM | 64 | NE2 | GLN | A | 53 | 220.723 | 92.031 | 167.411 | 1.00 | 83.94 | N |
| ATOM | 65 | N | ILE | A | 54 | 219.050 | 87.233 | 169.508 | 1.00 | 60.15 | N |
| ATOM | 66 | CA | ILE | A | 54 | 219.705 | 85.971 | 169.238 | 1.00 | 52.14 | C |
| ATOM | 67 | C | ILE | A | 54 | 220.190 | 85.896 | 167.802 | 1.00 | 51.88 | C |
| ATOM | 68 | O | ILE | A | 54 | 219.433 | 85.575 | 166.893 | 1.00 | 58.79 | O |
| ATOM | 69 | CB | ILE | A | 54 | 218.743 | 84.814 | 169.552 | 1.00 | 64.06 | C |
| ATOM | 70 | CG1 | ILE | A | 54 | 218.312 | 84.924 | 171.010 | 1.00 | 33.87 | C |
| ATOM | 71 | CG2 | ILE | A | 54 | 219.412 | 83.479 | 169.315 | 1.00 | 39.67 | C |
| ATOM | 72 | CD1 | ILE | A | 54 | 217.727 | 83.680 | 171.535 | 1.00 | 82.78 | C |
| ATOM | 73 | N | LYS | A | 55 | 221.464 | 86.197 | 167.611 | 1.00 | 48.72 | N |
| ATOM | 74 | CA | LYS | A | 55 | 222.064 | 86.182 | 166.287 | 1.00 | 49.52 | C |
| ATOM | 75 | C | LYS | A | 55 | 222.019 | 84.808 | 165.633 | 1.00 | 56.72 | C |
| ATOM | 76 | O | LYS | A | 55 | 222.270 | 83.808 | 166.283 | 1.00 | 70.19 | O |
| ATOM | 77 | CB | LYS | A | 55 | 223.512 | 86.661 | 166.383 | 1.00 | 51.25 | C |
| ATOM | 78 | CG | LYS | A | 55 | 223.628 | 88.111 | 166.815 | 1.00 | 49.44 | C |
| ATOM | 79 | CD | LYS | A | 55 | 225.059 | 88.584 | 166.817 | 1.00 | 89.37 | C |
| ATOM | 80 | CE | LYS | A | 55 | 225.114 | 90.085 | 167.040 | 1.00 | 73.14 | C |
| ATOM | 81 | NZ | LYS | A | 55 | 226.521 | 90.612 | 167.008 | 1.00 | 123.08 | N |
| ATOM | 82 | N | LYS | A | 56 | 221.710 | 84.758 | 164.343 | 1.00 | 41.46 | N |
| ATOM | 83 | CA | LYS | A | 56 | 221.644 | 83.482 | 163.643 | 1.00 | 66.57 | C |
| ATOM | 84 | C | LYS | A | 56 | 222.839 | 83.118 | 162.767 | 1.00 | 55.67 | C |
| ATOM | 85 | O | LYS | A | 56 | 223.028 | 81.945 | 162.455 | 1.00 | 66.55 | O |
| ATOM | 86 | CB | LYS | A | 56 | 220.379 | 83.413 | 162.793 | 1.00 | 48.95 | C |
| ATOM | 87 | CG | LYS | A | 56 | 219.242 | 82.751 | 163.486 | 1.00 | 57.91 | C |
| ATOM | 88 | CD | LYS | A | 56 | 219.248 | 83.157 | 164.927 | 1.00 | 78.89 | C |
| ATOM | 89 | CE | LYS | A | 56 | 217.907 | 82.899 | 165.554 | 1.00 | 71.88 | C |
| ATOM | 90 | NZ | LYS | A | 56 | 216.873 | 83.764 | 164.935 | 1.00 | 82.07 | N |
| ATOM | 91 | N | ASN | A | 57 | 223.640 | 84.096 | 162.361 | 1.00 | 48.62 | N |
| ATOM | 92 | CA | ASN | A | 57 | 224.788 | 83.802 | 161.508 | 1.00 | 52.30 | C |
| ATOM | 93 | C | ASN | A | 57 | 225.851 | 83.039 | 162.261 | 1.00 | 40.32 | C |
| ATOM | 94 | O | ASN | A | 57 | 225.977 | 83.197 | 163.467 | 1.00 | 58.36 | O |
| ATOM | 95 | CB | ASN | A | 57 | 225.380 | 85.083 | 161.004 | 1.00 | 42.83 | C |
| ATOM | 96 | CG | ASN | A | 57 | 225.743 | 86.007 | 162.123 | 1.00 | 73.68 | C |
| ATOM | 97 | OD1 | ASN | A | 57 | 224.859 | 86.577 | 162.794 | 1.00 | 48.52 | O |
| ATOM | 98 | ND2 | ASN | A | 57 | 227.056 | 86.182 | 162.340 | 1.00 | 36.35 | N |
| ATOM | 99 | N | ALA | A | 58 | 226.627 | 82.223 | 161.558 | 1.00 | 41.49 | N |
| ATOM | 100 | CA | ALA | A | 58 | 227.661 | 81.432 | 162.214 | 1.00 | 44.46 | C |
| ATOM | 101 | C | ALA | A | 58 | 228.613 | 82.283 | 163.040 | 1.00 | 44.31 | C |
| ATOM | 102 | O | ALA | A | 58 | 229.267 | 83.173 | 162.516 | 1.00 | 45.45 | O |
| ATOM | 103 | CB | ALA | A | 58 | 228.438 | 80.641 | 161.194 | 1.00 | 32.48 | C |
| ATOM | 104 | N | ILE | A | 59 | 228.694 | 81.998 | 164.334 | 1.00 | 46.98 | N |

TABLE 1-continued

Coordinates of the activated MAPKAP kinase-2/peptide complex

| ATOM | 105 | CA | ILE | A | 59 | 229.569 | 82.753 | 165.228 | 1.00 | 54.79 | C |
|---|---|---|---|---|---|---|---|---|---|---|---|
| ATOM | 106 | C | ILE | A | 59 | 231.007 | 82.870 | 164.670 | 1.00 | 63.43 | C |
| ATOM | 107 | O | ILE | A | 59 | 231.766 | 83.777 | 165.035 | 1.00 | 47.27 | O |
| ATOM | 108 | CB | ILE | A | 59 | 229.605 | 82.094 | 166.638 | 1.00 | 53.52 | C |
| ATOM | 109 | CG1 | ILE | A | 59 | 230.284 | 83.012 | 167.644 | 1.00 | 55.42 | C |
| ATOM | 110 | CG2 | ILE | A | 59 | 230.376 | 80.791 | 166.588 | 1.00 | 40.15 | C |
| ATOM | 111 | CD1 | ILE | A | 59 | 230.311 | 82.446 | 169.038 | 1.00 | 57.36 | C |
| ATOM | 112 | N | ILE | A | 60 | 231.375 | 81.956 | 163.777 | 1.00 | 43.08 | N |
| ATOM | 113 | CA | ILE | A | 60 | 232.743 | 81.902 | 163.274 | 1.00 | 57.78 | C |
| ATOM | 114 | C | ILE | A | 60 | 233.086 | 83.151 | 162.458 | 1.00 | 60.65 | C |
| ATOM | 115 | O | ILE | A | 60 | 234.226 | 83.590 | 162.377 | 1.00 | 72.20 | O |
| ATOM | 116 | CB | ILE | A | 60 | 232.866 | 80.659 | 162.393 | 1.00 | 38.44 | C |
| ATOM | 117 | CG1 | ILE | A | 60 | 231.615 | 80.513 | 161.518 | 1.00 | 50.72 | C |
| ATOM | 118 | CG2 | ILE | A | 60 | 232.965 | 79.403 | 163.277 | 1.00 | 49.86 | C |
| ATOM | 119 | CD1 | ILE | A | 60 | 231.798 | 79.479 | 160.407 | 1.00 | 46.70 | C |
| ATOM | 120 | N | ASP | A | 61 | 232.044 | 83.704 | 161.811 | 1.00 | 32.79 | N |
| ATOM | 121 | CA | ASP | A | 61 | 232.254 | 84.863 | 160.953 | 1.00 | 58.81 | C |
| ATOM | 122 | C | ASP | A | 61 | 232.607 | 86.117 | 161.758 | 1.00 | 50.10 | C |
| ATOM | 123 | O | ASP | A | 61 | 233.397 | 86.956 | 161.346 | 1.00 | 78.45 | O |
| ATOM | 124 | CB | ASP | A | 61 | 230.972 | 85.093 | 160.149 | 1.00 | 36.95 | C |
| ATOM | 125 | CG | ASP | A | 61 | 230.476 | 83.758 | 159.608 | 1.00 | 91.42 | C |
| ATOM | 126 | OD1 | ASP | A | 61 | 229.268 | 83.636 | 159.400 | 1.00 | 76.09 | O |
| ATOM | 127 | OD2 | ASP | A | 61 | 231.293 | 82.864 | 159.405 | 1.00 | 122.26 | O |
| ATOM | 128 | N | ASP | A | 62 | 231.954 | 86.250 | 162.929 | 1.00 | 62.40 | N |
| ATOM | 129 | CA | ASP | A | 62 | 232.213 | 87.422 | 163.761 | 1.00 | 63.46 | C |
| ATOM | 130 | C | ASP | A | 62 | 233.328 | 87.164 | 164.778 | 1.00 | 43.90 | C |
| ATOM | 131 | O | ASP | A | 62 | 233.994 | 88.071 | 165.261 | 1.00 | 74.39 | O |
| ATOM | 132 | CB | ASP | A | 62 | 230.918 | 87.786 | 164.492 | 1.00 | 33.21 | C |
| ATOM | 133 | CG | ASP | A | 62 | 229.843 | 88.135 | 163.473 | 1.00 | 76.80 | C |
| ATOM | 134 | OD1 | ASP | A | 62 | 230.116 | 88.979 | 162.618 | 1.00 | 99.65 | O |
| ATOM | 135 | OD2 | ASP | A | 62 | 228.754 | 87.573 | 163.546 | 1.00 | 84.30 | O |
| ATOM | 136 | N | TYR | A | 63 | 233.493 | 85.877 | 165.132 | 1.00 | 44.70 | N |
| ATOM | 137 | CA | TYR | A | 63 | 234.482 | 85.539 | 166.148 | 1.00 | 62.53 | C |
| ATOM | 138 | C | TYR | A | 63 | 235.502 | 84.519 | 165.641 | 1.00 | 58.43 | C |
| ATOM | 139 | O | TYR | A | 63 | 235.388 | 83.956 | 164.561 | 1.00 | 79.42 | O |
| ATOM | 140 | CB | TYR | A | 63 | 233.742 | 84.965 | 167.358 | 1.00 | 50.79 | C |
| ATOM | 141 | CG | TYR | A | 63 | 233.100 | 86.068 | 168.120 | 1.00 | 44.26 | C |
| ATOM | 142 | CD1 | TYR | A | 63 | 233.802 | 86.709 | 169.136 | 1.00 | 34.66 | C |
| ATOM | 143 | CD2 | TYR | A | 63 | 231.800 | 86.477 | 167.811 | 1.00 | 37.87 | C |
| ATOM | 144 | CE1 | TYR | A | 63 | 233.220 | 87.758 | 169.831 | 1.00 | 27.94 | C |
| ATOM | 145 | CE2 | TYR | A | 63 | 231.215 | 87.521 | 168.512 | 1.00 | 34.56 | C |
| ATOM | 146 | CZ | TYR | A | 63 | 231.916 | 88.158 | 169.519 | 1.00 | 56.82 | C |
| ATOM | 147 | OH | TYR | A | 63 | 231.353 | 89.224 | 170.192 | 1.00 | 41.90 | O |
| ATOM | 148 | N | LYS | A | 64 | 236.554 | 84.325 | 166.455 | 1.00 | 69.78 | N |
| ATOM | 149 | CA | LYS | A | 64 | 237.542 | 83.306 | 166.129 | 1.00 | 60.63 | C |
| ATOM | 150 | C | LYS | A | 64 | 237.831 | 82.420 | 167.340 | 1.00 | 67.37 | C |
| ATOM | 151 | O | LYS | A | 64 | 238.259 | 82.882 | 168.389 | 1.00 | 66.71 | O |
| ATOM | 152 | CB | LYS | A | 64 | 238.825 | 84.004 | 165.673 | 1.00 | 85.98 | C |
| ATOM | 153 | CG | LYS | A | 64 | 240.084 | 83.232 | 166.078 | 1.00 | 68.10 | C |
| ATOM | 154 | CD | LYS | A | 64 | 240.235 | 81.914 | 165.315 | 1.00 | 96.02 | C |
| ATOM | 155 | CE | LYS | A | 64 | 241.289 | 80.993 | 165.941 | 1.00 | 159.06 | C |
| ATOM | 156 | NZ | LYS | A | 64 | 241.422 | 79.778 | 165.141 | 1.00 | 151.29 | N |
| ATOM | 157 | N | VAL | A | 65 | 237.271 | 81.240 | 167.130 | 1.00 | 54.82 | N |
| ATOM | 158 | CA | VAL | A | 65 | 237.148 | 80.288 | 168.220 | 1.00 | 65.09 | C |
| ATOM | 159 | C | VAL | A | 65 | 238.437 | 79.492 | 168.298 | 1.00 | 65.21 | C |
| ATOM | 160 | O | VAL | A | 65 | 238.945 | 79.029 | 167.282 | 1.00 | 79.23 | O |
| ATOM | 161 | CB | VAL | A | 65 | 235.960 | 79.329 | 168.000 | 1.00 | 53.30 | C |
| ATOM | 162 | CG1 | VAL | A | 65 | 235.948 | 78.263 | 169.075 | 1.00 | 68.94 | C |
| ATOM | 163 | CG2 | VAL | A | 65 | 234.659 | 80.104 | 168.039 | 1.00 | 50.00 | C |
| ATOM | 164 | N | THR | A | 66 | 238.971 | 79.338 | 169.502 | 1.00 | 60.78 | N |
| ATOM | 165 | CA | THR | A | 66 | 240.214 | 78.602 | 169.680 | 1.00 | 73.39 | C |
| ATOM | 166 | C | THR | A | 66 | 240.032 | 77.346 | 170.515 | 1.00 | 76.31 | C |
| ATOM | 167 | O | THR | A | 66 | 238.969 | 77.107 | 171.080 | 1.00 | 77.40 | O |
| ATOM | 168 | CB | THR | A | 66 | 241.267 | 79.462 | 170.376 | 1.00 | 65.28 | C |
| ATOM | 169 | OG1 | THR | A | 66 | 241.150 | 79.289 | 171.798 | 1.00 | 71.85 | O |
| ATOM | 170 | CG2 | THR | A | 66 | 241.067 | 80.944 | 170.016 | 1.00 | 64.31 | C |
| ATOM | 171 | N | SER | A | 67 | 241.092 | 76.554 | 170.602 | 1.00 | 86.86 | N |
| ATOM | 172 | CA | SER | A | 67 | 241.065 | 75.318 | 171.369 | 1.00 | 86.84 | C |
| ATOM | 173 | C | SER | A | 67 | 241.359 | 75.528 | 172.838 | 1.00 | 78.98 | C |
| ATOM | 174 | O | SER | A | 67 | 241.140 | 74.631 | 173.646 | 1.00 | 92.44 | O |
| ATOM | 175 | CB | SER | A | 67 | 242.082 | 74.338 | 170.818 | 1.00 | 77.74 | C |
| ATOM | 176 | OG | SER | A | 67 | 241.681 | 73.901 | 169.540 | 1.00 | 131.17 | O |
| ATOM | 177 | N | GLN | A | 68 | 241.868 | 76.702 | 173.185 | 1.00 | 65.34 | N |
| ATOM | 178 | CA | GLN | A | 68 | 242.187 | 76.981 | 174.571 | 1.00 | 79.87 | C |
| ATOM | 179 | C | GLN | A | 68 | 240.955 | 76.819 | 175.448 | 1.00 | 75.61 | C |
| ATOM | 180 | O | GLN | A | 68 | 239.849 | 77.197 | 175.067 | 1.00 | 70.47 | O |
| ATOM | 181 | CB | GLN | A | 68 | 242.760 | 78.387 | 174.704 | 1.00 | 76.67 | C |
| ATOM | 182 | CG | GLN | A | 68 | 243.238 | 78.724 | 176.100 | 1.00 | 86.58 | C |

TABLE 1-continued

Coordinates of the activated MAPKAP kinase-2/peptide complex

| ATOM | 183 | CD | GLN | A | 68 | 244.346 | 79.757 | 176.087 | 1.00 | 151.90 | C |
|---|---|---|---|---|---|---|---|---|---|---|---|
| ATOM | 184 | OE1 | GLN | A | 68 | 244.745 | 80.271 | 177.134 | 1.00 | 147.03 | O |
| ATOM | 185 | NE2 | GLN | A | 68 | 244.860 | 80.060 | 174.895 | 1.00 | 166.06 | N |
| ATOM | 186 | N | VAL | A | 69 | 241.155 | 76.244 | 176.625 | 1.00 | 70.23 | N |
| ATOM | 187 | CA | VAL | A | 69 | 240.064 | 76.013 | 177.552 | 1.00 | 73.71 | C |
| ATOM | 188 | C | VAL | A | 69 | 240.157 | 76.908 | 178.775 | 1.00 | 65.57 | C |
| ATOM | 189 | O | VAL | A | 69 | 241.009 | 76.704 | 179.639 | 1.00 | 83.31 | O |
| ATOM | 190 | CB | VAL | A | 69 | 240.064 | 74.564 | 178.023 | 1.00 | 69.41 | C |
| ATOM | 191 | CG1 | VAL | A | 69 | 238.896 | 74.324 | 178.952 | 1.00 | 51.08 | C |
| ATOM | 192 | CG2 | VAL | A | 69 | 240.017 | 73.648 | 176.830 | 1.00 | 57.48 | C |
| ATOM | 193 | N | LEU | A | 70 | 239.276 | 77.899 | 178.847 | 1.00 | 74.02 | N |
| ATOM | 194 | CA | LEU | A | 70 | 239.259 | 78.816 | 179.977 | 1.00 | 88.16 | C |
| ATOM | 195 | C | LEU | A | 70 | 238.865 | 78.039 | 181.227 | 1.00 | 94.93 | C |
| ATOM | 196 | O | LEU | A | 70 | 239.171 | 78.458 | 182.343 | 1.00 | 86.96 | O |
| ATOM | 197 | CB | LEU | A | 70 | 238.268 | 79.956 | 179.718 | 1.00 | 80.15 | C |
| ATOM | 198 | CG | LEU | A | 70 | 238.660 | 81.015 | 178.680 | 1.00 | 66.85 | C |
| ATOM | 199 | CD1 | LEU | A | 70 | 237.420 | 81.668 | 178.097 | 1.00 | 90.30 | C |
| ATOM | 200 | CD2 | LEU | A | 70 | 239.553 | 82.049 | 179.322 | 1.00 | 79.20 | C |
| ATOM | 201 | N | GLY | A | 71 | 238.194 | 76.903 | 181.035 | 1.00 | 87.34 | N |
| ATOM | 202 | CA | GLY | A | 71 | 237.781 | 76.089 | 182.166 | 1.00 | 87.75 | C |
| ATOM | 203 | C | GLY | A | 71 | 236.707 | 75.077 | 181.825 | 1.00 | 83.77 | C |
| ATOM | 204 | O | GLY | A | 71 | 236.158 | 75.111 | 180.730 | 1.00 | 84.32 | O |
| ATOM | 205 | N | LEU | A | 72 | 236.405 | 74.175 | 182.757 | 1.00 | 88.68 | N |
| ATOM | 206 | CA | LEU | A | 72 | 235.381 | 73.155 | 182.534 | 1.00 | 82.29 | C |
| ATOM | 207 | C | LEU | A | 72 | 234.225 | 73.239 | 183.509 | 1.00 | 73.28 | C |
| ATOM | 208 | O | LEU | A | 72 | 234.318 | 73.871 | 184.557 | 1.00 | 95.04 | O |
| ATOM | 209 | CB | LEU | A | 72 | 235.976 | 71.751 | 182.621 | 1.00 | 77.46 | C |
| ATOM | 210 | CG | LEU | A | 72 | 236.877 | 71.305 | 181.473 | 1.00 | 94.19 | C |
| ATOM | 211 | CD1 | LEU | A | 72 | 237.217 | 69.818 | 181.595 | 1.00 | 139.26 | C |
| ATOM | 212 | CD2 | LEU | A | 72 | 236.150 | 71.568 | 180.172 | 1.00 | 109.03 | C |
| ATOM | 213 | N | GLY | A | 73 | 233.133 | 72.577 | 183.158 | 1.00 | 77.98 | N |
| ATOM | 214 | CA | GLY | A | 73 | 231.963 | 72.592 | 184.013 | 1.00 | 71.81 | C |
| ATOM | 215 | C | GLY | A | 73 | 230.762 | 71.853 | 183.446 | 1.00 | 99.78 | C |
| ATOM | 216 | O | GLY | A | 73 | 230.843 | 71.171 | 182.418 | 1.00 | 93.36 | O |
| ATOM | 217 | N | ILE | A | 74 | 229.635 | 72.004 | 184.136 | 1.00 | 112.58 | N |
| ATOM | 218 | CA | ILE | A | 74 | 228.376 | 71.365 | 183.765 | 1.00 | 114.50 | C |
| ATOM | 219 | C | ILE | A | 74 | 228.103 | 71.259 | 182.270 | 1.00 | 110.24 | C |
| ATOM | 220 | O | ILE | A | 74 | 227.890 | 70.162 | 181.750 | 1.00 | 94.78 | O |
| ATOM | 221 | CB | ILE | A | 74 | 227.189 | 72.085 | 184.439 | 1.00 | 120.25 | C |
| ATOM | 222 | CG1 | ILE | A | 74 | 227.145 | 71.707 | 185.921 | 1.00 | 127.29 | C |
| ATOM | 223 | CG2 | ILE | A | 74 | 225.889 | 71.745 | 183.724 | 1.00 | 110.29 | C |
| ATOM | 224 | CD1 | ILE | A | 74 | 225.968 | 72.285 | 186.673 | 1.00 | 178.93 | C |
| ATOM | 225 | N | ASN | A | 75 | 228.106 | 72.393 | 181.580 | 1.00 | 113.84 | N |
| ATOM | 226 | CA | ASN | A | 75 | 227.844 | 72.395 | 180.148 | 1.00 | 108.71 | C |
| ATOM | 227 | C | ASN | A | 75 | 229.044 | 72.005 | 179.296 | 1.00 | 100.52 | C |
| ATOM | 228 | O | ASN | A | 75 | 228.935 | 71.858 | 178.079 | 1.00 | 102.09 | O |
| ATOM | 229 | CB | ASN | A | 75 | 227.303 | 73.756 | 179.736 | 1.00 | 95.22 | C |
| ATOM | 230 | CG | ASN | A | 75 | 225.898 | 73.967 | 180.225 | 1.00 | 84.98 | C |
| ATOM | 231 | OD1 | ASN | A | 75 | 224.966 | 73.315 | 179.749 | 1.00 | 88.40 | O |
| ATOM | 232 | ND2 | ASN | A | 75 | 225.730 | 74.858 | 181.199 | 1.00 | 112.62 | N |
| ATOM | 233 | N | GLY | A | 76 | 230.186 | 71.820 | 179.940 | 1.00 | 99.31 | N |
| ATOM | 234 | CA | GLY | A | 76 | 231.360 | 71.428 | 179.198 | 1.00 | 93.20 | C |
| ATOM | 235 | C | GLY | A | 76 | 232.489 | 72.428 | 179.282 | 1.00 | 96.95 | C |
| ATOM | 236 | O | GLY | A | 76 | 232.666 | 73.117 | 180.285 | 1.00 | 101.12 | O |
| ATOM | 237 | N | LYS | A | 77 | 233.258 | 72.506 | 178.205 | 1.00 | 82.50 | N |
| ATOM | 238 | CA | LYS | A | 77 | 234.386 | 73.409 | 178.146 | 1.00 | 79.18 | C |
| ATOM | 239 | C | LYS | A | 77 | 233.986 | 74.820 | 177.757 | 1.00 | 66.93 | C |
| ATOM | 240 | O | LYS | A | 77 | 233.189 | 75.025 | 176.852 | 1.00 | 79.35 | O |
| ATOM | 241 | CB | LYS | A | 77 | 235.410 | 72.872 | 177.160 | 1.00 | 78.70 | C |
| ATOM | 242 | N | VAL | A | 78 | 234.523 | 75.794 | 178.470 | 1.00 | 57.33 | N |
| ATOM | 243 | CA | VAL | A | 78 | 234.267 | 77.179 | 178.150 | 1.00 | 49.75 | C |
| ATOM | 244 | C | VAL | A | 78 | 235.512 | 77.620 | 177.410 | 1.00 | 79.35 | C |
| ATOM | 245 | O | VAL | A | 78 | 236.545 | 77.888 | 178.028 | 1.00 | 64.43 | O |
| ATOM | 246 | CB | VAL | A | 78 | 234.138 | 78.020 | 179.386 | 1.00 | 54.95 | C |
| ATOM | 247 | CG1 | VAL | A | 78 | 234.267 | 79.482 | 179.023 | 1.00 | 45.00 | C |
| ATOM | 248 | CG2 | VAL | A | 78 | 232.810 | 77.742 | 180.029 | 1.00 | 52.90 | C |
| ATOM | 249 | N | LEU | A | 79 | 235.414 | 77.692 | 176.087 | 1.00 | 70.72 | N |
| ATOM | 250 | CA | LEU | A | 79 | 236.538 | 78.073 | 175.245 | 1.00 | 61.89 | C |
| ATOM | 251 | C | LEU | A | 79 | 236.825 | 79.563 | 175.185 | 1.00 | 64.76 | C |
| ATOM | 252 | O | LEU | A | 79 | 235.930 | 80.394 | 175.360 | 1.00 | 63.50 | O |
| ATOM | 253 | CB | LEU | A | 79 | 236.292 | 77.599 | 173.825 | 1.00 | 51.24 | C |
| ATOM | 254 | CG | LEU | A | 79 | 235.907 | 76.149 | 173.599 | 1.00 | 64.90 | C |
| ATOM | 255 | CD1 | LEU | A | 79 | 235.543 | 75.983 | 172.139 | 1.00 | 49.75 | C |
| ATOM | 256 | CD2 | LEU | A | 79 | 237.052 | 75.236 | 173.978 | 1.00 | 80.17 | C |
| ATOM | 257 | N | GLN | A | 80 | 238.090 | 79.889 | 174.919 | 1.00 | 72.17 | N |
| ATOM | 258 | CA | GLN | A | 80 | 238.505 | 81.274 | 174.765 | 1.00 | 77.62 | C |
| ATOM | 259 | C | GLN | A | 80 | 238.376 | 81.604 | 173.288 | 1.00 | 66.11 | C |
| ATOM | 260 | O | GLN | A | 80 | 238.775 | 80.813 | 172.437 | 1.00 | 64.63 | O |

TABLE 1-continued

Coordinates of the activated MAPKAP kinase-2/peptide complex

| ATOM | 261 | CB | GLN | A | 80 | 239.955 | 81.486 | 175.167 | 1.00 | 52.97 | C |
|---|---|---|---|---|---|---|---|---|---|---|---|
| ATOM | 262 | CG | GLN | A | 80 | 240.390 | 82.913 | 174.863 | 1.00 | 93.41 | C |
| ATOM | 263 | CD | GLN | A | 80 | 241.715 | 83.310 | 175.494 | 1.00 | 115.14 | C |
| ATOM | 264 | OE1 | GLN | A | 80 | 242.038 | 84.502 | 175.567 | 1.00 | 116.65 | O |
| ATOM | 265 | NE2 | GLN | A | 80 | 242.490 | 82.322 | 175.949 | 1.00 | 117.09 | N |
| ATOM | 266 | N | ILE | A | 81 | 237.792 | 82.754 | 172.982 | 1.00 | 57.33 | N |
| ATOM | 267 | CA | ILE | A | 81 | 237.629 | 83.150 | 171.596 | 1.00 | 57.32 | C |
| ATOM | 268 | C | ILE | A | 81 | 238.109 | 84.571 | 171.400 | 1.00 | 54.90 | C |
| ATOM | 269 | O | ILE | A | 81 | 238.310 | 85.320 | 172.362 | 1.00 | 61.04 | O |
| ATOM | 270 | CB | ILE | A | 81 | 236.160 | 83.072 | 171.114 | 1.00 | 62.17 | C |
| ATOM | 271 | CG1 | ILE | A | 81 | 235.289 | 84.050 | 171.897 | 1.00 | 51.03 | C |
| ATOM | 272 | CG2 | ILE | A | 81 | 235.628 | 81.679 | 171.285 | 1.00 | 42.99 | C |
| ATOM | 273 | CD1 | ILE | A | 81 | 233.852 | 84.088 | 171.391 | 1.00 | 59.46 | C |
| ATOM | 274 | N | PHE | A | 82 | 238.287 | 84.930 | 170.131 | 1.00 | 70.25 | N |
| ATOM | 275 | CA | PHE | A | 82 | 238.753 | 86.251 | 169.763 | 1.00 | 55.36 | C |
| ATOM | 276 | C | PHE | A | 82 | 237.815 | 86.911 | 168.787 | 1.00 | 62.80 | C |
| ATOM | 277 | O | PHE | A | 82 | 237.287 | 86.260 | 167.874 | 1.00 | 65.67 | O |
| ATOM | 278 | CB | PHE | A | 82 | 240.145 | 86.152 | 169.152 | 1.00 | 42.74 | C |
| ATOM | 279 | CG | PHE | A | 82 | 241.197 | 85.862 | 170.151 | 1.00 | 59.25 | C |
| ATOM | 280 | CD1 | PHE | A | 82 | 241.639 | 86.857 | 170.999 | 1.00 | 44.66 | C |
| ATOM | 281 | CD2 | PHE | A | 82 | 241.687 | 84.576 | 170.314 | 1.00 | 37.34 | C |
| ATOM | 282 | CE1 | PHE | A | 82 | 242.552 | 86.576 | 171.999 | 1.00 | 57.81 | C |
| ATOM | 283 | CE2 | PHE | A | 82 | 242.604 | 84.286 | 171.315 | 1.00 | 54.82 | C |
| ATOM | 284 | CZ | PHE | A | 82 | 243.032 | 85.287 | 172.156 | 1.00 | 58.83 | C |
| ATOM | 285 | N | ASN | A | 83 | 237.592 | 88.205 | 168.997 | 1.00 | 52.27 | N |
| ATOM | 286 | CA | ASN | A | 83 | 236.746 | 88.954 | 168.104 | 1.00 | 66.04 | C |
| ATOM | 287 | C | ASN | A | 83 | 237.605 | 89.492 | 166.971 | 1.00 | 53.09 | C |
| ATOM | 288 | O | ASN | A | 83 | 238.453 | 90.346 | 167.171 | 1.00 | 64.85 | O |
| ATOM | 289 | CB | ASN | A | 83 | 236.093 | 90.099 | 168.830 | 1.00 | 47.48 | C |
| ATOM | 290 | CG | ASN | A | 83 | 235.214 | 90.902 | 167.924 | 1.00 | 67.70 | C |
| ATOM | 291 | OD1 | ASN | A | 83 | 235.689 | 91.744 | 167.160 | 1.00 | 72.99 | O |
| ATOM | 292 | ND2 | ASN | A | 83 | 233.915 | 90.632 | 167.977 | 1.00 | 70.38 | N |
| ATOM | 293 | N | LYS | A | 84 | 237.383 | 88.974 | 165.774 | 1.00 | 63.87 | N |
| ATOM | 294 | CA | LYS | A | 84 | 238.133 | 89.376 | 164.590 | 1.00 | 68.20 | C |
| ATOM | 295 | C | LYS | A | 84 | 238.366 | 90.876 | 164.450 | 1.00 | 61.51 | C |
| ATOM | 296 | O | LYS | A | 84 | 239.492 | 91.340 | 164.537 | 1.00 | 74.81 | O |
| ATOM | 297 | CB | LYS | A | 84 | 237.412 | 88.859 | 163.345 | 1.00 | 55.26 | C |
| ATOM | 298 | CG | LYS | A | 84 | 237.312 | 87.343 | 163.283 | 1.00 | 33.38 | C |
| ATOM | 299 | CD | LYS | A | 84 | 236.425 | 86.918 | 162.154 | 1.00 | 30.89 | C |
| ATOM | 300 | CE | LYS | A | 84 | 236.759 | 85.521 | 161.719 | 1.00 | 46.41 | C |
| ATOM | 301 | NZ | LYS | A | 84 | 236.028 | 85.182 | 160.476 | 1.00 | 72.55 | N |
| ATOM | 302 | N | ARG | A | 85 | 237.290 | 91.622 | 164.235 | 1.00 | 63.12 | N |
| ATOM | 303 | CA | ARG | A | 85 | 237.359 | 93.066 | 164.043 | 1.00 | 51.69 | C |
| ATOM | 304 | C | ARG | A | 85 | 237.905 | 93.905 | 165.183 | 1.00 | 58.02 | C |
| ATOM | 305 | O | ARG | A | 85 | 238.197 | 95.075 | 164.991 | 1.00 | 86.09 | O |
| ATOM | 306 | CB | ARG | A | 85 | 235.978 | 93.589 | 163.647 | 1.00 | 60.23 | C |
| ATOM | 307 | CG | ARG | A | 85 | 235.862 | 95.086 | 163.509 | 1.00 | 76.93 | C |
| ATOM | 308 | CD | ARG | A | 85 | 235.516 | 95.725 | 164.835 | 1.00 | 84.92 | C |
| ATOM | 309 | NE | ARG | A | 85 | 234.121 | 96.140 | 164.907 | 1.00 | 93.42 | N |
| ATOM | 310 | CZ | ARG | A | 85 | 233.541 | 96.634 | 165.997 | 1.00 | 103.30 | C |
| ATOM | 311 | NH1 | ARG | A | 85 | 234.224 | 96.777 | 167.128 | 1.00 | 54.02 | N |
| ATOM | 312 | NH2 | ARG | A | 85 | 232.268 | 96.998 | 165.949 | 1.00 | 119.53 | N |
| ATOM | 313 | N | THR | A | 86 | 238.050 | 93.339 | 166.370 | 1.00 | 64.72 | N |
| ATOM | 314 | CA | THR | A | 86 | 238.565 | 94.123 | 167.489 | 1.00 | 54.27 | C |
| ATOM | 315 | C | THR | A | 86 | 239.717 | 93.398 | 168.140 | 1.00 | 52.40 | C |
| ATOM | 316 | O | THR | A | 86 | 240.520 | 93.980 | 168.856 | 1.00 | 57.78 | O |
| ATOM | 317 | CB | THR | A | 86 | 237.468 | 94.392 | 168.536 | 1.00 | 58.63 | C |
| ATOM | 318 | OG1 | THR | A | 86 | 236.471 | 95.246 | 167.968 | 1.00 | 54.24 | O |
| ATOM | 319 | CG2 | THR | A | 86 | 238.045 | 95.084 | 169.743 | 1.00 | 98.48 | C |
| ATOM | 320 | N | GLN | A | 87 | 239.772 | 92.106 | 167.883 | 1.00 | 54.70 | N |
| ATOM | 321 | CA | GLN | A | 87 | 240.819 | 91.260 | 168.397 | 1.00 | 49.69 | C |
| ATOM | 322 | C | GLN | A | 87 | 240.875 | 91.131 | 169.927 | 1.00 | 63.54 | C |
| ATOM | 323 | O | GLN | A | 87 | 241.936 | 90.881 | 170.491 | 1.00 | 78.48 | O |
| ATOM | 324 | CB | GLN | A | 87 | 242.148 | 91.761 | 167.854 | 1.00 | 44.04 | C |
| ATOM | 325 | CG | GLN | A | 87 | 243.145 | 90.675 | 167.561 | 1.00 | 87.54 | C |
| ATOM | 326 | CD | GLN | A | 87 | 242.722 | 89.811 | 166.413 | 1.00 | 70.54 | C |
| ATOM | 327 | OE1 | GLN | A | 87 | 243.394 | 88.840 | 166.083 | 1.00 | 95.76 | O |
| ATOM | 328 | NE2 | GLN | A | 87 | 241.601 | 90.157 | 165.789 | 1.00 | 75.13 | N |
| ATOM | 329 | N | GLU | A | 88 | 239.746 | 91.291 | 170.608 | 1.00 | 57.33 | N |
| ATOM | 330 | CA | GLU | A | 88 | 239.751 | 91.135 | 172.060 | 1.00 | 69.04 | C |
| ATOM | 331 | C | GLU | A | 88 | 239.352 | 89.723 | 172.442 | 1.00 | 68.23 | C |
| ATOM | 332 | O | GLU | A | 88 | 238.622 | 89.060 | 171.702 | 1.00 | 70.57 | O |
| ATOM | 333 | CB | GLU | A | 88 | 238.816 | 92.138 | 172.708 | 1.00 | 73.60 | C |
| ATOM | 334 | CG | GLU | A | 88 | 239.297 | 93.538 | 172.480 | 1.00 | 111.93 | C |
| ATOM | 335 | CD | GLU | A | 88 | 240.559 | 93.845 | 173.228 | 1.00 | 130.01 | C |
| ATOM | 336 | OE1 | GLU | A | 88 | 240.728 | 93.298 | 174.344 | 1.00 | 151.01 | O |
| ATOM | 337 | OE2 | GLU | A | 88 | 241.376 | 94.634 | 172.698 | 1.00 | 169.07 | O |
| ATOM | 338 | N | LYS | A | 89 | 239.837 | 89.261 | 173.592 | 1.00 | 80.21 | N |

TABLE 1-continued

Coordinates of the activated MAPKAP kinase-2/peptide complex

| ATOM | 339 | CA | LYS | A | 89 | 239.543 | 87.904 | 174.047 | 1.00 | 67.45 | C |
|---|---|---|---|---|---|---|---|---|---|---|---|
| ATOM | 340 | C | LYS | A | 89 | 238.171 | 87.815 | 174.709 | 1.00 | 67.74 | C |
| ATOM | 341 | O | LYS | A | 89 | 237.719 | 88.752 | 175.355 | 1.00 | 71.95 | O |
| ATOM | 342 | CB | LYS | A | 89 | 240.632 | 87.424 | 175.013 | 1.00 | 46.26 | C |
| ATOM | 343 | N | PHE | A | 90 | 237.504 | 86.681 | 174.537 | 1.00 | 68.69 | N |
| ATOM | 344 | CA | PHE | A | 90 | 236.195 | 86.481 | 175.128 | 1.00 | 63.31 | C |
| ATOM | 345 | C | PHE | A | 90 | 235.957 | 85.019 | 175.477 | 1.00 | 70.09 | C |
| ATOM | 346 | O | PHE | A | 90 | 236.571 | 84.121 | 174.892 | 1.00 | 76.39 | O |
| ATOM | 347 | CB | PHE | A | 90 | 235.100 | 86.935 | 174.169 | 1.00 | 52.49 | C |
| ATOM | 348 | CG | PHE | A | 90 | 234.975 | 88.434 | 174.031 | 1.00 | 61.34 | C |
| ATOM | 349 | CD1 | PHE | A | 90 | 235.523 | 89.091 | 172.952 | 1.00 | 63.36 | C |
| ATOM | 350 | CD2 | PHE | A | 90 | 234.238 | 89.170 | 174.942 | 1.00 | 60.92 | C |
| ATOM | 351 | CE1 | PHE | A | 90 | 235.330 | 90.429 | 172.781 | 1.00 | 38.41 | C |
| ATOM | 352 | CE2 | PHE | A | 90 | 234.048 | 90.529 | 174.762 | 1.00 | 57.58 | C |
| ATOM | 353 | CZ | PHE | A | 90 | 234.591 | 91.155 | 173.683 | 1.00 | 50.60 | C |
| ATOM | 354 | N | ALA | A | 91 | 235.055 | 84.788 | 176.431 | 1.00 | 67.69 | N |
| ATOM | 355 | CA | ALA | A | 91 | 234.692 | 83.444 | 176.853 | 1.00 | 44.28 | C |
| ATOM | 356 | C | ALA | A | 91 | 233.480 | 83.000 | 176.052 | 1.00 | 45.25 | C |
| ATOM | 357 | O | ALA | A | 91 | 232.569 | 83.788 | 175.795 | 1.00 | 60.93 | O |
| ATOM | 358 | CB | ALA | A | 91 | 234.360 | 83.443 | 178.302 | 1.00 | 52.11 | C |
| ATOM | 359 | N | LEU | A | 92 | 233.477 | 81.736 | 175.653 | 1.00 | 48.94 | N |
| ATOM | 360 | CA | LEU | A | 92 | 232.381 | 81.179 | 174.882 | 1.00 | 50.98 | C |
| ATOM | 361 | C | LEU | A | 92 | 231.771 | 79.995 | 175.610 | 1.00 | 66.99 | C |
| ATOM | 362 | O | LEU | A | 92 | 232.467 | 79.045 | 175.939 | 1.00 | 82.82 | O |
| ATOM | 363 | CB | LEU | A | 92 | 232.886 | 80.710 | 173.536 | 1.00 | 39.13 | C |
| ATOM | 364 | CG | LEU | A | 92 | 231.838 | 79.857 | 172.839 | 1.00 | 52.58 | C |
| ATOM | 365 | CD1 | LEU | A | 92 | 230.636 | 80.726 | 172.548 | 1.00 | 48.33 | C |
| ATOM | 366 | CD2 | LEU | A | 92 | 232.404 | 79.256 | 171.557 | 1.00 | 58.60 | C |
| ATOM | 367 | N | LYS | A | 93 | 230.469 | 80.053 | 175.856 | 1.00 | 66.30 | N |
| ATOM | 368 | CA | LYS | A | 93 | 229.650 | 79.022 | 176.486 | 1.00 | 62.11 | C |
| ATOM | 369 | C | LYS | A | 93 | 228.624 | 78.440 | 175.508 | 1.00 | 61.26 | C |
| ATOM | 370 | O | LYS | A | 93 | 227.945 | 79.148 | 174.774 | 1.00 | 77.67 | O |
| ATOM | 371 | CB | LYS | A | 93 | 228.936 | 79.645 | 177.689 | 1.00 | 79.47 | C |
| ATOM | 372 | CG | LYS | A | 93 | 228.640 | 78.617 | 178.785 | 1.00 | 69.18 | C |
| ATOM | 373 | CD | LYS | A | 93 | 227.896 | 79.231 | 179.974 | 1.00 | 74.19 | C |
| ATOM | 374 | CE | LYS | A | 93 | 227.871 | 78.303 | 181.194 | 1.00 | 107.78 | C |
| ATOM | 375 | NZ | LYS | A | 93 | 228.986 | 78.626 | 182.083 | 1.00 | 92.73 | N |
| ATOM | 376 | N | MET | A | 94 | 228.551 | 77.095 | 175.489 | 1.00 | 53.94 | N |
| ATOM | 377 | CA | MET | A | 94 | 227.639 | 76.436 | 174.560 | 1.00 | 63.34 | C |
| ATOM | 378 | C | MET | A | 94 | 226.517 | 75.693 | 175.290 | 1.00 | 67.05 | C |
| ATOM | 379 | O | MET | A | 94 | 226.740 | 74.805 | 176.101 | 1.00 | 77.93 | O |
| ATOM | 380 | CB | MET | A | 94 | 228.447 | 75.451 | 173.713 | 1.00 | 54.57 | C |
| ATOM | 381 | CG | MET | A | 94 | 229.751 | 76.056 | 173.188 | 1.00 | 66.95 | C |
| ATOM | 382 | SD | MET | A | 94 | 230.855 | 74.810 | 172.511 | 1.00 | 128.32 | S |
| ATOM | 383 | CE | MET | A | 94 | 231.935 | 75.912 | 171.587 | 1.00 | 110.84 | C |
| ATOM | 384 | N | LEU | A | 95 | 225.273 | 76.116 | 174.999 | 1.00 | 76.30 | N |
| ATOM | 385 | CA | LEU | A | 95 | 224.126 | 75.468 | 175.626 | 1.00 | 47.37 | C |
| ATOM | 386 | C | LEU | A | 95 | 223.284 | 74.703 | 174.601 | 1.00 | 61.07 | C |
| ATOM | 387 | O | LEU | A | 95 | 223.143 | 75.102 | 173.452 | 1.00 | 66.44 | O |
| ATOM | 388 | CB | LEU | A | 95 | 223.276 | 76.549 | 176.295 | 1.00 | 56.39 | C |
| ATOM | 389 | CG | LEU | A | 95 | 224.057 | 77.342 | 177.346 | 1.00 | 78.66 | C |
| ATOM | 390 | CD1 | LEU | A | 95 | 223.138 | 78.105 | 178.302 | 1.00 | 71.39 | C |
| ATOM | 391 | CD2 | LEU | A | 95 | 224.941 | 76.453 | 178.221 | 1.00 | 68.93 | C |
| ATOM | 392 | N | GLN | A | 96 | 222.574 | 73.621 | 174.890 | 1.00 | 60.77 | N |
| ATOM | 393 | CA | GLN | A | 96 | 221.662 | 73.075 | 173.906 | 1.00 | 63.29 | C |
| ATOM | 394 | C | GLN | A | 96 | 220.493 | 74.049 | 173.876 | 1.00 | 63.17 | C |
| ATOM | 395 | O | GLN | A | 96 | 219.998 | 74.481 | 174.915 | 1.00 | 63.30 | O |
| ATOM | 396 | CB | GLN | A | 96 | 221.193 | 71.700 | 174.326 | 1.00 | 70.27 | C |
| ATOM | 397 | N | ASP | A | 97 | 220.056 | 74.415 | 172.686 | 1.00 | 59.87 | N |
| ATOM | 398 | CA | ASP | A | 97 | 218.950 | 75.343 | 172.589 | 1.00 | 58.98 | C |
| ATOM | 399 | C | ASP | A | 97 | 217.669 | 74.640 | 173.022 | 1.00 | 73.48 | C |
| ATOM | 400 | O | ASP | A | 97 | 217.277 | 73.626 | 172.448 | 1.00 | 75.22 | O |
| ATOM | 401 | CB | ASP | A | 97 | 218.831 | 75.843 | 171.157 | 1.00 | 68.14 | C |
| ATOM | 402 | CG | ASP | A | 97 | 217.933 | 77.038 | 171.045 | 1.00 | 73.65 | C |
| ATOM | 403 | OD1 | ASP | A | 97 | 217.516 | 77.567 | 172.096 | 1.00 | 68.14 | O |
| ATOM | 404 | OD2 | ASP | A | 97 | 217.647 | 77.451 | 169.906 | 1.00 | 80.65 | O |
| ATOM | 405 | N | CYS | A | 98 | 217.023 | 75.189 | 174.041 | 1.00 | 67.24 | N |
| ATOM | 406 | CA | CYS | A | 98 | 215.801 | 74.626 | 174.586 | 1.00 | 52.14 | C |
| ATOM | 407 | C | CYS | A | 98 | 215.258 | 75.697 | 175.510 | 1.00 | 75.99 | C |
| ATOM | 408 | O | CYS | A | 98 | 216.018 | 76.483 | 176.068 | 1.00 | 86.44 | O |
| ATOM | 409 | CB | CYS | A | 98 | 216.122 | 73.415 | 175.421 | 1.00 | 52.47 | C |
| ATOM | 410 | SG | CYS | A | 98 | 216.922 | 73.906 | 176.969 | 1.00 | 68.25 | S |
| ATOM | 411 | N | PRO | A | 99 | 213.939 | 75.722 | 175.717 | 1.00 | 81.29 | N |
| ATOM | 412 | CA | PRO | A | 99 | 213.283 | 76.705 | 176.578 | 1.00 | 85.87 | C |
| ATOM | 413 | C | PRO | A | 99 | 213.996 | 77.083 | 177.868 | 1.00 | 82.76 | C |
| ATOM | 414 | O | PRO | A | 99 | 214.153 | 78.268 | 178.149 | 1.00 | 67.85 | O |
| ATOM | 415 | CB | PRO | A | 99 | 211.926 | 76.073 | 176.821 | 1.00 | 94.07 | C |
| ATOM | 416 | CG | PRO | A | 99 | 211.642 | 75.452 | 175.492 | 1.00 | 91.19 | C |

TABLE 1-continued

Coordinates of the activated MAPKAP kinase-2/peptide complex

| ATOM | 417 | CD | PRO | A | 99 | 212.959 | 74.756 | 175.201 | 1.00 | 93.97 | C |
|---|---|---|---|---|---|---|---|---|---|---|---|
| ATOM | 418 | N | LYS | A | 100 | 214.435 | 76.098 | 178.648 | 1.00 | 67.78 | N |
| ATOM | 419 | CA | LYS | A | 100 | 215.100 | 76.408 | 179.912 | 1.00 | 66.60 | C |
| ATOM | 420 | C | LYS | A | 100 | 216.341 | 77.236 | 179.702 | 1.00 | 80.42 | C |
| ATOM | 421 | O | LYS | A | 100 | 216.622 | 78.158 | 180.472 | 1.00 | 69.23 | O |
| ATOM | 422 | CB | LYS | A | 100 | 215.473 | 75.088 | 180.595 | 1.00 | 84.50 | C |
| ATOM | 423 | N | ALA | A | 101 | 217.085 | 76.885 | 178.656 | 1.00 | 76.33 | N |
| ATOM | 424 | CA | ALA | A | 101 | 218.320 | 77.570 | 178.319 | 1.00 | 66.38 | C |
| ATOM | 425 | C | ALA | A | 101 | 218.055 | 79.028 | 177.964 | 1.00 | 67.87 | C |
| ATOM | 426 | O | ALA | A | 101 | 218.639 | 79.922 | 178.563 | 1.00 | 70.18 | O |
| ATOM | 427 | CB | ALA | A | 101 | 219.022 | 76.849 | 177.175 | 1.00 | 55.84 | C |
| ATOM | 428 | N | ARG | A | 102 | 217.163 | 79.277 | 177.014 | 1.00 | 63.42 | N |
| ATOM | 429 | CA | ARG | A | 102 | 216.852 | 80.646 | 176.622 | 1.00 | 64.85 | C |
| ATOM | 430 | C | ARG | A | 102 | 216.409 | 81.491 | 177.812 | 1.00 | 68.04 | C |
| ATOM | 431 | O | ARG | A | 102 | 216.523 | 82.715 | 177.785 | 1.00 | 87.14 | O |
| ATOM | 432 | CB | ARG | A | 102 | 215.764 | 80.665 | 175.541 | 1.00 | 58.29 | C |
| ATOM | 433 | CG | ARG | A | 102 | 216.118 | 79.877 | 174.290 | 1.00 | 87.87 | C |
| ATOM | 434 | CD | ARG | A | 102 | 215.938 | 80.688 | 173.003 | 1.00 | 113.57 | C |
| ATOM | 435 | NE | ARG | A | 102 | 216.532 | 80.000 | 171.853 | 1.00 | 149.75 | N |
| ATOM | 436 | CZ | ARG | A | 102 | 216.645 | 80.517 | 170.626 | 1.00 | 161.97 | C |
| ATOM | 437 | NH1 | ARG | A | 102 | 216.200 | 81.742 | 170.361 | 1.00 | 169.18 | N |
| ATOM | 438 | NH2 | ARG | A | 102 | 217.209 | 79.808 | 169.658 | 1.00 | 123.53 | N |
| ATOM | 439 | N | ARG | A | 103 | 215.900 | 80.848 | 178.856 | 1.00 | 68.81 | N |
| ATOM | 440 | CA | ARG | A | 103 | 215.456 | 81.579 | 180.040 | 1.00 | 80.79 | C |
| ATOM | 441 | C | ARG | A | 103 | 216.664 | 82.065 | 180.812 | 1.00 | 74.21 | C |
| ATOM | 442 | O | ARG | A | 103 | 216.757 | 83.229 | 181.192 | 1.00 | 79.04 | O |
| ATOM | 443 | CB | ARG | A | 103 | 214.620 | 80.684 | 180.943 | 1.00 | 100.01 | C |
| ATOM | 444 | CG | ARG | A | 103 | 214.334 | 81.302 | 182.299 | 1.00 | 140.54 | C |
| ATOM | 445 | CD | ARG | A | 103 | 213.451 | 80.396 | 183.152 | 1.00 | 186.85 | C |
| ATOM | 446 | NE | ARG | A | 103 | 214.159 | 79.246 | 183.721 | 1.00 | 183.90 | N |
| ATOM | 447 | CZ | ARG | A | 103 | 213.851 | 77.974 | 183.469 | 1.00 | 163.96 | C |
| ATOM | 448 | NH1 | ARG | A | 103 | 212.848 | 77.669 | 182.641 | 1.00 | 83.48 | N |
| ATOM | 449 | NH2 | ARG | A | 103 | 214.523 | 77.008 | 184.082 | 1.00 | 172.74 | N |
| ATOM | 450 | N | GLU | A | 104 | 217.584 | 81.143 | 181.047 | 1.00 | 62.81 | N |
| ATOM | 451 | CA | GLU | A | 104 | 218.821 | 81.431 | 181.750 | 1.00 | 74.19 | C |
| ATOM | 452 | C | GLU | A | 104 | 219.481 | 82.643 | 181.094 | 1.00 | 76.22 | C |
| ATOM | 453 | O | GLU | A | 104 | 219.642 | 83.699 | 181.711 | 1.00 | 64.24 | O |
| ATOM | 454 | CB | GLU | A | 104 | 219.722 | 80.210 | 181.633 | 1.00 | 84.57 | C |
| ATOM | 455 | CG | GLU | A | 104 | 221.043 | 80.286 | 182.342 | 1.00 | 113.52 | C |
| ATOM | 456 | CD | GLU | A | 104 | 221.832 | 79.002 | 182.167 | 1.00 | 109.63 | C |
| ATOM | 457 | OE1 | GLU | A | 104 | 222.923 | 78.879 | 182.757 | 1.00 | 143.02 | O |
| ATOM | 458 | OE2 | GLU | A | 104 | 221.358 | 78.112 | 181.430 | 1.00 | 133.75 | O |
| ATOM | 459 | N | VAL | A | 105 | 219.845 | 82.462 | 179.828 | 1.00 | 72.46 | N |
| ATOM | 460 | CA | VAL | A | 105 | 220.488 | 83.485 | 179.010 | 1.00 | 67.75 | C |
| ATOM | 461 | C | VAL | A | 105 | 219.830 | 84.846 | 179.164 | 1.00 | 71.54 | C |
| ATOM | 462 | O | VAL | A | 105 | 220.506 | 85.851 | 179.366 | 1.00 | 75.44 | O |
| ATOM | 463 | CB | VAL | A | 105 | 220.450 | 83.096 | 177.524 | 1.00 | 70.64 | C |
| ATOM | 464 | CG1 | VAL | A | 105 | 221.057 | 84.183 | 176.695 | 1.00 | 60.07 | C |
| ATOM | 465 | CG2 | VAL | A | 105 | 221.196 | 81.796 | 177.312 | 1.00 | 75.62 | C |
| ATOM | 466 | N | GLU | A | 106 | 218.511 | 84.879 | 179.055 | 1.00 | 56.08 | N |
| ATOM | 467 | CA | GLU | A | 106 | 217.795 | 86.126 | 179.198 | 1.00 | 58.27 | C |
| ATOM | 468 | C | GLU | A | 106 | 218.087 | 86.715 | 180.569 | 1.00 | 62.94 | C |
| ATOM | 469 | O | GLU | A | 106 | 218.474 | 87.873 | 180.682 | 1.00 | 69.82 | O |
| ATOM | 470 | CB | GLU | A | 106 | 216.301 | 85.893 | 179.081 | 1.00 | 60.31 | C |
| ATOM | 471 | CG | GLU | A | 106 | 215.588 | 86.837 | 178.156 | 1.00 | 75.77 | C |
| ATOM | 472 | CD | GLU | A | 106 | 215.465 | 86.257 | 176.774 | 1.00 | 90.69 | C |
| ATOM | 473 | OE1 | GLU | A | 106 | 216.490 | 86.211 | 176.072 | 1.00 | 127.18 | O |
| ATOM | 474 | OE2 | GLU | A | 106 | 214.352 | 85.823 | 176.393 | 1.00 | 144.79 | O |
| ATOM | 475 | N | LEU | A | 107 | 217.896 | 85.921 | 181.617 | 1.00 | 59.54 | N |
| ATOM | 476 | CA | LEU | A | 107 | 218.132 | 86.409 | 182.964 | 1.00 | 60.25 | C |
| ATOM | 477 | C | LEU | A | 107 | 219.503 | 87.050 | 183.098 | 1.00 | 79.14 | C |
| ATOM | 478 | O | LEU | A | 107 | 219.649 | 88.148 | 183.623 | 1.00 | 55.44 | O |
| ATOM | 479 | CB | LEU | A | 107 | 218.013 | 85.269 | 183.967 | 1.00 | 82.80 | C |
| ATOM | 480 | CG | LEU | A | 107 | 216.618 | 84.741 | 184.297 | 1.00 | 74.03 | C |
| ATOM | 481 | CD1 | LEU | A | 107 | 216.740 | 83.679 | 185.368 | 1.00 | 68.79 | C |
| ATOM | 482 | CD2 | LEU | A | 107 | 215.731 | 85.866 | 184.783 | 1.00 | 64.45 | C |
| ATOM | 483 | N | HIS | A | 108 | 220.514 | 86.351 | 182.614 | 1.00 | 68.47 | N |
| ATOM | 484 | CA | HIS | A | 108 | 221.875 | 86.840 | 182.691 | 1.00 | 60.51 | C |
| ATOM | 485 | C | HIS | A | 108 | 222.058 | 88.075 | 181.819 | 1.00 | 51.27 | C |
| ATOM | 486 | O | HIS | A | 108 | 222.721 | 89.035 | 182.208 | 1.00 | 70.90 | O |
| ATOM | 487 | CB | HIS | A | 108 | 222.817 | 85.732 | 182.252 | 1.00 | 74.21 | C |
| ATOM | 488 | CG | HIS | A | 108 | 224.261 | 86.055 | 182.447 | 1.00 | 58.20 | C |
| ATOM | 489 | ND1 | HIS | A | 108 | 225.260 | 85.149 | 182.176 | 1.00 | 56.15 | N |
| ATOM | 490 | CD2 | HIS | A | 108 | 224.875 | 87.176 | 182.891 | 1.00 | 56.76 | C |
| ATOM | 491 | CE1 | HIS | A | 108 | 226.429 | 85.699 | 182.446 | 1.00 | 52.10 | C |
| ATOM | 492 | NE2 | HIS | A | 108 | 226.224 | 86.928 | 182.881 | 1.00 | 52.02 | N |
| ATOM | 493 | N | TRP | A | 109 | 221.480 | 88.046 | 180.628 | 1.00 | 57.29 | N |
| ATOM | 494 | CA | TRP | A | 109 | 221.633 | 89.219 | 179.779 | 1.00 | 60.60 | C |

TABLE 1-continued

Coordinates of the activated MAPKAP kinase-2/peptide complex

| ATOM | 495 | C | TRP | A | 109 | 220.952 | 90.440 | 180.401 | 1.00 | 49.86 | C |
|------|-----|----|-----|---|-----|---------|--------|---------|------|-------|---|
| ATOM | 496 | O | TRP | A | 109 | 221.365 | 91.583 | 180.231 | 1.00 | 77.39 | O |
| ATOM | 497 | CB | TRP | A | 109 | 221.000 | 88.905 | 178.423 | 1.00 | 58.21 | C |
| ATOM | 498 | CG | TRP | A | 109 | 220.711 | 90.158 | 177.691 | 1.00 | 62.11 | C |
| ATOM | 499 | CD1 | TRP | A | 109 | 219.493 | 90.874 | 177.686 | 1.00 | 77.34 | C |
| ATOM | 500 | CD2 | TRP | A | 109 | 221.631 | 90.902 | 176.855 | 1.00 | 77.76 | C |
| ATOM | 501 | NE1 | TRP | A | 109 | 219.557 | 92.006 | 176.931 | 1.00 | 78.01 | N |
| ATOM | 502 | CE2 | TRP | A | 109 | 220.933 | 92.041 | 176.375 | 1.00 | 87.90 | C |
| ATOM | 503 | CE3 | TRP | A | 109 | 222.954 | 90.700 | 176.473 | 1.00 | 105.10 | C |
| ATOM | 504 | CZ2 | TRP | A | 109 | 221.572 | 92.943 | 175.540 | 1.00 | 127.04 | C |
| ATOM | 505 | CZ3 | TRP | A | 109 | 223.594 | 91.606 | 175.640 | 1.00 | 107.99 | C |
| ATOM | 506 | CH2 | TRP | A | 109 | 222.895 | 92.731 | 175.167 | 1.00 | 111.87 | C |
| ATOM | 507 | N | ARG | A | 110 | 219.845 | 90.163 | 181.113 | 1.00 | 63.80 | N |
| ATOM | 508 | CA | ARG | A | 110 | 219.102 | 91.243 | 181.753 | 1.00 | 60.39 | C |
| ATOM | 509 | C | ARG | A | 110 | 219.807 | 91.738 | 183.019 | 1.00 | 56.74 | C |
| ATOM | 510 | O | ARG | A | 110 | 219.416 | 92.713 | 183.648 | 1.00 | 72.39 | O |
| ATOM | 511 | CB | ARG | A | 110 | 217.714 | 90.704 | 182.108 | 1.00 | 55.11 | C |
| ATOM | 512 | CG | ARG | A | 110 | 216.630 | 91.781 | 182.038 | 1.00 | 70.18 | C |
| ATOM | 513 | CD | ARG | A | 110 | 215.241 | 91.177 | 181.803 | 1.00 | 129.88 | C |
| ATOM | 514 | NE | ARG | A | 110 | 214.340 | 91.500 | 182.914 | 1.00 | 98.93 | N |
| ATOM | 515 | CZ | ARG | A | 110 | 214.072 | 90.515 | 183.794 | 1.00 | 97.18 | C |
| ATOM | 516 | NH1 | ARG | A | 110 | 213.537 | 90.802 | 184.969 | 1.00 | 106.39 | N |
| ATOM | 517 | NH2 | ARG | A | 110 | 214.325 | 89.245 | 183.464 | 1.00 | 84.21 | N |
| ATOM | 518 | N | ALA | A | 111 | 220.864 | 90.997 | 183.409 | 1.00 | 61.92 | N |
| ATOM | 519 | CA | ALA | A | 111 | 221.578 | 91.358 | 184.628 | 1.00 | 62.44 | C |
| ATOM | 520 | C | ALA | A | 111 | 223.023 | 91.776 | 184.343 | 1.00 | 78.96 | C |
| ATOM | 521 | O | ALA | A | 111 | 223.808 | 92.067 | 185.237 | 1.00 | 57.41 | O |
| ATOM | 522 | CB | ALA | A | 111 | 221.559 | 90.151 | 185.567 | 1.00 | 53.16 | C |
| ATOM | 523 | N | SER | A | 112 | 223.377 | 91.758 | 183.046 | 1.00 | 76.17 | N |
| ATOM | 524 | CA | SER | A | 112 | 224.737 | 92.128 | 182.670 | 1.00 | 71.16 | C |
| ATOM | 525 | C | SER | A | 112 | 224.979 | 93.632 | 182.825 | 1.00 | 64.82 | C |
| ATOM | 526 | O | SER | A | 112 | 226.104 | 94.113 | 182.806 | 1.00 | 63.34 | O |
| ATOM | 527 | CB | SER | A | 112 | 224.963 | 91.711 | 181.216 | 1.00 | 45.39 | C |
| ATOM | 528 | OG | SER | A | 112 | 224.992 | 90.282 | 181.135 | 1.00 | 81.43 | O |
| ATOM | 529 | N | GLN | A | 113 | 223.918 | 94.403 | 182.989 | 1.00 | 73.53 | N |
| ATOM | 530 | CA | GLN | A | 113 | 224.071 | 95.835 | 183.163 | 1.00 | 77.61 | C |
| ATOM | 531 | C | GLN | A | 113 | 224.644 | 96.132 | 184.545 | 1.00 | 70.17 | C |
| ATOM | 532 | O | GLN | A | 113 | 224.884 | 97.280 | 184.884 | 1.00 | 88.91 | O |
| ATOM | 533 | CB | GLN | A | 113 | 222.716 | 96.537 | 183.006 | 1.00 | 79.72 | C |
| ATOM | 534 | CG | GLN | A | 113 | 221.947 | 96.134 | 181.754 | 1.00 | 117.37 | C |
| ATOM | 535 | CD | GLN | A | 113 | 222.616 | 96.582 | 180.448 | 1.00 | 132.38 | C |
| ATOM | 536 | OE1 | GLN | A | 113 | 222.305 | 96.060 | 179.363 | 1.00 | 85.14 | O |
| ATOM | 537 | NE2 | GLN | A | 113 | 223.522 | 97.558 | 180.542 | 1.00 | 73.13 | N |
| ATOM | 538 | N | CYS | A | 114 | 224.854 | 95.098 | 185.348 | 1.00 | 77.28 | N |
| ATOM | 539 | CA | CYS | A | 114 | 225.395 | 95.280 | 186.692 | 1.00 | 65.33 | C |
| ATOM | 540 | C | CYS | A | 114 | 226.896 | 95.029 | 186.750 | 1.00 | 66.81 | C |
| ATOM | 541 | O | CYS | A | 114 | 227.365 | 93.910 | 186.553 | 1.00 | 70.94 | O |
| ATOM | 542 | CB | CYS | A | 114 | 224.699 | 94.346 | 187.679 | 1.00 | 68.99 | C |
| ATOM | 543 | SG | CYS | A | 114 | 225.606 | 94.158 | 189.225 | 1.00 | 70.19 | S |
| ATOM | 544 | N | PRO | A | 115 | 227.665 | 96.073 | 187.058 | 1.00 | 57.36 | N |
| ATOM | 545 | CA | PRO | A | 115 | 229.123 | 96.082 | 187.171 | 1.00 | 46.75 | C |
| ATOM | 546 | C | PRO | A | 115 | 229.770 | 94.790 | 187.650 | 1.00 | 60.90 | C |
| ATOM | 547 | O | PRO | A | 115 | 230.735 | 94.315 | 187.046 | 1.00 | 79.32 | O |
| ATOM | 548 | CB | PRO | A | 115 | 229.382 | 97.226 | 188.140 | 1.00 | 46.54 | C |
| ATOM | 549 | CG | PRO | A | 115 | 228.325 | 98.199 | 187.764 | 1.00 | 65.08 | C |
| ATOM | 550 | CD | PRO | A | 115 | 227.093 | 97.329 | 187.569 | 1.00 | 53.52 | C |
| ATOM | 551 | N | HIS | A | 116 | 229.242 | 94.217 | 188.726 | 1.00 | 50.47 | N |
| ATOM | 552 | CA | HIS | A | 116 | 229.827 | 93.015 | 189.294 | 1.00 | 62.43 | C |
| ATOM | 553 | C | HIS | A | 116 | 229.336 | 91.675 | 188.787 | 1.00 | 62.85 | C |
| ATOM | 554 | O | HIS | A | 116 | 229.654 | 90.634 | 189.366 | 1.00 | 86.03 | O |
| ATOM | 555 | CB | HIS | A | 116 | 229.709 | 93.085 | 190.804 | 1.00 | 66.18 | C |
| ATOM | 556 | CG | HIS | A | 116 | 230.547 | 94.163 | 191.405 | 1.00 | 74.19 | C |
| ATOM | 557 | ND1 | HIS | A | 116 | 231.923 | 94.104 | 191.422 | 1.00 | 58.68 | N |
| ATOM | 558 | CD2 | HIS | A | 116 | 230.214 | 95.360 | 191.945 | 1.00 | 50.93 | C |
| ATOM | 559 | CE1 | HIS | A | 116 | 232.404 | 95.220 | 191.945 | 1.00 | 106.08 | C |
| ATOM | 560 | NE2 | HIS | A | 116 | 231.386 | 95.999 | 192.269 | 1.00 | 97.40 | N |
| ATOM | 561 | N | ILE | A | 117 | 228.574 | 91.693 | 187.703 | 1.00 | 58.07 | N |
| ATOM | 562 | CA | ILE | A | 117 | 228.075 | 90.472 | 187.097 | 1.00 | 51.42 | C |
| ATOM | 563 | C | ILE | A | 117 | 228.790 | 90.375 | 185.769 | 1.00 | 57.68 | C |
| ATOM | 564 | O | ILE | A | 117 | 228.912 | 91.381 | 185.056 | 1.00 | 72.95 | O |
| ATOM | 565 | CB | ILE | A | 117 | 226.586 | 90.572 | 186.848 | 1.00 | 60.05 | C |
| ATOM | 566 | CG1 | ILE | A | 117 | 225.867 | 90.676 | 188.193 | 1.00 | 65.42 | C |
| ATOM | 567 | CG2 | ILE | A | 117 | 226.111 | 89.371 | 186.050 | 1.00 | 56.83 | C |
| ATOM | 568 | CD1 | ILE | A | 117 | 224.420 | 91.064 | 188.100 | 1.00 | 76.80 | C |
| ATOM | 569 | N | VAL | A | 118 | 229.275 | 89.188 | 185.427 | 1.00 | 60.67 | N |
| ATOM | 570 | CA | VAL | A | 118 | 229.979 | 89.028 | 184.160 | 1.00 | 56.50 | C |
| ATOM | 571 | C | VAL | A | 118 | 229.008 | 89.416 | 183.044 | 1.00 | 62.86 | C |
| ATOM | 572 | O | VAL | A | 118 | 227.844 | 89.008 | 183.071 | 1.00 | 61.80 | O |

TABLE 1-continued

Coordinates of the activated MAPKAP kinase-2/peptide complex

| ATOM | 573 | CB  | VAL | A | 118 | 230.469 | 87.583 | 183.975 | 1.00 | 59.65  | C |
|------|-----|-----|-----|---|-----|---------|--------|---------|------|--------|---|
| ATOM | 574 | CG1 | VAL | A | 118 | 229.288 | 86.642 | 183.812 | 1.00 | 58.62  | C |
| ATOM | 575 | CG2 | VAL | A | 118 | 231.389 | 87.503 | 182.776 | 1.00 | 72.68  | C |
| ATOM | 576 | N   | ARG | A | 119 | 229.483 | 90.204 | 182.075 | 1.00 | 59.87  | N |
| ATOM | 577 | CA  | ARG | A | 119 | 228.635 | 90.694 | 180.988 | 1.00 | 63.38  | C |
| ATOM | 578 | C   | ARG | A | 119 | 228.551 | 89.821 | 179.763 | 1.00 | 57.05  | C |
| ATOM | 579 | O   | ARG | A | 119 | 229.546 | 89.276 | 179.314 | 1.00 | 63.34  | O |
| ATOM | 580 | CB  | ARG | A | 119 | 229.083 | 92.079 | 180.566 | 1.00 | 37.88  | C |
| ATOM | 581 | N   | ILE | A | 120 | 227.348 | 89.698 | 179.217 | 1.00 | 52.84  | N |
| ATOM | 582 | CA  | ILE | A | 120 | 227.135 | 88.928 | 178.002 | 1.00 | 55.21  | C |
| ATOM | 583 | C   | ILE | A | 120 | 227.227 | 89.914 | 176.847 | 1.00 | 56.02  | C |
| ATOM | 584 | O   | ILE | A | 120 | 226.375 | 90.801 | 176.719 | 1.00 | 61.19  | O |
| ATOM | 585 | CB  | ILE | A | 120 | 225.742 | 88.298 | 177.985 | 1.00 | 63.39  | C |
| ATOM | 586 | CG1 | ILE | A | 120 | 225.707 | 87.100 | 178.931 | 1.00 | 59.03  | C |
| ATOM | 587 | CG2 | ILE | A | 120 | 225.368 | 87.898 | 176.570 | 1.00 | 45.00  | C |
| ATOM | 588 | CD1 | ILE | A | 120 | 224.390 | 86.384 | 178.896 | 1.00 | 71.76  | C |
| ATOM | 589 | N   | VAL | A | 121 | 228.259 | 89.766 | 176.013 | 1.00 | 69.54  | N |
| ATOM | 590 | CA  | VAL | A | 121 | 228.440 | 90.647 | 174.863 | 1.00 | 53.54  | C |
| ATOM | 591 | C   | VAL | A | 121 | 227.432 | 90.354 | 173.743 | 1.00 | 53.36  | C |
| ATOM | 592 | O   | VAL | A | 121 | 226.823 | 91.254 | 173.173 | 1.00 | 67.91  | O |
| ATOM | 593 | CB  | VAL | A | 121 | 229.875 | 90.482 | 174.354 | 1.00 | 52.53  | C |
| ATOM | 594 | CG1 | VAL | A | 121 | 230.153 | 91.471 | 173.224 | 1.00 | 91.60  | C |
| ATOM | 595 | CG2 | VAL | A | 121 | 230.854 | 90.737 | 175.486 | 1.00 | 71.15  | C |
| ATOM | 596 | N   | ASP | A | 122 | 227.299 | 89.060 | 173.389 | 1.00 | 45.30  | N |
| ATOM | 597 | CA  | ASP | A | 122 | 226.149 | 88.676 | 172.567 | 1.00 | 76.20  | C |
| ATOM | 598 | C   | ASP | A | 122 | 225.984 | 87.152 | 172.459 | 1.00 | 52.20  | C |
| ATOM | 599 | O   | ASP | A | 122 | 226.852 | 86.378 | 172.842 | 1.00 | 62.83  | O |
| ATOM | 600 | CB  | ASP | A | 122 | 226.337 | 89.280 | 171.173 | 1.00 | 81.39  | C |
| ATOM | 601 | CG  | ASP | A | 122 | 227.687 | 88.850 | 170.615 | 1.00 | 72.92  | C |
| ATOM | 602 | OD1 | ASP | A | 122 | 228.224 | 87.860 | 171.115 | 1.00 | 121.42 | O |
| ATOM | 603 | OD2 | ASP | A | 122 | 228.183 | 89.500 | 169.698 | 1.00 | 55.20  | O |
| ATOM | 604 | N   | VAL | A | 123 | 224.777 | 86.769 | 171.999 | 1.00 | 50.00  | N |
| ATOM | 605 | CA  | VAL | A | 123 | 224.398 | 85.361 | 171.982 | 1.00 | 55.40  | C |
| ATOM | 606 | C   | VAL | A | 123 | 223.988 | 84.917 | 170.574 | 1.00 | 50.66  | C |
| ATOM | 607 | O   | VAL | A | 123 | 223.350 | 85.650 | 169.830 | 1.00 | 50.76  | O |
| ATOM | 608 | CB  | VAL | A | 123 | 223.215 | 85.196 | 172.943 | 1.00 | 45.71  | C |
| ATOM | 609 | CG1 | VAL | A | 123 | 222.819 | 83.726 | 173.058 | 1.00 | 66.35  | C |
| ATOM | 610 | CG2 | VAL | A | 123 | 223.581 | 85.730 | 174.316 | 1.00 | 57.34  | C |
| ATOM | 611 | N   | TYR | A | 124 | 224.384 | 83.682 | 170.271 | 1.00 | 54.76  | N |
| ATOM | 612 | CA  | TYR | A | 124 | 224.108 | 83.092 | 168.964 | 1.00 | 59.15  | C |
| ATOM | 613 | C   | TYR | A | 124 | 223.286 | 81.813 | 169.047 | 1.00 | 61.11  | C |
| ATOM | 614 | O   | TYR | A | 124 | 223.356 | 81.063 | 170.021 | 1.00 | 77.18  | O |
| ATOM | 615 | CB  | TYR | A | 124 | 225.412 | 82.768 | 168.216 | 1.00 | 54.42  | C |
| ATOM | 616 | CG  | TYR | A | 124 | 226.292 | 83.973 | 167.929 | 1.00 | 64.97  | C |
| ATOM | 617 | CD1 | TYR | A | 124 | 227.031 | 84.574 | 168.941 | 1.00 | 36.17  | C |
| ATOM | 618 | CD2 | TYR | A | 124 | 226.352 | 84.532 | 166.649 | 1.00 | 68.56  | C |
| ATOM | 619 | CE1 | TYR | A | 124 | 227.793 | 85.681 | 168.700 | 1.00 | 56.00  | C |
| ATOM | 620 | CE2 | TYR | A | 124 | 227.117 | 85.653 | 166.393 | 1.00 | 49.47  | C |
| ATOM | 621 | CZ  | TYR | A | 124 | 227.835 | 86.220 | 167.428 | 1.00 | 51.06  | C |
| ATOM | 622 | OH  | TYR | A | 124 | 228.608 | 87.330 | 167.202 | 1.00 | 71.62  | O |
| ATOM | 623 | N   | GLU | A | 125 | 222.497 | 81.576 | 168.010 | 1.00 | 65.81  | N |
| ATOM | 624 | CA  | GLU | A | 125 | 221.697 | 80.374 | 167.910 | 1.00 | 49.40  | C |
| ATOM | 625 | C   | GLU | A | 125 | 222.164 | 79.747 | 166.601 | 1.00 | 50.33  | C |
| ATOM | 626 | O   | GLU | A | 125 | 221.610 | 80.007 | 165.535 | 1.00 | 63.99  | O |
| ATOM | 627 | CB  | GLU | A | 125 | 220.210 | 80.728 | 167.851 | 1.00 | 56.44  | C |
| ATOM | 628 | CG  | GLU | A | 125 | 219.285 | 79.525 | 167.952 | 1.00 | 64.02  | C |
| ATOM | 629 | CD  | GLU | A | 125 | 218.600 | 79.176 | 166.637 | 1.00 | 103.79 | C |
| ATOM | 630 | OE1 | GLU | A | 125 | 217.665 | 79.900 | 166.223 | 1.00 | 113.21 | O |
| ATOM | 631 | OE2 | GLU | A | 125 | 219.002 | 78.172 | 166.009 | 1.00 | 118.03 | O |
| ATOM | 632 | N   | ASN | A | 126 | 223.217 | 78.948 | 166.675 | 1.00 | 57.09  | N |
| ATOM | 633 | CA  | ASN | A | 126 | 223.752 | 78.304 | 165.480 | 1.00 | 63.39  | C |
| ATOM | 634 | C   | ASN | A | 126 | 223.370 | 76.842 | 165.453 | 1.00 | 68.35  | C |
| ATOM | 635 | O   | ASN | A | 126 | 222.770 | 76.334 | 166.393 | 1.00 | 78.79  | O |
| ATOM | 636 | CB  | ASN | A | 126 | 225.271 | 78.413 | 165.451 | 1.00 | 53.33  | C |
| ATOM | 637 | CG  | ASN | A | 126 | 225.738 | 79.824 | 165.237 | 1.00 | 50.86  | C |
| ATOM | 638 | OD1 | ASN | A | 126 | 226.934 | 80.105 | 165.254 | 1.00 | 53.47  | O |
| ATOM | 639 | ND2 | ASN | A | 126 | 224.786 | 80.732 | 165.026 | 1.00 | 57.45  | N |
| ATOM | 640 | N   | LEU | A | 127 | 223.729 | 76.167 | 164.370 | 1.00 | 72.36  | N |
| ATOM | 641 | CA  | LEU | A | 127 | 223.431 | 74.753 | 164.222 | 1.00 | 56.01  | C |
| ATOM | 642 | C   | LEU | A | 127 | 224.712 | 73.983 | 164.467 | 1.00 | 63.01  | C |
| ATOM | 643 | O   | LEU | A | 127 | 225.637 | 74.025 | 163.663 | 1.00 | 79.72  | O |
| ATOM | 644 | CB  | LEU | A | 127 | 222.926 | 74.467 | 162.817 | 1.00 | 57.56  | C |
| ATOM | 645 | CG  | LEU | A | 127 | 221.810 | 73.443 | 162.741 | 1.00 | 56.21  | C |
| ATOM | 646 | CD1 | LEU | A | 127 | 220.660 | 73.944 | 163.564 | 1.00 | 63.97  | C |
| ATOM | 647 | CD2 | LEU | A | 127 | 221.386 | 73.235 | 161.311 | 1.00 | 50.73  | C |
| ATOM | 648 | N   | TYR | A | 128 | 224.768 | 73.281 | 165.588 | 1.00 | 85.19  | N |
| ATOM | 649 | CA  | TYR | A | 128 | 225.949 | 72.511 | 165.932 | 1.00 | 78.91  | C |
| ATOM | 650 | C   | TYR | A | 128 | 225.657 | 71.015 | 166.036 | 1.00 | 99.93  | C |

TABLE 1-continued

Coordinates of the activated MAPKAP kinase-2/peptide complex

| ATOM | 651 | O   | TYR | A | 128 | 224.960 | 70.571 | 166.956 | 1.00 | 83.06  | O |
|------|-----|-----|-----|---|-----|---------|--------|---------|------|--------|---|
| ATOM | 652 | CB  | TYR | A | 128 | 226.513 | 72.996 | 167.259 | 1.00 | 73.34  | C |
| ATOM | 653 | CG  | TYR | A | 128 | 227.849 | 72.396 | 167.562 | 1.00 | 113.80 | C |
| ATOM | 654 | CD1 | TYR | A | 128 | 229.000 | 72.939 | 167.024 | 1.00 | 118.71 | C |
| ATOM | 655 | CD2 | TYR | A | 128 | 227.959 | 71.253 | 168.341 | 1.00 | 128.83 | C |
| ATOM | 656 | CE1 | TYR | A | 128 | 230.223 | 72.372 | 167.247 | 1.00 | 148.93 | C |
| ATOM | 657 | CE2 | TYR | A | 128 | 229.183 | 70.667 | 168.569 | 1.00 | 160.37 | C |
| ATOM | 658 | CZ  | TYR | A | 128 | 230.316 | 71.239 | 168.018 | 1.00 | 162.93 | C |
| ATOM | 659 | OH  | TYR | A | 128 | 231.559 | 70.688 | 168.244 | 1.00 | 162.00 | O |
| ATOM | 660 | N   | ALA | A | 129 | 226.204 | 70.240 | 165.098 | 1.00 | 112.77 | N |
| ATOM | 661 | CA  | ALA | A | 129 | 226.016 | 68.788 | 165.077 | 1.00 | 119.60 | C |
| ATOM | 662 | C   | ALA | A | 129 | 224.556 | 68.445 | 164.843 | 1.00 | 117.04 | C |
| ATOM | 663 | O   | ALA | A | 129 | 223.981 | 67.637 | 165.575 | 1.00 | 102.48 | O |
| ATOM | 664 | CB  | ALA | A | 129 | 226.482 | 68.181 | 166.398 | 1.00 | 105.12 | C |
| ATOM | 665 | N   | GLY | A | 130 | 223.957 | 69.056 | 163.823 | 1.00 | 115.24 | N |
| ATOM | 666 | CA  | GLY | A | 130 | 222.550 | 68.810 | 163.553 | 1.00 | 115.49 | C |
| ATOM | 667 | C   | GLY | A | 130 | 221.728 | 69.250 | 164.756 | 1.00 | 107.44 | C |
| ATOM | 668 | O   | GLY | A | 130 | 220.501 | 69.259 | 164.722 | 1.00 | 95.78  | O |
| ATOM | 669 | N   | ARG | A | 131 | 222.425 | 69.616 | 165.828 | 1.00 | 89.82  | N |
| ATOM | 670 | CA  | ARG | A | 131 | 221.791 | 70.067 | 167.055 | 1.00 | 92.75  | C |
| ATOM | 671 | C   | ARG | A | 131 | 221.754 | 71.593 | 167.105 | 1.00 | 80.22  | C |
| ATOM | 672 | O   | ARG | A | 131 | 222.756 | 72.265 | 166.892 | 1.00 | 63.19  | O |
| ATOM | 673 | CB  | ARG | A | 131 | 222.546 | 69.516 | 168.271 | 1.00 | 79.11  | C |
| ATOM | 674 | N   | LYS | A | 132 | 220.574 | 72.121 | 167.381 | 1.00 | 68.38  | N |
| ATOM | 675 | CA  | LYS | A | 132 | 220.349 | 73.553 | 167.487 | 1.00 | 64.95  | C |
| ATOM | 676 | C   | LYS | A | 132 | 220.944 | 74.013 | 168.828 | 1.00 | 56.62  | C |
| ATOM | 677 | O   | LYS | A | 132 | 220.449 | 73.648 | 169.889 | 1.00 | 63.01  | O |
| ATOM | 678 | CB  | LYS | A | 132 | 218.839 | 73.782 | 167.429 | 1.00 | 50.70  | C |
| ATOM | 679 | CG  | LYS | A | 132 | 218.340 | 75.188 | 167.516 | 1.00 | 60.30  | C |
| ATOM | 680 | CD  | LYS | A | 132 | 216.821 | 75.123 | 167.476 | 1.00 | 72.13  | C |
| ATOM | 681 | CE  | LYS | A | 132 | 216.171 | 76.486 | 167.371 | 1.00 | 106.61 | C |
| ATOM | 682 | NZ  | LYS | A | 132 | 214.692 | 76.354 | 167.313 | 1.00 | 65.96  | N |
| ATOM | 683 | N   | CYS | A | 133 | 222.011 | 74.805 | 168.787 | 1.00 | 77.15  | N |
| ATOM | 684 | CA  | CYS | A | 133 | 222.648 | 75.263 | 170.022 | 1.00 | 74.16  | C |
| ATOM | 685 | C   | CYS | A | 133 | 222.555 | 76.745 | 170.320 | 1.00 | 65.05  | C |
| ATOM | 686 | O   | CYS | A | 133 | 222.157 | 77.543 | 169.471 | 1.00 | 81.10  | O |
| ATOM | 687 | CB  | CYS | A | 133 | 224.114 | 74.877 | 170.024 | 1.00 | 92.23  | C |
| ATOM | 688 | SG  | CYS | A | 133 | 224.343 | 73.126 | 169.850 | 1.00 | 106.91 | S |
| ATOM | 689 | N   | LEU | A | 134 | 222.947 | 77.099 | 171.540 | 1.00 | 67.21  | N |
| ATOM | 690 | CA  | LEU | A | 134 | 222.921 | 78.478 | 171.986 | 1.00 | 67.45  | C |
| ATOM | 691 | C   | LEU | A | 134 | 224.326 | 78.865 | 172.431 | 1.00 | 63.74  | C |
| ATOM | 692 | O   | LEU | A | 134 | 224.804 | 78.446 | 173.488 | 1.00 | 71.31  | O |
| ATOM | 693 | CB  | LEU | A | 134 | 221.953 | 78.634 | 173.152 | 1.00 | 51.96  | C |
| ATOM | 694 | CG  | LEU | A | 134 | 221.107 | 79.902 | 173.189 | 1.00 | 72.36  | C |
| ATOM | 695 | CD1 | LEU | A | 134 | 220.129 | 79.885 | 172.025 | 1.00 | 66.47  | C |
| ATOM | 696 | CD2 | LEU | A | 134 | 220.342 | 79.981 | 174.503 | 1.00 | 63.46  | C |
| ATOM | 697 | N   | LEU | A | 135 | 224.992 | 79.663 | 171.608 | 1.00 | 69.76  | N |
| ATOM | 698 | CA  | LEU | A | 135 | 226.338 | 80.103 | 171.910 | 1.00 | 48.46  | C |
| ATOM | 699 | C   | LEU | A | 135 | 226.262 | 81.450 | 172.608 | 1.00 | 60.20  | C |
| ATOM | 700 | O   | LEU | A | 135 | 225.639 | 82.381 | 172.101 | 1.00 | 49.35  | O |
| ATOM | 701 | CB  | LEU | A | 135 | 227.130 | 80.192 | 170.609 | 1.00 | 69.61  | C |
| ATOM | 702 | CG  | LEU | A | 135 | 227.191 | 78.851 | 169.873 | 1.00 | 59.09  | C |
| ATOM | 703 | CD1 | LEU | A | 135 | 227.585 | 79.058 | 168.425 | 1.00 | 80.07  | C |
| ATOM | 704 | CD2 | LEU | A | 135 | 228.173 | 77.943 | 170.579 | 1.00 | 92.22  | C |
| ATOM | 705 | N   | ILE | A | 136 | 226.896 | 81.530 | 173.775 | 1.00 | 39.79  | N |
| ATOM | 706 | CA  | ILE | A | 136 | 226.913 | 82.744 | 174.581 | 1.00 | 48.18  | C |
| ATOM | 707 | C   | ILE | A | 136 | 228.321 | 83.324 | 174.691 | 1.00 | 54.20  | C |
| ATOM | 708 | O   | ILE | A | 136 | 229.219 | 82.672 | 175.204 | 1.00 | 63.12  | O |
| ATOM | 709 | CB  | ILE | A | 136 | 226.398 | 82.453 | 176.006 | 1.00 | 57.17  | C |
| ATOM | 710 | CG1 | ILE | A | 136 | 224.997 | 81.864 | 175.934 | 1.00 | 54.12  | C |
| ATOM | 711 | CG2 | ILE | A | 136 | 226.364 | 83.720 | 176.829 | 1.00 | 45.37  | C |
| ATOM | 712 | CD1 | ILE | A | 136 | 224.893 | 80.475 | 176.545 | 1.00 | 94.13  | C |
| ATOM | 713 | N   | VAL | A | 137 | 228.527 | 84.539 | 174.200 | 1.00 | 47.11  | N |
| ATOM | 714 | CA  | VAL | A | 137 | 229.812 | 85.185 | 174.376 | 1.00 | 51.92  | C |
| ATOM | 715 | C   | VAL | A | 137 | 229.827 | 86.081 | 175.615 | 1.00 | 62.30  | C |
| ATOM | 716 | O   | VAL | A | 137 | 228.925 | 86.871 | 175.875 | 1.00 | 65.38  | O |
| ATOM | 717 | CB  | VAL | A | 137 | 230.091 | 85.979 | 173.099 | 1.00 | 55.29  | C |
| ATOM | 718 | CG1 | VAL | A | 137 | 231.461 | 86.640 | 173.162 | 1.00 | 49.20  | C |
| ATOM | 719 | CG2 | VAL | A | 137 | 230.064 | 85.035 | 171.910 | 1.00 | 33.49  | C |
| ATOM | 720 | N   | MET | A | 138 | 230.893 | 85.889 | 176.417 | 1.00 | 63.64  | N |
| ATOM | 721 | CA  | MET | A | 138 | 231.026 | 86.598 | 177.685 | 1.00 | 47.48  | C |
| ATOM | 722 | C   | MET | A | 138 | 232.339 | 87.381 | 177.769 | 1.00 | 63.41  | C |
| ATOM | 723 | O   | MET | A | 138 | 233.371 | 86.975 | 177.246 | 1.00 | 60.31  | O |
| ATOM | 724 | CB  | MET | A | 138 | 231.044 | 85.548 | 178.796 | 1.00 | 76.63  | C |
| ATOM | 725 | CG  | MET | A | 138 | 229.707 | 84.836 | 178.965 | 1.00 | 72.52  | C |
| ATOM | 726 | SD  | MET | A | 138 | 229.779 | 83.570 | 180.236 | 1.00 | 81.89  | S |
| ATOM | 727 | CE  | MET | A | 138 | 228.109 | 82.937 | 180.029 | 1.00 | 180.26 | C |
| ATOM | 728 | N   | GLU | A | 139 | 232.281 | 88.555 | 178.427 | 1.00 | 44.14  | N |

TABLE 1-continued

Coordinates of the activated MAPKAP kinase-2/peptide complex

| ATOM | 729 | CA | GLU | A | 139 | 233.550 | 89.154 | 178.798 | 1.00 | 46.81 | C |
|---|---|---|---|---|---|---|---|---|---|---|---|
| ATOM | 730 | C | GLU | A | 139 | 234.381 | 88.099 | 179.511 | 1.00 | 61.98 | C |
| ATOM | 731 | O | GLU | A | 139 | 233.876 | 87.285 | 180.272 | 1.00 | 68.61 | O |
| ATOM | 732 | CB | GLU | A | 139 | 233.291 | 90.346 | 179.732 | 1.00 | 40.20 | C |
| ATOM | 733 | CG | GLU | A | 139 | 233.444 | 89.999 | 181.216 | 1.00 | 70.67 | C |
| ATOM | 734 | CD | GLU | A | 139 | 233.140 | 91.231 | 182.059 | 1.00 | 76.30 | C |
| ATOM | 735 | OE1 | GLU | A | 139 | 231.972 | 91.501 | 182.306 | 1.00 | 89.15 | O |
| ATOM | 736 | OE2 | GLU | A | 139 | 234.079 | 91.912 | 182.459 | 1.00 | 100.67 | O |
| ATOM | 737 | N | CYS | A | 140 | 235.664 | 88.142 | 179.172 | 1.00 | 69.16 | N |
| ATOM | 738 | CA | CYS | A | 140 | 236.625 | 87.167 | 179.666 | 1.00 | 69.69 | C |
| ATOM | 739 | C | CYS | A | 140 | 237.322 | 87.529 | 180.968 | 1.00 | 60.14 | C |
| ATOM | 740 | O | CYS | A | 140 | 238.227 | 88.349 | 180.990 | 1.00 | 82.48 | O |
| ATOM | 741 | CB | CYS | A | 140 | 237.676 | 86.903 | 178.587 | 1.00 | 74.24 | C |
| ATOM | 742 | SG | CYS | A | 140 | 238.996 | 85.811 | 179.117 | 1.00 | 73.10 | S |
| ATOM | 743 | N | LEU | A | 141 | 236.912 | 86.895 | 182.055 | 1.00 | 71.80 | N |
| ATOM | 744 | CA | LEU | A | 141 | 237.524 | 87.159 | 183.348 | 1.00 | 79.00 | C |
| ATOM | 745 | C | LEU | A | 141 | 238.785 | 86.304 | 183.509 | 1.00 | 76.59 | C |
| ATOM | 746 | O | LEU | A | 141 | 238.736 | 85.081 | 183.360 | 1.00 | 77.59 | O |
| ATOM | 747 | CB | LEU | A | 141 | 236.523 | 86.847 | 184.462 | 1.00 | 81.97 | C |
| ATOM | 748 | CG | LEU | A | 141 | 235.203 | 87.610 | 184.350 | 1.00 | 76.77 | C |
| ATOM | 749 | CD1 | LEU | A | 141 | 234.214 | 87.100 | 185.382 | 1.00 | 96.50 | C |
| ATOM | 750 | CD2 | LEU | A | 141 | 235.469 | 89.086 | 184.535 | 1.00 | 47.85 | C |
| ATOM | 751 | N | ASP | A | 142 | 239.913 | 86.940 | 183.818 | 1.00 | 90.64 | N |
| ATOM | 752 | CA | ASP | A | 142 | 241.158 | 86.197 | 183.977 | 1.00 | 92.77 | C |
| ATOM | 753 | C | ASP | A | 142 | 241.771 | 86.152 | 185.366 | 1.00 | 84.21 | C |
| ATOM | 754 | O | ASP | A | 142 | 242.387 | 85.153 | 185.725 | 1.00 | 120.09 | O |
| ATOM | 755 | CB | ASP | A | 142 | 242.202 | 86.698 | 182.984 | 1.00 | 92.82 | C |
| ATOM | 756 | CG | ASP | A | 142 | 241.951 | 86.182 | 181.586 | 1.00 | 110.94 | C |
| ATOM | 757 | OD1 | ASP | A | 142 | 241.710 | 84.961 | 181.450 | 1.00 | 82.18 | O |
| ATOM | 758 | OD2 | ASP | A | 142 | 242.003 | 86.987 | 180.632 | 1.00 | 115.53 | O |
| ATOM | 759 | N | GLY | A | 143 | 241.616 | 87.220 | 186.142 | 1.00 | 76.67 | N |
| ATOM | 760 | CA | GLY | A | 143 | 242.178 | 87.249 | 187.486 | 1.00 | 84.99 | C |
| ATOM | 761 | C | GLY | A | 143 | 242.128 | 85.940 | 188.269 | 1.00 | 83.56 | C |
| ATOM | 762 | O | GLY | A | 143 | 242.909 | 85.744 | 189.194 | 1.00 | 94.38 | O |
| ATOM | 763 | N | GLY | A | 144 | 241.216 | 85.040 | 187.913 | 1.00 | 81.49 | N |
| ATOM | 764 | CA | GLY | A | 144 | 241.132 | 83.778 | 188.621 | 1.00 | 72.81 | C |
| ATOM | 765 | C | GLY | A | 144 | 240.064 | 83.784 | 189.700 | 1.00 | 88.08 | C |
| ATOM | 766 | O | GLY | A | 144 | 239.527 | 84.839 | 190.045 | 1.00 | 76.11 | O |
| ATOM | 767 | N | GLU | A | 145 | 239.759 | 82.603 | 190.235 | 1.00 | 72.60 | N |
| ATOM | 768 | CA | GLU | A | 145 | 238.746 | 82.464 | 191.268 | 1.00 | 80.92 | C |
| ATOM | 769 | C | GLU | A | 145 | 239.050 | 83.249 | 192.539 | 1.00 | 85.24 | C |
| ATOM | 770 | O | GLU | A | 145 | 240.206 | 83.446 | 192.908 | 1.00 | 76.66 | O |
| ATOM | 771 | CB | GLU | A | 145 | 238.543 | 80.993 | 191.605 | 1.00 | 61.62 | C |
| ATOM | 772 | CG | GLU | A | 145 | 237.797 | 80.215 | 190.539 | 1.00 | 89.57 | C |
| ATOM | 773 | CD | GLU | A | 145 | 238.090 | 78.727 | 190.618 | 1.00 | 126.57 | C |
| ATOM | 774 | OE1 | GLU | A | 145 | 237.257 | 77.922 | 190.143 | 1.00 | 97.67 | O |
| ATOM | 775 | OE2 | GLU | A | 145 | 239.165 | 78.367 | 191.156 | 1.00 | 103.63 | O |
| ATOM | 776 | N | LEU | A | 146 | 237.988 | 83.679 | 193.210 | 1.00 | 97.07 | N |
| ATOM | 777 | CA | LEU | A | 146 | 238.095 | 84.479 | 194.419 | 1.00 | 86.04 | C |
| ATOM | 778 | C | LEU | A | 146 | 239.174 | 84.065 | 195.402 | 1.00 | 75.32 | C |
| ATOM | 779 | O | LEU | A | 146 | 240.049 | 84.852 | 195.732 | 1.00 | 72.90 | O |
| ATOM | 780 | CB | LEU | A | 146 | 236.743 | 84.530 | 195.138 | 1.00 | 83.71 | C |
| ATOM | 781 | CG | LEU | A | 146 | 236.768 | 85.402 | 196.395 | 1.00 | 84.94 | C |
| ATOM | 782 | CD1 | LEU | A | 146 | 237.338 | 86.754 | 196.044 | 1.00 | 92.90 | C |
| ATOM | 783 | CD2 | LEU | A | 146 | 235.382 | 85.551 | 196.975 | 1.00 | 116.24 | C |
| ATOM | 784 | N | PHE | A | 147 | 239.127 | 82.829 | 195.867 | 1.00 | 80.55 | N |
| ATOM | 785 | CA | PHE | A | 147 | 240.104 | 82.385 | 196.847 | 1.00 | 87.51 | C |
| ATOM | 786 | C | PHE | A | 147 | 241.526 | 82.244 | 196.332 | 1.00 | 92.39 | C |
| ATOM | 787 | O | PHE | A | 147 | 242.478 | 82.546 | 197.051 | 1.00 | 104.70 | O |
| ATOM | 788 | CB | PHE | A | 147 | 239.611 | 81.094 | 197.495 | 1.00 | 62.88 | C |
| ATOM | 789 | CG | PHE | A | 147 | 238.388 | 81.297 | 198.330 | 1.00 | 83.58 | C |
| ATOM | 790 | CD1 | PHE | A | 147 | 237.514 | 80.260 | 198.589 | 1.00 | 80.71 | C |
| ATOM | 791 | CD2 | PHE | A | 147 | 238.102 | 82.557 | 198.845 | 1.00 | 82.88 | C |
| ATOM | 792 | CE1 | PHE | A | 147 | 236.375 | 80.476 | 199.342 | 1.00 | 93.95 | C |
| ATOM | 793 | CE2 | PHE | A | 147 | 236.971 | 82.778 | 199.596 | 1.00 | 50.19 | C |
| ATOM | 794 | CZ | PHE | A | 147 | 236.105 | 81.740 | 199.844 | 1.00 | 97.28 | C |
| ATOM | 795 | N | SER | A | 148 | 241.680 | 81.805 | 195.090 | 1.00 | 81.24 | N |
| ATOM | 796 | CA | SER | A | 148 | 243.008 | 81.657 | 194.525 | 1.00 | 74.75 | C |
| ATOM | 797 | C | SER | A | 148 | 243.758 | 82.970 | 194.714 | 1.00 | 83.42 | C |
| ATOM | 798 | O | SER | A | 148 | 244.679 | 83.053 | 195.529 | 1.00 | 88.34 | O |
| ATOM | 799 | CB | SER | A | 148 | 242.902 | 81.301 | 193.051 | 1.00 | 76.50 | C |
| ATOM | 800 | OG | SER | A | 148 | 242.158 | 80.106 | 192.902 | 1.00 | 74.94 | O |
| ATOM | 801 | N | ARG | A | 149 | 243.347 | 83.999 | 193.978 | 1.00 | 81.76 | N |
| ATOM | 802 | CA | ARG | A | 149 | 243.974 | 85.316 | 194.077 | 1.00 | 102.63 | C |
| ATOM | 803 | C | ARG | A | 149 | 244.325 | 85.650 | 195.512 | 1.00 | 107.57 | C |
| ATOM | 804 | O | ARG | A | 149 | 245.399 | 86.169 | 195.796 | 1.00 | 115.11 | O |
| ATOM | 805 | CB | ARG | A | 149 | 243.038 | 86.396 | 193.537 | 1.00 | 92.17 | C |
| ATOM | 806 | CG | ARG | A | 149 | 242.950 | 86.427 | 192.033 | 1.00 | 96.27 | C |

TABLE 1-continued

Coordinates of the activated MAPKAP kinase-2/peptide complex

| ATOM | 807 | CD | ARG | A | 149 | 244.278 | 86.851 | 191.433 | 1.00 | 127.89 | C |
|---|---|---|---|---|---|---|---|---|---|---|---|
| ATOM | 808 | NE | ARG | A | 149 | 244.141 | 88.079 | 190.656 | 1.00 | 105.03 | N |
| ATOM | 809 | CZ | ARG | A | 149 | 243.698 | 89.227 | 191.155 | 1.00 | 106.80 | C |
| ATOM | 810 | NH1 | ARG | A | 149 | 243.350 | 89.307 | 192.434 | 1.00 | 91.41 | N |
| ATOM | 811 | NH2 | ARG | A | 149 | 243.597 | 90.293 | 190.377 | 1.00 | 81.30 | N |
| ATOM | 812 | N | ILE | A | 150 | 243.410 | 85.352 | 196.423 | 1.00 | 117.64 | N |
| ATOM | 813 | CA | ILE | A | 150 | 243.658 | 85.636 | 197.821 | 1.00 | 111.89 | C |
| ATOM | 814 | C | ILE | A | 150 | 244.890 | 84.907 | 198.320 | 1.00 | 111.27 | C |
| ATOM | 815 | O | ILE | A | 150 | 245.841 | 85.543 | 198.769 | 1.00 | 125.08 | O |
| ATOM | 816 | CB | ILE | A | 150 | 242.447 | 85.262 | 198.691 | 1.00 | 102.67 | C |
| ATOM | 817 | CG1 | ILE | A | 150 | 241.501 | 86.458 | 198.783 | 1.00 | 81.93 | C |
| ATOM | 818 | CG2 | ILE | A | 150 | 242.900 | 84.866 | 200.081 | 1.00 | 93.62 | C |
| ATOM | 819 | CD1 | ILE | A | 150 | 241.279 | 87.159 | 197.457 | 1.00 | 131.92 | C |
| ATOM | 820 | N | GLN | A | 151 | 244.898 | 83.583 | 198.221 | 1.00 | 93.05 | N |
| ATOM | 821 | CA | GLN | A | 151 | 246.045 | 82.836 | 198.708 | 1.00 | 112.82 | C |
| ATOM | 822 | C | GLN | A | 151 | 247.325 | 83.240 | 197.992 | 1.00 | 130.96 | C |
| ATOM | 823 | O | GLN | A | 151 | 248.373 | 83.378 | 198.624 | 1.00 | 146.77 | O |
| ATOM | 824 | CB | GLN | A | 151 | 245.825 | 81.329 | 198.565 | 1.00 | 96.24 | C |
| ATOM | 825 | CG | GLN | A | 151 | 246.123 | 80.751 | 197.203 | 1.00 | 107.91 | C |
| ATOM | 826 | CD | GLN | A | 151 | 246.134 | 79.231 | 197.224 | 1.00 | 135.63 | C |
| ATOM | 827 | OE1 | GLN | A | 151 | 246.326 | 78.584 | 196.193 | 1.00 | 152.64 | O |
| ATOM | 828 | NE2 | GLN | A | 151 | 245.929 | 78.654 | 198.406 | 1.00 | 63.64 | N |
| ATOM | 829 | N | ASP | A | 152 | 247.241 | 83.452 | 196.682 | 1.00 | 131.86 | N |
| ATOM | 830 | CA | ASP | A | 152 | 248.416 | 83.833 | 195.898 | 1.00 | 121.88 | C |
| ATOM | 831 | C | ASP | A | 152 | 248.697 | 85.331 | 195.974 | 1.00 | 119.03 | C |
| ATOM | 832 | O | ASP | A | 152 | 249.617 | 85.765 | 196.678 | 1.00 | 108.04 | O |
| ATOM | 833 | CB | ASP | A | 152 | 248.226 | 83.420 | 194.436 | 1.00 | 120.82 | C |
| ATOM | 834 | CG | ASP | A | 152 | 247.643 | 82.015 | 194.296 | 1.00 | 145.66 | C |
| ATOM | 835 | OD1 | ASP | A | 152 | 248.152 | 81.088 | 194.964 | 1.00 | 161.64 | O |
| ATOM | 836 | OD2 | ASP | A | 152 | 246.679 | 81.834 | 193.515 | 1.00 | 172.99 | O |
| TER | 836 | | ASP | A | 152 | | | | | | |
| ATOM | 837 | N | THR | A | 159 | 244.002 | 91.956 | 205.011 | 1.00 | 65.30 | N |
| ATOM | 838 | CA | THR | A | 159 | 243.414 | 92.956 | 205.898 | 1.00 | 99.51 | C |
| ATOM | 839 | C | THR | A | 159 | 241.893 | 92.871 | 205.964 | 1.00 | 87.22 | C |
| ATOM | 840 | O | THR | A | 159 | 241.221 | 92.755 | 204.944 | 1.00 | 90.56 | O |
| ATOM | 841 | CB | THR | A | 159 | 243.790 | 94.404 | 205.473 | 1.00 | 95.19 | C |
| ATOM | 842 | OG1 | THR | A | 159 | 243.610 | 94.560 | 204.061 | 1.00 | 103.02 | O |
| ATOM | 843 | CG2 | THR | A | 159 | 245.229 | 94.718 | 205.831 | 1.00 | 121.85 | C |
| ATOM | 844 | N | GLU | A | 160 | 241.360 | 92.931 | 207.178 | 1.00 | 90.46 | N |
| ATOM | 845 | CA | GLU | A | 160 | 239.921 | 92.876 | 207.395 | 1.00 | 95.08 | C |
| ATOM | 846 | C | GLU | A | 160 | 239.243 | 93.816 | 206.400 | 1.00 | 97.10 | C |
| ATOM | 847 | O | GLU | A | 160 | 238.191 | 93.498 | 205.844 | 1.00 | 77.77 | O |
| ATOM | 848 | CB | GLU | A | 160 | 239.606 | 93.302 | 208.836 | 1.00 | 84.05 | C |
| ATOM | 849 | CG | GLU | A | 160 | 238.135 | 93.255 | 209.218 | 1.00 | 102.30 | C |
| ATOM | 850 | CD | GLU | A | 160 | 237.888 | 93.636 | 210.675 | 1.00 | 107.68 | C |
| ATOM | 851 | OE1 | GLU | A | 160 | 238.512 | 93.022 | 211.566 | 1.00 | 102.89 | O |
| ATOM | 852 | OE2 | GLU | A | 160 | 237.063 | 94.542 | 210.931 | 1.00 | 116.03 | O |
| ATOM | 853 | N | ARG | A | 161 | 239.872 | 94.966 | 206.169 | 1.00 | 91.94 | N |
| ATOM | 854 | CA | ARG | A | 161 | 239.359 | 95.979 | 205.252 | 1.00 | 98.89 | C |
| ATOM | 855 | C | ARG | A | 161 | 239.188 | 95.480 | 203.826 | 1.00 | 94.53 | C |
| ATOM | 856 | O | ARG | A | 161 | 238.251 | 95.874 | 203.129 | 1.00 | 84.43 | O |
| ATOM | 857 | CB | ARG | A | 161 | 240.276 | 97.204 | 205.245 | 1.00 | 94.61 | C |
| ATOM | 858 | CG | ARG | A | 161 | 239.886 | 98.251 | 204.206 | 1.00 | 116.99 | C |
| ATOM | 859 | CD | ARG | A | 161 | 240.724 | 99.506 | 204.347 | 1.00 | 131.31 | C |
| ATOM | 860 | NE | ARG | A | 161 | 240.601 | 100.069 | 205.688 | 1.00 | 142.10 | N |
| ATOM | 861 | CZ | ARG | A | 161 | 241.205 | 101.180 | 206.092 | 1.00 | 132.03 | C |
| ATOM | 862 | NH1 | ARG | A | 161 | 241.982 | 101.855 | 205.257 | 1.00 | 142.54 | N |
| ATOM | 863 | NH2 | ARG | A | 161 | 241.026 | 101.620 | 207.330 | 1.00 | 138.86 | N |
| ATOM | 864 | N | GLU | A | 162 | 240.107 | 94.628 | 203.389 | 1.00 | 86.92 | N |
| ATOM | 865 | CA | GLU | A | 162 | 240.040 | 94.067 | 202.050 | 1.00 | 96.77 | C |
| ATOM | 866 | C | GLU | A | 162 | 238.899 | 93.063 | 201.991 | 1.00 | 93.54 | C |
| ATOM | 867 | O | GLU | A | 162 | 238.101 | 93.078 | 201.052 | 1.00 | 98.52 | O |
| ATOM | 868 | CB | GLU | A | 162 | 241.360 | 93.385 | 201.699 | 1.00 | 101.33 | C |
| ATOM | 869 | CG | GLU | A | 162 | 242.463 | 94.360 | 201.317 | 1.00 | 125.60 | C |
| ATOM | 870 | CD | GLU | A | 162 | 243.848 | 93.755 | 201.448 | 1.00 | 135.51 | C |
| ATOM | 871 | OE1 | GLU | A | 162 | 244.823 | 94.405 | 201.011 | 1.00 | 144.57 | O |
| ATOM | 872 | OE2 | GLU | A | 162 | 243.959 | 92.636 | 201.999 | 1.00 | 130.61 | O |
| ATOM | 873 | N | ALA | A | 163 | 238.822 | 92.199 | 203.002 | 1.00 | 93.78 | N |
| ATOM | 874 | CA | ALA | A | 163 | 237.772 | 91.187 | 203.071 | 1.00 | 86.54 | C |
| ATOM | 875 | C | ALA | A | 163 | 236.426 | 91.889 | 202.976 | 1.00 | 87.93 | C |
| ATOM | 876 | O | ALA | A | 163 | 235.509 | 91.418 | 202.297 | 1.00 | 94.67 | O |
| ATOM | 877 | CB | ALA | A | 163 | 237.871 | 90.419 | 204.371 | 1.00 | 72.07 | C |
| ATOM | 878 | N | SER | A | 164 | 236.319 | 93.021 | 203.662 | 1.00 | 75.33 | N |
| ATOM | 879 | CA | SER | A | 164 | 235.098 | 93.809 | 203.651 | 1.00 | 81.45 | C |
| ATOM | 880 | C | SER | A | 164 | 234.765 | 94.222 | 202.223 | 1.00 | 92.32 | C |
| ATOM | 881 | O | SER | A | 164 | 233.708 | 93.892 | 201.679 | 1.00 | 89.51 | O |
| ATOM | 882 | CB | SER | A | 164 | 235.281 | 95.057 | 204.511 | 1.00 | 61.52 | C |
| ATOM | 883 | OG | SER | A | 164 | 234.233 | 95.977 | 204.289 | 1.00 | 85.01 | O |

TABLE 1-continued

Coordinates of the activated MAPKAP kinase-2/peptide complex

| ATOM | 884 | N | GLU | A | 165 | 235.696 | 94.949 | 201.622 | 1.00 | 106.88 | N |
|---|---|---|---|---|---|---|---|---|---|---|---|
| ATOM | 885 | CA | GLU | A | 165 | 235.537 | 95.436 | 200.259 | 1.00 | 107.60 | C |
| ATOM | 886 | C | GLU | A | 165 | 235.138 | 94.312 | 199.306 | 1.00 | 98.22 | C |
| ATOM | 887 | O | GLU | A | 165 | 234.309 | 94.509 | 198.421 | 1.00 | 80.74 | O |
| ATOM | 888 | CB | GLU | A | 165 | 236.834 | 96.102 | 199.807 | 1.00 | 117.73 | C |
| ATOM | 889 | CG | GLU | A | 165 | 237.296 | 97.198 | 200.763 | 1.00 | 121.43 | C |
| ATOM | 890 | CD | GLU | A | 165 | 238.640 | 97.776 | 200.381 | 1.00 | 129.44 | C |
| ATOM | 891 | OE1 | GLU | A | 165 | 239.620 | 96.998 | 200.285 | 1.00 | 132.54 | O |
| ATOM | 892 | OE2 | GLU | A | 165 | 238.711 | 99.007 | 200.172 | 1.00 | 114.59 | O |
| ATOM | 893 | N | ILE | A | 166 | 235.722 | 93.134 | 199.483 | 1.00 | 87.57 | N |
| ATOM | 894 | CA | ILE | A | 166 | 235.354 | 92.020 | 198.628 | 1.00 | 78.81 | C |
| ATOM | 895 | C | ILE | A | 166 | 233.887 | 91.705 | 198.905 | 1.00 | 85.13 | C |
| ATOM | 896 | O | ILE | A | 166 | 233.068 | 91.644 | 197.975 | 1.00 | 86.94 | O |
| ATOM | 897 | CB | ILE | A | 166 | 236.207 | 90.755 | 198.905 | 1.00 | 76.17 | C |
| ATOM | 898 | CG1 | ILE | A | 166 | 237.628 | 90.972 | 198.376 | 1.00 | 76.65 | C |
| ATOM | 899 | CG2 | ILE | A | 166 | 235.567 | 89.534 | 198.255 | 1.00 | 77.07 | C |
| ATOM | 900 | CD1 | ILE | A | 166 | 238.532 | 89.759 | 198.515 | 1.00 | 56.87 | C |
| ATOM | 901 | N | MET | A | 167 | 233.546 | 91.520 | 200.179 | 1.00 | 80.82 | N |
| ATOM | 902 | CA | MET | A | 167 | 232.166 | 91.195 | 200.521 | 1.00 | 77.70 | C |
| ATOM | 903 | C | MET | A | 167 | 231.228 | 92.224 | 199.941 | 1.00 | 73.89 | C |
| ATOM | 904 | O | MET | A | 167 | 230.152 | 91.895 | 199.452 | 1.00 | 72.21 | O |
| ATOM | 905 | CB | MET | A | 167 | 231.978 | 91.110 | 202.035 | 1.00 | 67.42 | C |
| ATOM | 906 | CG | MET | A | 167 | 232.544 | 89.845 | 202.620 | 1.00 | 65.04 | C |
| ATOM | 907 | SD | MET | A | 167 | 232.087 | 88.398 | 201.648 | 1.00 | 75.11 | S |
| ATOM | 908 | CE | MET | A | 167 | 230.294 | 88.399 | 201.807 | 1.00 | 53.41 | C |
| ATOM | 909 | N | LYS | A | 168 | 231.659 | 93.472 | 199.962 | 1.00 | 54.97 | N |
| ATOM | 910 | CA | LYS | A | 168 | 230.830 | 94.534 | 199.449 | 1.00 | 60.76 | C |
| ATOM | 911 | C | LYS | A | 168 | 230.456 | 94.386 | 197.990 | 1.00 | 70.78 | C |
| ATOM | 912 | O | LYS | A | 168 | 229.307 | 94.607 | 197.629 | 1.00 | 66.11 | O |
| ATOM | 913 | CB | LYS | A | 168 | 231.502 | 95.876 | 199.659 | 1.00 | 65.32 | C |
| ATOM | 914 | CG | LYS | A | 168 | 230.616 | 97.027 | 199.293 | 1.00 | 49.49 | C |
| ATOM | 915 | CD | LYS | A | 168 | 231.208 | 98.313 | 199.780 | 1.00 | 103.77 | C |
| ATOM | 916 | CE | LYS | A | 168 | 230.191 | 99.429 | 199.714 | 1.00 | 87.12 | C |
| ATOM | 917 | NZ | LYS | A | 168 | 230.644 | 100.674 | 200.407 | 1.00 | 118.45 | N |
| ATOM | 918 | N | SER | A | 169 | 231.403 | 94.023 | 197.136 | 1.00 | 82.60 | N |
| ATOM | 919 | CA | SER | A | 169 | 231.061 | 93.885 | 195.723 | 1.00 | 89.11 | C |
| ATOM | 920 | C | SER | A | 169 | 230.176 | 92.665 | 195.484 | 1.00 | 81.07 | C |
| ATOM | 921 | O | SER | A | 169 | 229.262 | 92.726 | 194.657 | 1.00 | 75.01 | O |
| ATOM | 922 | CB | SER | A | 169 | 232.327 | 93.796 | 194.863 | 1.00 | 73.74 | C |
| ATOM | 923 | OG | SER | A | 169 | 233.058 | 92.620 | 195.165 | 1.00 | 77.68 | O |
| ATOM | 924 | N | ILE | A | 170 | 230.448 | 91.560 | 196.191 | 1.00 | 75.29 | N |
| ATOM | 925 | CA | ILE | A | 170 | 229.630 | 90.349 | 196.034 | 1.00 | 74.32 | C |
| ATOM | 926 | C | ILE | A | 170 | 228.232 | 90.743 | 196.437 | 1.00 | 63.33 | C |
| ATOM | 927 | O | ILE | A | 170 | 227.255 | 90.334 | 195.818 | 1.00 | 57.44 | O |
| ATOM | 928 | CB | ILE | A | 170 | 230.053 | 89.177 | 196.951 | 1.00 | 68.61 | C |
| ATOM | 929 | CG1 | ILE | A | 170 | 231.437 | 88.663 | 196.571 | 1.00 | 59.95 | C |
| ATOM | 930 | CG2 | ILE | A | 170 | 229.091 | 88.015 | 196.782 | 1.00 | 46.17 | C |
| ATOM | 931 | CD1 | ILE | A | 170 | 231.768 | 87.318 | 197.192 | 1.00 | 76.19 | C |
| ATOM | 932 | N | GLY | A | 171 | 228.154 | 91.560 | 197.484 | 1.00 | 56.09 | N |
| ATOM | 933 | CA | GLY | A | 171 | 226.870 | 92.026 | 197.958 | 1.00 | 75.47 | C |
| ATOM | 934 | C | GLY | A | 171 | 226.110 | 92.700 | 196.835 | 1.00 | 69.45 | C |
| ATOM | 935 | O | GLY | A | 171 | 224.947 | 92.390 | 196.568 | 1.00 | 76.12 | O |
| ATOM | 936 | N | GLU | A | 172 | 226.792 | 93.621 | 196.166 | 1.00 | 71.58 | N |
| ATOM | 937 | CA | GLU | A | 172 | 226.212 | 94.368 | 195.066 | 1.00 | 73.09 | C |
| ATOM | 938 | C | GLU | A | 172 | 225.715 | 93.446 | 193.960 | 1.00 | 69.34 | C |
| ATOM | 939 | O | GLU | A | 172 | 224.645 | 93.653 | 193.396 | 1.00 | 74.21 | O |
| ATOM | 940 | CB | GLU | A | 172 | 227.243 | 95.332 | 194.499 | 1.00 | 62.80 | C |
| ATOM | 941 | CG | GLU | A | 172 | 228.028 | 96.080 | 195.547 | 1.00 | 91.94 | C |
| ATOM | 942 | CD | GLU | A | 172 | 228.717 | 97.298 | 194.973 | 1.00 | 112.10 | C |
| ATOM | 943 | OE1 | GLU | A | 172 | 228.051 | 98.349 | 194.825 | 1.00 | 116.39 | O |
| ATOM | 944 | OE2 | GLU | A | 172 | 229.919 | 97.199 | 194.649 | 1.00 | 121.47 | O |
| ATOM | 945 | N | ALA | A | 173 | 226.487 | 92.427 | 193.635 | 1.00 | 50.91 | N |
| ATOM | 946 | CA | ALA | A | 173 | 226.039 | 91.525 | 192.599 | 1.00 | 55.42 | C |
| ATOM | 947 | C | ALA | A | 173 | 224.666 | 90.969 | 192.995 | 1.00 | 69.00 | C |
| ATOM | 948 | O | ALA | A | 173 | 223.779 | 90.793 | 192.156 | 1.00 | 68.62 | O |
| ATOM | 949 | CB | ALA | A | 173 | 227.036 | 90.392 | 192.429 | 1.00 | 59.45 | C |
| ATOM | 950 | N | ILE | A | 174 | 224.491 | 90.709 | 194.287 | 1.00 | 59.68 | N |
| ATOM | 951 | CA | ILE | A | 174 | 223.240 | 90.163 | 194.793 | 1.00 | 55.23 | C |
| ATOM | 952 | C | ILE | A | 174 | 222.137 | 91.199 | 194.912 | 1.00 | 66.27 | C |
| ATOM | 953 | O | ILE | A | 174 | 220.991 | 90.943 | 194.542 | 1.00 | 59.24 | O |
| ATOM | 954 | CB | ILE | A | 174 | 223.439 | 89.528 | 196.157 | 1.00 | 72.24 | C |
| ATOM | 955 | CG1 | ILE | A | 174 | 224.492 | 88.438 | 196.055 | 1.00 | 44.08 | C |
| ATOM | 956 | CG2 | ILE | A | 174 | 222.132 | 88.924 | 196.636 | 1.00 | 52.34 | C |
| ATOM | 957 | CD1 | ILE | A | 174 | 224.090 | 87.355 | 195.102 | 1.00 | 105.89 | C |
| ATOM | 958 | N | GLN | A | 175 | 222.473 | 92.368 | 195.444 | 1.00 | 46.22 | N |
| ATOM | 959 | CA | GLN | A | 175 | 221.477 | 93.407 | 195.586 | 1.00 | 60.91 | C |
| ATOM | 960 | C | GLN | A | 175 | 220.804 | 93.676 | 194.240 | 1.00 | 48.25 | C |
| ATOM | 961 | O | GLN | A | 175 | 219.581 | 93.742 | 194.155 | 1.00 | 62.61 | O |

TABLE 1-continued

Coordinates of the activated MAPKAP kinase-2/peptide complex

| ATOM | 962 | CB | GLN | A | 175 | 222.121 | 94.674 | 196.144 | 1.00 | 49.40 | C |
|---|---|---|---|---|---|---|---|---|---|---|---|
| ATOM | 963 | CG | GLN | A | 175 | 221.309 | 95.931 | 195.912 | 1.00 | 71.12 | C |
| ATOM | 964 | CD | GLN | A | 175 | 221.661 | 97.042 | 196.892 | 1.00 | 104.15 | C |
| ATOM | 965 | OE1 | GLN | A | 175 | 222.825 | 97.446 | 197.017 | 1.00 | 76.77 | O |
| ATOM | 966 | NE2 | GLN | A | 175 | 220.645 | 97.544 | 197.600 | 1.00 | 111.29 | N |
| ATOM | 967 | N | TYR | A | 176 | 221.602 | 93.798 | 193.184 | 1.00 | 72.76 | N |
| ATOM | 968 | CA | TYR | A | 176 | 221.025 | 94.078 | 191.873 | 1.00 | 74.81 | C |
| ATOM | 969 | C | TYR | A | 176 | 220.105 | 92.946 | 191.416 | 1.00 | 74.26 | C |
| ATOM | 970 | O | TYR | A | 176 | 218.933 | 93.142 | 191.122 | 1.00 | 61.26 | O |
| ATOM | 971 | CB | TYR | A | 176 | 222.168 | 94.255 | 190.874 | 1.00 | 79.17 | C |
| ATOM | 972 | CG | TYR | A | 176 | 221.628 | 94.703 | 189.563 | 1.00 | 53.89 | C |
| ATOM | 973 | CD1 | TYR | A | 176 | 221.692 | 96.048 | 189.209 | 1.00 | 73.14 | C |
| ATOM | 974 | CD2 | TYR | A | 176 | 221.054 | 93.785 | 188.683 | 1.00 | 78.08 | C |
| ATOM | 975 | CE1 | TYR | A | 176 | 221.197 | 96.471 | 187.985 | 1.00 | 58.55 | C |
| ATOM | 976 | CE2 | TYR | A | 176 | 220.550 | 94.209 | 187.463 | 1.00 | 60.19 | C |
| ATOM | 977 | CZ | TYR | A | 176 | 220.616 | 95.546 | 187.115 | 1.00 | 70.05 | C |
| ATOM | 978 | OH | TYR | A | 176 | 220.124 | 95.975 | 185.898 | 1.00 | 98.35 | O |
| ATOM | 979 | N | LEU | A | 177 | 220.626 | 91.729 | 191.357 | 1.00 | 69.60 | N |
| ATOM | 980 | CA | LEU | A | 177 | 219.824 | 90.582 | 190.986 | 1.00 | 65.69 | C |
| ATOM | 981 | C | LEU | A | 177 | 218.485 | 90.616 | 191.705 | 1.00 | 62.46 | C |
| ATOM | 982 | O | LEU | A | 177 | 217.437 | 90.563 | 191.057 | 1.00 | 73.48 | O |
| ATOM | 983 | CB | LEU | A | 177 | 220.562 | 89.297 | 191.333 | 1.00 | 59.94 | C |
| ATOM | 984 | CG | LEU | A | 177 | 221.671 | 88.955 | 190.357 | 1.00 | 54.02 | C |
| ATOM | 985 | CD1 | LEU | A | 177 | 222.252 | 87.585 | 190.679 | 1.00 | 59.89 | C |
| ATOM | 986 | CD2 | LEU | A | 177 | 221.078 | 88.962 | 188.964 | 1.00 | 77.33 | C |
| ATOM | 987 | N | HIS | A | 178 | 218.518 | 90.708 | 193.035 | 1.00 | 61.49 | N |
| ATOM | 988 | CA | HIS | A | 178 | 217.285 | 90.746 | 193.816 | 1.00 | 57.69 | C |
| ATOM | 989 | C | HIS | A | 178 | 216.419 | 91.952 | 193.466 | 1.00 | 56.16 | C |
| ATOM | 990 | O | HIS | A | 178 | 215.204 | 91.831 | 193.368 | 1.00 | 71.55 | O |
| ATOM | 991 | CB | HIS | A | 178 | 217.590 | 90.741 | 195.313 | 1.00 | 58.67 | C |
| ATOM | 992 | CG | HIS | A | 178 | 218.154 | 89.446 | 195.805 | 1.00 | 66.35 | C |
| ATOM | 993 | ND1 | HIS | A | 178 | 218.554 | 89.259 | 197.110 | 1.00 | 49.65 | N |
| ATOM | 994 | CD2 | HIS | A | 178 | 218.437 | 88.292 | 195.154 | 1.00 | 50.67 | C |
| ATOM | 995 | CE1 | HIS | A | 178 | 219.068 | 88.049 | 197.241 | 1.00 | 77.64 | C |
| ATOM | 996 | NE2 | HIS | A | 178 | 219.010 | 87.442 | 196.069 | 1.00 | 44.53 | N |
| ATOM | 997 | N | SER | A | 179 | 217.037 | 93.107 | 193.259 | 1.00 | 62.56 | N |
| ATOM | 998 | CA | SER | A | 179 | 216.270 | 94.292 | 192.906 | 1.00 | 56.93 | C |
| ATOM | 999 | C | SER | A | 179 | 215.575 | 94.094 | 191.567 | 1.00 | 44.23 | C |
| ATOM | 1000 | O | SER | A | 179 | 214.830 | 94.956 | 191.136 | 1.00 | 68.45 | O |
| ATOM | 1001 | CB | SER | A | 179 | 217.160 | 95.518 | 192.803 | 1.00 | 41.33 | C |
| ATOM | 1002 | OG | SER | A | 179 | 217.835 | 95.504 | 191.554 | 1.00 | 86.61 | O |
| ATOM | 1003 | N | ILE | A | 180 | 215.842 | 92.997 | 190.876 | 1.00 | 60.70 | N |
| ATOM | 1004 | CA | ILE | A | 180 | 215.135 | 92.778 | 189.629 | 1.00 | 66.56 | C |
| ATOM | 1005 | C | ILE | A | 180 | 214.483 | 91.409 | 189.667 | 1.00 | 76.38 | C |
| ATOM | 1006 | O | ILE | A | 180 | 214.223 | 90.783 | 188.641 | 1.00 | 67.28 | O |
| ATOM | 1007 | CB | ILE | A | 180 | 216.041 | 92.928 | 188.368 | 1.00 | 65.72 | C |
| ATOM | 1008 | CG1 | ILE | A | 180 | 217.061 | 91.804 | 188.280 | 1.00 | 98.00 | C |
| ATOM | 1009 | CG2 | ILE | A | 180 | 216.766 | 94.248 | 188.413 | 1.00 | 65.05 | C |
| ATOM | 1010 | CD1 | ILE | A | 180 | 217.787 | 91.783 | 186.962 | 1.00 | 42.99 | C |
| ATOM | 1011 | N | ASN | A | 181 | 214.229 | 90.940 | 190.880 | 1.00 | 62.76 | N |
| ATOM | 1012 | CA | ASN | A | 181 | 213.556 | 89.672 | 191.081 | 1.00 | 64.37 | C |
| ATOM | 1013 | C | ASN | A | 181 | 214.257 | 88.447 | 190.552 | 1.00 | 64.72 | C |
| ATOM | 1014 | O | ASN | A | 181 | 213.624 | 87.605 | 189.919 | 1.00 | 76.26 | O |
| ATOM | 1015 | CB | ASN | A | 181 | 212.156 | 89.726 | 190.464 | 1.00 | 52.97 | C |
| ATOM | 1016 | CG | ASN | A | 181 | 211.274 | 90.765 | 191.118 | 1.00 | 91.87 | C |
| ATOM | 1017 | OD1 | ASN | A | 181 | 210.607 | 91.549 | 190.435 | 1.00 | 70.51 | O |
| ATOM | 1018 | ND2 | ASN | A | 181 | 211.261 | 90.779 | 192.456 | 1.00 | 66.84 | N |
| ATOM | 1019 | N | ILE | A | 182 | 215.550 | 88.325 | 190.800 | 1.00 | 69.03 | N |
| ATOM | 1020 | CA | ILE | A | 182 | 216.251 | 87.140 | 190.343 | 1.00 | 58.61 | C |
| ATOM | 1021 | C | ILE | A | 182 | 217.060 | 86.582 | 191.510 | 1.00 | 64.49 | C |
| ATOM | 1022 | O | ILE | A | 182 | 217.652 | 87.335 | 192.289 | 1.00 | 75.24 | O |
| ATOM | 1023 | CB | ILE | A | 182 | 217.217 | 87.452 | 189.175 | 1.00 | 67.77 | C |
| ATOM | 1024 | CG1 | ILE | A | 182 | 216.498 | 88.204 | 188.058 | 1.00 | 51.81 | C |
| ATOM | 1025 | CG2 | ILE | A | 182 | 217.765 | 86.162 | 188.604 | 1.00 | 71.00 | C |
| ATOM | 1026 | CD1 | ILE | A | 182 | 217.397 | 88.520 | 186.870 | 1.00 | 51.04 | C |
| ATOM | 1027 | N | ALA | A | 183 | 217.068 | 85.261 | 191.639 | 1.00 | 74.62 | N |
| ATOM | 1028 | CA | ALA | A | 183 | 217.907 | 84.570 | 192.612 | 1.00 | 86.67 | C |
| ATOM | 1029 | C | ALA | A | 183 | 218.970 | 83.710 | 191.924 | 1.00 | 88.25 | C |
| ATOM | 1030 | O | ALA | A | 183 | 218.683 | 82.841 | 191.110 | 1.00 | 87.52 | O |
| ATOM | 1031 | CB | ALA | A | 183 | 217.006 | 83.691 | 193.480 | 1.00 | 82.75 | C |
| ATOM | 1032 | N | HIS | A | 184 | 220.241 | 84.008 | 192.248 | 1.00 | 80.72 | N |
| ATOM | 1033 | CA | HIS | A | 184 | 221.331 | 83.245 | 191.654 | 1.00 | 76.94 | C |
| ATOM | 1034 | C | HIS | A | 184 | 221.282 | 81.775 | 192.077 | 1.00 | 80.75 | C |
| ATOM | 1035 | O | HIS | A | 184 | 221.411 | 80.858 | 191.277 | 1.00 | 72.26 | O |
| ATOM | 1036 | CB | HIS | A | 184 | 222.652 | 83.872 | 192.102 | 1.00 | 71.67 | C |
| ATOM | 1037 | CG | HIS | A | 184 | 223.777 | 83.319 | 191.264 | 1.00 | 61.47 | C |
| ATOM | 1038 | ND1 | HIS | A | 184 | 224.599 | 84.095 | 190.515 | 1.00 | 83.49 | N |
| ATOM | 1039 | CD2 | HIS | A | 184 | 224.158 | 81.983 | 191.101 | 1.00 | 84.93 | C |

TABLE 1-continued

Coordinates of the activated MAPKAP kinase-2/peptide complex

| ATOM | 1040 | CE1 | HIS | A | 184 | 225.456 | 83.245 | 189.918 | 1.00 | 77.60 | C |
|---|---|---|---|---|---|---|---|---|---|---|---|
| ATOM | 1041 | NE2 | HIS | A | 184 | 225.215 | 81.974 | 190.250 | 1.00 | 94.64 | N |
| ATOM | 1042 | N | ARG | A | 185 | 221.128 | 81.570 | 193.401 | 1.00 | 76.53 | N |
| ATOM | 1043 | CA | ARG | A | 185 | 221.070 | 80.207 | 193.915 | 1.00 | 77.64 | C |
| ATOM | 1044 | C | ARG | A | 185 | 222.301 | 79.398 | 193.501 | 1.00 | 85.59 | C |
| ATOM | 1045 | O | ARG | A | 185 | 222.247 | 78.190 | 193.308 | 1.00 | 76.00 | O |
| ATOM | 1046 | CB | ARG | A | 185 | 219.805 | 79.546 | 193.368 | 1.00 | 60.05 | C |
| ATOM | 1047 | CG | ARG | A | 185 | 218.538 | 80.313 | 193.747 | 1.00 | 69.87 | C |
| ATOM | 1048 | CD | ARG | A | 185 | 217.293 | 79.421 | 193.714 | 1.00 | 88.79 | C |
| ATOM | 1049 | NE | ARG | A | 185 | 216.984 | 79.018 | 192.339 | 1.00 | 74.62 | N |
| ATOM | 1050 | CZ | ARG | A | 185 | 216.704 | 77.720 | 192.125 | 1.00 | 102.74 | C |
| ATOM | 1051 | NH1 | ARG | A | 185 | 216.704 | 76.865 | 193.132 | 1.00 | 105.16 | N |
| ATOM | 1052 | NH2 | ARG | A | 185 | 216.428 | 77.299 | 190.884 | 1.00 | 124.15 | N |
| ATOM | 1053 | N | ASP | A | 186 | 223.476 | 80.000 | 193.397 | 1.00 | 85.17 | N |
| ATOM | 1054 | CA | ASP | A | 186 | 224.677 | 79.238 | 193.128 | 1.00 | 65.94 | C |
| ATOM | 1055 | C | ASP | A | 186 | 225.857 | 80.161 | 193.327 | 1.00 | 63.69 | C |
| ATOM | 1056 | O | ASP | A | 186 | 226.821 | 80.122 | 192.573 | 1.00 | 76.80 | O |
| ATOM | 1057 | CB | ASP | A | 186 | 224.651 | 78.670 | 191.712 | 1.00 | 64.22 | C |
| ATOM | 1058 | CG | ASP | A | 186 | 225.560 | 77.461 | 191.555 | 1.00 | 69.83 | C |
| ATOM | 1059 | OD1 | ASP | A | 186 | 225.629 | 76.654 | 192.503 | 1.00 | 114.36 | O |
| ATOM | 1060 | OD2 | ASP | A | 186 | 226.197 | 77.304 | 190.492 | 1.00 | 103.36 | O |
| ATOM | 1061 | N | VAL | A | 187 | 225.757 | 80.991 | 194.364 | 1.00 | 65.08 | N |
| ATOM | 1062 | CA | VAL | A | 187 | 226.794 | 81.952 | 194.717 | 1.00 | 62.87 | C |
| ATOM | 1063 | C | VAL | A | 187 | 227.923 | 81.305 | 195.507 | 1.00 | 61.46 | C |
| ATOM | 1064 | O | VAL | A | 187 | 228.134 | 81.605 | 196.677 | 1.00 | 76.23 | O |
| ATOM | 1065 | CB | VAL | A | 187 | 226.218 | 83.132 | 195.539 | 1.00 | 56.36 | C |
| ATOM | 1066 | CG1 | VAL | A | 187 | 227.311 | 84.156 | 195.831 | 1.00 | 45.04 | C |
| ATOM | 1067 | CG2 | VAL | A | 187 | 225.099 | 83.791 | 194.774 | 1.00 | 49.15 | C |
| ATOM | 1068 | N | LYS | A | 188 | 228.644 | 80.407 | 194.852 | 1.00 | 71.26 | N |
| ATOM | 1069 | CA | LYS | A | 188 | 229.766 | 79.731 | 195.482 | 1.00 | 71.74 | C |
| ATOM | 1070 | C | LYS | A | 188 | 231.033 | 80.392 | 194.985 | 1.00 | 71.11 | C |
| ATOM | 1071 | O | LYS | A | 188 | 231.049 | 80.975 | 193.905 | 1.00 | 76.85 | O |
| ATOM | 1072 | CB | LYS | A | 188 | 229.770 | 78.246 | 195.123 | 1.00 | 59.58 | C |
| ATOM | 1073 | CG | LYS | A | 188 | 229.709 | 77.962 | 193.639 | 1.00 | 61.04 | C |
| ATOM | 1074 | CD | LYS | A | 188 | 228.939 | 76.679 | 193.367 | 1.00 | 96.00 | C |
| ATOM | 1075 | CE | LYS | A | 188 | 228.669 | 76.509 | 191.869 | 1.00 | 141.45 | C |
| ATOM | 1076 | NZ | LYS | A | 188 | 227.746 | 75.371 | 191.579 | 1.00 | 122.86 | N |
| ATOM | 1077 | N | PRO | A | 189 | 232.115 | 80.318 | 195.776 | 1.00 | 66.86 | N |
| ATOM | 1078 | CA | PRO | A | 189 | 233.409 | 80.911 | 195.433 | 1.00 | 82.94 | C |
| ATOM | 1079 | C | PRO | A | 189 | 233.746 | 80.698 | 193.967 | 1.00 | 81.19 | C |
| ATOM | 1080 | O | PRO | A | 189 | 233.989 | 81.641 | 193.231 | 1.00 | 92.51 | O |
| ATOM | 1081 | CB | PRO | A | 189 | 234.359 | 80.199 | 196.381 | 1.00 | 77.38 | C |
| ATOM | 1082 | CG | PRO | A | 189 | 233.511 | 80.063 | 197.620 | 1.00 | 79.38 | C |
| ATOM | 1083 | CD | PRO | A | 189 | 232.197 | 79.582 | 197.049 | 1.00 | 84.38 | C |
| ATOM | 1084 | N | GLU | A | 190 | 233.743 | 79.447 | 193.553 | 1.00 | 79.12 | N |
| ATOM | 1085 | CA | GLU | A | 190 | 234.019 | 79.080 | 192.178 | 1.00 | 82.41 | C |
| ATOM | 1086 | C | GLU | A | 190 | 233.441 | 80.092 | 191.159 | 1.00 | 81.32 | C |
| ATOM | 1087 | O | GLU | A | 190 | 234.121 | 80.487 | 190.213 | 1.00 | 102.09 | O |
| ATOM | 1088 | CB | GLU | A | 190 | 233.432 | 77.689 | 191.920 | 1.00 | 94.71 | C |
| ATOM | 1089 | CG | GLU | A | 190 | 233.784 | 76.609 | 192.978 | 1.00 | 121.01 | C |
| ATOM | 1090 | CD | GLU | A | 190 | 232.689 | 76.364 | 194.043 | 1.00 | 135.59 | C |
| ATOM | 1091 | OE1 | GLU | A | 190 | 231.485 | 76.334 | 193.693 | 1.00 | 113.86 | O |
| ATOM | 1092 | OE2 | GLU | A | 190 | 233.039 | 76.185 | 195.236 | 1.00 | 133.59 | O |
| ATOM | 1093 | N | ASN | A | 191 | 232.196 | 80.527 | 191.350 | 1.00 | 80.04 | N |
| ATOM | 1094 | CA | ASN | A | 191 | 231.584 | 81.457 | 190.405 | 1.00 | 59.50 | C |
| ATOM | 1095 | C | ASN | A | 191 | 231.991 | 82.905 | 190.569 | 1.00 | 72.63 | C |
| ATOM | 1096 | O | ASN | A | 191 | 231.360 | 83.796 | 189.998 | 1.00 | 60.72 | O |
| ATOM | 1097 | CB | ASN | A | 191 | 230.068 | 81.364 | 190.471 | 1.00 | 59.13 | C |
| ATOM | 1098 | CG | ASN | A | 191 | 229.566 | 79.975 | 190.189 | 1.00 | 57.02 | C |
| ATOM | 1099 | OD1 | ASN | A | 191 | 228.797 | 79.413 | 190.959 | 1.00 | 107.48 | O |
| ATOM | 1100 | ND2 | ASN | A | 191 | 230.005 | 79.406 | 189.077 | 1.00 | 62.85 | N |
| ATOM | 1101 | N | LEU | A | 192 | 233.042 | 83.149 | 191.342 | 1.00 | 64.74 | N |
| ATOM | 1102 | CA | LEU | A | 192 | 233.524 | 84.514 | 191.552 | 1.00 | 58.75 | C |
| ATOM | 1103 | C | LEU | A | 192 | 234.931 | 84.655 | 190.987 | 1.00 | 67.25 | C |
| ATOM | 1104 | O | LEU | A | 192 | 235.906 | 84.314 | 191.644 | 1.00 | 63.30 | O |
| ATOM | 1105 | CB | LEU | A | 192 | 233.512 | 84.856 | 193.047 | 1.00 | 64.92 | C |
| ATOM | 1106 | CG | LEU | A | 192 | 232.127 | 84.840 | 193.709 | 1.00 | 76.84 | C |
| ATOM | 1107 | CD1 | LEU | A | 192 | 232.285 | 84.706 | 195.207 | 1.00 | 63.79 | C |
| ATOM | 1108 | CD2 | LEU | A | 192 | 231.350 | 86.108 | 193.349 | 1.00 | 49.09 | C |
| ATOM | 1109 | N | LEU | A | 193 | 235.022 | 85.173 | 189.767 | 1.00 | 76.60 | N |
| ATOM | 1110 | CA | LEU | A | 193 | 236.299 | 85.334 | 189.077 | 1.00 | 68.12 | C |
| ATOM | 1111 | C | LEU | A | 193 | 236.765 | 86.779 | 189.008 | 1.00 | 67.18 | C |
| ATOM | 1112 | O | LEU | A | 193 | 235.957 | 87.700 | 189.001 | 1.00 | 70.12 | O |
| ATOM | 1113 | CB | LEU | A | 193 | 236.165 | 84.801 | 187.657 | 1.00 | 57.38 | C |
| ATOM | 1114 | CG | LEU | A | 193 | 235.346 | 83.517 | 187.573 | 1.00 | 67.03 | C |
| ATOM | 1115 | CD1 | LEU | A | 193 | 235.242 | 83.061 | 186.137 | 1.00 | 74.99 | C |
| ATOM | 1116 | CD2 | LEU | A | 193 | 235.985 | 82.449 | 188.445 | 1.00 | 80.12 | C |
| ATOM | 1117 | N | TYR | A | 194 | 238.073 | 86.982 | 188.950 | 1.00 | 66.38 | N |

TABLE 1-continued

Coordinates of the activated MAPKAP kinase-2/peptide complex

| ATOM | 1118 | CA | TYR | A | 194 | 238.603 | 88.333 | 188.846 | 1.00 | 70.20 | C |
|---|---|---|---|---|---|---|---|---|---|---|---|
| ATOM | 1119 | C | TYR | A | 194 | 238.833 | 88.697 | 187.382 | 1.00 | 65.05 | C |
| ATOM | 1120 | O | TYR | A | 194 | 239.219 | 87.856 | 186.578 | 1.00 | 55.59 | O |
| ATOM | 1121 | CB | TYR | A | 194 | 239.903 | 88.449 | 189.636 | 1.00 | 71.53 | C |
| ATOM | 1122 | CG | TYR | A | 194 | 239.692 | 88.807 | 191.085 | 1.00 | 83.55 | C |
| ATOM | 1123 | CD1 | TYR | A | 194 | 239.221 | 90.068 | 191.446 | 1.00 | 60.55 | C |
| ATOM | 1124 | CD2 | TYR | A | 194 | 239.959 | 87.889 | 192.095 | 1.00 | 54.69 | C |
| ATOM | 1125 | CE1 | TYR | A | 194 | 239.026 | 90.402 | 192.766 | 1.00 | 77.54 | C |
| ATOM | 1126 | CE2 | TYR | A | 194 | 239.764 | 88.216 | 193.423 | 1.00 | 72.23 | C |
| ATOM | 1127 | CZ | TYR | A | 194 | 239.300 | 89.472 | 193.749 | 1.00 | 80.69 | C |
| ATOM | 1128 | OH | TYR | A | 194 | 239.118 | 89.812 | 195.068 | 1.00 | 97.12 | O |
| ATOM | 1129 | N | THR | A | 195 | 238.585 | 89.952 | 187.035 | 1.00 | 56.71 | N |
| ATOM | 1130 | CA | THR | A | 195 | 238.754 | 90.389 | 185.660 | 1.00 | 63.48 | C |
| ATOM | 1131 | C | THR | A | 195 | 240.193 | 90.206 | 185.176 | 1.00 | 82.40 | C |
| ATOM | 1132 | O | THR | A | 195 | 240.436 | 89.542 | 184.164 | 1.00 | 96.10 | O |
| ATOM | 1133 | CB | THR | A | 195 | 238.334 | 91.865 | 185.494 | 1.00 | 66.82 | C |
| ATOM | 1134 | OG1 | THR | A | 195 | 239.028 | 92.668 | 186.452 | 1.00 | 70.80 | O |
| ATOM | 1135 | CG2 | THR | A | 195 | 236.829 | 92.022 | 185.688 | 1.00 | 54.17 | C |
| ATOM | 1136 | N | SER | A | 196 | 241.145 | 90.790 | 185.897 | 1.00 | 84.27 | N |
| ATOM | 1137 | CA | SER | A | 196 | 242.552 | 90.672 | 185.532 | 1.00 | 77.62 | C |
| ATOM | 1138 | C | SER | A | 196 | 243.388 | 90.202 | 186.716 | 1.00 | 88.08 | C |
| ATOM | 1139 | O | SER | A | 196 | 242.865 | 89.980 | 187.805 | 1.00 | 101.07 | O |
| ATOM | 1140 | CB | SER | A | 196 | 243.089 | 92.019 | 185.033 | 1.00 | 78.67 | C |
| ATOM | 1141 | OG | SER | A | 196 | 243.063 | 92.995 | 186.055 | 1.00 | 92.46 | O |
| ATOM | 1142 | N | LYS | A | 197 | 244.688 | 90.038 | 186.490 | 1.00 | 106.23 | N |
| ATOM | 1143 | CA | LYS | A | 197 | 245.601 | 89.609 | 187.542 | 1.00 | 100.72 | C |
| ATOM | 1144 | C | LYS | A | 197 | 246.055 | 90.885 | 188.230 | 1.00 | 93.19 | C |
| ATOM | 1145 | O | LYS | A | 197 | 246.509 | 90.870 | 189.373 | 1.00 | 91.43 | O |
| ATOM | 1146 | CB | LYS | A | 197 | 246.792 | 88.882 | 186.936 | 1.00 | 90.18 | C |
| ATOM | 1147 | N | ARG | A | 198 | 245.911 | 91.985 | 187.500 | 1.00 | 76.02 | N |
| ATOM | 1148 | CA | ARG | A | 198 | 246.275 | 93.318 | 187.959 | 1.00 | 111.08 | C |
| ATOM | 1149 | C | ARG | A | 198 | 245.815 | 93.469 | 189.412 | 1.00 | 105.33 | C |
| ATOM | 1150 | O | ARG | A | 198 | 244.993 | 92.696 | 189.885 | 1.00 | 104.59 | O |
| ATOM | 1151 | CB | ARG | A | 198 | 245.582 | 94.345 | 187.048 | 1.00 | 118.16 | C |
| ATOM | 1152 | CG | ARG | A | 198 | 246.321 | 95.666 | 186.798 | 1.00 | 144.07 | C |
| ATOM | 1153 | CD | ARG | A | 198 | 245.911 | 96.211 | 185.435 | 1.00 | 152.31 | C |
| ATOM | 1154 | NE | ARG | A | 198 | 246.262 | 97.611 | 185.210 | 1.00 | 171.50 | N |
| ATOM | 1155 | CZ | ARG | A | 198 | 245.920 | 98.290 | 184.115 | 1.00 | 162.32 | C |
| ATOM | 1156 | NH1 | ARG | A | 198 | 245.223 | 97.692 | 183.152 | 1.00 | 96.38 | N |
| ATOM | 1157 | NH2 | ARG | A | 198 | 246.265 | 99.565 | 183.984 | 1.00 | 146.82 | N |
| ATOM | 1158 | N | PRO | A | 199 | 246.347 | 94.461 | 190.144 | 1.00 | 115.43 | N |
| ATOM | 1159 | CA | PRO | A | 199 | 245.943 | 94.653 | 191.545 | 1.00 | 123.33 | C |
| ATOM | 1160 | C | PRO | A | 199 | 244.581 | 95.315 | 191.719 | 1.00 | 123.60 | C |
| ATOM | 1161 | O | PRO | A | 199 | 243.991 | 95.259 | 192.794 | 1.00 | 135.30 | O |
| ATOM | 1162 | CB | PRO | A | 199 | 247.061 | 95.524 | 192.105 | 1.00 | 121.70 | C |
| ATOM | 1163 | CG | PRO | A | 199 | 247.387 | 96.397 | 190.921 | 1.00 | 133.24 | C |
| ATOM | 1164 | CD | PRO | A | 199 | 247.411 | 95.409 | 189.775 | 1.00 | 125.16 | C |
| ATOM | 1165 | N | ASN | A | 200 | 244.090 | 95.943 | 190.656 | 1.00 | 122.57 | N |
| ATOM | 1166 | CA | ASN | A | 200 | 242.810 | 96.629 | 190.719 | 1.00 | 108.91 | C |
| ATOM | 1167 | C | ASN | A | 200 | 241.726 | 95.826 | 190.023 | 1.00 | 95.83 | C |
| ATOM | 1168 | O | ASN | A | 200 | 240.606 | 96.310 | 189.835 | 1.00 | 73.96 | O |
| ATOM | 1169 | CB | ASN | A | 200 | 242.923 | 98.019 | 190.090 | 1.00 | 118.71 | C |
| ATOM | 1170 | N | ALA | A | 201 | 242.059 | 94.598 | 189.637 | 1.00 | 75.18 | N |
| ATOM | 1171 | CA | ALA | A | 201 | 241.093 | 93.725 | 188.979 | 1.00 | 84.90 | C |
| ATOM | 1172 | C | ALA | A | 201 | 239.789 | 93.860 | 189.751 | 1.00 | 91.91 | C |
| ATOM | 1173 | O | ALA | A | 201 | 239.800 | 94.214 | 190.929 | 1.00 | 89.51 | O |
| ATOM | 1174 | CB | ALA | A | 201 | 241.579 | 92.278 | 189.022 | 1.00 | 81.83 | C |
| ATOM | 1175 | N | ILE | A | 202 | 238.660 | 93.607 | 189.097 | 1.00 | 78.80 | N |
| ATOM | 1176 | CA | ILE | A | 202 | 237.378 | 93.698 | 189.795 | 1.00 | 91.70 | C |
| ATOM | 1177 | C | ILE | A | 202 | 236.697 | 92.326 | 189.886 | 1.00 | 95.28 | C |
| ATOM | 1178 | O | ILE | A | 202 | 236.837 | 91.488 | 188.995 | 1.00 | 88.21 | O |
| ATOM | 1179 | CB | ILE | A | 202 | 236.454 | 94.707 | 189.121 | 1.00 | 76.30 | C |
| ATOM | 1180 | CG1 | ILE | A | 202 | 235.623 | 94.029 | 188.059 | 1.00 | 78.45 | C |
| ATOM | 1181 | CG2 | ILE | A | 202 | 237.278 | 95.772 | 188.468 | 1.00 | 61.72 | C |
| ATOM | 1182 | CD1 | ILE | A | 202 | 234.681 | 94.991 | 187.390 | 1.00 | 169.28 | C |
| ATOM | 1183 | N | LEU | A | 203 | 235.975 | 92.102 | 190.981 | 1.00 | 93.25 | N |
| ATOM | 1184 | CA | LEU | A | 203 | 235.308 | 90.821 | 191.231 | 1.00 | 66.28 | C |
| ATOM | 1185 | C | LEU | A | 203 | 233.935 | 90.746 | 190.587 | 1.00 | 67.61 | C |
| ATOM | 1186 | O | LEU | A | 203 | 233.137 | 91.681 | 190.695 | 1.00 | 68.70 | O |
| ATOM | 1187 | CB | LEU | A | 203 | 235.195 | 90.599 | 192.745 | 1.00 | 73.90 | C |
| ATOM | 1188 | CG | LEU | A | 203 | 234.947 | 89.189 | 193.273 | 1.00 | 52.16 | C |
| ATOM | 1189 | CD1 | LEU | A | 203 | 236.016 | 88.244 | 192.783 | 1.00 | 61.94 | C |
| ATOM | 1190 | CD2 | LEU | A | 203 | 234.956 | 89.228 | 194.779 | 1.00 | 85.31 | C |
| ATOM | 1191 | N | LYS | A | 204 | 233.665 | 89.628 | 189.919 | 1.00 | 58.34 | N |
| ATOM | 1192 | CA | LYS | A | 204 | 232.392 | 89.434 | 189.243 | 1.00 | 58.89 | C |
| ATOM | 1193 | C | LYS | A | 204 | 231.788 | 88.047 | 189.423 | 1.00 | 73.88 | C |
| ATOM | 1194 | O | LYS | A | 204 | 232.490 | 87.027 | 189.406 | 1.00 | 67.59 | O |
| ATOM | 1195 | CB | LYS | A | 204 | 232.540 | 89.740 | 187.750 | 1.00 | 68.02 | C |

TABLE 1-continued

Coordinates of the activated MAPKAP kinase-2/peptide complex

| ATOM | 1196 | CG  | LYS | A | 204 | 232.844 | 91.199 | 187.461 | 1.00 | 64.40  | C |
|------|------|-----|-----|---|-----|---------|--------|---------|------|--------|---|
| ATOM | 1197 | CD  | LYS | A | 204 | 232.603 | 91.552 | 186.008 | 1.00 | 62.63  | C |
| ATOM | 1198 | CE  | LYS | A | 204 | 232.786 | 93.033 | 185.788 | 1.00 | 71.16  | C |
| ATOM | 1199 | NZ  | LYS | A | 204 | 232.247 | 93.468 | 184.487 | 1.00 | 94.63  | N |
| ATOM | 1200 | N   | LEU | A | 205 | 230.472 | 88.023 | 189.586 | 1.00 | 66.05  | N |
| ATOM | 1201 | CA  | LEU | A | 205 | 229.750 | 86.781 | 189.782 | 1.00 | 63.28  | C |
| ATOM | 1202 | C   | LEU | A | 205 | 229.296 | 86.241 | 188.452 | 1.00 | 53.73  | C |
| ATOM | 1203 | O   | LEU | A | 205 | 228.884 | 87.001 | 187.583 | 1.00 | 55.72  | O |
| ATOM | 1204 | CB  | LEU | A | 205 | 228.540 | 87.024 | 190.680 | 1.00 | 64.69  | C |
| ATOM | 1205 | CG  | LEU | A | 205 | 227.514 | 85.905 | 190.813 | 1.00 | 47.19  | C |
| ATOM | 1206 | CD1 | LEU | A | 205 | 228.150 | 84.657 | 191.394 | 1.00 | 81.96  | C |
| ATOM | 1207 | CD2 | LEU | A | 205 | 226.397 | 86.387 | 191.695 | 1.00 | 64.88  | C |
| ATOM | 1208 | N   | THR | A | 206 | 229.374 | 84.926 | 188.300 | 1.00 | 53.81  | N |
| ATOM | 1209 | CA  | THR | A | 206 | 228.976 | 84.363 | 187.015 | 1.00 | 65.26  | C |
| ATOM | 1210 | C   | THR | A | 206 | 228.239 | 83.033 | 187.185 | 1.00 | 53.82  | C |
| ATOM | 1211 | O   | THR | A | 206 | 228.098 | 82.495 | 188.276 | 1.00 | 71.37  | O |
| ATOM | 1212 | CB  | THR | A | 206 | 230.236 | 84.153 | 186.174 | 1.00 | 61.13  | C |
| ATOM | 1213 | OG1 | THR | A | 206 | 231.023 | 83.115 | 186.762 | 1.00 | 57.86  | O |
| ATOM | 1214 | CG2 | THR | A | 206 | 231.064 | 85.441 | 186.137 | 1.00 | 74.17  | C |
| ATOM | 1215 | N   | ASP | A | 207 | 227.721 | 82.523 | 186.051 | 1.00 | 79.42  | N |
| ATOM | 1216 | CA  | ASP | A | 207 | 227.033 | 81.239 | 186.082 | 1.00 | 59.92  | C |
| ATOM | 1217 | C   | ASP | A | 207 | 225.577 | 81.381 | 186.532 | 1.00 | 58.53  | C |
| ATOM | 1218 | O   | ASP | A | 207 | 225.272 | 81.747 | 187.660 | 1.00 | 80.39  | O |
| ATOM | 1219 | CB  | ASP | A | 207 | 227.785 | 80.312 | 187.037 | 1.00 | 60.66  | C |
| ATOM | 1220 | CG  | ASP | A | 207 | 227.400 | 78.869 | 186.743 | 1.00 | 80.61  | C |
| ATOM | 1221 | OD1 | ASP | A | 207 | 226.540 | 78.671 | 185.884 | 1.00 | 83.40  | O |
| ATOM | 1222 | OD2 | ASP | A | 207 | 227.955 | 77.969 | 187.369 | 1.00 | 77.29  | O |
| ATOM | 1223 | N   | PHE | A | 208 | 224.661 | 81.117 | 185.582 | 1.00 | 57.58  | N |
| ATOM | 1224 | CA  | PHE | A | 208 | 223.242 | 81.177 | 185.911 | 1.00 | 65.42  | C |
| ATOM | 1225 | C   | PHE | A | 208 | 222.554 | 79.836 | 185.650 | 1.00 | 55.77  | C |
| ATOM | 1226 | O   | PHE | A | 208 | 221.342 | 79.748 | 185.504 | 1.00 | 71.33  | O |
| ATOM | 1227 | CB  | PHE | A | 208 | 222.597 | 82.267 | 185.055 | 1.00 | 41.42  | C |
| ATOM | 1228 | CG  | PHE | A | 208 | 222.872 | 83.615 | 185.655 | 1.00 | 55.64  | C |
| ATOM | 1229 | CD1 | PHE | A | 208 | 224.177 | 84.088 | 185.707 | 1.00 | 30.42  | C |
| ATOM | 1230 | CD2 | PHE | A | 208 | 221.825 | 84.390 | 186.125 | 1.00 | 49.87  | C |
| ATOM | 1231 | CE1 | PHE | A | 208 | 224.432 | 85.349 | 186.229 | 1.00 | 68.91  | C |
| ATOM | 1232 | CE2 | PHE | A | 208 | 222.089 | 85.654 | 186.645 | 1.00 | 47.56  | C |
| ATOM | 1233 | CZ  | PHE | A | 208 | 223.390 | 86.139 | 186.697 | 1.00 | 56.42  | C |
| ATOM | 1234 | N   | GLY | A | 209 | 223.362 | 78.788 | 185.594 | 1.00 | 61.07  | N |
| ATOM | 1235 | CA  | GLY | A | 209 | 222.825 | 77.461 | 185.343 | 1.00 | 72.68  | C |
| ATOM | 1236 | C   | GLY | A | 209 | 221.723 | 77.080 | 186.309 | 1.00 | 73.62  | C |
| ATOM | 1237 | O   | GLY | A | 209 | 220.958 | 76.161 | 186.039 | 1.00 | 77.98  | O |
| ATOM | 1238 | N   | PHE | A | 210 | 221.656 | 77.777 | 187.441 | 1.00 | 83.69  | N |
| ATOM | 1239 | CA  | PHE | A | 210 | 220.624 | 77.527 | 188.439 | 1.00 | 69.57  | C |
| ATOM | 1240 | C   | PHE | A | 210 | 219.818 | 78.787 | 188.732 | 1.00 | 81.37  | C |
| ATOM | 1241 | O   | PHE | A | 210 | 218.872 | 78.738 | 189.507 | 1.00 | 58.29  | O |
| ATOM | 1242 | CB  | PHE | A | 210 | 221.225 | 77.037 | 189.753 | 1.00 | 67.31  | C |
| ATOM | 1243 | CG  | PHE | A | 210 | 222.004 | 75.774 | 189.633 | 1.00 | 73.06  | C |
| ATOM | 1244 | CD1 | PHE | A | 210 | 221.429 | 74.645 | 189.085 | 1.00 | 114.78 | C |
| ATOM | 1245 | CD2 | PHE | A | 210 | 223.306 | 75.703 | 190.097 | 1.00 | 90.32  | C |
| ATOM | 1246 | CE1 | PHE | A | 210 | 222.134 | 73.459 | 189.000 | 1.00 | 109.98 | C |
| ATOM | 1247 | CE2 | PHE | A | 210 | 224.021 | 74.522 | 190.017 | 1.00 | 108.27 | C |
| ATOM | 1248 | CZ  | PHE | A | 210 | 223.432 | 73.398 | 189.467 | 1.00 | 132.84 | C |
| ATOM | 1249 | N   | ALA | A | 211 | 220.208 | 79.913 | 188.137 | 1.00 | 81.89  | N |
| ATOM | 1250 | CA  | ALA | A | 211 | 219.490 | 81.170 | 188.341 | 1.00 | 69.02  | C |
| ATOM | 1251 | C   | ALA | A | 211 | 218.028 | 80.898 | 188.075 | 1.00 | 58.89  | C |
| ATOM | 1252 | O   | ALA | A | 211 | 217.700 | 80.102 | 187.206 | 1.00 | 66.98  | O |
| ATOM | 1253 | CB  | ALA | A | 211 | 219.992 | 82.228 | 187.381 | 1.00 | 73.43  | C |
| ATOM | 1254 | N   | LYS | A | 212 | 217.147 | 81.552 | 188.817 | 1.00 | 66.85  | N |
| ATOM | 1255 | CA  | LYS | A | 212 | 215.726 | 81.329 | 188.624 | 1.00 | 74.67  | C |
| ATOM | 1256 | C   | LYS | A | 212 | 214.892 | 82.598 | 188.785 | 1.00 | 69.94  | C |
| ATOM | 1257 | O   | LYS | A | 212 | 215.106 | 83.387 | 189.709 | 1.00 | 68.45  | O |
| ATOM | 1258 | CB  | LYS | A | 212 | 215.242 | 80.249 | 189.600 | 1.00 | 70.15  | C |
| ATOM | 1259 | CG  | LYS | A | 212 | 213.744 | 80.022 | 189.558 | 1.00 | 104.51 | C |
| ATOM | 1260 | CD  | LYS | A | 212 | 213.371 | 78.669 | 188.952 | 1.00 | 157.53 | C |
| ATOM | 1261 | CE  | LYS | A | 212 | 211.877 | 78.354 | 189.164 | 1.00 | 119.37 | C |
| ATOM | 1262 | NZ  | LYS | A | 212 | 211.408 | 77.209 | 188.336 | 1.00 | 93.54  | N |
| ATOM | 1263 | N   | GLU | A | 213 | 214.141 | 82.794 | 187.868 | 1.00 | 15.00  |   |
| ATOM | 1264 | CA  | GLU | A | 213 | 213.459 | 84.043 | 187.550 | 1.00 | 15.00  |   |
| ATOM | 1265 | CB  | GLU | A | 213 | 213.339 | 84.210 | 186.033 | 1.00 | 15.00  |   |
| ATOM | 1266 | CG  | GLU | A | 213 | 212.159 | 83.475 | 185.419 | 1.00 | 15.00  |   |
| ATOM | 1267 | CD  | GLU | A | 213 | 212.043 | 83.702 | 183.925 | 1.00 | 15.00  |   |
| ATOM | 1268 | OE1 | GLU | A | 213 | 211.180 | 83.058 | 183.289 | 1.00 | 15.00  |   |
| ATOM | 1269 | OE2 | GLU | A | 213 | 212.815 | 84.522 | 183.385 | 1.00 | 15.00  |   |
| ATOM | 1270 | C   | GLU | A | 213 | 212.074 | 84.087 | 188.185 | 1.00 | 15.00  |   |
| ATOM | 1271 | O   | GLU | A | 213 | 211.548 | 83.061 | 188.604 | 1.00 | 15.36  |   |
| ATOM | 1272 | N   | THR | A | 214 | 211.491 | 85.288 | 188.256 | 1.00 | 15.00  |   |
| ATOM | 1273 | CA  | THR | A | 214 | 210.119 | 85.515 | 188.693 | 1.00 | 15.00  |   |

TABLE 1-continued

Coordinates of the activated MAPKAP kinase-2/peptide complex

| ATOM | 1274 | CB  | THR | A | 214 | 209.149 | 84.520 | 188.029 | 1.00 | 15.00 | |
|------|------|-----|-----|---|-----|---------|--------|---------|------|-------|---|
| ATOM | 1275 | OG1 | THR | A | 214 | 209.187 | 84.691 | 186.606 | 1.00 | 15.00 | |
| ATOM | 1276 | CG2 | THR | A | 214 | 207.729 | 84.751 | 188.525 | 1.00 | 15.00 | |
| ATOM | 1277 | C   | THR | A | 214 | 209.999 | 85.380 | 190.208 | 1.00 | 15.00 | |
| ATOM | 1278 | O   | THR | A | 214 | 208.821 | 85.220 | 190.684 | 1.00 | 20.56 | |
| ATOM | 1279 | N   | THR | A | 215 | 211.054 | 85.475 | 190.986 | 1.00 | 15.00 | |
| ATOM | 1280 | CA  | THR | A | 215 | 210.986 | 85.364 | 192.438 | 1.00 | 15.00 | |
| ATOM | 1281 | CB  | THR | A | 215 | 212.132 | 84.493 | 192.987 | 1.00 | 15.00 | |
| ATOM | 1282 | OG1 | THR | A | 215 | 212.031 | 83.170 | 192.444 | 1.00 | 15.00 | |
| ATOM | 1283 | CG2 | THR | A | 215 | 212.062 | 84.420 | 194.505 | 1.00 | 15.00 | |
| ATOM | 1284 | C   | THR | A | 215 | 211.057 | 86.739 | 193.095 | 1.00 | 15.00 | |
| ATOM | 1285 | O   | THR | A | 215 | 212.111 | 87.316 | 193.358 | 1.00 | 17.54 | |
| ATOM | 1286 | N   | SER | A | 216 | 209.845 | 87.327 | 193.310 | 1.00 | 15.00 | |
| ATOM | 1287 | CA  | SER | A | 216 | 209.645 | 88.633 | 193.871 | 1.00 | 15.00 | |
| ATOM | 1288 | CB  | SER | A | 216 | 208.582 | 89.393 | 193.087 | 1.00 | 15.00 | |
| ATOM | 1289 | OG  | SER | A | 216 | 207.344 | 88.725 | 193.050 | 1.00 | 15.00 | |
| ATOM | 1290 | C   | SER | A | 216 | 209.352 | 88.649 | 195.380 | 1.00 | 15.00 | |
| ATOM | 1291 | O   | SER | A | 216 | 209.553 | 89.753 | 195.944 | 1.00 | 24.37 | |
| ATOM | 1292 | N   | HIS | A | 217 | 208.923 | 87.546 | 195.889 | 1.00 | 15.00 | |
| ATOM | 1293 | CA  | HIS | A | 217 | 208.587 | 87.117 | 197.213 | 1.00 | 15.00 | |
| ATOM | 1294 | CB  | HIS | A | 217 | 208.248 | 88.231 | 198.187 | 1.00 | 15.00 | |
| ATOM | 1295 | CG  | HIS | A | 217 | 208.489 | 87.994 | 199.627 | 1.00 | 15.00 | |
| ATOM | 1296 | CD2 | HIS | A | 217 | 209.559 | 88.383 | 200.390 | 1.00 | 15.00 | |
| ATOM | 1297 | ND1 | HIS | A | 217 | 207.605 | 87.415 | 200.500 | 1.00 | 15.00 | |
| ATOM | 1298 | CE1 | HIS | A | 217 | 208.130 | 87.392 | 201.715 | 1.00 | 15.00 | |
| ATOM | 1299 | NE2 | HIS | A | 217 | 209.316 | 87.977 | 201.671 | 1.00 | 15.00 | |
| ATOM | 1300 | C   | HIS | A | 217 | 207.430 | 86.096 | 197.115 | 1.00 | 15.00 | |
| ATOM | 1301 | O   | HIS | A | 217 | 206.272 | 86.389 | 196.895 | 1.00 | 28.08 | |
| ATOM | 1302 | N   | ASN | A | 218 | 207.933 | 84.916 | 197.149 | 1.00 | 15.00 | |
| ATOM | 1303 | CA  | ASN | A | 218 | 208.098 | 83.782 | 196.497 | 1.00 | 15.00 | |
| ATOM | 1304 | CB  | ASN | A | 218 | 207.843 | 83.860 | 194.969 | 1.00 | 15.00 | |
| ATOM | 1305 | CG  | ASN | A | 218 | 206.412 | 83.605 | 194.590 | 1.00 | 15.00 | |
| ATOM | 1306 | OD1 | ASN | A | 218 | 205.835 | 82.541 | 194.841 | 1.00 | 15.00 | |
| ATOM | 1307 | ND2 | ASN | A | 218 | 205.794 | 84.575 | 193.913 | 1.00 | 15.00 | |
| ATOM | 1308 | C   | ASN | A | 218 | 209.199 | 82.856 | 196.804 | 1.00 | 15.00 | |
| ATOM | 1309 | O   | ASN | A | 218 | 210.327 | 83.158 | 197.160 | 1.00 | 16.81 | |
| ATOM | 1310 | N   | SER | A | 219 | 208.738 | 81.608 | 196.607 | 1.00 | 15.00 | |
| ATOM | 1311 | CA  | SER | A | 219 | 209.612 | 80.496 | 196.960 | 1.00 | 15.00 | |
| ATOM | 1312 | CB  | SER | A | 219 | 208.946 | 79.616 | 198.021 | 1.00 | 15.00 | |
| ATOM | 1313 | OG  | SER | A | 219 | 207.780 | 78.995 | 197.509 | 1.00 | 15.00 | |
| ATOM | 1314 | C   | SER | A | 219 | 209.953 | 79.658 | 195.732 | 1.00 | 15.00 | |
| ATOM | 1315 | O   | SER | A | 219 | 209.421 | 79.706 | 194.646 | 1.00 | 13.95 | |
| ATOM | 1316 | N   | LEU | A | 220 | 211.012 | 78.785 | 195.962 | 1.00 | 15.00 | |
| ATOM | 1317 | CA  | LEU | A | 220 | 211.564 | 77.825 | 195.013 | 1.00 | 15.00 | |
| ATOM | 1318 | CB  | LEU | A | 220 | 212.993 | 78.219 | 194.633 | 1.00 | 15.00 | |
| ATOM | 1319 | CG  | LEU | A | 220 | 213.161 | 79.569 | 193.932 | 1.00 | 15.00 | |
| ATOM | 1320 | CD1 | LEU | A | 220 | 214.636 | 79.928 | 193.843 | 1.00 | 15.00 | |
| ATOM | 1321 | CD2 | LEU | A | 220 | 212.537 | 79.516 | 192.547 | 1.00 | 15.00 | |
| ATOM | 1322 | C   | LEU | A | 220 | 211.553 | 76.415 | 195.594 | 1.00 | 15.00 | |
| ATOM | 1323 | O   | LEU | A | 220 | 211.679 | 76.279 | 196.816 | 1.00 | 14.38 | |
| ATOM | 1324 | N   | THR | A | 221 | 211.526 | 75.374 | 194.729 | 1.00 | 15.00 | |
| ATOM | 1325 | CA  | THR | A | 221 | 211.397 | 74.011 | 195.231 | 1.00 | 15.00 | |
| ATOM | 1326 | CB  | THR | A | 221 | 210.079 | 73.365 | 194.763 | 1.00 | 15.00 | |
| ATOM | 1327 | OG1 | THR | A | 221 | 208.970 | 74.121 | 195.264 | 1.00 | 15.00 | |
| ATOM | 1328 | CG2 | THR | A | 221 | 209.981 | 71.933 | 195.268 | 1.00 | 15.00 | |
| ATOM | 1329 | C   | THR | A | 221 | 212.562 | 73.144 | 194.764 | 1.00 | 15.00 | |
| ATOM | 1330 | O   | THR | A | 221 | 212.736 | 72.026 | 195.385 | 1.00 | 15.81 | |
| TER  | 1330 |     | THR | A | 221 |         |        |         |      |       | |
| ATOM | 1331 | N   | TPO | A | 222 | 213.399 | 73.479 | 193.800 | 1.00 | 15.00 | |
| ATOM | 1332 | CA  | TPO | A | 222 | 214.459 | 72.638 | 193.257 | 1.00 | 15.00 | |
| ATOM | 1333 | CB  | TPO | A | 222 | 215.056 | 73.250 | 191.976 | 1.00 | 15.00 | |
| ATOM | 1334 | OG1 | TPO | A | 222 | 214.002 | 73.557 | 191.055 | 1.00 | 15.00 | |
| ATOM | 1335 | CG2 | TPO | A | 222 | 216.025 | 72.275 | 191.324 | 1.00 | 15.00 | |
| ATOM | 1336 | P   | TPO | A | 222 | 213.808 | 74.828 | 190.542 | 1.00 | 15.80 | P |
| ATOM | 1337 | O1P | TPO | A | 222 | 214.914 | 75.324 | 189.669 | 1.00 | 15.57 | O |
| ATOM | 1338 | O2P | TPO | A | 222 | 213.482 | 75.613 | 191.784 | 1.00 | 15.91 | O |
| ATOM | 1339 | O3P | TPO | A | 222 | 212.591 | 74.609 | 189.572 | 1.00 | 15.73 | O |
| ATOM | 1340 | C   | TPO | A | 222 | 215.578 | 72.444 | 194.276 | 1.00 | 15.00 | |
| ATOM | 1341 | O   | TPO | A | 222 | 216.123 | 73.375 | 194.857 | 1.00 | 12.56 | |
| ATOM | 1342 | N   | PRO | A | 223 | 215.917 | 71.098 | 194.555 | 1.00 | 15.00 | |
| ATOM | 1343 | CD  | PRO | A | 223 | 215.209 | 69.889 | 194.261 | 1.00 | 15.00 | |
| ATOM | 1344 | CA  | PRO | A | 223 | 217.121 | 70.849 | 195.355 | 1.00 | 15.00 | |
| ATOM | 1345 | CB  | PRO | A | 223 | 216.915 | 69.424 | 195.868 | 1.00 | 15.00 | |
| ATOM | 1346 | CG  | PRO | A | 223 | 216.042 | 68.783 | 194.845 | 1.00 | 15.00 | |
| ATOM | 1347 | C   | PRO | A | 223 | 218.396 | 70.958 | 194.525 | 1.00 | 15.00 | |
| ATOM | 1348 | O   | PRO | A | 223 | 218.639 | 70.105 | 193.676 | 1.00 | 12.12 | |
| ATOM | 1349 | N   | CYS | A | 224 | 219.010 | 72.137 | 194.641 | 1.00 | 15.00 | |
| ATOM | 1350 | CA  | CYS | A | 224 | 220.180 | 72.438 | 193.826 | 1.00 | 15.00 | |

TABLE 1-continued

Coordinates of the activated MAPKAP kinase-2/peptide complex

| ATOM | 1351 | CB | CYS | A | 224 | 219.754 | 73.079 | 192.503 | 1.00 | 15.00 |
|---|---|---|---|---|---|---|---|---|---|---|
| ATOM | 1352 | SG | CYS | A | 224 | 219.284 | 71.899 | 191.217 | 1.00 | 15.00 |
| ATOM | 1353 | C | CYS | A | 224 | 221.138 | 73.367 | 194.565 | 1.00 | 15.00 |
| ATOM | 1354 | O | CYS | A | 224 | 220.831 | 73.947 | 195.595 | 1.00 | 9.31 |
| ATOM | 1355 | N | TYR | A | 225 | 222.314 | 73.544 | 193.951 | 1.00 | 15.00 |
| ATOM | 1356 | CA | TYR | A | 225 | 223.376 | 74.375 | 194.506 | 1.00 | 15.00 |
| ATOM | 1357 | CB | TYR | A | 225 | 223.004 | 74.838 | 195.916 | 1.00 | 15.00 |
| ATOM | 1358 | CG | TYR | A | 225 | 222.663 | 73.709 | 196.863 | 1.00 | 15.00 |
| ATOM | 1359 | CD1 | TYR | A | 225 | 223.543 | 72.652 | 197.060 | 1.00 | 15.00 |
| ATOM | 1360 | CE1 | TYR | A | 225 | 223.236 | 71.620 | 197.924 | 1.00 | 15.00 |
| ATOM | 1361 | CD2 | TYR | A | 225 | 221.461 | 73.699 | 197.556 | 1.00 | 15.00 |
| ATOM | 1362 | CE2 | TYR | A | 225 | 221.146 | 72.667 | 198.422 | 1.00 | 15.00 |
| ATOM | 1363 | CZ | TYR | A | 225 | 222.036 | 71.631 | 198.602 | 1.00 | 15.00 |
| ATOM | 1364 | OH | TYR | A | 225 | 221.725 | 70.605 | 199.464 | 1.00 | 15.00 |
| ATOM | 1365 | C | TYR | A | 225 | 224.699 | 73.618 | 194.543 | 1.00 | 15.00 |
| ATOM | 1366 | O | TYR | A | 225 | 224.872 | 72.695 | 193.743 | 1.00 | 11.69 |
| ATOM | 1367 | N | THR | A | 226 | 225.564 | 74.018 | 195.383 | 1.00 | 15.00 |
| ATOM | 1368 | CA | THR | A | 226 | 226.833 | 73.340 | 195.622 | 1.00 | 15.00 |
| ATOM | 1369 | CB | THR | A | 226 | 228.026 | 74.279 | 195.362 | 1.00 | 15.00 |
| ATOM | 1370 | OG1 | THR | A | 226 | 229.137 | 73.880 | 196.175 | 1.00 | 15.00 |
| ATOM | 1371 | CG2 | THR | A | 226 | 227.653 | 75.716 | 195.691 | 1.00 | 15.00 |
| ATOM | 1372 | C | THR | A | 226 | 226.916 | 72.827 | 197.056 | 1.00 | 15.00 |
| ATOM | 1373 | O | THR | A | 226 | 226.576 | 73.621 | 197.967 | 1.00 | 9.55 |
| ATOM | 1374 | N | PRO | A | 227 | 227.140 | 71.546 | 197.345 | 1.00 | 15.00 |
| ATOM | 1375 | CD | PRO | A | 227 | 228.192 | 71.043 | 196.515 | 1.00 | 15.00 |
| ATOM | 1376 | CA | PRO | A | 227 | 227.065 | 70.837 | 198.626 | 1.00 | 15.00 |
| ATOM | 1377 | CB | PRO | A | 227 | 227.911 | 69.587 | 198.389 | 1.00 | 15.00 |
| ATOM | 1378 | CG | PRO | A | 227 | 228.885 | 69.992 | 197.336 | 1.00 | 15.00 |
| ATOM | 1379 | C | PRO | A | 227 | 227.621 | 71.670 | 199.777 | 1.00 | 15.00 |
| ATOM | 1380 | O | PRO | A | 227 | 226.859 | 71.868 | 200.794 | 1.00 | 10.86 |
| ATOM | 1381 | N | TYR | A | 228 | 228.838 | 72.168 | 199.777 | 1.00 | 15.00 |
| ATOM | 1382 | CA | TYR | A | 228 | 229.509 | 72.872 | 200.863 | 1.00 | 15.00 |
| ATOM | 1383 | CB | TYR | A | 228 | 230.999 | 73.029 | 200.552 | 1.00 | 15.00 |
| ATOM | 1384 | CG | TYR | A | 228 | 231.748 | 71.718 | 200.461 | 1.00 | 15.00 |
| ATOM | 1385 | CD1 | TYR | A | 228 | 232.077 | 71.168 | 199.228 | 1.00 | 15.00 |
| ATOM | 1386 | CE1 | TYR | A | 228 | 232.762 | 69.972 | 199.141 | 1.00 | 15.00 |
| ATOM | 1387 | CD2 | TYR | A | 228 | 232.124 | 71.030 | 201.607 | 1.00 | 15.00 |
| ATOM | 1388 | CE2 | TYR | A | 228 | 232.808 | 69.831 | 201.527 | 1.00 | 15.00 |
| ATOM | 1389 | CZ | TYR | A | 228 | 233.124 | 69.307 | 200.293 | 1.00 | 15.00 |
| ATOM | 1390 | OH | TYR | A | 228 | 233.805 | 68.114 | 200.210 | 1.00 | 15.00 |
| ATOM | 1391 | C | TYR | A | 228 | 228.883 | 74.243 | 201.095 | 1.00 | 15.00 |
| ATOM | 1392 | O | TYR | A | 228 | 229.096 | 74.833 | 202.195 | 1.00 | 10.82 |
| ATOM | 1393 | N | TYR | A | 229 | 228.075 | 74.767 | 200.161 | 1.00 | 15.00 |
| ATOM | 1394 | CA | TYR | A | 229 | 227.513 | 76.111 | 200.221 | 1.00 | 15.00 |
| ATOM | 1395 | CB | TYR | A | 229 | 227.822 | 76.871 | 198.929 | 1.00 | 15.00 |
| ATOM | 1396 | CG | TYR | A | 229 | 229.281 | 77.238 | 198.768 | 1.00 | 15.00 |
| ATOM | 1397 | CD1 | TYR | A | 229 | 229.951 | 76.991 | 197.577 | 1.00 | 15.00 |
| ATOM | 1398 | CE1 | TYR | A | 229 | 231.283 | 77.325 | 197.425 | 1.00 | 15.00 |
| ATOM | 1399 | CD2 | TYR | A | 229 | 229.987 | 77.829 | 199.807 | 1.00 | 15.00 |
| ATOM | 1400 | CE2 | TYR | A | 229 | 231.320 | 78.165 | 199.661 | 1.00 | 15.00 |
| ATOM | 1401 | CZ | TYR | A | 229 | 231.962 | 77.911 | 198.470 | 1.00 | 15.00 |
| ATOM | 1402 | OH | TYR | A | 229 | 233.289 | 78.245 | 198.324 | 1.00 | 15.00 |
| ATOM | 1403 | C | TYR | A | 229 | 226.005 | 76.064 | 200.443 | 1.00 | 15.00 |
| ATOM | 1404 | O | TYR | A | 229 | 225.390 | 77.180 | 200.548 | 1.00 | 10.79 |
| ATOM | 1405 | N | VAL | A | 230 | 225.363 | 74.929 | 200.540 | 1.00 | 15.00 |
| ATOM | 1406 | CA | VAL | A | 230 | 223.918 | 74.808 | 200.689 | 1.00 | 15.00 |
| ATOM | 1407 | CB | VAL | A | 230 | 223.468 | 73.336 | 200.596 | 1.00 | 15.00 |
| ATOM | 1408 | CG1 | VAL | A | 230 | 224.223 | 72.492 | 201.612 | 1.00 | 15.00 |
| ATOM | 1409 | CG2 | VAL | A | 230 | 221.967 | 73.230 | 200.819 | 1.00 | 15.00 |
| ATOM | 1410 | C | VAL | A | 230 | 223.457 | 75.378 | 202.027 | 1.00 | 15.00 |
| ATOM | 1411 | O | VAL | A | 230 | 224.048 | 75.172 | 203.074 | 1.00 | 9.09 |
| ATOM | 1412 | CB | ALA | A | 231 | 220.726 | 77.807 | 202.673 | 1.00 | 15.00 |
| ATOM | 1413 | C | ALA | A | 231 | 220.871 | 75.607 | 203.851 | 1.00 | 15.00 |
| ATOM | 1414 | O | ALA | A | 231 | 220.417 | 74.655 | 203.184 | 1.00 | 9.49 |
| ATOM | 1415 | N | ALA | A | 231 | 222.349 | 76.103 | 201.918 | 1.00 | 15.00 |
| ATOM | 1416 | CA | ALA | A | 231 | 221.655 | 76.680 | 203.104 | 1.00 | 15.00 |
| ATOM | 1417 | N | PRO | A | 232 | 220.755 | 75.645 | 205.185 | 1.00 | 15.00 |
| ATOM | 1418 | CD | PRO | A | 232 | 220.885 | 76.873 | 205.909 | 1.00 | 15.00 |
| ATOM | 1419 | CA | PRO | A | 232 | 220.064 | 74.616 | 205.968 | 1.00 | 15.00 |
| ATOM | 1420 | CB | PRO | A | 232 | 220.102 | 75.171 | 207.392 | 1.00 | 15.00 |
| ATOM | 1421 | CG | PRO | A | 232 | 220.173 | 76.648 | 207.213 | 1.00 | 15.00 |
| ATOM | 1422 | C | PRO | A | 232 | 218.629 | 74.402 | 205.498 | 1.00 | 15.00 |
| ATOM | 1423 | O | PRO | A | 232 | 218.155 | 73.251 | 205.520 | 1.00 | 10.53 |
| ATOM | 1424 | N | GLU | A | 233 | 217.931 | 75.458 | 205.055 | 1.00 | 15.00 |
| ATOM | 1425 | CA | GLU | A | 233 | 216.540 | 75.343 | 204.633 | 1.00 | 15.00 |
| ATOM | 1426 | CB | GLU | A | 233 | 215.917 | 76.732 | 204.474 | 1.00 | 15.00 |
| ATOM | 1427 | CG | GLU | A | 233 | 214.503 | 76.844 | 205.020 | 1.00 | 15.00 |
| ATOM | 1428 | CD | GLU | A | 233 | 213.601 | 77.678 | 204.133 | 1.00 | 15.00 |

TABLE 1-continued

Coordinates of the activated MAPKAP kinase-2/peptide complex

| ATOM | 1429 | OE1 | GLU | A | 233 | 212.376 | 77.703 | 204.384 | 1.00 | 15.00 | |
|------|------|-----|-----|---|-----|---------|--------|---------|------|-------|---|
| ATOM | 1430 | OE2 | GLU | A | 233 | 214.114 | 78.309 | 203.185 | 1.00 | 15.00 | |
| ATOM | 1431 | C | GLU | A | 233 | 216.428 | 74.573 | 203.321 | 1.00 | 15.00 | |
| ATOM | 1432 | O | GLU | A | 233 | 215.392 | 73.897 | 203.095 | 1.00 | 10.95 | |
| ATOM | 1433 | N | VAL | A | 234 | 217.465 | 74.585 | 202.462 | 1.00 | 15.00 | |
| ATOM | 1434 | CA | VAL | A | 234 | 217.484 | 73.810 | 201.227 | 1.00 | 15.00 | |
| ATOM | 1435 | CB | VAL | A | 234 | 218.603 | 74.293 | 200.282 | 1.00 | 15.00 | |
| ATOM | 1436 | CG1 | VAL | A | 234 | 218.713 | 73.363 | 199.084 | 1.00 | 15.00 | |
| ATOM | 1437 | CG2 | VAL | A | 234 | 218.331 | 75.720 | 199.832 | 1.00 | 15.00 | |
| ATOM | 1438 | C | VAL | A | 234 | 217.690 | 72.327 | 201.515 | 1.00 | 15.00 | |
| ATOM | 1439 | O | VAL | A | 234 | 217.255 | 71.447 | 200.787 | 1.00 | 10.86 | |
| ATOM | 1440 | N | LEU | A | 235 | 218.265 | 72.046 | 202.723 | 1.00 | 15.00 | |
| ATOM | 1441 | CA | LEU | A | 235 | 218.512 | 70.679 | 203.169 | 1.00 | 15.00 | |
| ATOM | 1442 | CB | LEU | A | 235 | 219.760 | 70.629 | 204.053 | 1.00 | 15.00 | |
| ATOM | 1443 | CG | LEU | A | 235 | 221.077 | 71.046 | 203.392 | 1.00 | 15.00 | |
| ATOM | 1444 | CD1 | LEU | A | 235 | 222.165 | 71.181 | 204.445 | 1.00 | 15.00 | |
| ATOM | 1445 | CD2 | LEU | A | 235 | 221.473 | 70.027 | 202.337 | 1.00 | 15.00 | |
| ATOM | 1446 | C | LEU | A | 235 | 217.313 | 70.129 | 203.934 | 1.00 | 15.00 | |
| ATOM | 1447 | O | LEU | A | 235 | 217.361 | 69.014 | 204.500 | 1.00 | 10.16 | |
| ATOM | 1448 | N | GLY | A | 236 | 216.252 | 70.887 | 203.946 | 1.00 | 15.00 | |
| ATOM | 1449 | CA | GLY | A | 236 | 214.958 | 70.501 | 204.475 | 1.00 | 15.00 | |
| ATOM | 1450 | C | GLY | A | 236 | 213.924 | 70.292 | 203.386 | 1.00 | 15.00 | |
| ATOM | 1451 | O | GLY | A | 236 | 214.223 | 70.745 | 202.251 | 1.00 | 15.43 | |
| ATOM | 1452 | N | PRO | A | 237 | 212.800 | 69.571 | 203.652 | 1.00 | 15.00 | |
| ATOM | 1453 | CD | PRO | A | 237 | 212.368 | 68.973 | 204.879 | 1.00 | 15.00 | |
| ATOM | 1454 | CA | PRO | A | 237 | 211.813 | 69.401 | 202.581 | 1.00 | 15.00 | |
| ATOM | 1455 | CB | PRO | A | 237 | 210.885 | 68.315 | 203.124 | 1.00 | 15.00 | |
| ATOM | 1456 | CG | PRO | A | 237 | 210.988 | 68.445 | 204.605 | 1.00 | 15.00 | |
| ATOM | 1457 | C | PRO | A | 237 | 211.047 | 70.688 | 202.295 | 1.00 | 15.00 | |
| ATOM | 1458 | O | PRO | A | 237 | 211.186 | 71.681 | 202.987 | 1.00 | 19.34 | |
| ATOM | 1459 | N | GLU | A | 238 | 210.242 | 70.629 | 201.243 | 1.00 | 15.00 | |
| ATOM | 1460 | CA | GLU | A | 238 | 209.352 | 71.651 | 200.704 | 1.00 | 15.00 | |
| ATOM | 1461 | CB | GLU | A | 238 | 208.401 | 72.153 | 201.793 | 1.00 | 15.00 | |
| ATOM | 1462 | CG | GLU | A | 238 | 207.415 | 71.107 | 202.287 | 1.00 | 15.00 | |
| ATOM | 1463 | CD | GLU | A | 238 | 206.523 | 71.625 | 203.397 | 1.00 | 15.00 | |
| ATOM | 1464 | OE1 | GLU | A | 238 | 205.595 | 70.894 | 203.807 | 1.00 | 15.00 | |
| ATOM | 1465 | OE2 | GLU | A | 238 | 206.747 | 72.764 | 203.860 | 1.00 | 15.00 | |
| ATOM | 1466 | C | GLU | A | 238 | 210.146 | 72.820 | 200.131 | 1.00 | 15.00 | |
| ATOM | 1467 | O | GLU | A | 238 | 211.191 | 72.629 | 199.449 | 1.00 | 25.64 | |
| ATOM | 1468 | N | LYS | A | 239 | 209.723 | 74.116 | 200.341 | 1.00 | 15.00 | |
| ATOM | 1469 | CA | LYS | A | 239 | 210.244 | 75.246 | 199.582 | 1.00 | 15.00 | |
| ATOM | 1470 | CB | LYS | A | 239 | 209.094 | 76.047 | 198.966 | 1.00 | 15.00 | |
| ATOM | 1471 | CG | LYS | A | 239 | 208.369 | 75.328 | 197.840 | 1.00 | 15.00 | |
| ATOM | 1472 | CD | LYS | A | 239 | 207.259 | 76.189 | 197.261 | 1.00 | 15.00 | |
| ATOM | 1473 | CE | LYS | A | 239 | 206.534 | 75.469 | 196.134 | 1.00 | 15.00 | |
| ATOM | 1474 | NZ | LYS | A | 239 | 205.442 | 76.301 | 195.556 | 1.00 | 15.00 | |
| ATOM | 1475 | C | LYS | A | 239 | 211.090 | 76.155 | 200.466 | 1.00 | 15.00 | |
| ATOM | 1476 | O | LYS | A | 239 | 211.196 | 76.171 | 201.667 | 1.00 | 16.81 | |
| ATOM | 1477 | N | TYR | A | 240 | 211.840 | 77.115 | 199.704 | 1.00 | 15.00 | |
| ATOM | 1478 | CA | TYR | A | 240 | 212.736 | 78.087 | 200.316 | 1.00 | 15.00 | |
| ATOM | 1479 | CB | TYR | A | 240 | 214.163 | 77.536 | 200.363 | 1.00 | 15.00 | |
| ATOM | 1480 | CG | TYR | A | 240 | 214.299 | 76.138 | 199.801 | 1.00 | 15.00 | |
| ATOM | 1481 | CD1 | TYR | A | 240 | 214.813 | 75.929 | 198.526 | 1.00 | 15.00 | |
| ATOM | 1482 | CE1 | TYR | A | 240 | 214.940 | 74.655 | 198.009 | 1.00 | 15.00 | |
| ATOM | 1483 | CD2 | TYR | A | 240 | 213.913 | 75.030 | 200.542 | 1.00 | 15.00 | |
| ATOM | 1484 | CE2 | TYR | A | 240 | 214.038 | 73.752 | 200.030 | 1.00 | 15.00 | |
| ATOM | 1485 | CZ | TYR | A | 240 | 214.550 | 73.570 | 198.765 | 1.00 | 15.00 | |
| ATOM | 1486 | OH | TYR | A | 240 | 214.674 | 72.298 | 198.252 | 1.00 | 15.00 | |
| ATOM | 1487 | C | TYR | A | 240 | 212.717 | 79.406 | 199.552 | 1.00 | 15.00 | |
| ATOM | 1488 | O | TYR | A | 240 | 212.436 | 79.469 | 198.354 | 1.00 | 13.90 | |
| ATOM | 1489 | N | ASP | A | 241 | 213.113 | 80.515 | 200.250 | 1.00 | 15.00 | |
| ATOM | 1490 | CA | ASP | A | 241 | 213.048 | 81.860 | 199.690 | 1.00 | 15.00 | |
| ATOM | 1491 | CB | ASP | A | 241 | 212.482 | 82.836 | 200.725 | 1.00 | 15.00 | |
| ATOM | 1492 | CG | ASP | A | 241 | 211.007 | 82.608 | 200.994 | 1.00 | 15.00 | |
| ATOM | 1493 | OD1 | ASP | A | 241 | 210.289 | 82.190 | 200.062 | 1.00 | 15.00 | |
| ATOM | 1494 | OD2 | ASP | A | 241 | 210.567 | 82.847 | 202.138 | 1.00 | 15.00 | |
| ATOM | 1495 | C | ASP | A | 241 | 214.426 | 82.330 | 199.237 | 1.00 | 15.00 | |
| ATOM | 1496 | O | ASP | A | 241 | 215.421 | 81.629 | 199.180 | 1.00 | 12.46 | |
| ATOM | 1497 | N | LYS | A | 242 | 214.597 | 83.587 | 198.906 | 1.00 | 106.74 | N |
| ATOM | 1498 | CA | LYS | A | 242 | 215.786 | 84.284 | 198.467 | 1.00 | 86.50 | C |
| ATOM | 1499 | C | LYS | A | 242 | 216.900 | 84.299 | 199.494 | 1.00 | 99.35 | C |
| ATOM | 1500 | O | LYS | A | 242 | 217.948 | 84.893 | 199.254 | 1.00 | 106.37 | O |
| ATOM | 1501 | CB | LYS | A | 242 | 215.446 | 85.726 | 198.107 | 1.00 | 97.76 | C |
| ATOM | 1502 | CG | LYS | A | 242 | 214.108 | 86.236 | 198.608 | 1.00 | 71.36 | C |
| ATOM | 1503 | CD | LYS | A | 242 | 213.651 | 87.417 | 197.771 | 1.00 | 103.00 | C |
| ATOM | 1504 | CE | LYS | A | 242 | 212.555 | 88.212 | 198.477 | 1.00 | 138.19 | C |
| ATOM | 1505 | NZ | LYS | A | 242 | 212.180 | 89.484 | 197.778 | 1.00 | 123.67 | N |
| ATOM | 1506 | N | SER | A | 243 | 216.681 | 83.659 | 200.637 | 1.00 | 97.75 | N |

TABLE 1-continued

Coordinates of the activated MAPKAP kinase-2/peptide complex

| ATOM | 1507 | CA | SER | A | 243 | 217.683 | 83.627 | 201.704 | 1.00 | 84.81 | C |
|------|------|-----|-----|---|-----|---------|--------|---------|------|--------|---|
| ATOM | 1508 | C | SER | A | 243 | 218.986 | 82.926 | 201.333 | 1.00 | 82.48 | C |
| ATOM | 1509 | O | SER | A | 243 | 220.025 | 83.174 | 201.948 | 1.00 | 74.56 | O |
| ATOM | 1510 | CB | SER | A | 243 | 217.097 | 82.973 | 202.940 | 1.00 | 77.67 | C |
| ATOM | 1511 | OG | SER | A | 243 | 215.950 | 83.691 | 203.344 | 1.00 | 121.59 | O |
| ATOM | 1512 | N | CYS | A | 244 | 218.944 | 82.044 | 200.343 | 1.00 | 67.22 | N |
| ATOM | 1513 | CA | CYS | A | 244 | 220.098 | 81.217 | 200.052 | 1.00 | 78.41 | C |
| ATOM | 1514 | C | CYS | A | 244 | 221.259 | 82.130 | 199.674 | 1.00 | 64.58 | C |
| ATOM | 1515 | O | CYS | A | 244 | 222.377 | 81.930 | 200.139 | 1.00 | 67.24 | O |
| ATOM | 1516 | CB | CYS | A | 244 | 219.790 | 80.254 | 198.911 | 1.00 | 64.99 | C |
| ATOM | 1517 | SG | CYS | A | 244 | 219.163 | 81.050 | 197.435 | 1.00 | 91.08 | S |
| ATOM | 1518 | N | ASP | A | 245 | 220.988 | 83.129 | 198.834 | 1.00 | 49.99 | N |
| ATOM | 1519 | CA | ASP | A | 245 | 222.016 | 84.076 | 198.416 | 1.00 | 45.00 | C |
| ATOM | 1520 | C | ASP | A | 245 | 222.720 | 84.635 | 199.651 | 1.00 | 60.39 | C |
| ATOM | 1521 | O | ASP | A | 245 | 223.952 | 84.702 | 199.688 | 1.00 | 67.65 | O |
| ATOM | 1522 | CB | ASP | A | 245 | 221.410 | 85.236 | 197.620 | 1.00 | 69.55 | C |
| ATOM | 1523 | CG | ASP | A | 245 | 221.092 | 84.874 | 196.180 | 1.00 | 60.27 | C |
| ATOM | 1524 | OD1 | ASP | A | 245 | 221.535 | 83.802 | 195.715 | 1.00 | 73.75 | O |
| ATOM | 1525 | OD2 | ASP | A | 245 | 220.410 | 85.679 | 195.506 | 1.00 | 70.27 | O |
| ATOM | 1526 | N | MET | A | 246 | 221.937 | 85.033 | 200.659 | 1.00 | 43.54 | N |
| ATOM | 1527 | CA | MET | A | 246 | 222.494 | 85.577 | 201.898 | 1.00 | 64.86 | C |
| ATOM | 1528 | C | MET | A | 246 | 223.266 | 84.526 | 202.684 | 1.00 | 67.48 | C |
| ATOM | 1529 | O | MET | A | 246 | 224.198 | 84.855 | 203.425 | 1.00 | 67.31 | O |
| ATOM | 1530 | CB | MET | A | 246 | 221.401 | 86.146 | 202.790 | 1.00 | 52.62 | C |
| ATOM | 1531 | CG | MET | A | 246 | 220.635 | 87.263 | 202.163 | 1.00 | 60.79 | C |
| ATOM | 1532 | SD | MET | A | 246 | 221.708 | 88.445 | 201.385 | 1.00 | 66.30 | S |
| ATOM | 1533 | CE | MET | A | 246 | 222.403 | 89.309 | 202.804 | 1.00 | 55.43 | C |
| ATOM | 1534 | N | TRP | A | 247 | 222.868 | 83.265 | 202.536 | 1.00 | 54.14 | N |
| ATOM | 1535 | CA | TRP | A | 247 | 223.551 | 82.177 | 203.215 | 1.00 | 62.36 | C |
| ATOM | 1536 | C | TRP | A | 247 | 224.934 | 82.015 | 202.592 | 1.00 | 62.90 | C |
| ATOM | 1537 | O | TRP | A | 247 | 225.951 | 82.071 | 203.287 | 1.00 | 62.42 | O |
| ATOM | 1538 | CB | TRP | A | 247 | 222.748 | 80.888 | 203.074 | 1.00 | 69.04 | C |
| ATOM | 1539 | CG | TRP | A | 247 | 223.470 | 79.670 | 203.559 | 1.00 | 86.20 | C |
| ATOM | 1540 | CD1 | TRP | A | 247 | 224.327 | 78.896 | 202.844 | 1.00 | 72.11 | C |
| ATOM | 1541 | CD2 | TRP | A | 247 | 223.430 | 79.110 | 204.885 | 1.00 | 75.65 | C |
| ATOM | 1542 | NE1 | TRP | A | 247 | 224.827 | 77.885 | 203.636 | 1.00 | 81.90 | N |
| ATOM | 1543 | CE2 | TRP | A | 247 | 224.293 | 77.999 | 204.893 | 1.00 | 68.57 | C |
| ATOM | 1544 | CE3 | TRP | A | 247 | 222.749 | 79.446 | 206.064 | 1.00 | 91.13 | C |
| ATOM | 1545 | CZ2 | TRP | A | 247 | 224.500 | 77.221 | 206.030 | 1.00 | 68.02 | C |
| ATOM | 1546 | CZ3 | TRP | A | 247 | 222.952 | 78.669 | 207.193 | 1.00 | 82.48 | C |
| ATOM | 1547 | CH2 | TRP | A | 247 | 223.821 | 77.572 | 207.166 | 1.00 | 74.62 | C |
| ATOM | 1548 | N | SER | A | 248 | 224.959 | 81.829 | 201.274 | 1.00 | 77.02 | N |
| ATOM | 1549 | CA | SER | A | 248 | 226.203 | 81.676 | 200.531 | 1.00 | 73.53 | C |
| ATOM | 1550 | C | SER | A | 248 | 227.156 | 82.786 | 200.892 | 1.00 | 80.75 | C |
| ATOM | 1551 | O | SER | A | 248 | 228.369 | 82.583 | 200.943 | 1.00 | 84.06 | O |
| ATOM | 1552 | CB | SER | A | 248 | 225.930 | 81.731 | 199.043 | 1.00 | 67.92 | C |
| ATOM | 1553 | OG | SER | A | 248 | 225.112 | 80.642 | 198.668 | 1.00 | 118.25 | O |
| ATOM | 1554 | N | LEU | A | 249 | 226.593 | 83.967 | 201.130 | 1.00 | 76.04 | N |
| ATOM | 1555 | CA | LEU | A | 249 | 227.378 | 85.132 | 201.506 | 1.00 | 82.09 | C |
| ATOM | 1556 | C | LEU | A | 249 | 228.081 | 84.869 | 202.845 | 1.00 | 84.27 | C |
| ATOM | 1557 | O | LEU | A | 249 | 229.298 | 85.035 | 202.960 | 1.00 | 83.90 | O |
| ATOM | 1558 | CB | LEU | A | 249 | 226.473 | 86.363 | 201.610 | 1.00 | 85.62 | C |
| ATOM | 1559 | CG | LEU | A | 249 | 227.049 | 87.629 | 200.964 | 1.00 | 77.42 | C |
| ATOM | 1560 | CD1 | LEU | A | 249 | 227.250 | 87.346 | 199.493 | 1.00 | 68.42 | C |
| ATOM | 1561 | CD2 | LEU | A | 249 | 226.119 | 88.832 | 201.153 | 1.00 | 95.64 | C |
| ATOM | 1562 | N | GLY | A | 250 | 227.318 | 84.449 | 203.851 | 1.00 | 64.22 | N |
| ATOM | 1563 | CA | GLY | A | 250 | 227.915 | 84.165 | 205.147 | 1.00 | 62.72 | C |
| ATOM | 1564 | C | GLY | A | 250 | 229.103 | 83.231 | 204.998 | 1.00 | 63.71 | C |
| ATOM | 1565 | O | GLY | A | 250 | 230.220 | 83.544 | 205.418 | 1.00 | 57.98 | O |
| ATOM | 1566 | N | VAL | A | 251 | 228.855 | 82.076 | 204.387 | 1.00 | 57.35 | N |
| ATOM | 1567 | CA | VAL | A | 251 | 229.902 | 81.091 | 204.152 | 1.00 | 72.77 | C |
| ATOM | 1568 | C | VAL | A | 251 | 231.130 | 81.779 | 203.587 | 1.00 | 65.76 | C |
| ATOM | 1569 | O | VAL | A | 251 | 232.239 | 81.624 | 204.093 | 1.00 | 72.08 | O |
| ATOM | 1570 | CB | VAL | A | 251 | 229.474 | 80.052 | 203.129 | 1.00 | 72.02 | C |
| ATOM | 1571 | CG1 | VAL | A | 251 | 230.627 | 79.119 | 202.852 | 1.00 | 48.81 | C |
| ATOM | 1572 | CG2 | VAL | A | 251 | 228.255 | 79.312 | 203.617 | 1.00 | 45.51 | C |
| ATOM | 1573 | N | ILE | A | 252 | 230.927 | 82.544 | 202.525 | 1.00 | 65.58 | N |
| ATOM | 1574 | CA | ILE | A | 252 | 232.036 | 83.248 | 201.899 | 1.00 | 68.61 | C |
| ATOM | 1575 | C | ILE | A | 252 | 232.722 | 84.197 | 202.876 | 1.00 | 77.12 | C |
| ATOM | 1576 | O | ILE | A | 252 | 233.932 | 84.098 | 203.088 | 1.00 | 79.18 | O |
| ATOM | 1577 | CB | ILE | A | 252 | 231.564 | 84.008 | 200.634 | 1.00 | 65.58 | C |
| ATOM | 1578 | CG1 | ILE | A | 252 | 231.151 | 82.989 | 199.570 | 1.00 | 42.53 | C |
| ATOM | 1579 | CG2 | ILE | A | 252 | 232.679 | 84.891 | 200.102 | 1.00 | 53.46 | C |
| ATOM | 1580 | CD1 | ILE | A | 252 | 230.557 | 83.587 | 198.355 | 1.00 | 59.04 | C |
| ATOM | 1581 | N | MET | A | 253 | 231.956 | 85.091 | 203.498 | 1.00 | 72.95 | N |
| ATOM | 1582 | CA | MET | A | 253 | 232.553 | 86.028 | 204.444 | 1.00 | 81.03 | C |
| ATOM | 1583 | C | MET | A | 253 | 233.367 | 85.286 | 205.497 | 1.00 | 75.68 | C |
| ATOM | 1584 | O | MET | A | 253 | 234.460 | 85.724 | 205.883 | 1.00 | 79.62 | O |

TABLE 1-continued

Coordinates of the activated MAPKAP kinase-2/peptide complex

| ATOM | 1585 | CB  | MET | A | 253 | 231.486 | 86.866 | 205.149 | 1.00 | 64.17  | C |
|------|------|-----|-----|---|-----|---------|--------|---------|------|--------|---|
| ATOM | 1586 | CG  | MET | A | 253 | 232.083 | 88.081 | 205.819 | 1.00 | 54.30  | C |
| ATOM | 1587 | SD  | MET | A | 253 | 230.954 | 88.969 | 206.885 | 1.00 | 85.00  | S |
| ATOM | 1588 | CE  | MET | A | 253 | 229.555 | 89.250 | 205.802 | 1.00 | 83.83  | C |
| ATOM | 1589 | N   | TYR | A | 254 | 232.829 | 84.161 | 205.960 | 1.00 | 81.14  | N |
| ATOM | 1590 | CA  | TYR | A | 254 | 233.513 | 83.370 | 206.969 | 1.00 | 68.03  | C |
| ATOM | 1591 | C   | TYR | A | 254 | 234.879 | 83.008 | 206.419 | 1.00 | 74.50  | C |
| ATOM | 1592 | O   | TYR | A | 254 | 235.901 | 83.519 | 206.879 | 1.00 | 78.65  | O |
| ATOM | 1593 | CB  | TYR | A | 254 | 232.711 | 82.107 | 207.279 | 1.00 | 66.09  | C |
| ATOM | 1594 | CG  | TYR | A | 254 | 233.253 | 81.291 | 208.427 | 1.00 | 68.80  | C |
| ATOM | 1595 | CD1 | TYR | A | 254 | 234.285 | 80.388 | 208.230 | 1.00 | 93.85  | C |
| ATOM | 1596 | CD2 | TYR | A | 254 | 232.739 | 81.434 | 209.713 | 1.00 | 66.37  | C |
| ATOM | 1597 | CE1 | TYR | A | 254 | 234.797 | 79.640 | 209.281 | 1.00 | 93.85  | C |
| ATOM | 1598 | CE2 | TYR | A | 254 | 233.238 | 80.696 | 210.775 | 1.00 | 60.25  | C |
| ATOM | 1599 | CZ  | TYR | A | 254 | 234.270 | 79.797 | 210.553 | 1.00 | 78.16  | C |
| ATOM | 1600 | OH  | TYR | A | 254 | 234.780 | 79.043 | 211.592 | 1.00 | 83.85  | O |
| ATOM | 1601 | N   | ILE | A | 255 | 234.876 | 82.148 | 205.405 | 1.00 | 71.34  | N |
| ATOM | 1602 | CA  | ILE | A | 255 | 236.099 | 81.690 | 204.774 | 1.00 | 61.37  | C |
| ATOM | 1603 | C   | ILE | A | 255 | 237.128 | 82.782 | 204.558 | 1.00 | 76.55  | C |
| ATOM | 1604 | O   | ILE | A | 255 | 238.298 | 82.590 | 204.870 | 1.00 | 92.35  | O |
| ATOM | 1605 | CB  | ILE | A | 255 | 235.810 | 81.046 | 203.443 | 1.00 | 62.35  | C |
| ATOM | 1606 | CG1 | ILE | A | 255 | 234.928 | 79.819 | 203.653 | 1.00 | 62.67  | C |
| ATOM | 1607 | CG2 | ILE | A | 255 | 237.107 | 80.661 | 202.790 | 1.00 | 76.47  | C |
| ATOM | 1608 | CD1 | ILE | A | 255 | 234.514 | 79.131 | 202.387 | 1.00 | 57.99  | C |
| ATOM | 1609 | N   | LEU | A | 256 | 236.709 | 83.925 | 204.024 | 1.00 | 73.36  | N |
| ATOM | 1610 | CA  | LEU | A | 256 | 237.647 | 85.022 | 203.809 | 1.00 | 76.61  | C |
| ATOM | 1611 | C   | LEU | A | 256 | 238.466 | 85.295 | 205.065 | 1.00 | 80.02  | C |
| ATOM | 1612 | O   | LEU | A | 256 | 239.681 | 85.116 | 205.074 | 1.00 | 95.93  | O |
| ATOM | 1613 | CB  | LEU | A | 256 | 236.921 | 86.316 | 203.430 | 1.00 | 82.53  | C |
| ATOM | 1614 | CG  | LEU | A | 256 | 236.503 | 86.623 | 201.991 | 1.00 | 67.94  | C |
| ATOM | 1615 | CD1 | LEU | A | 256 | 236.199 | 88.119 | 201.870 | 1.00 | 83.50  | C |
| ATOM | 1616 | CD2 | LEU | A | 256 | 237.615 | 86.248 | 201.038 | 1.00 | 61.15  | C |
| ATOM | 1617 | N   | LEU | A | 257 | 237.780 | 85.718 | 206.124 | 1.00 | 64.99  | N |
| ATOM | 1618 | CA  | LEU | A | 257 | 238.407 | 86.060 | 207.399 | 1.00 | 83.07  | C |
| ATOM | 1619 | C   | LEU | A | 257 | 239.336 | 85.046 | 208.090 | 1.00 | 92.07  | C |
| ATOM | 1620 | O   | LEU | A | 257 | 240.175 | 85.450 | 208.897 | 1.00 | 79.63  | O |
| ATOM | 1621 | CB  | LEU | A | 257 | 237.331 | 86.467 | 208.402 | 1.00 | 65.07  | C |
| ATOM | 1622 | CG  | LEU | A | 257 | 236.445 | 87.661 | 208.054 | 1.00 | 72.20  | C |
| ATOM | 1623 | CD1 | LEU | A | 257 | 235.475 | 87.888 | 209.185 | 1.00 | 109.20 | C |
| ATOM | 1624 | CD2 | LEU | A | 257 | 237.282 | 88.906 | 207.843 | 1.00 | 77.76  | C |
| ATOM | 1625 | N   | CYS | A | 258 | 239.211 | 83.751 | 207.805 | 1.00 | 84.06  | N |
| ATOM | 1626 | CA  | CYS | A | 258 | 240.068 | 82.782 | 208.486 | 1.00 | 65.38  | C |
| ATOM | 1627 | C   | CYS | A | 258 | 240.811 | 81.822 | 207.572 | 1.00 | 79.35  | C |
| ATOM | 1628 | O   | CYS | A | 258 | 241.865 | 81.305 | 207.936 | 1.00 | 89.35  | O |
| ATOM | 1629 | CB  | CYS | A | 258 | 239.250 | 81.952 | 209.465 | 1.00 | 74.82  | C |
| ATOM | 1630 | SG  | CYS | A | 258 | 238.333 | 80.661 | 208.627 | 1.00 | 88.33  | S |
| ATOM | 1631 | N   | GLY | A | 259 | 240.259 | 81.552 | 206.397 | 1.00 | 77.77  | N |
| ATOM | 1632 | CA  | GLY | A | 259 | 240.927 | 80.636 | 205.491 | 1.00 | 86.18  | C |
| ATOM | 1633 | C   | GLY | A | 259 | 240.211 | 79.311 | 205.306 | 1.00 | 84.64  | C |
| ATOM | 1634 | O   | GLY | A | 259 | 240.562 | 78.538 | 204.415 | 1.00 | 91.47  | O |
| ATOM | 1635 | N   | TYR | A | 260 | 239.219 | 79.030 | 206.145 | 1.00 | 80.25  | N |
| ATOM | 1636 | CA  | TYR | A | 260 | 238.454 | 77.788 | 206.024 | 1.00 | 85.40  | C |
| ATOM | 1637 | C   | TYR | A | 260 | 236.969 | 78.064 | 206.208 | 1.00 | 92.78  | C |
| ATOM | 1638 | O   | TYR | A | 260 | 236.587 | 79.064 | 206.813 | 1.00 | 109.20 | O |
| ATOM | 1639 | CB  | TYR | A | 260 | 238.936 | 76.760 | 207.050 | 1.00 | 90.73  | C |
| ATOM | 1640 | CG  | TYR | A | 260 | 239.030 | 77.305 | 208.451 | 1.00 | 78.95  | C |
| ATOM | 1641 | CD1 | TYR | A | 260 | 237.942 | 77.261 | 209.312 | 1.00 | 99.14  | C |
| ATOM | 1642 | CD2 | TYR | A | 260 | 240.204 | 77.892 | 208.904 | 1.00 | 82.37  | C |
| ATOM | 1643 | CE1 | TYR | A | 260 | 238.023 | 77.785 | 210.585 | 1.00 | 88.16  | C |
| ATOM | 1644 | CE2 | TYR | A | 260 | 240.292 | 78.420 | 210.173 | 1.00 | 97.24  | C |
| ATOM | 1645 | CZ  | TYR | A | 260 | 239.201 | 78.364 | 211.007 | 1.00 | 67.63  | C |
| ATOM | 1646 | OH  | TYR | A | 260 | 239.298 | 78.896 | 212.269 | 1.00 | 84.01  | O |
| ATOM | 1647 | N   | PRO | A | 261 | 236.114 | 77.183 | 205.676 | 1.00 | 89.49  | N |
| ATOM | 1648 | CA  | PRO | A | 261 | 234.656 | 77.296 | 205.753 | 1.00 | 103.35 | C |
| ATOM | 1649 | C   | PRO | A | 261 | 234.107 | 77.095 | 207.161 | 1.00 | 96.36  | C |
| ATOM | 1650 | O   | PRO | A | 261 | 234.743 | 76.459 | 207.995 | 1.00 | 100.89 | O |
| ATOM | 1651 | CB  | PRO | A | 261 | 234.185 | 76.209 | 204.791 | 1.00 | 98.88  | C |
| ATOM | 1652 | CG  | PRO | A | 261 | 235.208 | 75.152 | 204.996 | 1.00 | 95.80  | C |
| ATOM | 1653 | CD  | PRO | A | 261 | 236.493 | 75.962 | 204.950 | 1.00 | 91.52  | C |
| ATOM | 1654 | N   | PRO | A | 262 | 232.918 | 77.653 | 207.444 | 1.00 | 94.45  | N |
| ATOM | 1655 | CA  | PRO | A | 262 | 232.337 | 77.488 | 208.773 | 1.00 | 85.15  | C |
| ATOM | 1656 | C   | PRO | A | 262 | 232.015 | 76.028 | 209.043 | 1.00 | 68.20  | C |
| ATOM | 1657 | O   | PRO | A | 262 | 232.519 | 75.448 | 209.998 | 1.00 | 106.94 | O |
| ATOM | 1658 | CB  | PRO | A | 262 | 231.092 | 78.368 | 208.717 | 1.00 | 75.57  | C |
| ATOM | 1659 | CG  | PRO | A | 262 | 230.721 | 78.337 | 207.278 | 1.00 | 64.63  | C |
| ATOM | 1660 | CD  | PRO | A | 262 | 232.053 | 78.504 | 206.609 | 1.00 | 99.03  | C |
| ATOM | 1661 | N   | PHE | A | 263 | 231.200 | 75.419 | 208.191 | 1.00 | 73.57  | N |
| ATOM | 1662 | CA  | PHE | A | 263 | 230.838 | 74.021 | 208.393 | 1.00 | 79.36  | C |

TABLE 1-continued

Coordinates of the activated MAPKAP kinase-2/peptide complex

| ATOM | 1663 | C   | PHE | A | 263 | 231.864 | 73.093 | 207.757 | 1.00 | 106.15 | C |
|------|------|-----|-----|---|-----|---------|--------|---------|------|--------|---|
| ATOM | 1664 | O   | PHE | A | 263 | 231.972 | 73.009 | 206.530 | 1.00 | 105.28 | O |
| ATOM | 1665 | CB  | PHE | A | 263 | 229.428 | 73.777 | 207.848 | 1.00 | 69.85  | C |
| ATOM | 1666 | CG  | PHE | A | 263 | 228.420 | 74.759 | 208.374 | 1.00 | 81.28  | C |
| ATOM | 1667 | CD1 | PHE | A | 263 | 228.128 | 75.917 | 207.677 | 1.00 | 113.87 | C |
| ATOM | 1668 | CD2 | PHE | A | 263 | 227.845 | 74.573 | 209.613 | 1.00 | 117.67 | C |
| ATOM | 1669 | CE1 | PHE | A | 263 | 227.285 | 76.867 | 208.205 | 1.00 | 85.69  | C |
| ATOM | 1670 | CE2 | PHE | A | 263 | 227.004 | 75.520 | 210.145 | 1.00 | 108.39 | C |
| ATOM | 1671 | CZ  | PHE | A | 263 | 226.729 | 76.670 | 209.437 | 1.00 | 117.73 | C |
| ATOM | 1672 | N   | TYR | A | 264 | 232.620 | 72.408 | 208.622 | 1.00 | 134.25 | N |
| ATOM | 1673 | CA  | TYR | A | 264 | 233.681 | 71.497 | 208.197 | 1.00 | 147.77 | C |
| ATOM | 1674 | C   | TYR | A | 264 | 233.192 | 70.094 | 207.848 | 1.00 | 140.09 | C |
| ATOM | 1675 | O   | TYR | A | 264 | 232.006 | 69.787 | 207.979 | 1.00 | 138.93 | O |
| ATOM | 1676 | CB  | TYR | A | 264 | 234.775 | 71.405 | 209.284 | 1.00 | 153.86 | C |
| ATOM | 1677 | CG  | TYR | A | 264 | 236.191 | 71.629 | 208.760 | 1.00 | 157.09 | C |
| ATOM | 1678 | CD1 | TYR | A | 264 | 237.265 | 70.886 | 209.250 | 1.00 | 193.79 | C |
| ATOM | 1679 | CD2 | TYR | A | 264 | 236.448 | 72.574 | 207.768 | 1.00 | 140.55 | C |
| ATOM | 1680 | CE1 | TYR | A | 264 | 238.553 | 71.074 | 208.764 | 1.00 | 220.80 | C |
| ATOM | 1681 | CE2 | TYR | A | 264 | 237.734 | 72.771 | 207.279 | 1.00 | 201.56 | C |
| ATOM | 1682 | CZ  | TYR | A | 264 | 238.782 | 72.015 | 207.781 | 1.00 | 222.82 | C |
| ATOM | 1683 | OH  | TYR | A | 264 | 240.069 | 72.185 | 207.307 | 1.00 | 220.52 | O |
| ATOM | 1684 | N   | SER | A | 265 | 234.118 | 69.246 | 207.409 | 1.00 | 141.69 | N |
| ATOM | 1685 | CA  | SER | A | 265 | 233.785 | 67.877 | 207.044 | 1.00 | 135.35 | C |
| ATOM | 1686 | C   | SER | A | 265 | 234.560 | 66.896 | 207.915 | 1.00 | 131.47 | C |
| ATOM | 1687 | O   | SER | A | 265 | 235.792 | 66.945 | 207.976 | 1.00 | 126.66 | O |
| ATOM | 1688 | CB  | SER | A | 265 | 234.113 | 67.628 | 205.566 | 1.00 | 138.65 | C |
| ATOM | 1689 | OG  | SER | A | 265 | 233.591 | 66.386 | 205.130 | 1.00 | 107.77 | O |
| TER  | 1689 |     | SER | A | 265 |         |        |         |      |        |   |
| ATOM | 1690 | N   | GLY | A | 274 | 229.307 | 63.721 | 209.431 | 1.00 | 106.41 | N |
| ATOM | 1691 | CA  | GLY | A | 274 | 228.030 | 64.307 | 209.816 | 1.00 | 119.68 | C |
| ATOM | 1692 | C   | GLY | A | 274 | 227.987 | 65.812 | 209.615 | 1.00 | 113.16 | C |
| ATOM | 1693 | O   | GLY | A | 274 | 227.553 | 66.551 | 210.496 | 1.00 | 95.55  | O |
| ATOM | 1694 | N   | MET | A | 275 | 228.446 | 66.261 | 208.449 | 1.00 | 110.29 | N |
| ATOM | 1695 | CA  | MET | A | 275 | 228.463 | 67.676 | 208.112 | 1.00 | 95.81  | C |
| ATOM | 1696 | C   | MET | A | 275 | 227.067 | 68.162 | 207.746 | 1.00 | 94.19  | C |
| ATOM | 1697 | O   | MET | A | 275 | 226.633 | 69.206 | 208.220 | 1.00 | 75.71  | O |
| ATOM | 1698 | CB  | MET | A | 275 | 229.412 | 67.938 | 206.943 | 1.00 | 90.51  | C |
| ATOM | 1699 | CG  | MET | A | 275 | 229.404 | 69.380 | 206.472 | 1.00 | 83.11  | C |
| ATOM | 1700 | SD  | MET | A | 275 | 230.324 | 69.611 | 204.942 | 1.00 | 99.84  | S |
| ATOM | 1701 | CE  | MET | A | 275 | 229.028 | 69.352 | 203.750 | 1.00 | 79.14  | C |
| ATOM | 1702 | N   | LYS | A | 276 | 226.362 | 67.411 | 206.904 | 1.00 | 80.06  | N |
| ATOM | 1703 | CA  | LYS | A | 276 | 225.018 | 67.816 | 206.511 | 1.00 | 81.42  | C |
| ATOM | 1704 | C   | LYS | A | 276 | 224.233 | 68.145 | 207.770 | 1.00 | 67.18  | C |
| ATOM | 1705 | O   | LYS | A | 276 | 223.297 | 68.931 | 207.738 | 1.00 | 87.18  | O |
| ATOM | 1706 | CB  | LYS | A | 276 | 224.327 | 66.705 | 205.731 | 1.00 | 70.05  | C |
| ATOM | 1707 | N   | THR | A | 277 | 224.641 | 67.552 | 208.886 | 1.00 | 90.20  | N |
| ATOM | 1708 | CA  | THR | A | 277 | 223.982 | 67.776 | 210.167 | 1.00 | 86.79  | C |
| ATOM | 1709 | C   | THR | A | 277 | 224.402 | 69.103 | 210.790 | 1.00 | 88.87  | C |
| ATOM | 1710 | O   | THR | A | 277 | 223.570 | 69.987 | 211.004 | 1.00 | 90.25  | O |
| ATOM | 1711 | CB  | THR | A | 277 | 224.316 | 66.657 | 211.170 | 1.00 | 94.65  | C |
| ATOM | 1712 | OG1 | THR | A | 277 | 223.953 | 65.387 | 210.614 | 1.00 | 124.83 | O |
| ATOM | 1713 | CG2 | THR | A | 277 | 223.559 | 66.871 | 212.464 | 1.00 | 101.58 | C |
| ATOM | 1714 | N   | ARG | A | 278 | 225.696 | 69.224 | 211.083 | 1.00 | 83.15  | N |
| ATOM | 1715 | CA  | ARG | A | 278 | 226.273 | 70.425 | 211.683 | 1.00 | 85.59  | C |
| ATOM | 1716 | C   | ARG | A | 278 | 225.653 | 71.666 | 211.039 | 1.00 | 80.18  | C |
| ATOM | 1717 | O   | ARG | A | 278 | 225.537 | 72.716 | 211.673 | 1.00 | 83.67  | O |
| ATOM | 1718 | CB  | ARG | A | 278 | 227.792 | 70.413 | 211.479 | 1.00 | 76.56  | C |
| ATOM | 1719 | CG  | ARG | A | 278 | 228.346 | 68.998 | 211.313 | 1.00 | 94.91  | C |
| ATOM | 1720 | CD  | ARG | A | 278 | 229.398 | 68.600 | 212.352 | 1.00 | 109.01 | C |
| ATOM | 1721 | NE  | ARG | A | 278 | 230.699 | 69.199 | 212.072 | 1.00 | 121.75 | N |
| ATOM | 1722 | CZ  | ARG | A | 278 | 231.384 | 69.003 | 210.944 | 1.00 | 131.02 | C |
| ATOM | 1723 | NH1 | ARG | A | 278 | 230.892 | 68.216 | 209.988 | 1.00 | 101.83 | N |
| ATOM | 1724 | NH2 | ARG | A | 278 | 232.556 | 69.613 | 210.763 | 1.00 | 135.84 | N |
| ATOM | 1725 | N   | ILE | A | 279 | 225.250 | 71.516 | 209.778 | 1.00 | 83.10  | N |
| ATOM | 1726 | CA  | ILE | A | 279 | 224.615 | 72.579 | 209.001 | 1.00 | 82.30  | C |
| ATOM | 1727 | C   | ILE | A | 279 | 223.167 | 72.765 | 209.421 | 1.00 | 76.46  | C |
| ATOM | 1728 | O   | ILE | A | 279 | 222.778 | 73.847 | 209.847 | 1.00 | 90.20  | O |
| ATOM | 1729 | CB  | ILE | A | 279 | 224.609 | 72.257 | 207.498 | 1.00 | 84.92  | C |
| ATOM | 1730 | CG1 | ILE | A | 279 | 226.006 | 72.436 | 206.913 | 1.00 | 77.12  | C |
| ATOM | 1731 | CG2 | ILE | A | 279 | 223.611 | 73.144 | 206.789 | 1.00 | 57.01  | C |
| ATOM | 1732 | CD1 | ILE | A | 279 | 226.093 | 72.021 | 205.455 | 1.00 | 73.72  | C |
| ATOM | 1733 | N   | ARG | A | 280 | 222.371 | 71.709 | 209.270 | 1.00 | 68.55  | N |
| ATOM | 1734 | CA  | ARG | A | 280 | 220.965 | 71.757 | 209.640 | 1.00 | 66.51  | C |
| ATOM | 1735 | C   | ARG | A | 280 | 220.886 | 72.218 | 211.090 | 1.00 | 62.26  | C |
| ATOM | 1736 | O   | ARG | A | 280 | 220.039 | 73.038 | 211.456 | 1.00 | 69.34  | O |
| ATOM | 1737 | CB  | ARG | A | 280 | 220.326 | 70.383 | 209.475 | 1.00 | 49.45  | C |
| ATOM | 1738 | N   | MET | A | 281 | 221.787 | 71.693 | 211.912 | 1.00 | 62.31  | N |
| ATOM | 1739 | CA  | MET | A | 281 | 221.846 | 72.058 | 213.323 | 1.00 | 71.30  | C |

TABLE 1-continued

Coordinates of the activated MAPKAP kinase-2/peptide complex

| ATOM | 1740 | C | MET | A | 281 | 222.348 | 73.489 | 213.438 | 1.00 | 78.13 | C |
|---|---|---|---|---|---|---|---|---|---|---|---|
| ATOM | 1741 | O | MET | A | 281 | 222.151 | 74.152 | 214.450 | 1.00 | 79.48 | O |
| ATOM | 1742 | CB | MET | A | 281 | 222.794 | 71.122 | 214.075 | 1.00 | 73.13 | C |
| ATOM | 1743 | CG | MET | A | 281 | 222.253 | 69.721 | 214.315 | 1.00 | 98.38 | C |
| ATOM | 1744 | SD | MET | A | 281 | 220.850 | 69.703 | 215.434 | 1.00 | 82.33 | S |
| ATOM | 1745 | CE | MET | A | 281 | 221.659 | 70.065 | 216.963 | 1.00 | 94.31 | C |
| ATOM | 1746 | N | GLY | A | 282 | 223.000 | 73.953 | 212.379 | 1.00 | 80.51 | N |
| ATOM | 1747 | CA | GLY | A | 282 | 223.536 | 75.298 | 212.354 | 1.00 | 70.03 | C |
| ATOM | 1748 | C | GLY | A | 282 | 224.577 | 75.481 | 213.435 | 1.00 | 89.35 | C |
| ATOM | 1749 | O | GLY | A | 282 | 224.566 | 76.482 | 214.146 | 1.00 | 77.94 | O |
| ATOM | 1750 | N | GLN | A | 283 | 225.479 | 74.514 | 213.576 | 1.00 | 81.75 | N |
| ATOM | 1751 | CA | GLN | A | 283 | 226.509 | 74.624 | 214.602 | 1.00 | 104.61 | C |
| ATOM | 1752 | C | GLN | A | 283 | 227.939 | 74.764 | 214.094 | 1.00 | 94.71 | C |
| ATOM | 1753 | O | GLN | A | 283 | 228.503 | 73.843 | 213.505 | 1.00 | 88.07 | O |
| ATOM | 1754 | CB | GLN | A | 283 | 226.421 | 73.450 | 215.583 | 1.00 | 113.16 | C |
| ATOM | 1755 | CG | GLN | A | 283 | 226.575 | 72.075 | 214.982 | 1.00 | 114.78 | C |
| ATOM | 1756 | CD | GLN | A | 283 | 226.574 | 71.002 | 216.057 | 1.00 | 133.39 | C |
| ATOM | 1757 | OE1 | GLN | A | 283 | 227.356 | 71.068 | 217.005 | 1.00 | 133.52 | O |
| ATOM | 1758 | NE2 | GLN | A | 283 | 225.691 | 70.012 | 215.922 | 1.00 | 112.55 | N |
| ATOM | 1759 | N | TYR | A | 284 | 228.516 | 75.935 | 214.347 | 1.00 | 90.04 | N |
| ATOM | 1760 | CA | TYR | A | 284 | 229.875 | 76.242 | 213.934 | 1.00 | 64.09 | C |
| ATOM | 1761 | C | TYR | A | 284 | 230.474 | 77.137 | 215.008 | 1.00 | 65.66 | C |
| ATOM | 1762 | O | TYR | A | 284 | 229.806 | 77.468 | 215.981 | 1.00 | 88.03 | O |
| ATOM | 1763 | CB | TYR | A | 284 | 229.864 | 77.002 | 212.620 | 1.00 | 82.88 | C |
| ATOM | 1764 | CG | TYR | A | 284 | 229.040 | 78.259 | 212.690 | 1.00 | 50.94 | C |
| ATOM | 1765 | CD1 | TYR | A | 284 | 227.656 | 78.208 | 212.619 | 1.00 | 72.36 | C |
| ATOM | 1766 | CD2 | TYR | A | 284 | 229.645 | 79.496 | 212.856 | 1.00 | 79.70 | C |
| ATOM | 1767 | CE1 | TYR | A | 284 | 226.901 | 79.355 | 212.709 | 1.00 | 69.83 | C |
| ATOM | 1768 | CE2 | TYR | A | 284 | 228.896 | 80.646 | 212.951 | 1.00 | 57.96 | C |
| ATOM | 1769 | CZ | TYR | A | 284 | 227.527 | 80.569 | 212.877 | 1.00 | 57.53 | C |
| ATOM | 1770 | OH | TYR | A | 284 | 226.778 | 81.716 | 212.978 | 1.00 | 94.22 | O |
| ATOM | 1771 | N | GLU | A | 285 | 231.725 | 77.538 | 214.821 | 1.00 | 80.73 | N |
| ATOM | 1772 | CA | GLU | A | 285 | 232.399 | 78.388 | 215.785 | 1.00 | 81.22 | C |
| ATOM | 1773 | C | GLU | A | 285 | 233.397 | 79.305 | 215.101 | 1.00 | 90.67 | C |
| ATOM | 1774 | O | GLU | A | 285 | 233.713 | 79.119 | 213.926 | 1.00 | 106.16 | O |
| ATOM | 1775 | CB | GLU | A | 285 | 233.113 | 77.527 | 216.807 | 1.00 | 87.46 | C |
| ATOM | 1776 | N | PHE | A | 286 | 233.875 | 80.303 | 215.839 | 1.00 | 86.81 | N |
| ATOM | 1777 | CA | PHE | A | 286 | 234.880 | 81.236 | 215.334 | 1.00 | 97.06 | C |
| ATOM | 1778 | C | PHE | A | 286 | 236.110 | 80.887 | 216.167 | 1.00 | 100.16 | C |
| ATOM | 1779 | O | PHE | A | 286 | 236.527 | 81.662 | 217.028 | 1.00 | 110.05 | O |
| ATOM | 1780 | CB | PHE | A | 286 | 234.476 | 82.697 | 215.602 | 1.00 | 78.01 | C |
| ATOM | 1781 | CG | PHE | A | 286 | 233.214 | 83.127 | 214.904 | 1.00 | 98.13 | C |
| ATOM | 1782 | CD1 | PHE | A | 286 | 232.172 | 83.698 | 215.615 | 1.00 | 92.96 | C |
| ATOM | 1783 | CD2 | PHE | A | 286 | 233.064 | 82.959 | 213.538 | 1.00 | 102.41 | C |
| ATOM | 1784 | CE1 | PHE | A | 286 | 231.003 | 84.092 | 214.980 | 1.00 | 96.16 | C |
| ATOM | 1785 | CE2 | PHE | A | 286 | 231.892 | 83.353 | 212.897 | 1.00 | 82.36 | C |
| ATOM | 1786 | CZ | PHE | A | 286 | 230.865 | 83.918 | 213.620 | 1.00 | 71.90 | C |
| ATOM | 1787 | N | PRO | A | 287 | 236.707 | 79.715 | 215.909 | 1.00 | 96.70 | N |
| ATOM | 1788 | CA | PRO | A | 287 | 237.883 | 79.170 | 216.586 | 1.00 | 103.18 | C |
| ATOM | 1789 | C | PRO | A | 287 | 239.086 | 80.081 | 216.730 | 1.00 | 112.32 | C |
| ATOM | 1790 | O | PRO | A | 287 | 239.531 | 80.709 | 215.770 | 1.00 | 114.13 | O |
| ATOM | 1791 | CB | PRO | A | 287 | 238.210 | 77.940 | 215.754 | 1.00 | 105.25 | C |
| ATOM | 1792 | CG | PRO | A | 287 | 237.828 | 78.359 | 214.411 | 1.00 | 92.44 | C |
| ATOM | 1793 | CD | PRO | A | 287 | 236.474 | 78.978 | 214.659 | 1.00 | 100.51 | C |
| ATOM | 1794 | N | ASN | A | 288 | 239.608 | 80.133 | 217.950 | 1.00 | 119.25 | N |
| ATOM | 1795 | CA | ASN | A | 288 | 240.796 | 80.913 | 218.239 | 1.00 | 131.90 | C |
| ATOM | 1796 | C | ASN | A | 288 | 241.953 | 79.964 | 217.949 | 1.00 | 138.51 | C |
| ATOM | 1797 | O | ASN | A | 288 | 241.808 | 78.742 | 218.021 | 1.00 | 143.95 | O |
| ATOM | 1798 | CB | ASN | A | 288 | 240.826 | 81.347 | 219.708 | 1.00 | 133.89 | C |
| ATOM | 1799 | CG | ASN | A | 288 | 239.631 | 82.211 | 220.092 | 1.00 | 158.92 | C |
| ATOM | 1800 | OD1 | ASN | A | 288 | 239.383 | 83.259 | 219.485 | 1.00 | 172.68 | O |
| ATOM | 1801 | ND2 | ASN | A | 288 | 238.890 | 81.779 | 221.114 | 1.00 | 139.14 | N |
| ATOM | 1802 | N | PRO | A | 289 | 243.119 | 80.510 | 217.602 | 1.00 | 145.89 | N |
| ATOM | 1803 | CA | PRO | A | 289 | 243.399 | 81.940 | 217.477 | 1.00 | 147.78 | C |
| ATOM | 1804 | C | PRO | A | 289 | 242.632 | 82.643 | 216.367 | 1.00 | 140.12 | C |
| ATOM | 1805 | O | PRO | A | 289 | 242.027 | 83.678 | 216.608 | 1.00 | 145.48 | O |
| ATOM | 1806 | CB | PRO | A | 289 | 244.904 | 81.967 | 217.231 | 1.00 | 160.27 | C |
| ATOM | 1807 | CG | PRO | A | 289 | 245.107 | 80.724 | 216.415 | 1.00 | 158.40 | C |
| ATOM | 1808 | CD | PRO | A | 289 | 244.286 | 79.712 | 217.185 | 1.00 | 149.68 | C |
| ATOM | 1809 | N | GLU | A | 290 | 242.665 | 82.064 | 215.166 | 1.00 | 135.89 | N |
| ATOM | 1810 | CA | GLU | A | 290 | 242.019 | 82.602 | 213.959 | 1.00 | 122.33 | C |
| ATOM | 1811 | C | GLU | A | 290 | 241.100 | 83.810 | 214.141 | 1.00 | 111.48 | C |
| ATOM | 1812 | O | GLU | A | 290 | 241.314 | 84.858 | 213.531 | 1.00 | 94.90 | O |
| ATOM | 1813 | CB | GLU | A | 290 | 241.230 | 81.502 | 213.236 | 1.00 | 121.58 | C |
| ATOM | 1814 | CG | GLU | A | 290 | 241.934 | 80.155 | 213.147 | 1.00 | 140.70 | C |
| ATOM | 1815 | CD | GLU | A | 290 | 241.650 | 79.287 | 214.360 | 1.00 | 183.86 | C |
| ATOM | 1816 | OE1 | GLU | A | 290 | 241.898 | 79.762 | 215.484 | 1.00 | 193.44 | O |
| ATOM | 1817 | OE2 | GLU | A | 290 | 241.178 | 78.137 | 214.193 | 1.00 | 182.20 | O |

TABLE 1-continued

Coordinates of the activated MAPKAP kinase-2/peptide complex

| ATOM | 1818 | N | TRP | A | 291 | 240.080 | 83.655 | 214.980 | 1.00 | 102.18 | N |
|---|---|---|---|---|---|---|---|---|---|---|---|
| ATOM | 1819 | CA | TRP | A | 291 | 239.105 | 84.715 | 215.221 | 1.00 | 106.95 | C |
| ATOM | 1820 | C | TRP | A | 291 | 239.335 | 85.573 | 216.457 | 1.00 | 115.40 | C |
| ATOM | 1821 | O | TRP | A | 291 | 238.474 | 86.375 | 216.824 | 1.00 | 120.18 | O |
| ATOM | 1822 | CB | TRP | A | 291 | 237.712 | 84.106 | 215.295 | 1.00 | 110.40 | C |
| ATOM | 1823 | CG | TRP | A | 291 | 237.364 | 83.374 | 214.056 | 1.00 | 104.11 | C |
| ATOM | 1824 | CD1 | TRP | A | 291 | 237.782 | 82.121 | 213.692 | 1.00 | 84.92 | C |
| ATOM | 1825 | CD2 | TRP | A | 291 | 236.556 | 83.857 | 212.982 | 1.00 | 106.19 | C |
| ATOM | 1826 | NE1 | TRP | A | 291 | 237.282 | 81.799 | 212.456 | 1.00 | 103.99 | N |
| ATOM | 1827 | CE2 | TRP | A | 291 | 236.529 | 82.848 | 211.996 | 1.00 | 102.71 | C |
| ATOM | 1828 | CE3 | TRP | A | 291 | 235.857 | 85.048 | 212.753 | 1.00 | 70.56 | C |
| ATOM | 1829 | CZ2 | TRP | A | 291 | 235.827 | 82.992 | 210.807 | 1.00 | 86.03 | C |
| ATOM | 1830 | CZ3 | TRP | A | 291 | 235.165 | 85.189 | 211.578 | 1.00 | 73.88 | C |
| ATOM | 1831 | CH2 | TRP | A | 291 | 235.154 | 84.171 | 210.616 | 1.00 | 114.55 | C |
| ATOM | 1832 | N | SER | A | 292 | 240.491 | 85.404 | 217.091 | 1.00 | 129.00 | N |
| ATOM | 1833 | CA | SER | A | 292 | 240.851 | 86.158 | 218.287 | 1.00 | 124.04 | C |
| ATOM | 1834 | C | SER | A | 292 | 240.910 | 87.670 | 218.051 | 1.00 | 123.03 | C |
| ATOM | 1835 | O | SER | A | 292 | 240.661 | 88.455 | 218.966 | 1.00 | 113.67 | O |
| ATOM | 1836 | CB | SER | A | 292 | 242.199 | 85.658 | 218.825 | 1.00 | 125.10 | C |
| ATOM | 1837 | OG | SER | A | 292 | 243.196 | 85.669 | 217.817 | 1.00 | 135.63 | O |
| ATOM | 1838 | N | GLU | A | 293 | 241.237 | 88.081 | 216.829 | 1.00 | 123.41 | N |
| ATOM | 1839 | CA | GLU | A | 293 | 241.321 | 89.508 | 216.513 | 1.00 | 127.66 | C |
| ATOM | 1840 | C | GLU | A | 293 | 240.108 | 90.026 | 215.724 | 1.00 | 121.92 | C |
| ATOM | 1841 | O | GLU | A | 293 | 240.091 | 91.178 | 215.285 | 1.00 | 115.91 | O |
| ATOM | 1842 | CB | GLU | A | 293 | 242.600 | 89.792 | 215.737 | 1.00 | 138.28 | C |
| ATOM | 1843 | N | VAL | A | 294 | 239.094 | 89.181 | 215.555 | 1.00 | 111.91 | N |
| ATOM | 1844 | CA | VAL | A | 294 | 237.898 | 89.568 | 214.818 | 1.00 | 95.15 | C |
| ATOM | 1845 | C | VAL | A | 294 | 236.811 | 90.136 | 215.721 | 1.00 | 103.25 | C |
| ATOM | 1846 | O | VAL | A | 294 | 236.506 | 89.573 | 216.771 | 1.00 | 98.28 | O |
| ATOM | 1847 | CB | VAL | A | 294 | 237.322 | 88.378 | 214.066 | 1.00 | 92.93 | C |
| ATOM | 1848 | CG1 | VAL | A | 294 | 236.182 | 88.840 | 213.168 | 1.00 | 91.77 | C |
| ATOM | 1849 | CG2 | VAL | A | 294 | 238.418 | 87.705 | 213.269 | 1.00 | 94.47 | C |
| ATOM | 1850 | N | SER | A | 295 | 236.218 | 91.249 | 215.292 | 1.00 | 84.68 | N |
| ATOM | 1851 | CA | SER | A | 295 | 235.168 | 91.914 | 216.056 | 1.00 | 92.73 | C |
| ATOM | 1852 | C | SER | A | 295 | 233.919 | 91.072 | 216.244 | 1.00 | 88.74 | C |
| ATOM | 1853 | O | SER | A | 295 | 233.568 | 90.250 | 215.399 | 1.00 | 88.58 | O |
| ATOM | 1854 | CB | SER | A | 295 | 234.745 | 93.201 | 215.365 | 1.00 | 102.34 | C |
| ATOM | 1855 | OG | SER | A | 295 | 233.464 | 93.030 | 214.784 | 1.00 | 114.40 | O |
| ATOM | 1856 | N | GLU | A | 296 | 233.244 | 91.301 | 217.362 | 1.00 | 92.37 | N |
| ATOM | 1857 | CA | GLU | A | 296 | 232.008 | 90.600 | 217.658 | 1.00 | 104.61 | C |
| ATOM | 1858 | C | GLU | A | 296 | 230.970 | 91.166 | 216.694 | 1.00 | 112.98 | C |
| ATOM | 1859 | O | GLU | A | 296 | 229.956 | 90.523 | 216.406 | 1.00 | 105.91 | O |
| ATOM | 1860 | CB | GLU | A | 296 | 231.593 | 90.857 | 219.108 | 1.00 | 99.76 | C |
| ATOM | 1861 | CG | GLU | A | 296 | 230.316 | 90.154 | 219.543 | 1.00 | 121.36 | C |
| ATOM | 1862 | CD | GLU | A | 296 | 230.324 | 88.663 | 219.236 | 1.00 | 136.85 | C |
| ATOM | 1863 | OE1 | GLU | A | 296 | 231.304 | 87.970 | 219.609 | 1.00 | 131.43 | O |
| ATOM | 1864 | OE2 | GLU | A | 296 | 229.340 | 88.185 | 218.619 | 1.00 | 136.46 | O |
| ATOM | 1865 | N | GLU | A | 297 | 231.237 | 92.379 | 216.203 | 1.00 | 112.50 | N |
| ATOM | 1866 | CA | GLU | A | 297 | 230.357 | 93.045 | 215.247 | 1.00 | 99.85 | C |
| ATOM | 1867 | C | GLU | A | 297 | 230.420 | 92.241 | 213.960 | 1.00 | 92.47 | C |
| ATOM | 1868 | O | GLU | A | 297 | 229.396 | 91.854 | 213.400 | 1.00 | 93.48 | O |
| ATOM | 1869 | CB | GLU | A | 297 | 230.838 | 94.472 | 214.998 | 1.00 | 98.76 | C |
| ATOM | 1870 | CG | GLU | A | 297 | 230.226 | 95.146 | 213.787 | 1.00 | 102.64 | C |
| ATOM | 1871 | CD | GLU | A | 297 | 230.489 | 96.642 | 213.773 | 1.00 | 129.34 | C |
| ATOM | 1872 | OE1 | GLU | A | 297 | 229.777 | 97.379 | 214.497 | 1.00 | 134.48 | O |
| ATOM | 1873 | OE2 | GLU | A | 297 | 231.415 | 97.081 | 213.049 | 1.00 | 104.72 | O |
| ATOM | 1874 | N | VAL | A | 298 | 231.638 | 91.993 | 213.499 | 1.00 | 80.38 | N |
| ATOM | 1875 | CA | VAL | A | 298 | 231.843 | 91.200 | 212.305 | 1.00 | 87.49 | C |
| ATOM | 1876 | C | VAL | A | 298 | 231.282 | 89.809 | 212.579 | 1.00 | 80.88 | C |
| ATOM | 1877 | O | VAL | A | 298 | 230.690 | 89.176 | 211.702 | 1.00 | 71.80 | O |
| ATOM | 1878 | CB | VAL | A | 298 | 233.333 | 91.057 | 211.993 | 1.00 | 64.02 | C |
| ATOM | 1879 | CG1 | VAL | A | 298 | 233.542 | 89.953 | 210.980 | 1.00 | 84.65 | C |
| ATOM | 1880 | CG2 | VAL | A | 298 | 233.873 | 92.364 | 211.466 | 1.00 | 112.61 | C |
| ATOM | 1881 | N | LYS | A | 299 | 231.479 | 89.331 | 213.801 | 1.00 | 79.83 | N |
| ATOM | 1882 | CA | LYS | A | 299 | 230.990 | 88.015 | 214.162 | 1.00 | 75.16 | C |
| ATOM | 1883 | C | LYS | A | 299 | 229.478 | 87.983 | 214.138 | 1.00 | 80.77 | C |
| ATOM | 1884 | O | LYS | A | 299 | 228.872 | 87.052 | 213.618 | 1.00 | 62.14 | O |
| ATOM | 1885 | CB | LYS | A | 299 | 231.517 | 87.616 | 215.539 | 1.00 | 74.57 | C |
| ATOM | 1886 | CG | LYS | A | 299 | 232.979 | 87.229 | 215.509 | 1.00 | 75.11 | C |
| ATOM | 1887 | CD | LYS | A | 299 | 233.432 | 86.563 | 216.790 | 1.00 | 92.06 | C |
| ATOM | 1888 | CE | LYS | A | 299 | 234.841 | 86.005 | 216.623 | 1.00 | 125.81 | C |
| ATOM | 1889 | NZ | LYS | A | 299 | 235.368 | 85.378 | 217.867 | 1.00 | 126.47 | N |
| ATOM | 1890 | N | MET | A | 300 | 228.872 | 89.021 | 214.691 | 1.00 | 78.00 | N |
| ATOM | 1891 | CA | MET | A | 300 | 227.428 | 89.116 | 214.735 | 1.00 | 80.36 | C |
| ATOM | 1892 | C | MET | A | 300 | 226.822 | 89.120 | 213.327 | 1.00 | 69.48 | C |
| ATOM | 1893 | O | MET | A | 300 | 225.732 | 88.587 | 213.118 | 1.00 | 75.70 | O |
| ATOM | 1894 | CB | MET | A | 300 | 227.033 | 90.378 | 215.502 | 1.00 | 87.97 | C |
| ATOM | 1895 | CG | MET | A | 300 | 226.011 | 90.131 | 216.601 | 1.00 | 118.90 | C |

TABLE 1-continued

Coordinates of the activated MAPKAP kinase-2/peptide complex

| ATOM | 1896 | SD | MET | A | 300 | 226.231 | 88.508 | 217.393 | 1.00 | 128.71 | S |
|---|---|---|---|---|---|---|---|---|---|---|---|
| ATOM | 1897 | CE | MET | A | 300 | 224.516 | 87.872 | 217.267 | 1.00 | 113.92 | C |
| ATOM | 1898 | N | LEU | A | 301 | 227.538 | 89.707 | 212.369 | 1.00 | 73.89 | N |
| ATOM | 1899 | CA | LEU | A | 301 | 227.079 | 89.782 | 210.972 | 1.00 | 63.96 | C |
| ATOM | 1900 | C | LEU | A | 301 | 227.048 | 88.406 | 210.301 | 1.00 | 70.75 | C |
| ATOM | 1901 | O | LEU | A | 301 | 226.145 | 88.086 | 209.532 | 1.00 | 60.38 | O |
| ATOM | 1902 | CB | LEU | A | 301 | 227.977 | 90.735 | 210.177 | 1.00 | 63.62 | C |
| ATOM | 1903 | CG | LEU | A | 301 | 227.617 | 91.019 | 208.720 | 1.00 | 52.63 | C |
| ATOM | 1904 | CD1 | LEU | A | 301 | 226.130 | 91.284 | 208.596 | 1.00 | 65.57 | C |
| ATOM | 1905 | CD2 | LEU | A | 301 | 228.414 | 92.212 | 208.225 | 1.00 | 73.24 | C |
| ATOM | 1906 | N | ILE | A | 302 | 228.046 | 87.588 | 210.592 | 1.00 | 67.57 | N |
| ATOM | 1907 | CA | ILE | A | 302 | 228.090 | 86.250 | 210.037 | 1.00 | 61.70 | C |
| ATOM | 1908 | C | ILE | A | 302 | 226.900 | 85.455 | 210.582 | 1.00 | 75.97 | C |
| ATOM | 1909 | O | ILE | A | 302 | 226.226 | 84.741 | 209.837 | 1.00 | 58.38 | O |
| ATOM | 1910 | CB | ILE | A | 302 | 229.422 | 85.565 | 210.402 | 1.00 | 70.53 | C |
| ATOM | 1911 | CG1 | ILE | A | 302 | 230.562 | 86.271 | 209.659 | 1.00 | 76.98 | C |
| ATOM | 1912 | CG2 | ILE | A | 302 | 229.369 | 84.086 | 210.071 | 1.00 | 65.01 | C |
| ATOM | 1913 | CD1 | ILE | A | 302 | 231.930 | 85.670 | 209.869 | 1.00 | 71.99 | C |
| ATOM | 1914 | N | ARG | A | 303 | 226.630 | 85.611 | 211.878 | 1.00 | 73.53 | N |
| ATOM | 1915 | CA | ARG | A | 303 | 225.526 | 84.913 | 212.532 | 1.00 | 61.85 | C |
| ATOM | 1916 | C | ARG | A | 303 | 224.162 | 85.201 | 211.898 | 1.00 | 74.05 | C |
| ATOM | 1917 | O | ARG | A | 303 | 223.370 | 84.286 | 211.695 | 1.00 | 79.80 | O |
| ATOM | 1918 | CB | ARG | A | 303 | 225.461 | 85.279 | 214.009 | 1.00 | 61.93 | C |
| ATOM | 1919 | CG | ARG | A | 303 | 226.666 | 84.917 | 214.852 | 1.00 | 78.75 | C |
| ATOM | 1920 | CD | ARG | A | 303 | 226.402 | 85.392 | 216.284 | 1.00 | 71.93 | C |
| ATOM | 1921 | NE | ARG | A | 303 | 227.608 | 85.725 | 217.038 | 1.00 | 101.37 | N |
| ATOM | 1922 | CZ | ARG | A | 303 | 228.488 | 84.827 | 217.457 | 1.00 | 93.09 | C |
| ATOM | 1923 | NH1 | ARG | A | 303 | 228.286 | 83.540 | 217.191 | 1.00 | 90.11 | N |
| ATOM | 1924 | NH2 | ARG | A | 303 | 229.561 | 85.211 | 218.140 | 1.00 | 76.11 | N |
| ATOM | 1925 | N | ASN | A | 304 | 223.865 | 86.458 | 211.596 | 1.00 | 61.15 | N |
| ATOM | 1926 | CA | ASN | A | 304 | 222.575 | 86.775 | 210.982 | 1.00 | 77.76 | C |
| ATOM | 1927 | C | ASN | A | 304 | 222.517 | 86.277 | 209.535 | 1.00 | 74.95 | C |
| ATOM | 1928 | O | ASN | A | 304 | 221.449 | 86.208 | 208.929 | 1.00 | 67.98 | O |
| ATOM | 1929 | CB | ASN | A | 304 | 222.312 | 88.291 | 211.016 | 1.00 | 83.64 | C |
| ATOM | 1930 | CG | ASN | A | 304 | 222.000 | 88.806 | 212.421 | 1.00 | 112.22 | C |
| ATOM | 1931 | OD1 | ASN | A | 304 | 222.399 | 89.919 | 212.802 | 1.00 | 84.27 | O |
| ATOM | 1932 | ND2 | ASN | A | 304 | 221.269 | 88.004 | 213.197 | 1.00 | 69.02 | N |
| ATOM | 1933 | N | LEU | A | 305 | 223.671 | 85.943 | 208.973 | 1.00 | 63.99 | N |
| ATOM | 1934 | CA | LEU | A | 305 | 223.711 | 85.458 | 207.605 | 1.00 | 54.76 | C |
| ATOM | 1935 | C | LEU | A | 305 | 223.590 | 83.952 | 207.666 | 1.00 | 73.10 | C |
| ATOM | 1936 | O | LEU | A | 305 | 222.929 | 83.313 | 206.841 | 1.00 | 58.22 | O |
| ATOM | 1937 | CB | LEU | A | 305 | 225.032 | 85.860 | 206.948 | 1.00 | 52.05 | C |
| ATOM | 1938 | CG | LEU | A | 305 | 225.127 | 87.316 | 206.481 | 1.00 | 58.75 | C |
| ATOM | 1939 | CD1 | LEU | A | 305 | 226.511 | 87.621 | 205.932 | 1.00 | 69.80 | C |
| ATOM | 1940 | CD2 | LEU | A | 305 | 224.075 | 87.560 | 205.421 | 1.00 | 47.92 | C |
| ATOM | 1941 | N | LEU | A | 306 | 224.240 | 83.401 | 208.681 | 1.00 | 57.81 | N |
| ATOM | 1942 | CA | LEU | A | 306 | 224.256 | 81.975 | 208.915 | 1.00 | 59.22 | C |
| ATOM | 1943 | C | LEU | A | 306 | 223.087 | 81.525 | 209.779 | 1.00 | 70.17 | C |
| ATOM | 1944 | O | LEU | A | 306 | 223.205 | 80.586 | 210.565 | 1.00 | 86.15 | O |
| ATOM | 1945 | CB | LEU | A | 306 | 225.581 | 81.582 | 209.559 | 1.00 | 54.83 | C |
| ATOM | 1946 | CG | LEU | A | 306 | 226.752 | 81.718 | 208.599 | 1.00 | 56.28 | C |
| ATOM | 1947 | CD1 | LEU | A | 306 | 228.035 | 81.262 | 209.237 | 1.00 | 46.67 | C |
| ATOM | 1948 | CD2 | LEU | A | 306 | 226.445 | 80.883 | 207.385 | 1.00 | 50.52 | C |
| ATOM | 1949 | N | LYS | A | 307 | 221.960 | 82.212 | 209.648 | 1.00 | 70.52 | N |
| ATOM | 1950 | CA | LYS | A | 307 | 220.772 | 81.832 | 210.394 | 1.00 | 64.84 | C |
| ATOM | 1951 | C | LYS | A | 307 | 220.251 | 80.593 | 209.676 | 1.00 | 65.05 | C |
| ATOM | 1952 | O | LYS | A | 307 | 220.153 | 80.570 | 208.449 | 1.00 | 73.22 | O |
| ATOM | 1953 | CB | LYS | A | 307 | 219.720 | 82.930 | 210.337 | 1.00 | 60.26 | C |
| ATOM | 1954 | CG | LYS | A | 307 | 220.137 | 84.247 | 210.952 | 1.00 | 76.35 | C |
| ATOM | 1955 | CD | LYS | A | 307 | 219.620 | 84.411 | 212.371 | 1.00 | 75.87 | C |
| ATOM | 1956 | CE | LYS | A | 307 | 220.487 | 83.696 | 213.389 | 1.00 | 92.33 | C |
| ATOM | 1957 | NZ | LYS | A | 307 | 219.963 | 83.886 | 214.773 | 1.00 | 94.73 | N |
| ATOM | 1958 | N | THR | A | 308 | 219.925 | 79.558 | 210.439 | 1.00 | 87.36 | N |
| ATOM | 1959 | CA | THR | A | 308 | 219.432 | 78.314 | 209.864 | 1.00 | 86.54 | C |
| ATOM | 1960 | C | THR | A | 308 | 218.057 | 78.489 | 209.219 | 1.00 | 80.07 | C |
| ATOM | 1961 | O | THR | A | 308 | 217.722 | 77.809 | 208.248 | 1.00 | 80.48 | O |
| ATOM | 1962 | CB | THR | A | 308 | 219.382 | 77.198 | 210.945 | 1.00 | 80.31 | C |
| ATOM | 1963 | OG1 | THR | A | 308 | 220.615 | 76.457 | 210.929 | 1.00 | 85.50 | O |
| ATOM | 1964 | CG2 | THR | A | 308 | 218.211 | 76.265 | 210.701 | 1.00 | 108.80 | C |
| ATOM | 1965 | N | GLU | A | 309 | 217.264 | 79.407 | 209.755 | 1.00 | 86.56 | N |
| ATOM | 1966 | CA | GLU | A | 309 | 215.934 | 79.647 | 209.217 | 1.00 | 80.34 | C |
| ATOM | 1967 | C | GLU | A | 309 | 215.964 | 80.820 | 208.253 | 1.00 | 80.14 | C |
| ATOM | 1968 | O | GLU | A | 309 | 216.353 | 81.933 | 208.614 | 1.00 | 72.43 | O |
| ATOM | 1969 | CB | GLU | A | 309 | 214.937 | 79.945 | 210.345 | 1.00 | 79.03 | C |
| ATOM | 1970 | CG | GLU | A | 309 | 213.461 | 79.716 | 209.976 | 1.00 | 107.32 | C |
| ATOM | 1971 | CD | GLU | A | 309 | 213.028 | 78.264 | 210.160 | 1.00 | 128.86 | C |
| ATOM | 1972 | OE1 | GLU | A | 309 | 213.354 | 77.691 | 211.227 | 1.00 | 100.32 | O |
| ATOM | 1973 | OE2 | GLU | A | 309 | 212.364 | 77.699 | 209.252 | 1.00 | 91.75 | O |

TABLE 1-continued

Coordinates of the activated MAPKAP kinase-2/peptide complex

| ATOM | 1974 | N   | PRO | A | 310 | 215.554 | 80.585 | 207.002 | 1.00 | 69.20  | N |
|------|------|-----|-----|---|-----|---------|--------|---------|------|--------|---|
| ATOM | 1975 | CA  | PRO | A | 310 | 215.536 | 81.644 | 205.988 | 1.00 | 75.56  | C |
| ATOM | 1976 | C   | PRO | A | 310 | 214.955 | 82.953 | 206.540 | 1.00 | 73.13  | C |
| ATOM | 1977 | O   | PRO | A | 310 | 215.697 | 83.886 | 206.848 | 1.00 | 70.20  | O |
| ATOM | 1978 | CB  | PRO | A | 310 | 214.675 | 81.041 | 204.888 | 1.00 | 58.28  | C |
| ATOM | 1979 | CG  | PRO | A | 310 | 215.049 | 79.598 | 204.957 | 1.00 | 61.31  | C |
| ATOM | 1980 | CD  | PRO | A | 310 | 215.073 | 79.312 | 206.442 | 1.00 | 64.66  | C |
| ATOM | 1981 | N   | THR | A | 311 | 213.633 | 83.004 | 206.683 | 1.00 | 57.71  | N |
| ATOM | 1982 | CA  | THR | A | 311 | 212.952 | 84.188 | 207.194 | 1.00 | 63.44  | C |
| ATOM | 1983 | C   | THR | A | 311 | 213.671 | 84.899 | 208.338 | 1.00 | 65.40  | C |
| ATOM | 1984 | O   | THR | A | 311 | 213.424 | 86.078 | 208.585 | 1.00 | 70.08  | O |
| ATOM | 1985 | CB  | THR | A | 311 | 211.552 | 83.839 | 207.666 | 1.00 | 52.68  | C |
| ATOM | 1986 | OG1 | THR | A | 311 | 211.650 | 82.936 | 208.763 | 1.00 | 76.00  | O |
| ATOM | 1987 | CG2 | THR | A | 311 | 210.781 | 83.179 | 206.574 | 1.00 | 44.79  | C |
| ATOM | 1988 | N   | GLN | A | 312 | 214.551 | 84.198 | 209.043 | 1.00 | 61.23  | N |
| ATOM | 1989 | CA  | GLN | A | 312 | 215.271 | 84.831 | 210.145 | 1.00 | 58.30  | C |
| ATOM | 1990 | C   | GLN | A | 312 | 216.527 | 85.518 | 209.629 | 1.00 | 63.30  | C |
| ATOM | 1991 | O   | GLN | A | 312 | 216.995 | 86.509 | 210.189 | 1.00 | 65.70  | O |
| ATOM | 1992 | CB  | GLN | A | 312 | 215.675 | 83.798 | 211.202 | 1.00 | 78.77  | C |
| ATOM | 1993 | CG  | GLN | A | 312 | 215.203 | 84.120 | 212.625 | 1.00 | 101.21 | C |
| ATOM | 1994 | CD  | GLN | A | 312 | 215.952 | 83.321 | 213.691 | 1.00 | 105.49 | C |
| ATOM | 1995 | OE1 | GLN | A | 312 | 217.112 | 83.612 | 214.004 | 1.00 | 110.73 | O |
| ATOM | 1996 | NE2 | GLN | A | 312 | 215.294 | 82.305 | 214.243 | 1.00 | 82.13  | N |
| ATOM | 1997 | N   | ARG | A | 313 | 217.057 | 84.974 | 208.545 | 1.00 | 75.75  | N |
| ATOM | 1998 | CA  | ARG | A | 313 | 218.278 | 85.463 | 207.924 | 1.00 | 58.86  | C |
| ATOM | 1999 | C   | ARG | A | 313 | 218.184 | 86.894 | 207.391 | 1.00 | 51.81  | C |
| ATOM | 2000 | O   | ARG | A | 313 | 217.125 | 87.341 | 206.952 | 1.00 | 85.05  | O |
| ATOM | 2001 | CB  | ARG | A | 313 | 218.663 | 84.495 | 206.807 | 1.00 | 52.47  | C |
| ATOM | 2002 | CG  | ARG | A | 313 | 220.131 | 84.401 | 206.516 | 1.00 | 74.86  | C |
| ATOM | 2003 | CD  | ARG | A | 313 | 220.355 | 83.299 | 205.506 | 1.00 | 84.86  | C |
| ATOM | 2004 | NE  | ARG | A | 313 | 219.851 | 82.018 | 205.984 | 1.00 | 53.52  | N |
| ATOM | 2005 | CZ  | ARG | A | 313 | 219.467 | 81.032 | 205.186 | 1.00 | 62.95  | C |
| ATOM | 2006 | NH1 | ARG | A | 313 | 219.528 | 81.192 | 203.874 | 1.00 | 85.30  | N |
| ATOM | 2007 | NH2 | ARG | A | 313 | 219.039 | 79.888 | 205.697 | 1.00 | 49.87  | N |
| ATOM | 2008 | N   | MET | A | 314 | 219.318 | 87.590 | 207.430 | 1.00 | 75.49  | N |
| ATOM | 2009 | CA  | MET | A | 314 | 219.450 | 88.981 | 206.980 | 1.00 | 62.90  | C |
| ATOM | 2010 | C   | MET | A | 314 | 219.115 | 89.160 | 205.496 | 1.00 | 68.20  | C |
| ATOM | 2011 | O   | MET | A | 314 | 219.267 | 88.229 | 204.694 | 1.00 | 78.91  | O |
| ATOM | 2012 | CB  | MET | A | 314 | 220.888 | 89.463 | 207.248 | 1.00 | 79.70  | C |
| ATOM | 2013 | CG  | MET | A | 314 | 221.145 | 90.951 | 206.994 | 1.00 | 74.01  | C |
| ATOM | 2014 | SD  | MET | A | 314 | 222.873 | 91.447 | 207.330 | 1.00 | 84.44  | S |
| ATOM | 2015 | CE  | MET | A | 314 | 222.742 | 92.071 | 208.957 | 1.00 | 104.75 | C |
| ATOM | 2016 | N   | THR | A | 315 | 218.660 | 90.357 | 205.135 | 1.00 | 63.73  | N |
| ATOM | 2017 | CA  | THR | A | 315 | 218.319 | 90.652 | 203.750 | 1.00 | 64.98  | C |
| ATOM | 2018 | C   | THR | A | 315 | 219.470 | 91.347 | 203.030 | 1.00 | 68.09  | C |
| ATOM | 2019 | O   | THR | A | 315 | 220.317 | 91.969 | 203.658 | 1.00 | 63.59  | O |
| ATOM | 2020 | CB  | THR | A | 315 | 217.075 | 91.545 | 203.661 | 1.00 | 62.15  | C |
| ATOM | 2021 | OG1 | THR | A | 315 | 217.322 | 92.813 | 204.286 | 1.00 | 58.05  | O |
| ATOM | 2022 | CG2 | THR | A | 315 | 215.929 | 90.868 | 204.338 | 1.00 | 61.97  | C |
| ATOM | 2023 | N   | ILE | A | 316 | 219.498 | 91.236 | 201.707 | 1.00 | 65.76  | N |
| ATOM | 2024 | CA  | ILE | A | 316 | 220.566 | 91.854 | 200.935 | 1.00 | 66.14  | C |
| ATOM | 2025 | C   | ILE | A | 316 | 220.564 | 93.351 | 201.167 | 1.00 | 71.26  | C |
| ATOM | 2026 | O   | ILE | A | 316 | 221.618 | 93.981 | 201.192 | 1.00 | 67.36  | O |
| ATOM | 2027 | CB  | ILE | A | 316 | 220.417 | 91.583 | 199.426 | 1.00 | 60.35  | C |
| ATOM | 2028 | CG1 | ILE | A | 316 | 221.714 | 91.937 | 198.710 | 1.00 | 52.24  | C |
| ATOM | 2029 | CG2 | ILE | A | 316 | 219.314 | 92.435 | 198.854 | 1.00 | 56.27  | C |
| ATOM | 2030 | CD1 | ILE | A | 316 | 222.942 | 91.410 | 199.405 | 1.00 | 55.83  | C |
| ATOM | 2031 | N   | THR | A | 317 | 219.381 | 93.926 | 201.346 | 1.00 | 60.50  | N |
| ATOM | 2032 | CA  | THR | A | 317 | 219.301 | 95.356 | 201.591 | 1.00 | 58.94  | C |
| ATOM | 2033 | C   | THR | A | 317 | 219.858 | 95.658 | 202.964 | 1.00 | 61.73  | C |
| ATOM | 2034 | O   | THR | A | 317 | 220.533 | 96.659 | 203.161 | 1.00 | 69.91  | O |
| ATOM | 2035 | CB  | THR | A | 317 | 217.865 | 95.875 | 201.554 | 1.00 | 68.58  | C |
| ATOM | 2036 | OG1 | THR | A | 317 | 217.301 | 95.636 | 200.259 | 1.00 | 67.56  | O |
| ATOM | 2037 | CG2 | THR | A | 317 | 217.844 | 97.364 | 201.860 | 1.00 | 50.05  | C |
| ATOM | 2038 | N   | GLU | A | 318 | 219.577 | 94.794 | 203.923 | 1.00 | 54.23  | N |
| ATOM | 2039 | CA  | GLU | A | 318 | 220.082 | 95.027 | 205.266 | 1.00 | 69.88  | C |
| ATOM | 2040 | C   | GLU | A | 318 | 221.586 | 94.796 | 205.348 | 1.00 | 72.99  | C |
| ATOM | 2041 | O   | GLU | A | 318 | 222.262 | 95.329 | 206.221 | 1.00 | 64.78  | O |
| ATOM | 2042 | CB  | GLU | A | 318 | 219.336 | 94.138 | 206.269 | 1.00 | 82.03  | C |
| ATOM | 2043 | CG  | GLU | A | 318 | 217.903 | 94.596 | 206.496 | 1.00 | 64.99  | C |
| ATOM | 2044 | CD  | GLU | A | 318 | 217.152 | 93.742 | 207.486 | 1.00 | 85.92  | C |
| ATOM | 2045 | OE1 | GLU | A | 318 | 216.415 | 94.327 | 208.315 | 1.00 | 91.71  | O |
| ATOM | 2046 | OE2 | GLU | A | 318 | 217.288 | 92.497 | 207.424 | 1.00 | 88.17  | O |
| ATOM | 2047 | N   | PHE | A | 319 | 222.103 | 94.005 | 204.421 | 1.00 | 75.36  | N |
| ATOM | 2048 | CA  | PHE | A | 319 | 223.519 | 93.700 | 204.380 | 1.00 | 69.31  | C |
| ATOM | 2049 | C   | PHE | A | 319 | 224.279 | 94.883 | 203.800 | 1.00 | 79.85  | C |
| ATOM | 2050 | O   | PHE | A | 319 | 225.281 | 95.324 | 204.359 | 1.00 | 86.43  | O |
| ATOM | 2051 | CB  | PHE | A | 319 | 223.744 | 92.455 | 203.523 | 1.00 | 78.91  | C |

TABLE 1-continued

Coordinates of the activated MAPKAP kinase-2/peptide complex

| ATOM | 2052 | CG | PHE | A | 319 | 225.193 | 92.144 | 203.250 | 1.00 | 82.05 | C |
|---|---|---|---|---|---|---|---|---|---|---|---|
| ATOM | 2053 | CD1 | PHE | A | 319 | 225.978 | 91.538 | 204.210 | 1.00 | 64.69 | C |
| ATOM | 2054 | CD2 | PHE | A | 319 | 225.757 | 92.432 | 202.011 | 1.00 | 68.65 | C |
| ATOM | 2055 | CE1 | PHE | A | 319 | 227.287 | 91.219 | 203.940 | 1.00 | 55.30 | C |
| ATOM | 2056 | CE2 | PHE | A | 319 | 227.060 | 92.114 | 201.744 | 1.00 | 75.06 | C |
| ATOM | 2057 | CZ | PHE | A | 319 | 227.826 | 91.506 | 202.711 | 1.00 | 57.56 | C |
| ATOM | 2058 | N | MET | A | 320 | 223.805 | 95.404 | 202.679 | 1.00 | 64.36 | N |
| ATOM | 2059 | CA | MET | A | 320 | 224.489 | 96.527 | 202.066 | 1.00 | 69.16 | C |
| ATOM | 2060 | C | MET | A | 320 | 224.525 | 97.753 | 202.973 | 1.00 | 78.25 | C |
| ATOM | 2061 | O | MET | A | 320 | 225.304 | 98.673 | 202.745 | 1.00 | 86.13 | O |
| ATOM | 2062 | CB | MET | A | 320 | 223.848 | 96.889 | 200.725 | 1.00 | 73.27 | C |
| ATOM | 2063 | CG | MET | A | 320 | 224.120 | 95.877 | 199.635 | 1.00 | 72.98 | C |
| ATOM | 2064 | SD | MET | A | 320 | 225.832 | 95.315 | 199.691 | 1.00 | 87.32 | S |
| ATOM | 2065 | CE | MET | A | 320 | 226.586 | 96.413 | 198.528 | 1.00 | 70.20 | C |
| ATOM | 2066 | N | ASN | A | 321 | 223.695 | 97.772 | 204.006 | 1.00 | 77.28 | N |
| ATOM | 2067 | CA | ASN | A | 321 | 223.691 | 98.907 | 204.912 | 1.00 | 79.74 | C |
| ATOM | 2068 | C | ASN | A | 321 | 224.489 | 98.692 | 206.174 | 1.00 | 76.50 | C |
| ATOM | 2069 | O | ASN | A | 321 | 224.868 | 99.651 | 206.836 | 1.00 | 95.86 | O |
| ATOM | 2070 | CB | ASN | A | 321 | 222.271 | 99.296 | 205.267 | 1.00 | 79.55 | C |
| ATOM | 2071 | CG | ASN | A | 321 | 221.783 | 100.428 | 204.427 | 1.00 | 104.33 | C |
| ATOM | 2072 | OD1 | ASN | A | 321 | 222.191 | 101.578 | 204.622 | 1.00 | 115.09 | O |
| ATOM | 2073 | ND2 | ASN | A | 321 | 220.926 | 100.121 | 203.456 | 1.00 | 119.81 | N |
| ATOM | 2074 | N | HIS | A | 322 | 224.744 | 97.439 | 206.521 | 1.00 | 82.50 | N |
| ATOM | 2075 | CA | HIS | A | 322 | 225.527 | 97.179 | 207.707 | 1.00 | 80.78 | C |
| ATOM | 2076 | C | HIS | A | 322 | 226.837 | 97.948 | 207.555 | 1.00 | 84.39 | C |
| ATOM | 2077 | O | HIS | A | 322 | 227.483 | 97.895 | 206.506 | 1.00 | 83.28 | O |
| ATOM | 2078 | CB | HIS | A | 322 | 225.812 | 95.691 | 207.851 | 1.00 | 75.27 | C |
| ATOM | 2079 | CG | HIS | A | 322 | 226.690 | 95.370 | 209.013 | 1.00 | 76.67 | C |
| ATOM | 2080 | ND1 | HIS | A | 322 | 227.927 | 95.950 | 209.189 | 1.00 | 84.96 | N |
| ATOM | 2081 | CD2 | HIS | A | 322 | 226.504 | 94.548 | 210.070 | 1.00 | 67.42 | C |
| ATOM | 2082 | CE1 | HIS | A | 322 | 228.464 | 95.502 | 210.308 | 1.00 | 85.58 | C |
| ATOM | 2083 | NE2 | HIS | A | 322 | 227.622 | 94.649 | 210.862 | 1.00 | 86.63 | N |
| ATOM | 2084 | N | PRO | A | 323 | 227.234 | 98.686 | 208.603 | 1.00 | 91.61 | N |
| ATOM | 2085 | CA | PRO | A | 323 | 228.447 | 99.501 | 208.680 | 1.00 | 84.82 | C |
| ATOM | 2086 | C | PRO | A | 323 | 229.697 | 98.867 | 208.087 | 1.00 | 79.23 | C |
| ATOM | 2087 | O | PRO | A | 323 | 230.318 | 99.436 | 207.193 | 1.00 | 85.59 | O |
| ATOM | 2088 | CB | PRO | A | 323 | 228.567 | 99.772 | 210.170 | 1.00 | 74.59 | C |
| ATOM | 2089 | CG | PRO | A | 323 | 227.135 | 99.952 | 210.553 | 1.00 | 86.91 | C |
| ATOM | 2090 | CD | PRO | A | 323 | 226.484 | 98.767 | 209.868 | 1.00 | 92.14 | C |
| ATOM | 2091 | N | TRP | A | 324 | 230.066 | 97.692 | 208.578 | 1.00 | 81.53 | N |
| ATOM | 2092 | CA | TRP | A | 324 | 231.247 | 97.002 | 208.070 | 1.00 | 80.47 | C |
| ATOM | 2093 | C | TRP | A | 324 | 231.260 | 97.039 | 206.541 | 1.00 | 76.75 | C |
| ATOM | 2094 | O | TRP | A | 324 | 232.288 | 97.293 | 205.917 | 1.00 | 63.50 | O |
| ATOM | 2095 | CB | TRP | A | 324 | 231.225 | 95.553 | 208.537 | 1.00 | 79.62 | C |
| ATOM | 2096 | CG | TRP | A | 324 | 232.549 | 94.881 | 208.546 | 1.00 | 68.42 | C |
| ATOM | 2097 | CD1 | TRP | A | 324 | 233.579 | 95.118 | 209.408 | 1.00 | 97.23 | C |
| ATOM | 2098 | CD2 | TRP | A | 324 | 232.973 | 93.806 | 207.704 | 1.00 | 91.77 | C |
| ATOM | 2099 | NE1 | TRP | A | 324 | 234.614 | 94.254 | 209.162 | 1.00 | 96.32 | N |
| ATOM | 2100 | CE2 | TRP | A | 324 | 234.268 | 93.437 | 208.120 | 1.00 | 90.15 | C |
| ATOM | 2101 | CE3 | TRP | A | 324 | 232.382 | 93.118 | 206.639 | 1.00 | 85.73 | C |
| ATOM | 2102 | CZ2 | TRP | A | 324 | 234.979 | 92.411 | 207.515 | 1.00 | 55.96 | C |
| ATOM | 2103 | CZ3 | TRP | A | 324 | 233.091 | 92.099 | 206.038 | 1.00 | 78.54 | C |
| ATOM | 2104 | CH2 | TRP | A | 324 | 234.375 | 91.755 | 206.475 | 1.00 | 83.38 | C |
| ATOM | 2105 | N | ILE | A | 325 | 230.099 | 96.785 | 205.952 | 1.00 | 61.98 | N |
| ATOM | 2106 | CA | ILE | A | 325 | 229.956 | 96.764 | 204.513 | 1.00 | 63.34 | C |
| ATOM | 2107 | C | ILE | A | 325 | 229.832 | 98.156 | 203.920 | 1.00 | 81.46 | C |
| ATOM | 2108 | O | ILE | A | 325 | 230.518 | 98.483 | 202.956 | 1.00 | 101.97 | O |
| ATOM | 2109 | CB | ILE | A | 325 | 228.723 | 95.941 | 204.092 | 1.00 | 64.13 | C |
| ATOM | 2110 | CG1 | ILE | A | 325 | 229.156 | 94.621 | 203.470 | 1.00 | 57.81 | C |
| ATOM | 2111 | CG2 | ILE | A | 325 | 227.909 | 96.703 | 203.076 | 1.00 | 79.69 | C |
| ATOM | 2112 | CD1 | ILE | A | 325 | 230.005 | 93.796 | 204.357 | 1.00 | 99.33 | C |
| ATOM | 2113 | N | MET | A | 326 | 228.971 | 98.986 | 204.497 | 1.00 | 86.84 | N |
| ATOM | 2114 | CA | MET | A | 326 | 228.766 | 100.327 | 203.962 | 1.00 | 97.80 | C |
| ATOM | 2115 | C | MET | A | 326 | 229.941 | 101.291 | 204.108 | 1.00 | 88.82 | C |
| ATOM | 2116 | O | MET | A | 326 | 230.023 | 102.271 | 203.375 | 1.00 | 96.42 | O |
| ATOM | 2117 | CB | MET | A | 326 | 227.509 | 100.951 | 204.573 | 1.00 | 99.22 | C |
| ATOM | 2118 | CG | MET | A | 326 | 227.134 | 102.287 | 203.957 | 1.00 | 109.19 | C |
| ATOM | 2119 | SD | MET | A | 326 | 225.425 | 102.771 | 204.309 | 1.00 | 131.16 | S |
| ATOM | 2120 | CE | MET | A | 326 | 224.679 | 102.571 | 202.683 | 1.00 | 123.49 | C |
| ATOM | 2121 | N | GLN | A | 327 | 230.847 | 101.016 | 205.042 | 1.00 | 99.42 | N |
| ATOM | 2122 | CA | GLN | A | 327 | 232.005 | 101.880 | 205.253 | 1.00 | 100.47 | C |
| ATOM | 2123 | C | GLN | A | 327 | 233.330 | 101.120 | 205.290 | 1.00 | 109.31 | C |
| ATOM | 2124 | O | GLN | A | 327 | 234.060 | 101.184 | 206.279 | 1.00 | 116.79 | O |
| ATOM | 2125 | CB | GLN | A | 327 | 231.856 | 102.668 | 206.557 | 1.00 | 90.31 | C |
| ATOM | 2126 | CG | GLN | A | 327 | 230.780 | 103.743 | 206.538 | 1.00 | 124.03 | C |
| ATOM | 2127 | CD | GLN | A | 327 | 230.929 | 104.713 | 205.370 | 1.00 | 165.27 | C |
| ATOM | 2128 | OE1 | GLN | A | 327 | 232.047 | 105.051 | 204.958 | 1.00 | 160.87 | O |
| ATOM | 2129 | NE2 | GLN | A | 327 | 229.795 | 105.178 | 204.841 | 1.00 | 148.79 | N |

TABLE 1-continued

Coordinates of the activated MAPKAP kinase-2/peptide complex

| ATOM | 2130 | N   | SER | A | 328 | 233.644 | 100.406 | 204.215 | 1.00 | 109.39 | N |
|------|------|-----|-----|---|-----|---------|---------|---------|------|--------|---|
| ATOM | 2131 | CA  | SER | A | 328 | 234.888 | 99.643  | 204.157 | 1.00 | 117.56 | C |
| ATOM | 2132 | C   | SER | A | 328 | 236.084 | 100.539 | 204.457 | 1.00 | 126.63 | C |
| ATOM | 2133 | O   | SER | A | 328 | 236.892 | 100.239 | 205.332 | 1.00 | 122.39 | O |
| ATOM | 2134 | CB  | SER | A | 328 | 235.055 | 99.008  | 202.777 | 1.00 | 106.48 | C |
| ATOM | 2135 | OG  | SER | A | 328 | 233.976 | 98.139  | 202.490 | 1.00 | 101.32 | O |
| ATOM | 2136 | N   | THR | A | 329 | 236.189 | 101.642 | 203.725 | 1.00 | 147.22 | N |
| ATOM | 2137 | CA  | THR | A | 329 | 237.283 | 102.582 | 203.919 | 1.00 | 153.16 | C |
| ATOM | 2138 | C   | THR | A | 329 | 237.668 | 102.713 | 205.393 | 1.00 | 151.36 | C |
| ATOM | 2139 | O   | THR | A | 329 | 238.849 | 102.680 | 205.736 | 1.00 | 165.48 | O |
| ATOM | 2140 | CB  | THR | A | 329 | 236.918 | 103.986 | 203.365 | 1.00 | 159.02 | C |
| ATOM | 2141 | OG1 | THR | A | 329 | 237.929 | 104.930 | 203.748 | 1.00 | 164.35 | O |
| ATOM | 2142 | CG2 | THR | A | 329 | 235.553 | 104.443 | 203.893 | 1.00 | 171.23 | C |
| ATOM | 2143 | N   | LYS | A | 330 | 236.670 | 102.840 | 206.262 | 1.00 | 138.67 | N |
| ATOM | 2144 | CA  | LYS | A | 330 | 236.916 | 102.994 | 207.691 | 1.00 | 128.38 | C |
| ATOM | 2145 | C   | LYS | A | 330 | 236.937 | 101.670 | 208.457 | 1.00 | 134.38 | C |
| ATOM | 2146 | O   | LYS | A | 330 | 236.425 | 101.586 | 209.580 | 1.00 | 138.61 | O |
| ATOM | 2147 | CB  | LYS | A | 330 | 235.867 | 103.931 | 208.298 | 1.00 | 134.91 | C |
| ATOM | 2148 | N   | VAL | A | 331 | 237.526 | 100.637 | 207.860 | 1.00 | 122.49 | N |
| ATOM | 2149 | CA  | VAL | A | 331 | 237.608 | 99.340  | 208.531 | 1.00 | 120.28 | C |
| ATOM | 2150 | C   | VAL | A | 331 | 239.066 | 98.890  | 208.689 | 1.00 | 111.19 | C |
| ATOM | 2151 | O   | VAL | A | 331 | 239.850 | 98.899  | 207.739 | 1.00 | 85.41  | O |
| ATOM | 2152 | CB  | VAL | A | 331 | 236.770 | 98.239  | 207.785 | 1.00 | 120.15 | C |
| ATOM | 2153 | CG1 | VAL | A | 331 | 237.342 | 97.971  | 206.422 | 1.00 | 125.69 | C |
| ATOM | 2154 | CG2 | VAL | A | 331 | 236.740 | 96.946  | 208.595 | 1.00 | 124.20 | C |
| ATOM | 2155 | N   | PRO | A | 332 | 239.433 | 98.496  | 209.916 | 1.00 | 102.76 | N |
| ATOM | 2156 | CA  | PRO | A | 332 | 240.737 | 98.021  | 210.385 | 1.00 | 105.52 | C |
| ATOM | 2157 | C   | PRO | A | 332 | 241.528 | 97.215  | 209.363 | 1.00 | 112.97 | C |
| ATOM | 2158 | O   | PRO | A | 332 | 241.016 | 96.262  | 208.779 | 1.00 | 111.93 | O |
| ATOM | 2159 | CB  | PRO | A | 332 | 240.369 | 97.193  | 211.609 | 1.00 | 105.70 | C |
| ATOM | 2160 | CG  | PRO | A | 332 | 239.247 | 97.970  | 212.184 | 1.00 | 122.25 | C |
| ATOM | 2161 | CD  | PRO | A | 332 | 238.418 | 98.332  | 210.971 | 1.00 | 100.61 | C |
| ATOM | 2162 | N   | GLN | A | 333 | 242.782 | 97.604  | 209.154 | 1.00 | 109.39 | N |
| ATOM | 2163 | CA  | GLN | A | 333 | 243.645 | 96.908  | 208.206 | 1.00 | 106.56 | C |
| ATOM | 2164 | C   | GLN | A | 333 | 244.265 | 95.714  | 208.913 | 1.00 | 99.10  | C |
| ATOM | 2165 | O   | GLN | A | 333 | 245.347 | 95.251  | 208.554 | 1.00 | 97.72  | O |
| ATOM | 2166 | CB  | GLN | A | 333 | 244.744 | 97.842  | 207.696 | 1.00 | 117.29 | C |
| ATOM | 2167 | CG  | GLN | A | 333 | 244.224 | 99.042  | 206.922 | 1.00 | 121.73 | C |
| ATOM | 2168 | CD  | GLN | A | 333 | 244.771 | 99.095  | 205.510 | 1.00 | 144.41 | C |
| ATOM | 2169 | OE1 | GLN | A | 333 | 244.442 | 99.996  | 204.735 | 1.00 | 153.63 | O |
| ATOM | 2170 | NE2 | GLN | A | 333 | 245.613 | 98.124  | 205.165 | 1.00 | 138.94 | N |
| ATOM | 2171 | N   | THR | A | 334 | 243.565 | 95.229  | 209.931 | 1.00 | 88.60  | N |
| ATOM | 2172 | CA  | THR | A | 334 | 244.023 | 94.081  | 210.693 | 1.00 | 112.85 | C |
| ATOM | 2173 | C   | THR | A | 334 | 244.310 | 92.878  | 209.797 | 1.00 | 123.95 | C |
| ATOM | 2174 | O   | THR | A | 334 | 243.438 | 92.392  | 209.086 | 1.00 | 128.29 | O |
| ATOM | 2175 | CB  | THR | A | 334 | 242.989 | 93.668  | 211.738 | 1.00 | 105.19 | C |
| ATOM | 2176 | OG1 | THR | A | 334 | 243.011 | 92.243  | 211.887 | 1.00 | 102.93 | O |
| ATOM | 2177 | CG2 | THR | A | 334 | 241.607 | 94.120  | 211.315 | 1.00 | 106.97 | C |
| ATOM | 2178 | N   | PRO | A | 335 | 245.549 | 92.372  | 209.832 | 1.00 | 124.58 | N |
| ATOM | 2179 | CA  | PRO | A | 335 | 245.911 | 91.224  | 209.005 | 1.00 | 124.62 | C |
| ATOM | 2180 | C   | PRO | A | 335 | 245.058 | 89.999  | 209.317 | 1.00 | 119.67 | C |
| ATOM | 2181 | O   | PRO | A | 335 | 244.513 | 89.878  | 210.416 | 1.00 | 108.06 | O |
| ATOM | 2182 | CB  | PRO | A | 335 | 247.383 | 91.002  | 209.358 | 1.00 | 134.66 | C |
| ATOM | 2183 | CG  | PRO | A | 335 | 247.857 | 92.390  | 209.673 | 1.00 | 120.03 | C |
| ATOM | 2184 | CD  | PRO | A | 335 | 246.730 | 92.881  | 210.547 | 1.00 | 120.76 | C |
| ATOM | 2185 | N   | LEU | A | 336 | 244.926 | 89.110  | 208.333 | 1.00 | 110.96 | N |
| ATOM | 2186 | CA  | LEU | A | 336 | 244.175 | 87.867  | 208.499 | 1.00 | 98.45  | C |
| ATOM | 2187 | C   | LEU | A | 336 | 245.087 | 86.726  | 208.066 | 1.00 | 87.77  | C |
| ATOM | 2188 | O   | LEU | A | 336 | 245.851 | 86.877  | 207.117 | 1.00 | 92.64  | O |
| ATOM | 2189 | CB  | LEU | A | 336 | 242.909 | 87.852  | 207.632 | 1.00 | 95.92  | C |
| ATOM | 2190 | CG  | LEU | A | 336 | 241.694 | 88.725  | 207.963 | 1.00 | 81.15  | C |
| ATOM | 2191 | CD1 | LEU | A | 336 | 241.641 | 88.972  | 209.461 | 1.00 | 94.01  | C |
| ATOM | 2192 | CD2 | LEU | A | 336 | 241.773 | 90.034  | 207.215 | 1.00 | 82.79  | C |
| ATOM | 2193 | N   | HIS | A | 337 | 244.999 | 85.595  | 208.762 | 1.00 | 86.05  | N |
| ATOM | 2194 | CA  | HIS | A | 337 | 245.813 | 84.410  | 208.469 | 1.00 | 100.05 | C |
| ATOM | 2195 | C   | HIS | A | 337 | 245.401 | 83.709  | 207.170 | 1.00 | 103.25 | C |
| ATOM | 2196 | O   | HIS | A | 337 | 246.075 | 82.782  | 206.712 | 1.00 | 110.52 | O |
| ATOM | 2197 | CB  | HIS | A | 337 | 245.687 | 83.390  | 209.610 | 1.00 | 118.04 | C |
| ATOM | 2198 | CG  | HIS | A | 337 | 246.205 | 83.874  | 210.930 | 1.00 | 151.49 | C |
| ATOM | 2199 | ND1 | HIS | A | 337 | 246.241 | 85.210  | 211.271 | 1.00 | 169.76 | N |
| ATOM | 2200 | CD2 | HIS | A | 337 | 246.675 | 83.198  | 212.010 | 1.00 | 160.51 | C |
| ATOM | 2201 | CE1 | HIS | A | 337 | 246.713 | 85.337  | 212.502 | 1.00 | 129.99 | C |
| ATOM | 2202 | NE2 | HIS | A | 337 | 246.984 | 84.132  | 212.971 | 1.00 | 150.26 | N |
| ATOM | 2203 | N   | THR | A | 338 | 244.294 | 84.167  | 206.589 | 1.00 | 111.23 | N |
| ATOM | 2204 | CA  | THR | A | 338 | 243.713 | 83.590  | 205.375 | 1.00 | 105.16 | C |
| ATOM | 2205 | C   | THR | A | 338 | 244.649 | 82.822  | 204.440 | 1.00 | 106.58 | C |
| ATOM | 2206 | O   | THR | A | 338 | 244.708 | 81.589  | 204.504 | 1.00 | 102.89 | O |
| ATOM | 2207 | CB  | THR | A | 338 | 242.957 | 84.658  | 204.557 | 1.00 | 100.36 | C |

TABLE 1-continued

Coordinates of the activated MAPKAP kinase-2/peptide complex

| ATOM | 2208 | OG1 | THR | A | 338 | 242.218 | 85.494 | 205.451 | 1.00 | 103.82 | O |
|---|---|---|---|---|---|---|---|---|---|---|---|
| ATOM | 2209 | CG2 | THR | A | 338 | 241.961 | 83.993 | 203.605 | 1.00 | 97.07 | C |
| ATOM | 2210 | N | SER | A | 339 | 245.370 | 83.532 | 203.573 | 1.00 | 100.67 | N |
| ATOM | 2211 | CA | SER | A | 339 | 246.276 | 82.877 | 202.622 | 1.00 | 106.75 | C |
| ATOM | 2212 | C | SER | A | 339 | 246.957 | 81.641 | 203.202 | 1.00 | 117.17 | C |
| ATOM | 2213 | O | SER | A | 339 | 246.862 | 80.555 | 202.634 | 1.00 | 126.71 | O |
| ATOM | 2214 | CB | SER | A | 339 | 247.341 | 83.855 | 202.137 | 1.00 | 100.87 | C |
| ATOM | 2215 | OG | SER | A | 339 | 246.771 | 84.880 | 201.348 | 1.00 | 116.32 | O |
| ATOM | 2216 | N | ARG | A | 340 | 247.643 | 81.811 | 204.329 | 1.00 | 108.64 | N |
| ATOM | 2217 | CA | ARG | A | 340 | 248.325 | 80.697 | 204.971 | 1.00 | 101.87 | C |
| ATOM | 2218 | C | ARG | A | 340 | 247.391 | 79.508 | 205.121 | 1.00 | 94.03 | C |
| ATOM | 2219 | O | ARG | A | 340 | 247.554 | 78.480 | 204.454 | 1.00 | 80.82 | O |
| ATOM | 2220 | CB | ARG | A | 340 | 248.848 | 81.112 | 206.347 | 1.00 | 117.73 | C |
| ATOM | 2221 | CG | ARG | A | 340 | 250.041 | 82.055 | 206.292 | 1.00 | 162.36 | C |
| ATOM | 2222 | CD | ARG | A | 340 | 249.770 | 83.353 | 207.068 | 1.00 | 208.75 | C |
| ATOM | 2223 | NE | ARG | A | 340 | 249.607 | 83.107 | 208.504 | 1.00 | 216.90 | N |
| ATOM | 2224 | CZ | ARG | A | 340 | 249.378 | 84.053 | 209.416 | 1.00 | 203.42 | C |
| ATOM | 2225 | NH1 | ARG | A | 340 | 249.279 | 85.330 | 209.055 | 1.00 | 186.56 | N |
| ATOM | 2226 | NH2 | ARG | A | 340 | 249.255 | 83.719 | 210.696 | 1.00 | 191.24 | N |
| ATOM | 2227 | N | VAL | A | 341 | 246.412 | 79.653 | 206.004 | 1.00 | 84.97 | N |
| ATOM | 2228 | CA | VAL | A | 341 | 245.455 | 78.585 | 206.239 | 1.00 | 88.40 | C |
| ATOM | 2229 | C | VAL | A | 341 | 244.913 | 78.128 | 204.891 | 1.00 | 93.56 | C |
| ATOM | 2230 | O | VAL | A | 341 | 244.917 | 76.939 | 204.566 | 1.00 | 86.14 | O |
| ATOM | 2231 | CB | VAL | A | 341 | 244.269 | 79.077 | 207.078 | 1.00 | 86.60 | C |
| ATOM | 2232 | CG1 | VAL | A | 341 | 243.692 | 77.928 | 207.866 | 1.00 | 93.99 | C |
| ATOM | 2233 | CG2 | VAL | A | 341 | 244.700 | 80.214 | 207.975 | 1.00 | 87.95 | C |
| ATOM | 2234 | N | LEU | A | 342 | 244.463 | 79.101 | 204.107 | 1.00 | 98.12 | N |
| ATOM | 2235 | CA | LEU | A | 342 | 243.887 | 78.847 | 202.798 | 1.00 | 97.33 | C |
| ATOM | 2236 | C | LEU | A | 342 | 244.771 | 77.929 | 201.976 | 1.00 | 103.21 | C |
| ATOM | 2237 | O | LEU | A | 342 | 244.280 | 77.134 | 201.181 | 1.00 | 108.03 | O |
| ATOM | 2238 | CB | LEU | A | 342 | 243.666 | 80.171 | 202.065 | 1.00 | 101.09 | C |
| ATOM | 2239 | CG | LEU | A | 342 | 242.513 | 80.212 | 201.065 | 1.00 | 102.01 | C |
| ATOM | 2240 | CD1 | LEU | A | 342 | 241.211 | 79.865 | 201.761 | 1.00 | 89.86 | C |
| ATOM | 2241 | CD2 | LEU | A | 342 | 242.428 | 81.595 | 200.463 | 1.00 | 76.62 | C |
| ATOM | 2242 | N | LYS | A | 343 | 246.078 | 78.031 | 202.177 | 1.00 | 118.91 | N |
| ATOM | 2243 | CA | LYS | A | 343 | 246.980 | 77.154 | 201.447 | 1.00 | 128.99 | C |
| ATOM | 2244 | C | LYS | A | 343 | 247.211 | 75.800 | 202.144 | 1.00 | 129.81 | C |
| ATOM | 2245 | O | LYS | A | 343 | 247.730 | 74.859 | 201.559 | 1.00 | 124.36 | O |
| ATOM | 2246 | CB | LYS | A | 343 | 248.308 | 77.894 | 201.320 | 1.00 | 131.78 | C |
| ATOM | 2247 | CG | LYS | A | 343 | 249.233 | 77.265 | 200.274 | 1.00 | 133.47 | C |
| ATOM | 2248 | CD | LYS | A | 343 | 250.528 | 78.061 | 200.106 | 1.00 | 161.36 | C |
| ATOM | 2249 | CE | LYS | A | 343 | 251.591 | 77.288 | 199.318 | 1.00 | 189.16 | C |
| ATOM | 2250 | NZ | LYS | A | 343 | 252.882 | 77.968 | 199.425 | 1.00 | 166.57 | N |
| ATOM | 2251 | N | GLU | A | 344 | 246.842 | 75.714 | 203.442 | 1.00 | 128.07 | N |
| ATOM | 2252 | CA | GLU | A | 344 | 247.254 | 74.549 | 204.240 | 1.00 | 135.55 | C |
| ATOM | 2253 | C | GLU | A | 344 | 246.429 | 73.272 | 203.985 | 1.00 | 137.12 | C |
| ATOM | 2254 | O | GLU | A | 344 | 246.915 | 72.156 | 204.102 | 1.00 | 147.11 | O |
| ATOM | 2255 | CB | GLU | A | 344 | 247.196 | 74.935 | 205.720 | 1.00 | 144.51 | C |
| ATOM | 2256 | CG | GLU | A | 344 | 248.480 | 74.589 | 206.485 | 1.00 | 182.52 | C |
| ATOM | 2257 | CD | GLU | A | 344 | 249.414 | 75.782 | 206.484 | 1.00 | 205.75 | C |
| ATOM | 2258 | OE1 | GLU | A | 344 | 249.252 | 76.650 | 207.336 | 1.00 | 195.59 | O |
| ATOM | 2259 | OE2 | GLU | A | 344 | 250.270 | 75.861 | 205.607 | 1.00 | 217.38 | O |
| ATOM | 2260 | N | ASP | A | 345 | 245.127 | 73.456 | 203.702 | 1.00 | 134.97 | N |
| ATOM | 2261 | CA | ASP | A | 345 | 244.310 | 72.298 | 203.321 | 1.00 | 153.39 | C |
| ATOM | 2262 | C | ASP | A | 345 | 243.429 | 72.611 | 202.107 | 1.00 | 164.28 | C |
| ATOM | 2263 | O | ASP | A | 345 | 243.779 | 73.413 | 201.250 | 1.00 | 177.09 | O |
| ATOM | 2264 | CB | ASP | A | 345 | 243.435 | 71.892 | 204.514 | 1.00 | 147.36 | C |
| ATOM | 2265 | CG | ASP | A | 345 | 242.851 | 70.495 | 204.291 | 1.00 | 174.56 | C |
| ATOM | 2266 | OD1 | ASP | A | 345 | 243.455 | 69.731 | 203.533 | 1.00 | 191.84 | O |
| ATOM | 2267 | OD2 | ASP | A | 345 | 241.820 | 70.182 | 204.883 | 1.00 | 169.86 | O |
| TER | 2267 | | ASP | A | 345 | | | | | | |
| ATOM | 1 | N | LEU | C | 4 | 242.399 | 73.184 | 199.539 | 1.00 | 15.00 | |
| ATOM | 2 | CA | LEU | C | 4 | 240.997 | 73.382 | 199.193 | 1.00 | 15.00 | |
| ATOM | 3 | CB | LEU | C | 4 | 240.688 | 74.874 | 199.065 | 1.00 | 15.00 | |
| ATOM | 4 | CG | LEU | C | 4 | 239.462 | 75.245 | 198.226 | 1.00 | 15.00 | |
| ATOM | 5 | CD1 | LEU | C | 4 | 238.302 | 75.613 | 199.137 | 1.00 | 15.00 | |
| ATOM | 6 | CD2 | LEU | C | 4 | 239.801 | 76.397 | 197.295 | 1.00 | 15.00 | |
| ATOM | 7 | C | LEU | C | 4 | 240.650 | 72.668 | 197.890 | 1.00 | 15.00 | |
| ATOM | 8 | O | LEU | C | 4 | 241.075 | 72.982 | 196.773 | 1.00 | 22.73 | |
| ATOM | 9 | N | GLN | C | 5 | 239.765 | 71.671 | 197.981 | 1.00 | 15.00 | |
| ATOM | 10 | CA | GLN | C | 5 | 239.268 | 70.862 | 196.875 | 1.00 | 15.00 | |
| ATOM | 11 | CB | GLN | C | 5 | 238.690 | 69.547 | 197.399 | 1.00 | 15.00 | |
| ATOM | 12 | CG | GLN | C | 5 | 238.232 | 69.602 | 198.847 | 1.00 | 15.00 | |
| ATOM | 13 | CD | GLN | C | 5 | 238.424 | 68.283 | 199.571 | 1.00 | 15.00 | |
| ATOM | 14 | OE1 | GLN | C | 5 | 237.494 | 67.758 | 200.184 | 1.00 | 15.00 | |
| ATOM | 15 | NE2 | GLN | C | 5 | 239.634 | 67.743 | 199.504 | 1.00 | 15.00 | |
| ATOM | 16 | C | GLN | C | 5 | 238.205 | 71.615 | 196.082 | 1.00 | 15.00 | |
| ATOM | 17 | O | GLN | C | 5 | 237.316 | 72.263 | 196.691 | 1.00 | 15.04 | |

TABLE 1-continued

Coordinates of the activated MAPKAP kinase-2/peptide complex

| | | | | | | | | | | | |
|---|---|---|---|---|---|---|---|---|---|---|---|
| ATOM | 18 | N | ARG | C | 6 | 238.236 | 71.564 | 194.739 | 1.00 | 18.35 | N |
| ATOM | 19 | CA | ARG | C | 6 | 237.243 | 72.209 | 193.873 | 1.00 | 18.05 | C |
| ATOM | 20 | C | ARG | C | 6 | 235.863 | 71.634 | 194.126 | 1.00 | 17.37 | C |
| ATOM | 21 | O | ARG | C | 6 | 235.711 | 70.424 | 194.303 | 1.00 | 16.29 | O |
| ATOM | 22 | CB | ARG | C | 6 | 237.578 | 72.015 | 192.398 | 1.00 | 20.66 | C |
| ATOM | 23 | CG | ARG | C | 6 | 238.842 | 72.678 | 191.953 | 1.00 | 23.47 | C |
| ATOM | 24 | CD | ARG | C | 6 | 238.840 | 72.882 | 190.445 | 1.00 | 23.04 | C |
| ATOM | 25 | NE | ARG | C | 6 | 237.880 | 73.892 | 189.981 | 1.00 | 22.74 | N |
| ATOM | 26 | CZ | ARG | C | 6 | 237.975 | 75.204 | 190.210 | 1.00 | 20.22 | C |
| ATOM | 27 | NH1 | ARG | C | 6 | 238.987 | 75.699 | 190.913 | 1.00 | 19.12 | N |
| ATOM | 28 | NH2 | ARG | C | 6 | 237.069 | 76.031 | 189.710 | 1.00 | 20.28 | N |
| ATOM | 29 | N | GLN | C | 7 | 234.864 | 72.520 | 194.186 | 1.00 | 15.00 | |
| ATOM | 30 | CA | GLN | C | 7 | 233.488 | 72.105 | 194.427 | 1.00 | 15.00 | |
| ATOM | 31 | CB | GLN | C | 7 | 232.904 | 72.869 | 195.617 | 1.00 | 15.00 | |
| ATOM | 32 | CG | GLN | C | 7 | 233.852 | 72.996 | 196.798 | 1.00 | 15.00 | |
| ATOM | 33 | CD | GLN | C | 7 | 233.258 | 73.799 | 197.940 | 1.00 | 15.00 | |
| ATOM | 34 | OE1 | GLN | C | 7 | 232.067 | 74.116 | 197.937 | 1.00 | 15.00 | |
| ATOM | 35 | NE2 | GLN | C | 7 | 234.086 | 74.132 | 198.923 | 1.00 | 15.00 | |
| ATOM | 36 | C | GLN | C | 7 | 232.623 | 72.336 | 193.191 | 1.00 | 15.00 | |
| ATOM | 37 | O | GLN | C | 7 | 232.724 | 73.384 | 192.538 | 1.00 | 20.09 | |
| ATOM | 38 | N | LEU | C | 8 | 231.805 | 71.324 | 192.833 | 1.00 | 15.00 | |
| ATOM | 39 | CA | LEU | C | 8 | 230.922 | 71.415 | 191.677 | 1.00 | 15.00 | |
| ATOM | 40 | CB | LEU | C | 8 | 231.160 | 70.233 | 190.734 | 1.00 | 15.00 | |
| ATOM | 41 | CG | LEU | C | 8 | 231.208 | 70.558 | 189.238 | 1.00 | 15.00 | |
| ATOM | 42 | CD1 | LEU | C | 8 | 232.592 | 70.252 | 188.686 | 1.00 | 15.00 | |
| ATOM | 43 | CD2 | LEU | C | 8 | 230.147 | 69.759 | 188.500 | 1.00 | 15.00 | |
| ATOM | 44 | C | LEU | C | 8 | 229.459 | 71.446 | 192.108 | 1.00 | 15.00 | |
| ATOM | 45 | O | LEU | C | 8 | 229.098 | 70.977 | 193.190 | 1.00 | 13.73 | |
| ATOM | 46 | N | SER | C | 9 | 228.611 | 72.005 | 191.242 | 1.00 | 13.08 | N |
| ATOM | 47 | CA | SER | C | 9 | 227.183 | 72.104 | 191.526 | 1.00 | 12.87 | C |
| ATOM | 48 | C | SER | C | 9 | 226.402 | 70.843 | 191.151 | 1.00 | 13.16 | C |
| ATOM | 49 | O | SER | C | 9 | 226.930 | 69.943 | 190.490 | 1.00 | 14.95 | O |
| ATOM | 50 | CB | SER | C | 9 | 226.569 | 73.323 | 190.823 | 1.00 | 14.61 | C |
| ATOM | 51 | OG | SER | C | 9 | 226.326 | 73.072 | 189.444 | 1.00 | 14.77 | O |
| ATOM | 52 | N | ILE | C | 10 | 225.174 | 70.780 | 191.613 | 1.00 | 15.00 | |
| ATOM | 53 | CA | ILE | C | 10 | 224.249 | 69.694 | 191.311 | 1.00 | 15.00 | |
| ATOM | 54 | CB | ILE | C | 10 | 223.837 | 68.939 | 192.591 | 1.00 | 15.00 | |
| ATOM | 55 | CG2 | ILE | C | 10 | 225.025 | 68.817 | 193.532 | 1.00 | 15.00 | |
| ATOM | 56 | CG1 | ILE | C | 10 | 222.681 | 69.664 | 193.280 | 1.00 | 15.00 | |
| ATOM | 57 | CD1 | ILE | C | 10 | 222.397 | 69.168 | 194.682 | 1.00 | 15.00 | |
| ATOM | 58 | C | ILE | C | 10 | 222.992 | 70.220 | 190.626 | 1.00 | 15.00 | |
| ATOM | 59 | O | ILE | C | 10 | 222.755 | 71.452 | 190.654 | 1.00 | 12.25 | |
| ATOM | 60 | N | ALA | C | 11 | 222.224 | 69.342 | 190.029 | 1.00 | 14.49 | N |
| ATOM | 61 | CA | ALA | C | 11 | 220.983 | 69.676 | 189.342 | 1.00 | 16.79 | C |
| ATOM | 62 | C | ALA | C | 11 | 220.122 | 68.421 | 189.365 | 1.00 | 19.44 | C |
| ATOM | 63 | O | ALA | C | 11 | 220.552 | 67.360 | 188.901 | 1.00 | 19.58 | O |
| ATOM | 64 | CB | ALA | C | 11 | 221.252 | 70.125 | 187.902 | 1.00 | 15.87 | C |
| TER | 64 | | ALA | C | 11 | | | | | | |
| END | | | | | | | | | | | |

TABLE 2

Pairs of contacting atoms in the MAPKAP kinase-2/peptide complex

| Atom in activated MAPKAP kinase-2 | Atom in peptide | Distance |
|---|---|---|
| ILE74 CD1 | SER9 OG | 2.90275 |
| GLU145 OE1 | ARG6 NH2 | 1.94903 |
| LYS188 NZ | SER9 CB | 2.48016 |
| GLU190 CD | GLN7 O | 3.33866 |
| PHE210 CE2 | SER9 OG | 2.78278 |
| PHE210 CZ | ILE10 O | 2.37786 |
| CYS224 SG | ALA11 CA | 3.36808 |
| TYR225 O | SER9 CA | 3.25655 |
| TYR225 O | ILE10 N | 2.88016 |
| THR 226 OG1 | GLN 7 OE1 | 3.42713 |
| PRO 227 CD | LEU 8 O | 3.44686 |
| TYR 228 CB | GLN 7 OE1 | 3.02662 |
| TYR 229 CE1 | GLN 7 OE1 | 3.34283 |
| ASP 345 O | LEU 4 N | 2.21006 |

RNA Interference (RNAi) and Recombinant DNA.

siRNA duplexes consisting of twenty-one base pairs with a two-base deoxynucleotide overhang were purchased from Dharmacon Research. Cells were transfected with siRNAs using oligofectamine (Invitrogen) according to the manufacturer's instructions. Cells were typically harvested for further experiments after forty-eight hours. U2OS cells stably expressing shRNA constructs were generated by lentiviral gene transfer. The RNAi hairpins were cloned into the multiple cloning site of the lentiviral transfer vector pLentiLox-3.7puro or -3.7GFP. Amphotropic VSV-G pseudotyped lentivirus was used for all infections in a BL2+ facility. All transfer and packaging constructs were a kind gift from C. P. Dillon, (MIT). Targeted cells were selected in 8 µg/ml puromycin for four days. Sequences used for RNAi were: luciferase (shRNA), 5'pTGA CCA GGC ATT CAC AGA AAT TCA AGA GAT TTC TGT GAA TGC CTG GTC TTT TTT C-3' (SEQ ID NO: 24); hMAPKAP kinase-2 (shRNA), 5'-pTTG ACC ATC ACC GAG TTT ATT TCA AGA GAA TA AAC TCG GTG ATG GTC ATT TTT TC-3' (SEQ ID NO: 25); mMAPKAP kinase-2 (shRNA), 5'-pTCG ATG CGT GTT GAC TAT GAT TCA AGA GAT CAT AGT CAA CAC GCA TCG TTT TTT C-3' (SEQ ID NO: 26); GFP (siRNA) sense 5'-UCC CGG CUA UGU GCA GGA GdTdT-3' (SEQ ID NO: 27) and antisense strand 5'-CUCCUG CAC AUA GCC GGG AdTdT-3' (SEQ ID NO: 28); mMAPKAP kinase-2 (siRNA), sense 5'-CGA UGC GUG UUG ACU AUG AdTdT-3' (SEQ ID NO: 29) and antisense strand 5'-UCA UAG UCA ACA CGC AUC GdTdT-3' (SEQ ID NO: 30); hMAPKAP kinase-2 (siRNA), sense 5'-UGA CCA UCA CCG AGU UUA UdTdT-3' (SEQ ID NO: 31) and anti-sense strand 5'-AUA AAC UCG GUG AUG GUC AdTdT-3' (SEQ ID NO: 32); Chk1 (siRNA), 5'-UGG CAA CAG UAU UUC GGU AdTdT-3' (SEQ ID NO: 33) and antisense strand 5'-UAC CGA AAU ACU GUU GCC AdTdT-3' (SEQ ID NO: 34).

For overexpression studies, FLAG-6×His-tagged human Chk1 cDNA was PCR amplified and subcloned into the Mlu-1 and Not-1 sites of pHURRA downstream from the CMV promoter. pHURRA was a kind gift from Dr. H. Pavenstadt (U. of Munster).

Therapy

Therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the patient's disease or disorder, and how the patient responds to the treatment. Additionally, a person having a greater risk of developing a disease or disorder that may be treated by the methods of the invention (e.g., a person who is genetically predisposed) may receive prophylactic treatment to inhibit or delay symptoms of the disease. Drug administration may be performed at different intervals (e.g., daily, weekly, or monthly). Therapy may be given in on-and-off cycles that include rest periods so that the patient's body has a chance to build healthy new cells and regain its strength. Therapy may be used to extend the patient's lifespan.

For cancer treatment, depending on the type of cancer and its stage of development, the therapy can be used to slow the spreading of the cancer, to slow the cancer's growth, to kill or arrest cancer cells that may have spread to other parts of the body from the original tumor, to relieve symptoms caused by the cancer, or to prevent cancer in the first place.

Administration of Therapeutic Compounds

By selectively disrupting or preventing a compound from binding to its natural partner(s) through its binding site, one may inhibit the biological activity or the biological function of a MAPKAP kinase-2 polypeptide. The methods of the invention feature the use of compounds that inhibit an activity of a MAPKAP kinase-2 polypeptide, whether by reducing expression of the polypeptide (e.g., RNAi or antisense therapy), or by binding directly to a MAPKAP kinase-2 polypeptide and inhibiting its substrate-binding activity. In some instances, MAPKAP kinase-2 inhibitory compounds are administered to patients having one or more p53-deficient cells, e.g., tumor cells. Exemplary inhibitory compounds will be described further below.

Diseases or disorders characterized by inappropriate cell cycle regulation include cellular proliferative disorders, such as neoplasias. Examples of neoplasias include, without limitation, acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor. Any of these diseases or disorders can include, or be associated with, one or more p53-deficient cells, e.g., tumor cells.

A MAPKAP kinase-2-binding peptide, small molecule, or other compound may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Combination Therapy

As described above, if desired, treatment with compounds that inhibit MAPKAP kinase-2 polypeptides may be combined with therapies for the treatment of proliferative disease, such as radiotherapy, surgery, or chemotherapy. Chemotherapeutic agents that may be administered with compounds (e.g., UCN-01) that interact with a MAPKAP kinase-2 polypeptide include, but are not limited to, alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, to hexamethylmelamine, hydroxyurea, hypericin, ifosfamide, imatinib, interferon, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, and vinorelbine. One or more chemotherapeutic agents may be administered in combination with one or more compounds that inhibit MAPKAP kinase-2 polypeptides. In some instances, combination therapy is administered to patients having one or more p53-deficient cells, e.g., tumor cells.

In the combination therapies of the invention, the therapy components are administered simultaneously, or within twenty-eight days of each other, in amounts sufficient to inhibit the growth of said neoplasm.

Depending on the type of cancer and its stage of development, the combination therapy can be used to treat cancer, to slow the spreading of the cancer, to slow the cancer's growth, to kill or arrest cancer cells that may have spread to other parts of the body from the original tumor, to relieve symptoms caused by the cancer, or to prevent cancer in the first place. Combination therapy can also help people live more comfortably by eliminating cancer cells that cause pain or discomfort.

The administration of a combination of the present invention allows for the administration of lower doses of each compound, providing similar efficacy and lower toxicity compared to administration of either compound alone. Alternatively, such combinations result in improved efficacy in treating neoplasms with similar or reduced toxicity.

RNA Interference Therapy

The invention features the novel and therapeutically important discovery that the use of RNA interference (RNAi) to reduce MAPKAP kinase-2 expression renders cells more susceptible to chemotherapeutic agents. Accordingly, using the methods of the invention, nucleobase oligomers may be employed in double-stranded RNAs for RNAi-mediated knockdown of MAPKAP kinase-2 expression. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). In RNAi, gene silencing is typically triggered post-transcriptionally by the presence of double-stranded RNA (dsRNA) in a cell. This dsRNA is processed intracellularly into shorter pieces called small interfering RNAs (siRNAs). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs consist of a stem-loop structure with optional 3' UU-overhangs. While there may be variation, stems can range from twenty-one to thirty-one base pairs (desirably twenty-five to twenty-nine base pairs), and the loops can range from four to thirty base pairs (desirably four to twenty-three base pairs). For expression of shRNAs within cells, plasmid vectors containing, e.g., the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Computer programs that employ rational design of oligos are useful in predicting regions of the MAPKAP kinase-2 sequence that may be targeted by RNAi. For example, see Reynolds et al., Nat. Biotechnol., 22:326-330, 2004, for a description of the Dharmacon siDESIGN tool. Table 3 lists several exemplary nucleotide sequences within MAPKAP kinase-2 that may be targeted for purposes of RNA interference. siRNA or shRNA oligos may be made corresponding to the sequences shown and including an overhang, e.g., a 3' dTdT overhang and/or a loop.

TABLE 3

| MAPKAP kinase-2 RNAi target sequences | |
|---|---|
| Sequence (5' to 3') | SEQ ID NO: |
| GACCAGGCATTCACAGAAA | 35 |
| TTGACCACTCCTTGTTATA | 36 |
| GACCACTCCTTGTTATACA | 37 |
| TGACCATCACCGAGTTTAT | 38 |
| TCACCGAGTTTATGAACCA | 39 |
| TCAAGAAGAACGCCATCAT | 40 |
| AAGCATCCGAAATCATGAA | 41 |
| AGTATCTGCATTCAATCAA | 42 |
| CTTTGACCACTCCTTGTTA | 43 |
| TTTGACCACTCCTTGTTAT | 44 |
| TACGGATCGTGGATGTGTA | 45 |
| GGACGGTGGAGAACTCTTT | 46 |
| CTTGTTATACACCGTACTA | 47 |
| GACGGTGGAGAACTCTTTA | 48 |
| GGAGAACTCTTTAGCCGAA | 49 |

Antisense Therapy

As an alternative to RNAi-based approaches, therapeutic strategies utilizing MAPKAP kinase-2 antisense nucleic acids may be employed in the methods of the invention. The technique is based on the principle that sequence-specific suppression of gene expression can be achieved by intracellular hybridization between mRNA and a complementary antisense species. The formation of a hybrid RNA duplex may then interfere with the processing/transport/translation and/or stability of the target MAPKAP kinase-2 mRNA. Antisense strategies may use a variety of approaches, including the use to of antisense oligonucleotides and injection of antisense RNA. An exemplary approach features transfection of antisense RNA expression vectors into targeted cells. Antisense effects can be induced by control (sense) sequences;

however, the extent of phenotypic changes are highly variable. Phenotypic effects induced by antisense effects are based on changes in criteria such as protein levels, protein activity measurement, and target mRNA levels.

Computer programs such as OLIGO (previously distributed by National Biosciences Inc.) may be used to select candidate nucleobase oligomers for antisense therapy based on the following criteria:

1) no more than 75% GC content, and no more than 75% AT content;
2) preferably no nucleobase oligomers with four or more consecutive G residues (due to reported toxic effects, although one was chosen as a toxicity control);
3) no nucleobase oligomers with the ability to form stable dimers or hairpin structures; and
4) sequences around the translation start site are a preferred region.

In addition, accessible regions of the target mRNA may be predicted with the help of the RNA secondary structure folding program MFOLD (M. Zuker, D. H. Mathews & D. H. Turner, Algorithms and Thermodynamics for RNA Secondary Structure Prediction: A Practical Guide. In: RNA Biochemistry and Biotechnology, J. Barciszewski & B. F. C. Clark, eds., NATO ASI Series, Kluwer Academic Publishers, (1999). Sub-optimal folds with a free energy value within 5% of the predicted most stable fold of the mRNA may be predicted using a window of 200 bases within which a residue can find a complimentary base to form a base pair bond. Open regions that do not form a base pair may be summed together with each suboptimal fold, and areas that consistently are predicted as open may be considered more accessible to the binding to nucleobase oligomers. Additional nucleobase oligomer that only partially fulfill some of the above selection criteria may also be chosen as possible candidates if they recognize a predicted open region of the target mRNA.

Therapeutically Useful Compounds and Pharmaceutical Compositions

Any compound or pharmaceutical composition that inhibits an activity of MAPKAP kinase-2 may be useful in the methods of the invention. The model of the activated MAPKAP kinase-2/peptide complex described above (Table 1) indicates that peptides, or peptide-like compounds, e.g., peptidomimetics, may be useful for inhibiting MAPKAP kinase-2. Such compounds achieve this effect by mimicking the natural peptide substrate of MAPKAP kinase-2 and decreasing the extent or rate with which a MAPKAP kinase-2 polypeptide is able to bind to its natural substrates in vivo. Accordingly, methods of synthesis or modification of peptides and peptide-like compounds is described below.

Peptide Synthesis and Conjugation

A compound of the invention that includes a peptide is prepared as detailed above. Alternatively, peptides can be prepared using standard FMOC chemistry on 2-chlorotrityl chloride resin (Int. J. Pept. Prot. Res. 38, 1991, 555-61). Cleavage from the resin is performed using 20% acetic acid in dichloromehane (DCM), which leaves the side chain still blocked. Free terminal carboxylate peptide is then coupled to 4' (aminomethy)-fluorescein (Molecular Probes, A-1351; Eugene, Oreg.) using excess diisopropylcarbodiimide (DIC) in dimethylformamide (DMF) at room temperature. The to fluorescent N—C blocked peptide is purified by silica gel chromatography (10% methanol in DCM). The N terminal FMOC group is then removed using piperidine (20%) in DMF, and the N-free peptide, purified by silica gel chromatography (20% methanol in DCM, 0.5% HOAc). Finally, any t-butyl side chain protective groups are removed using 95% trifluoroacetic acid containing 2.5% water and 2.5% triisopropyl silane. The peptide obtained in such a manner should give a single peak by HPLC and is sufficiently pure for carrying on with the assay described below.

Peptide Modifications and Unnatural Amino Acids

It is understood that modifications can be made to the amino acid residues of the peptide-containing compounds of the invention, to enhance or prolong the therapeutic efficacy and/or bioavailability of the compound. Accordingly, α-amino acids having the following general formula (I):

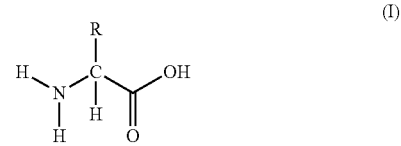

where R defines the specific amino acid residue, may undergo various modifications. Exemplary modifications of α-amino acids, include, but are not limited to, the following formula (II):

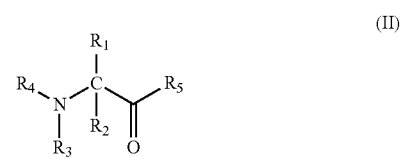

$R_1$, $R_2$, $R_3$, $R_4$, and $R_5$, are independently hydrogen, hydroxy, nitro, halo, $C_{1-5}$ branched or linear alkyl, $C_{1-5}$ alkaryl, heteroaryl, and aryl; wherein the alkyl, alkaryl, heteroaryl, and aryl may be unsubstituted or substituted by one or more substituents selected from the group consisting of $C_{1-5}$ alkyl, hydroxy, halo, nitro, $C_{1-5}$ alkoxy, $C_{1-5}$ alkylthio, trihalomethyl, $C_{1-5}$ acyl, arylcarbonyl, heteroarylcarbonyl, nitrile, $C_{1-5}$ alkoxycarbonyl, oxo, arylalkyl (wherein the alkyl group has from 1 to 5 carbon atoms) and heteroarylalkyl (wherein the alkyl group has from 1 to 5 carbon atoms); alternatively, $R_1$ and $R_2$ are joined to form a $C_{3-8}$ cyclic ring, optionally including oxygen, sulfur or hydrogen, or $C_{1-5}$ alkyl, optionally substituted by hydroxyl; or $R_2$ and $R_3$ are joined to form a $C_{3-8}$ cyclic ring, optionally substituted by hydroxyl and optionally including oxygen, sulfur, $C_{1-5}$ aminoalkyl, or $C_{1-5}$ alkyl.

A compound of the invention that includes a peptide may include, but it is not limited to, an unnatural N-terminal amino acid of the formula (III):

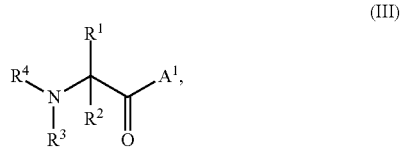

where $A^1$ is an amino acid or peptide chain linked via an α-amino group; $R^1$ and $R^3$ are independently hydrogen, $C_{1-5}$ branched or linear $C_{1-5}$ alkyl, $C_{1-5}$ alkaryl, heteroaryl, and aryl, each of which are unsubstituted or substituted with a substitutent selected from: 1 to 3 of $C_{1-5}$ alkyl, 1 to 3 of halogen, 1 to 2 of —$OR^5$, $N(R^5)(R^6)$, $SR^5$, N—$C(NR^5)$ $NR^6R^7$, methylenedioxy, —$S(O)_m R^5$, 1 to 2 of —$CF_3$, —OCF$_3$, nitro, —N(R$^5$)C(O)(R$^6$), —C(O)OR$^5$, —C(O)N(R$^5$)(R$^6$), -1H-tetrazol-5-yl, —SO$_2$N(R$^5$)(R$^6$), —N(R$^5$)SO$_2$ aryl, or —N(R$^5$)SO$_2$R$^6$; R$^5$, R$^6$ and R$^7$ are independently selected from hydrogen, C$_{1-5}$ linear or branched alkyl, C$_{1-5}$ alkaryl, aryl, heteroaryl, and C$_{3-7}$ cycloalkyl, and where two C$_{1-5}$ alkyl groups are present on one atom, they optionally are joined to form a C$_{3-8}$ cyclic ring, optionally including oxygen, sulfur or NR$^7$, where R$^7$ is hydrogen, or C$_{1-5}$ alkyl, optionally substituted by hydroxyl; R$^2$ is hydrogen, F, C$_{1-5}$ linear or branched alkyl, C$_{1-5}$ alkaryl; or R$^2$ and R$^1$ are joined to form a C$_{3-8}$ cyclic ring, optionally including oxygen, sulfur, or NR$^7$, where R$^7$ is hydrogen, or C$_{1-5}$ alkyl, optionally substituted by hydroxyl, or R$^2$ and R$^3$ are joined to form a C$_{3-8}$ cyclic ring, optionally substituted by hydroxyl and optionally including oxygen, sulfur or NR$^7$, where R$^7$ is hydrogen, or C$_{1-5}$ alkyl; R$^2$ is hydrogen, F, C$_{1-5}$ linear or branched alkyl, C$_{1-5}$ alkaryl; and R$^4$ is hydrogen, C$_{1-5}$ branched or linear C$_{1-5}$ alkyl, C$_{1-5}$ alkaryl, heteroaryl, and aryl, each of which are unsubstituted or substituted with a substituent selected from: 1 to 3 of C$_{1-5}$ alkyl, 1 to 3 of halogen, 1 to 2 of —OR$^5$, N(R$^5$)(R$^6$), N—C(NR$^5$)NR$^6$R$^7$, methylenedioxy, —S(O)$_m$R$^5$ (where m is 0-2), 1 to 2 of —CF$_3$, —OCF$_3$, nitro, —N(R$^5$)C(O)(R$^6$), —N(R$^5$)C(O)(OR$^6$), —C(O)OR$^5$, —C(O)N(R)(R$^6$), -1H-tetrazol-5-yl, —SO$_2$N(R$^5$)(R$^6$), —N(R$^5$)SO$_2$ aryl, or —N(R$^5$)SO$_2$R$^6$, R$^5$, R$^6$ and R$^7$ are independently selected from hydrogen, C$_{1-5}$ linear or branched alkyl, C$_{1-5}$ alkaryl, aryl, heteroaryl, and C$_{3-7}$ cycloalkyl, and where two C$_{1-5}$ alkyl groups are present on one atom, they optionally are joined to form a C$_{3-8}$ cyclic ring, optionally including oxygen, sulfur or NR$^7$, where R$^7$ is hydrogen, or C$_{1-5}$ alkyl, optionally substituted by hydroxyl.

A compound of the invention may also include an unnatural internal amino acid of the formula:

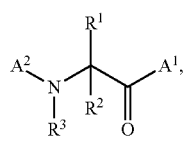

(IV)

where A$^2$ is an amino acid or peptide chain linked via an t-carboxy group; A$^1$ is an amino acid or peptide chain linked via an α-amino group; R$^1$ and R$^3$ are independently hydrogen, C$_{1-5}$ branched or linear C$_{1-5}$ alkyl, C$_{1-5}$ alkaryl, heteroaryl, and aryl, each of which are unsubstituted or substituted with a substituent selected from: 1 to 3 of C$_{1-5}$ alkyl, 1 to 3 of halogen, 1 to 2 of —OR$^5$, N(R$^5$)(R$^6$), SR$^5$, N—C(NR$^5$)NR$^6$R$^7$, methylenedioxy, —S(O)$_m$R$^5$ (m is 1-2), 1 to 2 of —CF$_3$, —OCF$_3$, nitro, —N(R$^5$)C(O)(R$^6$), —C(O)OR$^5$, —C(O)N(R$^5$)(R$^6$), -1H-tetrazol-5-yl, —SO$_2$N(R$^5$)(R$^6$), —N(R$^5$)SO$_2$ aryl, or —N(R$^5$)SO$_2$R$^6$; R$^5$, R$^6$ and R$^7$ are independently selected from hydrogen, C$_{1-5}$ linear or branched alkyl, C$_{1-5}$ alkaryl, aryl, heteroaryl, and C$_{3-7}$ cycloalkyl, and where two C$_{1-5}$ alkyl groups are present on one atom, they optionally are joined to form a C$_{3-8}$ cyclic ring, optionally including oxygen, sulfur or NR$^7$, where R$^7$ is hydrogen, or C$_{1-5}$ alkyl, optionally substituted by hydroxyl; and R$^2$ is hydrogen, F, C$_{1-5}$ linear or branched alkyl, C$_{1-5}$ alkaryl; or R$^2$ and R$^1$ are joined to form a C$_{3-8}$ cyclic ring, optionally including oxygen, sulfur or NR$^7$, where R$^7$ is hydrogen, or C$_{1-5}$ alkyl, optionally substituted by hydroxyl, or R$^2$ and R$^3$ are joined to form a C$_{3-8}$ cyclic ring, optionally substituted by hydroxyl and optionally including oxygen, sulfur or NR$^7$, where R$^7$ is hydrogen, or C$_{1-5}$ alkyl.

The invention also includes modifications of the peptide-containing compounds of the invention, wherein an unnatural internal amino acid of the formula:

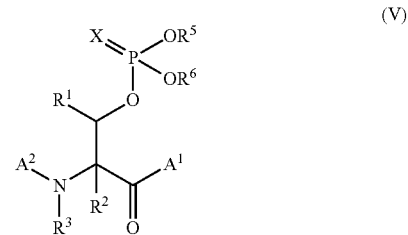

(V)

is present, where A$^2$ is an amino acid or peptide chain linked via an α-carboxy group; A$^1$ is an amino acid or peptide chain linked via an α-amino group; R$^1$ and R$^3$ are independently hydrogen, C$_{1-5}$ branched or linear C$_{1-5}$ alkyl, and C$_{1-5}$ alkaryl; R$^2$ is hydrogen, F, C$_{1-5}$ linear or branched alkyl, C$_{1-5}$ alkaryl; or R$^2$ and R$^1$ are joined to form a C$_{3-8}$ cyclic ring, optionally including oxygen, sulfur or NR$^7$, where R$^7$ is hydrogen, or C$_{1-5}$ alkyl, optionally substituted by hydroxyl; X is O or S; and R$^5$ and R$^6$ are independently selected from hydrogen, C$_{1-5}$ linear or branched alkyl, C$_{1-5}$ alkaryl, aryl, heteroaryl, and C$_{3-7}$ cycloalkyl, and where two C$_{1-5}$ alkyl groups are present on one atom, they optionally are joined to form a C$_{3-8}$ cyclic ring, optionally including oxygen, sulfur or NR$^7$, where R$^7$ is hydrogen, or C$_{1-5}$ alkyl, optionally substituted by hydroxyl; or R$^5$ and R$^6$ are joined to form a C$_{3-8}$ cyclic ring, optionally including oxygen, sulfur or NR$^7$, where R$^7$ is hydrogen, or C$_{1-5}$ alkyl, optionally substituted by hydroxyl.

A compound of the invention may also include a C-terminal unnatural internal amino acid of the formula:

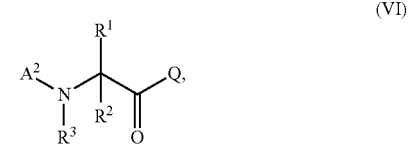

(VI)

where A$^2$ is an amino acid or peptide chain linked via an α-carboxy group; R$^1$ and R$^3$ are independently hydrogen, C$_{1-5}$ branched or linear C$_{1-5}$ alkyl, C$_{1-5}$ alkaryl, heteroaryl, and aryl, each of which are unsubstituted or substituted with a substituent selected from: 1 to 3 of C$_{1-5}$ alkyl, 1 to 3 of halogen, 1 to 2 of —OR$^5$, N(R$^5$)(R$^6$), SR$^5$, N—C(NR$^5$)NR$^6$R$^7$, methylenedioxy, —S(O)$_m$R$^5$, 1 to 2 of —CF$_3$, —OCF$_3$, nitro, —N(R$^5$)C(O)(R$^6$), —C(O)OR$^5$, —C(O)N(R$^5$)(R$^6$), -1H-tetrazol-5-yl, —SO$_2$N(R$^5$)(R$^6$), —N(R$^5$)SO$_2$ aryl, or —N(R$^5$)SO$_2$R$^6$; R$^5$, R$^6$ and R$^7$ are independently selected from hydrogen, C$_{1-5}$ linear or branched alkyl, C$_{1-5}$ alkaryl, aryl, heteroaryl, and C$_{3-7}$ cycloalkyl, and where two C$_{1-5}$ alkyl groups are present on one atom, they optionally are joined to form a C$_{3-8}$ cyclic ring, optionally including oxygen, sulfur or NR$^7$, where R$^7$ is hydrogen, or C$_{1-5}$ alkyl, optionally substituted by hydroxyl; R$^2$ is hydrogen, F, C$_{1-5}$ linear or branched alkyl, C$_{1-5}$ alkaryl; or R$^2$ and R$^1$ are joined to form a C$_{3-8}$ cyclic ring, optionally including oxygen, sulfur or NR$^7$, where R$^7$ is hydrogen, or C$_{1-5}$ alkyl, optionally substituted by hydroxyl; or R$^2$ and R$^3$ are joined to form a C$_{3-8}$ cyclic ring, optionally substituted by hydroxyl and optionally including oxygen, sulfur or NR$^7$, where R$^7$ is hydrogen, or C$_{1-5}$ alkyl; R$^2$ is hydrogen, F, C$_{1-5}$ linear or branched alkyl, C$_{1-5}$ alkaryl;

and Q is OH, OR$^5$, or NR$^5$R$^6$, where R$^5$, R$^6$ are independently selected from hydrogen, C$_{1-5}$ linear or branched alkyl, C$_{1-5}$ alkaryl, aryl, heteroaryl, and C$_{3-7}$ cycloalkyl, and where two C$_{1-5}$ alkyl groups are present on one atom, they optionally are joined to form a C$_{3-8}$ cyclic ring, optionally including oxygen, sulfur or NR$^7$, where R$^7$ is hydrogen, or C$_{1-5}$ alkyl, optionally substituted by hydroxyl. Methods well known in the art for modifying peptides are found, for example, in "Remington: The Science and Practice of Pharmacy," (20th ed., ed. A. R. Gennaro, 2000, Lippincott Williams & Wilkins, Philadelphia).

Peptidomimetics

Peptide derivatives (e.g., peptidomimetics) include cyclic peptides, peptides obtained by substitution of a natural amino acid residue by the corresponding D-stereoisomer, or by an unnatural amino acid residue, chemical derivatives of the peptides, dual peptides, multimers of the peptides, and peptides fused to other proteins or carriers. A cyclic derivative of a peptide of the invention is one having two or more additional amino acid residues suitable for cyclization. These residues are often added at the carboxyl terminus and at the amino terminus. A peptide derivative may have one or more amino acid residues replaced by the corresponding D-amino acid residue. In one example, a peptide or peptide derivative of the invention is all-L, all-D, or a mixed D,L-peptide. In another example, an amino acid residue is replaced by an unnatural amino acid residue. Examples of unnatural or derivatized unnatural amino acids include Nα-methyl amino acids, Cα-methyl amino acids, and n-methyl amino acids.

A chemical derivative of a peptide of the invention includes, but is not limited to, a derivative containing additional chemical moieties not normally a part of the peptide. Examples of such derivatives include: (a) N-acyl derivatives of the amino terminal or of another free amino group, where the acyl group may be either an alkanoyl group, e.g., acetyl, hexanoyl, octanoyl, an aroyl group, e.g., benzoyl, or a blocking group such as Fmoc (fluorenylmethyl-O—CO—), carbobenzoxy (benzyl-O—CO—), monomethoxysuccinyl, naphthyl-NH—CO—, acetylamino-caproyl, adamantyl-NH—CO—; (b) esters of the carboxyl terminal or of another free carboxyl or hydroxy groups; (c) amides of the carboxyl terminal or of another free carboxyl groups produced by reaction with ammonia or with a suitable amine; (d) glycosylated derivatives; (e) phosphorylated derivatives; (f) derivatives conjugated to lipophilic moieties, e.g., caproyl, lauryl, stearoyl; and (g) derivatives conjugated to an antibody or other biological ligand. Also included among the chemical derivatives are those derivatives obtained by modification of the peptide bond —CO—NH—, for example, by: (a) reduction to —CH$_2$—NH—; (b) alkylation to —CO—N(alkyl)—; and (c) inversion to —NH—CO—. Peptidomimetics may also comprise phosphonate or sulfonate moieties.

A dual peptide of the invention consists of two of the same, or two different, peptides of the invention covalently linked to one another, either directly or through a spacer.

Multimers of the invention consist of polymer molecules formed from a number of the same or different peptides or derivatives thereof.

In one example, a peptide derivative is more resistant to proteolytic degradation than the corresponding non-derivatized peptide. For example, a peptide derivative having D-amino acid substitution(s) in place of one or more L-amino acid residue(s) resists proteolytic cleavage.

In another example, the peptide derivative has increased permeability across a cell membrane as compared to the corresponding non-derivatized peptide. For example, a peptide derivative may have a lipophilic moiety coupled at the amino terminus and/or carboxyl terminus and/or an internal site. Such derivatives are highly preferred when targeting intracellular protein-protein interactions, provided they retain the desired functional activity.

In another example, a peptide derivative binds with increased affinity to a ligand (e.g., a MAPKAP kinase-2 polypeptide).

The peptides or peptide derivatives of the invention are obtained by any method of peptide synthesis known to those skilled in the art, including synthetic and recombinant techniques. For example, the peptides or peptide derivatives can be obtained by solid phase peptide synthesis which, in brief, consists of coupling the carboxyl group of the C-terminal amino acid to a resin and successively adding N-alpha protected amino acids. The protecting groups may be any such groups known in the art. Before each new amino acid is added to the growing chain, the protecting group of the previous amino acid added to the chain is removed. The coupling of amino acids to appropriate resins has been described by Rivier et al. (U.S. Pat. No. 4,244,946). Such solid phase syntheses have been described, for example, by Merrifield, J. Am. Chem. Soc. 85:2149, 1964; Vale et al., Science 213: 1394-1397, 1984; Marki et al., J. Am. Chem. Soc. 10:3178, 1981, and in U.S. Pat. Nos. 4,305,872 and 4,316,891. Desirably, an automated peptide synthesizer is employed.

Purification of the synthesized peptides or peptide derivatives is carried out by standard methods, including chromatography (e.g., ion exchange, affinity, and sizing column chromatography), centrifugation, differential solubility, hydrophobicity, or by any other standard technique for the purification of proteins. In one embodiment, thin layer chromatography is employed. In another embodiment, reverse phase HPLC (high performance liquid chromatography) is employed.

Finally, structure-function relationships determined from the peptides, peptide derivatives, and other small molecules of the invention may also be used to prepare analogous molecular structures having similar properties. Thus, the invention is contemplated to include molecules in addition to those expressly disclosed that share the structure, hydrophobicity, charge characteristics and side chain properties of the specific embodiments exemplified herein.

In one example, such derivatives or analogs that have the desired binding activity can be used for binding to a molecule or other target of interest, such as any MAPKAP kinase-2 polypeptide. Derivatives or analogs that retain, or alternatively lack or inhibit, a desired property-of-interest (e.g., inhibit MAPKAP kinase-2 binding to a natural ligand), can be used to inhibit the biological activity of a MAPKAP kinase-2 polypeptide.

In particular, peptide derivatives are made by altering amino acid sequences by substitutions, additions, or deletions that provide for functionally equivalent molecules, or for functionally enhanced or diminished molecules, as desired. Due to the degeneracy of the genetic code, other nucleic acid sequences that encode substantially the same amino acid sequence may be used for the production of recombinant peptides. These include, but are not limited to, nucleotide sequences comprising all or portions of a peptide of the invention that is altered by the substitution of different codons that encode a functionally equivalent amino acid residue within the sequence, thus producing a silent change.

The derivatives and analogs of the invention can be produced by various methods known in the art. The manipulations that result in their production can occur at the gene or protein level. For example, a cloned nucleic acid sequence can be modified by any of numerous strategies known in the art (Sambrook et al., 1989, Molecular Cloning, A Laboratory Manual, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro.

MAPKAP Kinase-2 Inhibitors

Based on the present discovery that RNAi knockdown of MAPKAP kinase-2 expression sensitizes cells to chemotherapeutic agents, any compound that inhibits MAPKAP kinase-2, whether specifically or nonspecifically, may be of utility in antineoplastic therapy. Suitable MAPKAP kinase-2 inhibitors that may be used in the methods and compositions of the invention include UCN-01, 2-(3-aminopropyl)-8-(methylthio)-2,4,5,6-tetrahydropyrazolo[3,4-e]indazole-3-carboxylic acid dihydrochloride, 2-(3-aminopropyl)-2,4,5,6-tetrahydropyrazolo[3,4-e]indazole-3-carboxylic acid hydrochloride, 2-(3-{[2-(4-bromophenyl)ethyl]amino}propyl)-2,4,5,6-tetrahydropyrazolo[3,4-e]indazole-3-carboxylic acid hydrochloride, 2-(2-aminoethyl)-2,4,5,6-tetrahydropyrazolo[3,4-e]indazole-3-carboxylic acid hydrochloride, 8-(allylthio)-2-(3-aminopropyl)-2,4,5,6-tetrahydropyrazolo[3,4-e]indazole-3-carboxylic acid dihydrochloride, 2-(3-aminopropyl)-8-(benzylthio)-2,4,5,6-tetrahydropyrazolo[3,4-e]indazole-3-carboxylic acid dihydrochloride, 2-{3-[(2-thien-2-ylethyl)amino]propyl}-2,4,5,6-tetrahydropyrazolo[3,4-e]indazole-3-carboxylic acid, 2-{3-[(2-thien-3-ylethyl)amino]propyl}-2,4,5,6-tetrahydropyrazolo[3,4-e]indazole-3-carboxylic acid hydrochloride, ethyl 2-(3-{[2-(4-bromophenyl)ethyl]amino}propyl)-2,4,5,6-tetrahydropyrazolo[3,4-e]indazole-3-carboxylate, 2-(3-aminopropyl)-8-quinolin-3-yl-4,5-dihydro-2H-pyrazolo[4,3-h]quinazoline-3-carboxylic acid dihydrochloride, 2-(3-aminopropyl)-8-(1,3-benzodioxol-5-yl)-4,5-dihydro-2H-pyrazolo[4,3-h]quinazoline-3-carboxylic acid hydrochloride, 2-(3-aminopropyl)-8-phenyl-4,5-dihydro-2H-pyrazolo[4,3-h]quinazoline-3-carboxylic acid hydrochloride, 2-quinolin-3-yl-5,6,8,9,10,11-hexahydro-7H-[1,4]diazepino[1',2':1,5]pyrazolo[4,3-h]quinazolin-7-one, 2-pyridin-3-yl-5,6,8,9,10,11-hexahydro-7H-(1,4)diazepino[1',2':1,5]pyrazolo[4,3-h]quinazolin-7-one, 8-quinolin-3-yl-2-[3-(tritylamino)propyl]-4,5-dihydro-2H-pyrazolo[4,3-h]quinazoline-3-carboxylic acid hydrochloride, 2-(1,3-benzodioxol-5-yl)-5,6,8,9,10,11-hexahydro-7H-[1,4]diazepino[1',2':1,5]pyrazolo[4,3-h]quinazolin-7-one, 2-(4-methoxyphenyl)-5,6,8,9,10,11-hexahydro-7H-[1,4]diazepino[1',2':1,5]pyrazolo[4,3-h]quinazolin-7-one, 2-pyridin-4-yl-5,6,8,9,10,11-hexahydro-7H-[1,4]diazepino[1',2':1,5]pyrazolo[4,3-h]quinazolin-7-one hydrochloride, 2-(3-aminopropyl)-8-quinolin-3-yl-4,5-dihydro-2H-pyrazolo[3,4-f]isoquinoline-3-carboxylic acid trifluoroacetate, 2-(3-aminopropyl)-8-(3-nitrophenyl)-4,5-dihydro-2H-pyrazolo[3,4-f]isoquinoline-3-carboxylic acid trifluoroacetate, 2-(3-aminopropyl)-8-(4-hydroxyphenyl)-4,5-dihydro-2H-pyrazolo[3,4-f]isoquinoline-3-carboxylic acid hydrobromide, 2-(3-aminopropyl)-8-(3-hydroxyphenyl)-4,5-dihydro-2H-pyrazolo[3,4-f]isoquinoline-3-carboxylic acid hydrobromide, 2-(3-aminopropyl)-8-(2-naphthyl)-4,5-dihydro-2H-pyrazolo[3,-f]isoquinoline-3-carboxylic acid trifluoroacetate, 2-(3-aminopropyl)-8-(3,5-difluorophenyl)-4,5-dihydro-2H-pyrazolo[3,4-f]isoquinoline-3-carboxylic acid trifluoroacetate, 2-(3-aminopropyl)-8-(1,3-benzodioxol-5-yl)-4,5-dihydro-2H-pyrazolo[3,4-q]isoquinoline-3-carboxylic acid trifluoroacetate, 2-(3-aminopropyl)-8-(3-cyanophenyl)-4,5-dihydro-2H-pyrazolo[3,4-q]isoquinoline-3-carboxylic acid trifluoroacetate, 9-(hydroxymethyl)-2-quinolin-3-yl-5,6,9,10-tetrahydropyrazino[1',2':1,5]pyrazolo[3,4-f]isoquinolin-7(8H)-one trifluoroacetate, 2-(3-aminopropyl)-8-(4-methoxyphenyl)-4,5-dihydro-2H-pyrazolo[3,4-q]isoquinoline-3-carboxylic acid trifluoroacetate, 2-(3-aminopropyl)-8-[3-(methyl-sulfonyl)phenyl]-4,5-dihydro-2H-pyrazolo[3,4-q]isoquinoline-3-carboxylic acid trifluoroacetate, 2-(3-aminopropyl)-8-[3-(trifluoromethyl)phenyl]-4,5-dihydro-2H-pyrazolo[3,4-q]isoquinoline-3-carboxylic acid trifluoroacetate, 2-(1H-imidazol-1-yl)-5,6,9,10-tetrahydropyrazino[1',2':1,5]pyrazolo[3,4-q]isoquinolin-7(8H)-one trifluoroacetate, 2-(3-aminopropyl)-8-(3-methoxyphenyl)-4,5-dihydro-2H-pyrazolo[3,4-f]isoquinoline-3-carboxylic acid trifluoroacetate, 2-(3-aminopropyl)-8-[4-(trifluoromethyl)phenyl]-4,5-dihydro-2H-pyrazolo[3,4-f]isoquinoline-3-carboxylic acid trifluoroacetate, 2-(3-aminopropyl)-8-anilino-4,5-dihydro-2H-pyrazolo[3,4-f]isoquinoline-3-carboxylic acid, 2-(3-aminopropyl)-8-(3,4-difluorophenyl)-4,5-dihydro-2H-pyrazolo[3,4-f]isoquinoline-3-carboxylic acid trifluoroacetate, 2-(3-{[2-(4'-carboxy-1,1'-biphenyl-4-yl)ethyl]amino}) propyl)-4,5-dihydro-2H-pyrazolo[3,4-f]isoquinoline-3-carboxylic acid trifluoroacetate, 2-(4-hydroxyphenyl)-5,6,9,10-tetrahydropyrazino[1',2':1,5]pyrazolo[3,4-f]isoquinolin-7(8H)-one trifluoroacetate, 2-propyl-8-quinolin-3-yl-4,5-dihydro-2H-pyrazolo[3,4-f]isoquinoline-3-carboxylic acid, 2-[3-({2-[3'-(trifluoromethyl)-1,1'-biphenyl-4-yl]ethyl}amino)propyl]-4,5-dihydro-2H-pyrazolo[3,4-f]isoquinoline-3-carboxylic acid trifluoroacetate, 2-(3-aminopropyl)-8-(4-tert-butylphenyl)-4,5-dihydro-2H-pyrazolo[3,4-f]isoquinoline-3-carboxylic acid trifluoroacetate, 2-[3-({2-[4-(3-furyl)phenyl]ethyl}amino)propyl]-4,5-dihydro-2H-pyrazolo[3,4-f]isoquinoline-3-carboxylic acid trifluoroacetate, 2-(3-{[2-(3'-chloro-1,1'-biphenyl-4-yl)ethyl]amino}propyl)-4,5-dihydro-2H-pyrazolo[3,4-f]isoquinoline-3-carboxylic acid trifluoroacetate, 2-(4-methoxyphenyl)-5,6,8,9,10,11-hexahydro-7H-[1,4]diazepino[1',2':1,5]pyrazolo[3,4-f]isoquinolin-7-one, 2-[3-({2-[4'-(trifluoromethyl)-1,1'-biphenyl-4-yl]ethyl}amino)propyl]-4,5-dihydro-2H-pyrazolo[3,4-f]isoquinoline-3-carboxylic acid trifluoroacetate, 2-(3-hydroxyphenyl)-5,6,9,10-tetrahydropyrazino[1',2':-1,5]pyrazolo[3,4-f]isoquinolin-7(8H)-one, 2-(3-aminopropyl)-N-hydroxy-8-quinolin-3-yl-4,5-dihydro-2H-pyrazolo[3,4-f-]isoquinoline-3-carboxamide hydrochloride, 2-[(E)-2-(4-hydroxyphenyl)ethenyl]-5,6,9,10-tetrahydropyrazino[1',2':1,5]pyrazolo[3,4-f]isoquinolin-7(8H)-one trifluoroacetate, 2-quinolin-3-yl-5,6,8,9,10,11-hexahydro-7H-[1,4]diazepino[1',2':1,5]pyrazolo[3,4-f]isoquinolin-7-one, 2-(4-hydroxyphenyl)-5,6,8,9,10,11-hexahydro-7H-[1,4]diazepino[1',2':1,5]pyrazolo[3,4-f]isoquinolin-7-one, 2-(3-{[2-(2'-chloro-1,1'-biphenyl-4-yl)ethyl]amino}propyl)-4,5-dihydro-2H-pyrazolo[3,4-f]isoquinoline-3-carboxylic acid trifluoroacetate, 2-(3-{[2-(4'-tert-butyl-1,1'-biphenyl-4-yl)ethyl]amino}propyl)-4,5-dihydro-2H-pyrazolo[3,4-f]isoquinoline-3-carboxylic acid trifluoroacetate, 2-(3-{[2-(3,4-dichlorophenyl)ethyl]amino}propyl)-4,5-dihydro-2H-pyrazolo[3,4-f]isoquinoline-3-carboxylic acid trifluoroacetate, 2-(3-{[3-(3-chlorophenyl)propyl]amino}propyl)-4,5-dihydro-2H-pyrazolo[3,4-f]isoquinoline-3-carboxylic acid trifluoroacetate, 2-[(E)-2-phenylethenyl]-5,6,9,10-tetrahydropyrazino[1',2':1,5]pyrazolo[3,4-f]isoquinolin-7(8H)-one trifluoroacetate, 2-(3-{[2-(4-pyridin-4-ylphenyl)ethyl]amino}propyl)-4,5-dihydro-2H-pyrazolo[3,4-f]isoquinoline-3-carboxylic acid trifluoroacetate, 2-(3-{[3-(4-bromophenyl)propyl]amino}propyl)-4,5-dihydro-2H-pyrazolo[3,4-f]isoquinoline-3-carboxylic acid trifluoroacetate, 2-(3-{([3-(4-tert-butylphenyl)propyl]amino}propyl)-4,5-dihydro-2H-pyrazolo[3,4-f]isoquinoline-3-carboxylic acid trifluoroacetate, 2-(3-{[2-(3'-isopropyl-1,1'-biphenyl-4-yl)ethyl]amino}propyl)-4,5-dihydro-2H-pyrazolo[3,4-f]isoquinoline-3-carboxylic acid trifluoroacetate, 2-{3-[(2-thien-2-ylethyl)amino]propyl}-4,5-dihydro-2H-pyrazolo[3,4-f]isoquinoline-3-carboxylic acid trifluoroacetate, 2-[4-(dimethylamino)phenyl]-5,6,9,10-tetrahydropyrazino[1',2':1,5]pyrazolo[3,4-f]isoquinolin-7(8H)-one, 2-(3-{[2-(1,1'-biphenyl-4-yl)ethyl]amino}propyl)-4,5-dihydro-2H-pyrazolo[3,4-f]isoquinoline-3-carboxylic acid trifluoroacetate, 2-(3-methoxyphenyl)-5,6,9,10-tetrahydropyrazino[1',2':1,5]pyrazolo[3,4-f]-isoquinolin-7(8H)-one, 2-(3-([2-(4-bromophenyl)ethyl]amino propyl)-4,5-dihydro-2H-pyrazolo[3,4-f]isoquinoline-3-carboxylic acid trifluoroacetate, 2-(3-{[2-(2,4-dichlorophenyl)ethyl]amino}propyl)-4,5-dihydro-2H-pyrazolo[3,4-f]isoquinoline-3-carboxylic acid trifluoroacetate, 2-{3-[(benzylsulfonyl)amino]propyl}-8-quinolin-3-yl-4,5-dihydro-2H-pyrazolo[3,4-f]isoquinoline-3-carboxylic acid, 9-(aminomethyl)-5,6,9,10-tetrahydropyrazino[1',2':1,5]pyrazolo[3,4-f]isoquinolin-7(8H)-one trifluoroacetate, 2-(3-nitrophenyl)-5,6,8,9,10,11-hexahydro-7H-[1,4]diazepino[1',2':1,5]pyrazolo[3,4-f]isoquinolin-7-one, 2-(3-aminopropyl)-8-quinolin-3-yl-4,5-dihydro-2H-pyrazolo[3,4-f]isoquinoline-3-carboxamide hydrochloride, 2-(3-{[3-(4-chlorophenyl)propyl]amino}propyl)-4,5-dihydro-2H-pyrazolo[3,4-f]isoquinoline-3-carboxylic acid trifluoroacetate, 2-[3-(dimethylamino)phenyl]-5,6,8,9,10,11-hexahydro-7H-[1,4]diazepino[1',2':1,5]pyrazolo[3,4-f]isoquinolin-7-one, 2-(3-{[(4-chlorobenzyl)sulfonyl]amino}propyl)-8-quinolin-3-yl-4,5-dihydro-2H-pyrazolo[3,4-f]isoquinoline-3-carboxylic acid, 2-(3-{[2-(4-pyridin-3-ylphenyl)ethyl]amino}propyl)-4,5-dihydro-2H-pyrazolo[3,4-f]isoquinoline-3-carboxylic acid trifluoroacetate, 2-(3-{[2-(4-chlorophenyl)ethyl]amino)}propyl)-4,5-dihydro-2H-pyrazolo[3,4-f]isoquinoline-3-carboxylic acid trifluoroacetate, 2-(3-{[2-(5-chlorothien-2-yl)ethyl]amino}propyl)-4,5-dihydro-2H-pyrazolo[3,4-f]isoquinoline-3-carboxylic acid trifluoroacetate, 2-(3-{[3-(4-cyanophenyl)propyl]amino}propyl)-4,5-dihydro-2H-pyrazolo[3,4-f]isoquinoline-3-carboxylic acid trifluoroacetate, 2-(3-{[3-(5-methyl-2-furyl)butyl]amino}propyl)-4,5-dihydro-2H-pyrazolo[3,4-f]isoquinoline-3-carboxylic acid trifluoroacetate, 2-[3-({2-[4-(1-benzothien-3-yl)phenyl]ethyl}amino)propyl]-4,5-dihydro-2H-pyrazolo[3,4-f]isoquinoline-3-carboxylic acid trifluoroacetate, 2-(3-ammoniopropyl)-3-carboxy-4,5-dihydro-2H-pyrazolo[3,4-f]isoquinolin-7-ium dichloride, 2-(4-methoxyphenyl)-5,6,9,10-tetrahydropyrazino[1',2':1,5]pyrazolo[3,4-f]isoquinolin-7(8H)-one, 2-(3-{[3-(4-acetylphenyl)propyl]amino}propyl)-4,5-dihydro-2H-pyrazolo[3,4-f]isoquinoline-3-carboxylic acid trifluoroacetate, 2-(3-aminopropyl)-4,5-dihydro-2H-pyrazolo[3,4-f]isoquinoline-3-carboxylic acid trifluoroacetate, 2-[3-({3-[4-(methylsulfonyl)phenyl]propyl}amino)propyl]-4,5-dihydro-2H-pyrazolo[3,4-f]isoquinoline-3-carboxylic acid trifluoroacetate, 2-(3-aminopropyl)-8-(2-methoxyphenyl)-4,5-dihydro-2H-pyrazolo[3,4-f]isoquinoline-3-carboxylic acid trifluoroacetate, 2-[3-({2-[3'-(aminomethyl)-1,1'-biphenyl-4-yl]ethyl}amino)propyl]-4,5-dihydro-2H-pyrazolo[3,4-f]isoquinoline-3-carboxylic acid trifluoroacetate, 2-(2-aminoethyl)-4,5-dihydro-2H-pyrazolo[3,4-f]isoquinoline-3-carboxylic acid dihydrochloride, 2-(3-{[2-(4-nitrophenyl)ethyl]amino}propyl)-4,5-dihydro-2H-pyrazolo[3,4-f]isoquinoline-3-carboxylic acid trifluoroacetate, 2-[3-({2-[2'-(trifluoromethyl)-1,1'-biphenyl-4-yl]ethyl}amino)propyl]-4,5-dihydro-2H-pyrazolo[3,4-f]isoquinoline-3-carboxylic acid trifluoroacetate, 9-(hydroxymethyl)-5,6,9,10-tetrahydropyrazino[1',2':1,5] pyrazolo[3,4-f]isoquinolin-7(8H)-one, 2-(3-{[2-(4-methylphenyl)ethyl]amino}) propyl)-4,5-dihydro-2H-pyrazolo[3,4-f]isoquinoline-3-carboxylic acid trifluoroacetate, 9-{[(2-thien-2-ylethyl)amino]methyl}-5,6,9,10-tetrahydropyrazino[1',2':1,5]pyrazolo[3,4-f]isoquinolin-7(8H)-one, 2-(3-{[2-(4-ethoxyphenyl)ethyl]amino}propyl)-4,5-dihydro-2H-pyrazolo[3,4-f]isoquinoline-3-carboxylic acid trifluoroacetate, 2-(1,3-benzodioxol-5-yl)-5,6,8,9,10,11-hexahydro-7H-[1,4]diazepino[1',2':1,5]pyrazolo[3,4-f]isoquinolin-7-one, 2-(3-{[2-(4-methoxyphenyl)ethyl]amino}propyl)-4,5-dihydro-2H-pyrazolo[3,4-f]isoquinoline-3-carboxylic acid trifluoroacetate, 3-[3-(1H-tetraazol-5-yl)-4,5-dihydro-2H-pyrazolo[3,4-f]isoquinolin-2-yl]propan-1-amine hydrochloride, 2-(3-aminopropyl)-8-chloro-4,5-dihydro-2H-pyrazolo[3,4-q]isoquinoline-3-carboxylic acid trifluoroacetate, 2-(3-{[(1R,2S)-2-phenylcyclopropyl]amino}propyl)-4,5-dihydro-2H-pyrazolo[3,4-f]isoquinoline-3-carboxylic acid trifluoroacetate, 2-{3-[(3,3-diphenylpropyl)amino]propyl}-4,5-dihydro-2H-pyrazolo[3,4-f]isoquinoline-3-carboxylic acid trifluoroacetate, 2-(3-{[2-(3-bromo-4-methoxyphenyl)ethyl]amino}propyl)-4,5-dihydro-2H-pyrazolo[3,4-f]isoquinoline-3-carboxylic acid trifluoroacetate, 2-{3-[(4-phenylbutyl)amino]propyl}-4,5-dihydro-2H-pyrazolo[3,4-f]isoquinoline-3-carboxylic acid trifluoroacetate, 2-[3-(2,3-dihydro-1H-inden-2-ylamino)propyl]-4,5-dihydro-2H-pyrazolo[3,4-f]isoquinoline-3-carboxylic acid trifluoroacetate, 2-(2-naphthyl)-5,6,8,9,-10,11-hexahydro-7H-[1,4]diazepino[1',2':1,5]pyrazolo[3,4-f]isoquinolin-7-one, 2-{3-[(3-phenylpropyl)amino]propyl}-4,5-dihydro-2H-pyrazolo[3,4-f]isoquinoline-3-carboxylic acid trifluoroacetate, 2-(3-{[2-(4-fluorophenyl)ethyl]amino}propyl)-4,5-dihydro-2H-pyrazolo[3,4-f]isoquinoline-3-carboxylic acid trifluoroacetate, 2-{3-[(2-thien-3-ylethyl)amino]propyl}-4,5-dihydro-2H-pyrazolo[3,4-f]isoquinoline-3-carboxylic acid dihydrochloride, 5,6,9,10-tetrahydropyrazino[1,2':1,5]pyrazolo[3,4-f]isoquinolin-7(8H)-one, 2-[3-(glycoloylamino)propyl]-8-quinolin-3-yl-4,5-dihydro-2H-pyrazolo[3,4-f]isoquinoline-3-carboxylic acid hydrochloride, 8-quinolin-3-yl-4,5-dihydro-2H-pyrazolo[3,4-f]isoquinoline-3-carboxylic acid, 2-(3-{[2-(4-ethylphenyl)ethyl]amino}propyl)-4,5-dihydro-2H-pyrazolo[3,4-f]isoquinoline-3-carboxylic acid trifluoroacetate, 2-(3-{[2-(2-chlorophenyl)ethyl]amino}propyl)-4,5-dihydro-2H-pyrazolo[3,4-f]isoquinoline-3-carboxylic acid trifluoroacetate, 2-{3-[(2-ethylbutyl)amino]propyl}-4,5-dihydro-2H-pyrazolo[3,4-f]isoquinoline-3-carboxylic acid trifluoroacetate, 8-quinolin-3-yl-4,5-dihydro-2H-pyrazolo[3,4-f]isoquinoline-3-carboxamide, 2-{3-[(2-pyridin-4-ylethyl)amino]propyl}-4,5-dihydro-2H-pyrazolo[3,4-f]isoquinoline-3-carboxylic acid trifluoroacetate, 2-(3-{[2-(4-chlorophenyl)propyl]amino}propyl)-4,5-dihydro-2H-pyrazolo[3,4-f]isoquinoline-3-carboxylic acid to trifluoroacetate, 2-(3-{[2-(3-chlorophenyl)ethyl]amino}propyl)-4,5-dihydro-2H-pyrazolo[3,4-f]isoquinoline-3-carboxylic acid trifluoroacetate, 2-[3-(glycoloylamino)propyl]-4,5-dihydro-2H-pyrazolo[3,4-f]isoquinoline-3-carboxylic acid trifluoroacetate, 2-(3-{[2-(3,4-dimethoxyphenyl)ethyl]amino}propyl)-4,5-dihydro-2H-pyrazolo[3,4-f]isoquinoline-3-carboxylic acid trifluoroacetate, 2-(1-benzofuran-2-yl)-5,6,8,9,10,11-hexahydro-7H-[1,4]diazepino[1',2':1,5]pyrazolo[3,4-f]isoquinolin-7-one, 2-(3-{[4-(2-aminoethyl)phenyl]amino}propyl)-4,5-dihydro-2H-pyrazolo[3,4-f]isoquinoline-3-carboxylic acid trifluoroacetate, 2-(1-naphthyl)-5,6,9,10-tetrahydropyrazino[1',2':1,5]pyrazolo[3,4-f]isoquinolin-7(8H)-one, 8-(3-aminopropyl)-5,6,8,9,10, 11-hexahydro-7H-[1,4]diazepino[1',2':1,5]pyrazolo[3,4-f]isoquinolin-7-one dihydrochloride, 2-anilino-5,6,9,10-tetrahydropyrazino[1',2':1,5]pyrazolo[3,4-f]isoquinolin-7(8H)-one, 2-(3-aminopropyl)-8-[2-(trifluoromethyl)phenyl]-4,5-dihydro-2H-pyrazolo[3,4-f]isoquinoline-3-carboxylic acid trifluoroacetate, 9-(azidomethyl)-5,6,9,10-tetrahydropyrazino[1',2':1,5]pyrazolo[3,4-f]isoquinolin-7(8H)-one, 9-({[2-(4-chlorophenyl)ethyl]amino}methyl)-5,6,9,10-tetrahydropyrazino[1',2':1,5]pyrazolo[3,4-f]isoquinolin-7(8H)-one, 2-phenyl-5,6,8,9,10,11-hexahydro-7H-[1,4]diazepino[1',2':1,5]pyrazolo[3,4-f]isoquinolin-7-one, 2-[3-(pentylamino)propyl]-4,5-dihydro-2H-pyrazolo[3,4-f]isoquinoline-3-carboxylic acid trifluoroacetate, 10-(2-aminoethyl)-5,6,9,10-tetrahydropyrazino[1',2':1,5]pyrazolo[3,4-f]isoquinolin-7(8H)-one, 2-[3-(allylamino)propyl]-4,5-dihydro-2H-pyrazolo[3,4-f]isoquinoline-3-carboxylic acid trifluoroacetate, 2-(4-aminobutyl)-4,5-dihydro-2H-pyrazolo[3,4-f]isoquinoline-3-carboxylic acid dihydrochloride, 2-(3-{[2-(4-aminophenyl)ethyl]amino}propyl)-4,5-dihydro-2H-pyrazolo[3,4-f]isoquinoline-3-carboxylic acid trifluoroacetate, 2-[(1E)-3,3-dimethylbut-1-enyl]-5,6,9,10-tetrahydropyrazino[1',2':1,5]pyrazolo[3,4-f]isoquinolin-7(8H)-one-trifluoroacetate, 10-(nitromethyl)-5,6,9,10-tetrahydropyrazino[1',2':1,5]pyrazolo[3,4-f]isoquinolin-7(8H)-one, 3-carboxy-2-[3-(methylammonio)propyl]-4,5-dihydro-2H-pyrazolo[3,4-f]isoquinolin-7-ium dichloride, 2-[3-({[(4-butoxyphenyl)amino]carbonyl}amino)propyl]-4,5-dihydro-2H-pyrazolo[3,4-f]isoquinoline-3-carboxylic acid, 2-{(3-[(2-pyridin-3-ylethyl)amino]propyl}-4,5-dihydro-2H-pyrazolo[3,4-f]isoquinoline-3-carboxylic acid trifluoroacetate, 2-{3-[(2-pyridin-2-ylethyl)amino]propyl}-4,5-dihydro-2H-pyrazolo[3,4-f]isoquinoline-3-carboxylic acid trifluoroacetate, 2-{3-[(cyclopropylmethyl)amino]propyl}-4,5-dihydro-2H-pyrazolo[3,4-f]isoquinoline-3-carboxylic acid trifluoroacetate, 2-{3-[(2-thien-2-ylpropyl)amino]propyl})-4,5-dihydro-2H-pyrazolo[3,4-f]isoquinoline-3-carboxylic acid trifluoroacetate, 2-methoxy-5,6,9,10-tetrahydropyrazino[1',2':1,5]pyrazolo[3,4-f]isoquinolin-7(8H)-one, 2-[3-(dimethylamino)phenyl]-5,6,9,10-tetrahydropyrazino[1',2':1,5]pyrazolo[3,4-q]isoquinolin-7(8H)-one, 2-(3-{[2-(1H-pyrrol-1-yl)ethyl]amino}propyl)-4,5-dihydro-2H-pyrazolo[3,4-f]isoquinoline-3-carboxylic acid trifluoroacetate, 2-[3-(benzyloxy)propyl]-8-quinolin-3-yl-4,5-dihydro-2H-pyrazolo[3,4-f]isoquinoline-3-carboxylic acid, 2-{3-[(4-butoxybenzyl)amino]propyl}-4,5-dihydro-2H-pyrazolo[3,4-f]isoquinoline-3-carboxylic acid trifluoroacetate, 2-(1,3-benzodioxol-5-yl)-5-,6,9,10-tetrahydropyrazino[1',2':1,5]pyrazolo[3,4-f]isoquinolin-7(8H)-one, 2-[(E)-2-(2-fluorophenyl)ethenyl]-5,6,9,10-tetrahydropyrazino[1',2':1,5]pyrazolo[3,4-q]isoquinolin-7(8H)-one, 2-[(1E)-hex-1-enyl]-5,6,9,10-tetrahydropyrazino[1',2':1,5]pyrazolo[3,4-f]isoquinolin-7(8H)-one trifluoroacetate, 2-anilino-5,6,8,9,10,11-hexahydro-7H-[1,4]diazepino[1',2':1,5]pyrazolo[3,4-f]isoquinolin-7-one, 5,6,8,9,10,11-hexahydro-7H-[1,4]diazepino[1',2':1,5]pyrazolo[3,4-f]isoquinolin-7-one, 2-chloro-5,6,9,10-tetrahydropyrazino[1',2':1,5]pyrazolo[3,4-f]isoquinolin-7(8H)-one, 2-[(E)-2-(4-methoxyphenyl)ethenyl]-5,6,9,10-tetrahydropyrazino[1',2':1,5]pyrazolo[3,4-f]isoquinolin-7(8H)-one, 2-(methylthio)-5,6,9,10-tetrahydropyrazino[1',2':1,5]pyrazolo[3,4-f]isoquinolin-7(8H)-one, 2-{3-[(2-furylmethyl)amino]propyl}-4,5-dihydro-2H-pyrazolo[3,4-f]isoquinoline-3-carboxylic acid trifluoroacetate, 2-azepan-1-yl-5,6,9,10-tetrahydropyrazino[1',2':1,5]pyrazolo[3,4-f]isoquinolin-7(8H)-one trifluoroacetate, 2-(3,6-dihydropyridin-1(2H)-yl)-5,6,9,10-tetrahydropyrazino[1',2':1,5]pyrazolo[3,4-f]isoquinolin-7(8H)-one trifluoroacetate, 9-methyl-5,6,9,10-tetrahydropyrazino[1',2':1,5]pyrazolo[3,4-f]isoquinolin-7(8H)-one, 2-(piperidin-3-ylmethyl)-4,5-dihydro-2H-pyrazolo[3,4-f]isoquinoline-3-carboxylic acid hydrochloride, 9-(chloromethyl)-5,6,9,10-tetrahydropyrazino[1',2':1,5]pyrazolo[3,4-f]isoquinolin-7(8H)-one, 2-[(4-methoxybenzyl)amino]-5,6,9,10-tetrahydropyrazino[1',2':1,5]pyrazolo[3,4-f]isoquinolin-7(8H)-one trifluoroacetate, 2-(3-([2-(1H-imidazol-4-yl)ethyl]amino}propyl)-4,5-dihydro-2H-pyrazolo[3,4-f]isoquinoline-3-carboxyli-c acid trifluoroacetate, 2-(benzylamino)-5,6,9,10-tetrahydropyrazino[1',2':1,5]pyrazolo[3,4-f]isoquinolin-7(8H)-one trifluoroacetate, 2-(methylthio)-5,6,8,9,10,11-hexahydro-7H-[1,4]diazepino[1',2':1,5]pyrazolo[3,4-f]isoquinolin-7-one, 2-{3-[(2-chlorobenzyl)amino]propyl}-4,5-dihydro-2H-pyrazolo[3,4-f]isoquinoline-3-carboxylic acid trifluoroacetate, 2-[3-(benzylamino)propyl]-4,5-dihydro-2H-pyrazolo[3,4-f]isoquinoline-3-carboxylic acid trifluoroacetate; 2-[3-({[(4-methoxyphenyl)amino]carbonyl}amino)propyl]-4,5-dihydro-2H-pyrazolo[3,4-f]isoquinoline-3-carboxylic acid, 2-{3-[(2-phenylethyl)amino]propyl}-4,5-dihydro-2H-pyrazolo[3,4-f]isoquinoline-3-carboxylic acid trifluoroacetate, 2-{3-[(thien-2-ylmethyl)amino]propyl}-4,5-dihydro-2H-pyrazolo[3,4-f]isoquinoline-3-carboxylic acid trifluoroacetate, 2-benzyl-5,6,9,10-tetrahydropyrazino[1',2':1,5]pyrazolo[3,4-f]isoquinolin-7(8H)-one, 5,6,8,9,10,11-hexahydro-7H-[1,4]diazepino[1',2':1,5]pyrazolo[3,4-f]isoquinolin-7-one, 2-{3-[(4-chlorobenzyl)amino]propyl}-4,5-dihydro-2H-pyrazolo[3,4-f]isoquinoline-3-carboxylic acid trifluoroacetate, 2-{3-[(2-phenylpropyl)amino]propyl}-4,5-dihydro-2H-pyrazolo[3,4-f]isoquinoline-3-carboxylic acid trifluoroacetate, 7-oxo-5,6,7,8,9,10-hexahydropyrazino[1',2':1,5]pyrazolo[3,4-f]isoquinoline-9-carboxamide trifluoroacetate, 2-(3-hydroxypropyl)-4,5-dihydro-2H-pyrazolo[3,4-f]isoquinoline-3-carboxylic acid, 2-(1,3-dihydro-2H-isoindol-2-yl)-5,6,9,10-tetrahydropyrazino[1',2':1,5]pyrazolo[3,4-f]isoquinolin-7(8H)-one trifluoroacetate, 2-{3-[(4-aminophenyl)amino]propyl}-4,5-dihydro-2H-pyrazolo[3,4-f]isoquinoline-3-carboxylic acid trifluoroacetate, 2-(4-hydroxypiperidin-1-yl)-5,6,9,10-tetrahydropyrazino[1',2':1,5]pyrazolo[3,4-f]isoquinolin-7(8H)-one trifluoroacetate, 2-(3-aminopropyl)-7-hydroxy-8-(3-nitrophenyl)-4,5-dihydro-2H-benzo[g]indazole-3-carboxylic acid trifluoroacetate, 2-(2-aminoethyl)-7-hydroxy-8-(3-nitrophenyl)-4,5-dihydro-2H-benzo[g]indazole-3-carboxylic acid trifluoroacetate, 3-hydroxy-2-(3-nitrophenyl)-5,6,8,9,10,11-hexahydro-7H-benzo[g][1,4]diazepino[1,2-b]indazol-7-one trifluoroacetate, 2-(3-aminopropyl)-7-hydroxy-4,5-dihydro-2H-benzo[g]indazole-3-carboxylic acid dihydrochloride, 2-(2-aminoethyl)-8-bromo-7-hydroxy-4,5-dihydro-2H-benzo[g]indazole-3-carboxylic acid trifluoroacetate, 2-(3-aminopropyl)-8-[2-(4-chlorophenyl)ethyl]-7-hydroxy-4,5-dihydro-2H-benzo[g]indazole-3-carboxylic acid trifluoroacetate, 3-hydroxy-2-(3-nitrophenyl)-5,6,9,10-tetrahydrobenzo[g]pyrazino[1,2-b]indazol-7(8H)-one hydrobromide, 2-(3-aminopropyl)-8-bromo-7-hydroxy-4,5-dihydro-2H-benzo[g]indazole-3-carboxylic acid hydrobromide, 2-(3-aminopropyl)-7-hydroxy-8-(4-nitrophenyl)-4,5-dihydro-2H-benzo[g]indazole-3-carboxylic acid trifluoroacetate, 2-(3-aminopropyl)-8-(3-cyanophenyl)-7-hydroxy-4,5-dihydro-2H-benzo[g]indazole-3-carboxylic acid trifluoroacetate, 2-(3-aminopropyl)-7-hydroxy-8-[3-(trifluoromethyl)phenyl]-4,5-dihydro-2H-benzo[g]indazole-3-carboxylic acid trifluoroacetate, and 2-(3-aminopropyl)-7-hydroxy-8-(3,3,3-trifluoropropyl)-4,5-dihydro-2H-benzo[g]indazole-3-carboxylic acid trifluoroacetate, 7-hydroxy-3,4,5,10-tetrahydro-1H-2,5-methanoazepino[3,4-b]indole-1-carboxylic acid, 2,3,8,10,11,12-hexahydro-1H,7H-9,12-methanoazepino[3, 4-b]pyrano[3,2-e]indole-8-carboxylic acid, 7-methoxy-3,4,5,10-tetrahydro-1H-2,5-methanoazepino[3,4-b]indole-1-carboxylic acid, 7-(methylthio)-3,4,5,10-tetrahydro-1H-2,5-methanoazepino[3,4-b]indole-1-carboxylic acid, 7-(benzyloxy)-3,4,5,10-tetrahydro-1H-2,5-methanoazepino[3,4-b]indole-1-carboxylic acid, 7-(methylthio)-3,4,5,10-tetrahydro-1H-2,5-methanoazepino[3,4-b]indole-1-carboxylic acid, 2,2,2-trifluoroethyl 7-methoxy-3,4,5,10-tetrahydro-1H-2,5-methanoazepino[3,4-b]indole-1-carboxylate, 2,3-dihydroxypropyl 7-methoxy-3,4,5,10-tetrahydro-1H-2,5-methanoazepino[3,4-b]indole-1-carboxylate, pyridin-4-ylmethyl 7-methoxy-3,4,5,10-tetrahydro-1H-2,5-methanoazepino[3,4-b]indole-1-carboxylate, 2-fluoroethyl 7-methoxy-3,4,5,10-tetrahydro-1H-2,5-methanoazepino[3,4-b]indole-1-carboxylate, allyl 7-methoxy-3,4,5,10-tetrahydro-1H-2,5-methanoazepino[3,4-b]indole-1-carboxylate, benzyl 7-methoxy-3,4,5,10-tetrahydro-1H-2,5-methanoazepino[3,4-b]indole-1-carboxylate, 2-(methylthio)ethyl 7-methoxy-3,4,5,10-tetrahydro-1H-2,5-methanoazepino[3,4-b]indole-1-carboxylate, 2-methoxyethyl 7-methoxy-3,4,5,10-tetrahydro-1H-2,5-methanoazepino[3,4-b]indole-1-carboxylatem, 7-methoxy-3,4,5,10-tetrahydro-1H-2,5-methanoazepino[3,4-b]indole-1-carboxylic acid, 7-hydroxy-3,4,5,10-tetrahydro-1H-2,5-methanoazepino[3,4-b]indole-1-carboxylic acid, 2,3,8,10,11,12-hexahydro-1H,7H-9,12-methanoazepino[3,4-b]pyrano[3,2-e]indole-8-carboxylic acid, 7-methoxy-3,4,5,10-tetrahydro-1H-2,5-methanoazepino[3,4-b]indole-1-carboxylic acid, 7-(methylthio)-3,4,5,10-tetrahydro-1H-2,5-methanoazepino[3,4-b]indole-1-carboxylic acid, 7-methoxy-3,4,5,10-tetrahydro-1H-2,5-methanoazepino[3,4-b]indole-1-carboxylic acid, 7-(benzyloxy)-3,4,5,10-tetrahydro-1H-2,5-methanoazepino[3,4-b]indole-1-carboxylic acid, 7-(methylthio)-3,4,5,10-tetrahydro-1H-2,5-methanoazepino[3,4-b]indole-1-carboxylic acid, 6-methoxy-2,3,4,9-tetrahydro-1H-beta-carboline-1-carboxylic acid, 6-(2-oxo-2-phenylethoxy)-2,3,4,9-tetrahydro-1H-beta-carboline-1-carboxylic acid, 6-methoxy-2-methyl-2,3,4,9-tetrahydro-1H-beta-carboline-1-carboxylic acid, 2,2,2-trifluoroethyl 7-methoxy-3,4,5,10-tetrahydro-1H-2,5-methanoazepino[3,4-b]indole-1-carboxylate, 6-methoxy-2,3,4,9-tetrahydro-1H-beta-carboline-1-carboxylic acid, 7-hydroxy-3,4,5,10-tetrahydro-1H-2,5-methanoazepino[3,4-b]indole-1-carboxylic acid, 6-hydroxy-2-methyl-2,3,4,9-tetrahydro-1H-beta-carboline-1-carboxylic acid, 7-methoxy-3,4,5,10-tetrahydro-1H-2,5-methanoazepino[3,4-b]indole-1-carboxylic acid, 6-methoxy-2-methyl-2,3,4,9-tetrahydro-1H-beta-carboline-1-carboxylic acid, 2,3-dihydroxypropyl 7-methoxy-3,4,5,10-tetrahydro-1H-2,5-methanoazepino[3,4-b]indole-1-carboxylate, 4-ethyl-6-methoxy-2,3,4,9-tetrahydro-1H-beta-carboline-1-carboxylic acid, 6-methoxy-4-methyl-2,3,4,9-tetrahydro-1H-beta-carboline-1-carboxylic acid, 8,9,10,11-tetrahydro-7H-pyrido[3',4':4,5]pyrrolo[2,3-f]isoquinolin-7-one trifluoroacetate, 3-(aminomethyl)-6-methoxy-2,3,4,9-tetrahydro-1H-beta-carbolin-1-one trifluoroacetate, 3-(aminomethyl)-6-methoxy-2,3,4,9-tetrahydro-1H-beta-carbolin-1-one hydrochloride, 7-methoxy-3,4,5,10-tetrahydroazepino[3,4-b]indol-1(2H)-one, 6-methoxy-2,3,4,9-tetrahydro-1H-beta-carbolin-1-one, 6-methoxy-2,9-dihydro-1H-beta-carbolin-1-one, 6-hydroxy-2,3,4,9-tetrahydro-1H-beta-carbolin-1-one, 8,9,10,11-tetrahydro-7H-pyrido[3',4':4,5]pyrrolo-[2,3-f]isoquinolin-7-one, 3-(aminomethyl)-6-methoxy-2,3,4,9-tetrahydro-1H-beta-carbolin-1-one, 3-(aminomethyl)-6-methoxy-2,3,4,9-tetrahydro-1H-beta-carbolin-1-one, 6-methoxy-3-{3-[(2-phenylethyl)amino]propyl}-2,3,4,9-tetrahydro-1H-beta-carbolin-1-one, (1E)-6-methoxy-2,3,4,9-tetrahydro-1H-carbazol-1-one oxime, (1Z)-6-methoxy-2,3,4,9-tetrahydro-1H-carbazol-1-one oxime, 6-methoxy-3-{3-[(3-phenylpropyl)amino]propyl}-2,3,4,9-tetrahydro-1H-beta-carbolin-1-one, methyl 1-oxo-2,3,4,5-tetrahydro-1H-pyrido[4,3-b]indole-6-carboxylate, 3-(hydroxymethyl)-6-methoxy-2,3,4,9-tetrahydro-1H-beta-carbolin-1-one, 3-(3-aminopropyl)-6-methoxy-2,3,4,9-tetrahydro-1H-beta-carbolin-1-one, 3-(2-aminoethyl)-6-methoxy-2,3,4,9-tetrahydro-1H-beta-carbolin-1-one, ethyl 1-(hydroxyimino)-2,3,4,9-tetrahydro-1H-carbazole-6-carboxylate, 2-methoxy-7,8,9,10-tetrahydrocyclohepta[b]indol-6(5H)-one oxime, 3-(hydroxymethyl)-6-methoxy-2,3,4,9-tetrahydro-1H-beta-carbolin-1-one, 3-(3-aminopropyl)-6-methoxy-2,3,4,9-tetrahydro-1H-beta-carbolin-1-one, 3-(2-aminoethyl)-6-methoxy-2,3,4,9-tetrahydro-1H-beta-carbolin-1-one, ethyl 1-(hydroxyimino)-2,3,4,9-tetrahydro-1H-carbazole-6-carboxylate, 2-methoxy-7,8,9,10-tetrahydrocyclohepta[b]indol-6(5H)-one oxime, 3-[3-(benzylamino)propyl]-6-methoxy-2,3,4,9-tetrahydro-1H-beta-carbolin-1-one, 6-methoxy-2,3,4,9-tetrahydro-1H-carbazol-1-one oxime, 6-iodo-2,3,4,9-tetrahydro-1H-carbazol-1-one oxime, 6-methoxy-2-methyl-2,3,4,9-tetrahydro-1H-carbazol-1-one oxime, 3-(3-hydroxypropyl)-6-methoxy-2,3,4,9-tetrahydro-1H-beta-carbolin-1-one, ethyl 1-oxo-2,3,4,5-tetrahydro-1H-pyrido[4,3-b]indole-6-carboxylate, 6-methoxy-2,3,4,9-tetrahydro-1H-beta-carboline-1-thione, methyl 4-oxo-2,3,4,9-tetrahydro-1H-carbazole-8-carboxylate, and 2,3,4,9-tetrahydro-1H-carbazol-1-one oxime. Others are described in U.S. Patent Application Publication Nos. 2004-0127492, 2005-0101623, 2005-0137220, and 2005-0143371.

Prodrugs and Other Modified Compounds

Interaction of a molecule, e.g., a drug, with a MAPKAP kinase-2 polypeptide can be used to promote enhanced sensitivity of cells to chemotherapy or radiation treatment. The treatment, stabilization, or prevention of a disease or disorder associated with MAPKAP kinase-2 can be mediated by administering a compound, peptide, or nucleic acid molecule. In some cases, however, a compound that is effective in vitro in to disrupting the interaction of a MAPKAP kinase-2 polypeptide and a natural substrate is not an effective therapeutic agent in vivo. For example, this could be due to low bioavailability of the compound. One way to circumvent this difficulty is to administer a modified drug, or prodrug, with improved bioavailability that converts naturally to the original compound following administration. Such prodrugs may undergo transformation before exhibiting their full pharmacological effects. Prodrugs contain one or more specialized protective groups that are specifically designed to alter or to eliminate undesirable properties in the parent molecule. In one embodiment, a prodrug masks one or more charged or hydrophobic groups of a parent molecule. Once administered, a prodrug is metabolized in vivo into an active compound.

Prodrugs may be useful for improving one or more of the following characteristics of a drug: solubility, absorption, distribution, metabolization, excretion, site specificity, stability, patient acceptability, reduced toxicity, or problems of formulation. For example, an active compound may have poor oral bioavailability, but by attaching an appropriately-chosen covalent linkage that may be metabolized in the body, oral bioavailability may improve sufficiently to enable the prodrug to be administered orally without adversely affecting the parent compound's activity within the body.

A prodrug may be carrier-linked, meaning that it contains a group such as an ester that can be removed enzymatically. Optimally, the additional chemical group has little or no pharmacologic activity, and the bond connecting this group to the parent compound is labile to allow for efficient in vivo activation. Such a carrier group may be linked directly to the parent compound (bipartate), or it may be bonded via a linker region (tripartate). Common examples of chemical groups attached to parent compounds to form prodrugs include esters, methyl esters, sulfates, sulfonates, phosphates, alcohols, amides, imines, phenyl carbamates, and carbonyls.

As one example, methylprednisolone is a poorly water-soluble corticosteroid drug. In order to be useful for aqueous injection or ophthalmic administration, this drug must be converted into a prodrug of enhanced solubility. Methylprednisolone sodium succinate ester is much more soluble than the parent compound, and it is rapidly and extensively hydrolysed in vivo by cholinesterases to free methylprednisolone.

Caged compounds may also be used as prodrugs. A caged compound may have, e.g., one or more photolyzable chemical groups attached that renders the compound biologically inactive. In this example, flash photolysis releases the caging group (and activates the compound) in a spatially or temporally controlled manner. Caged compounds may be made or designed by any method known to those of skill in the art.

For further description of the design and use of prodrugs, see Testa and Mayer, Hydrolysis in Drug and Prodrug Metabolism: Chemistry, Biochemistry and Enzymology, published by Vch. Verlagsgesellschaft Mbh. (2003). Other modified compounds are also possible in the methods of the invention. For example, a modified compound need not be metabolized to form a parent molecule. Rather, in some embodiments, a compound may contain a non-removable moiety that, e.g., increases bioavailability without substantially diminishing the activity of the parent molecule. Such a moiety could, for example, be covalently-linked to the parent molecule and could be capable of translocating across a biological membrane such as a cell membrane, in order to enhance cellular uptake. Exemplary moieties include peptides, e.g., penetratin or TAT. An exemplary penetratin-containing compound according to the invention is, e.g., a peptide comprising the sixteen amino acid sequence from the homeodomain of the Antennapedia protein (Derossi et al., J. Biol. Chem. 269:10444-10450, 1994), particularly a peptide having the amino acid sequence RQIKIWFQNRRMKWKK (SEQ ID NO: 50), or including a peptide sequence disclosed by Lin et al. (J. Biol. Chem. 270:14255-14258, 1995). Others are described in U.S. Patent Application Publication No. 2004-0209797 and U.S. Pat. Nos. 5,804,604, 5,747,641, 5,674,980, 5,670,617, and 5,652,122. In addition, a compound of the invention could be attached, for example, to a solid support.

Screening Assays

Fluorescence polarization assays can be used in displacement assays to identify small molecule peptidomimetics or other compounds useful in the methods of the invention. The following is an exemplary method for use of fluorescence polarization, and should not be viewed as limiting in any way. For screening, all reagents are diluted at the appropriate concentration and the working solution, kept on ice. The working stock concentration for GST and GST fusion proteins are ~4 ng/μL, Fluorescein-labeled peptides can be used at a concentration of 1.56 fmol/μL, while cold peptides at 25 pmol/μL. Samples are incubated at a total volume of 200 μL per well in black flat bottom plates, Biocoat, #359135 low binding (BD BioSciences; Bedford, Mass.). Assays are started with the successive addition using a Labsystem Multi-Drop 96/384 device (Labsystem; Franklin, Mass.) of 50 μL test compounds, diluted in 10% DMSO (average concentration of 28 μM), 50 μL of 50 mM MES-pH 6.5, 50 μL of Fluorescein-peptide, 50 μL of GST-MAPKAP kinase-2 polypeptide, or 500 μL of unlabeled polypeptide can be used as a negative control. Once added, all the plates are placed at 4° C. Following overnight incubation at 4° C., the fluorescence polarization is measured using a Polarion plate reader (Tecan, Research Triangle Park, N.C.). A xenon flash lamp equipped with an excitation filter of 485 nm and an emission filter of 535 nm. The number of flashes is set at 30. Raw data can then be converted into a percentage of total interaction(s). All further analysis can be performed using SPOTFIRE data analysis software (SPOTFIRE, Somerville, Mass.)

Upon selection of active compounds, auto-fluorescence of the hits is measured as well as the fluorescein quenching effect, where a measurement of 2,000 or more units indicates auto-fluorescence, while a measurement of 50 units indicates a quenching effect. Confirmed hits can then be analyzed in dose-response curves ($IC_{50}$) for reconfirmation. Best hits in dose-response curves can then be assessed by isothermal titration calorimetry using a GST-MAPKAP kinase-2 polypeptide fusion.

Assays with a candidate compound may be performed in the presence of a compound known to bind MAPKAP kinase-2, and the difference in binding the presence and absence of the compound known to bind may be a useful measure of the candidate compound's ability to bind to MAPKAP kinase-2. This assay may be done in any format known to those of skill in the art, e.g., as a displacement assay.

Alternate Binding and Displacement Assays

Fluorescence polarization assays are but one means to measure compound-protein interactions in a screening strategy. Alternate methods for measuring compound-protein interactions are known to the skilled artisan. Such methods include, but are not limited to mass spectrometry (Nelson and Krone, J. Mol. Recognit., 12:77-93, 1999), surface plasmon resonance (Spiga et al., FEBS Lett., 511:33-35, 2002; Rich and Mizka, J. Mol. Recognit., 14:223-8, 2001; Abrantes et al., Anal. Chem., 73:2828-35, 2001), fluorescence resonance energy transfer (FRET) (Bader et al., J. Biomol. Screen, 6:255-64, 2001; Song et al., Anal. Biochem. 291:133-41, 2001; Brockhoff et al., Cytometry, 44:338-48, 2001), bioluminescence resonance energy transfer (BRET) (Angers et al., Proc. Natl. Acad. Sci. USA, 97:3684-9, 2000; Xu et al., Proc. Natl. Acad. Sci. USA, 96:151-6, 1999), fluorescence quenching (Engelborghs, Spectrochim. Acta A. Mol. Biomol. Spectrosc., 57:2255-70, 70; Geoghegan et al., Bioconjug. Chem. 11:71-7, 2000), fluorescence activated cell scanning/sorting (Barth et al., J. Mol. Biol., 301:751-7, 2000), ELISA, and radioimmunoassay (RIA).

Pharmaceutical Compositions

The pharmaceutical compositions of the present invention are prepared in a manner known per se, for example by means of conventional dissolving, lyophilizing, mixing, granulating or confectioning processes. Methods well known in the art for making compositions and formulations are found, for example, in "Remington: The Science and Practice of Pharmacy," (20th ed., ed. A. R. Gennaro, 2000, Lippincott Williams & Wilkins, Philadelphia).

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting and/or emulsifying agents, to solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, poly vinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of anti oxidants, for example, vitamins E, β-carotene, or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (poly oxyethylene glycerol trioleate, Gattefoss, Paris), "Miglyol 812" (triglyceride of saturated fatty acids with a chain length of $C_8$ to $C_{12}$, Huls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, drage cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinyl-pyrrolidone, and/or, if desired, disintegrates, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Drage cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or drage coatings or the capsule casings, for example for identification purposes or to indicate different doses of active ingredient.

The pharmaceutical compositions comprise from approximately 1% to approximately 95%, preferably from approximately 20% to approximately 90%, active ingredient. Pharmaceutical compositions according to the invention may be, for example, to in unit dose form, such as in the form of ampoules, vials, suppositories, drages, tablets or capsules.

The formulations can be administered to human patients in a therapeutically effective amount (e.g., an amount that decreases, suppresses, attenuates, diminishes, arrests, or stabilizes the development or progression of a disease, disorder, or infection in a eukaryotic host organism). The preferred dosage of therapeutic agent to be administered is likely to depend on such variables as the type and extent of the disorder, the overall health status of the particular patient, the formulation of the compound excipients, and its route of administration.

For any of the methods of application described above, a compound that interacts with a MAPKAP kinase-2 polypeptide may be applied to the site of the needed therapeutic event (for example, by injection, e.g., direct injection into one or more tumors), or to tissue in the vicinity of the predicted therapeutic event or to a blood vessel supplying the cells predicted to require enhanced therapy.

The dosages of compounds that interact with a MAPKAP kinase-2 polypeptide depend on a number of factors, including the size and health of the individual patient, but, generally, between 0.1 mg and 1000 mg inclusive are administered per day to an adult in any pharmaceutically acceptable formulation. In addition, treatment by any of the approaches described herein may be combined with more traditional therapies.

EXAMPLES

Example 1

The p38MAPK-MK2 Pathway is Activated by Drugs that Directly Damage DNA

Figure 10A:
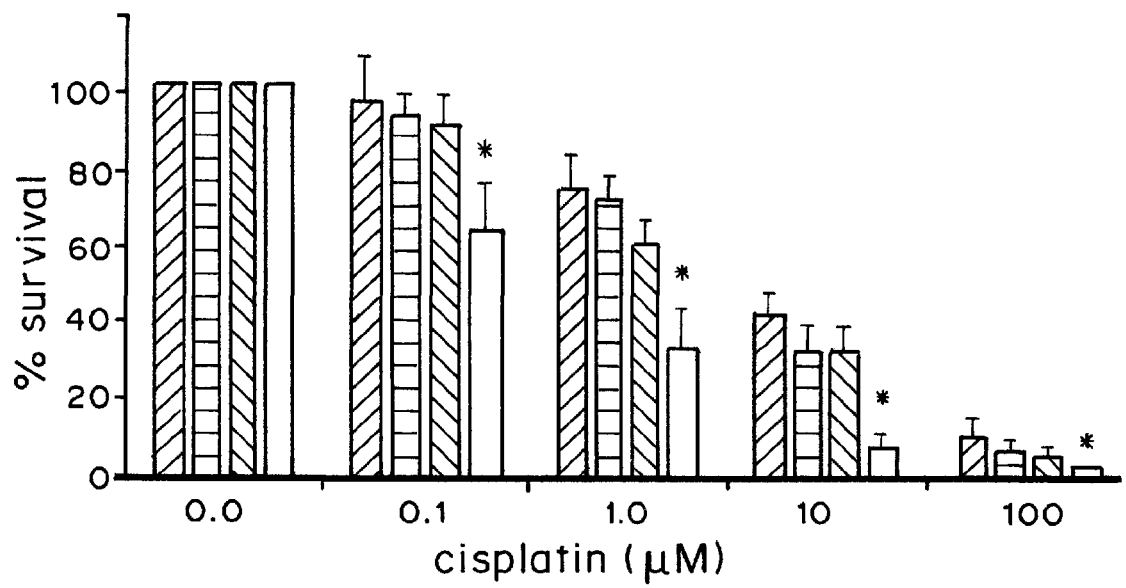
FIGS. 10A-10B are graphs showing the results of a colony survival assay in which mouse embryonic fibroblasts (MEFs) were treated with increasing doses of doxorubicin or cisplatin for eight hours, rinsed twice with PBS and once with media, and re-plated at an initial density of 5,000 cells/10 cm² dish. After eleven days, the number of colonies on the plate was counted and normalized to the number of colonies formed by the same cell type in the absence of treatment with chemotherapeutic drugs. RNA interference using short hairpin RNAs was used with both the p53 wild-type MEFs and the p53−/− MEFs to knock down the levels of MAPKAP kinase-2 (MK2 shRNA). Short hairpin RNAs against luciferase (luciferase shRNA) were used as a control. Loss of MAPKAP kinase-2 activity resulted in increased sensitivity to both doxorubicin and cisplatin (i.e. decreased survival after treatment) only in the MEFs that lacked p53.

To investigate whether the p38 MAPK/MK2 pathway was involved in the DNA damage response of cells following exposure to clinically useful chemotherapeutic agents, we treated human U2OS osteosarcoma cells with the DNA crosslinking agent cis-Platinum (cisplatin), the topoisomerase I inhibitor camptothecin, or the topoisomerase II inhibitor doxorubicin. p38 MAPK activation was assessed using an antibody specific for the Thr-180/Tyr-182 doubly phosphorylated active form of the kinase. Activation of MK2 was monitored by its altered mobility on SDS-PAGE, and by immunoblotting using a phospho-specific antibody for pThr-344, a site in the auto-inhibitory domain whose phosphorylation by p38MAPK results in a dramatic elevation of MK2 activity. Prior to exposure of cells to DNA damaging compounds, or in cells treated with DMSO (vehicle) alone, MK2 ran as a single band that did not cross-react with the anti-pThr-344 antibody. Within one hour after exposure of the cells to cisplatin and doxorubicin, or within four hour following treatment with camptothecin, MK2 displayed a significant reduction in its electrophoretic mobility. The upshifted MK2 band appeared with the same kinetics as both the MK2 pThr-344- and the p38MAPK pThr-180/pTyr-182 immunoreactive bands. Activation of MK2 was entirely dependent on p38MAPK, since addition of the p38MAPK selective inhibitor SB203580 to the growth media 30 minutes prior to application of the DNA damaging agents completely abolished MK2 activation, while preserving activation of p38MAPK. Similar results for MK2 activation in response to cisplatin, camptothecin and doxorubicin were also observed in HeLa cervical carcinoma cells, U87MG human glioblastoma cells, and primary MEFs (FIG. 10A and data not shown). The time course of MK2 activation upon treatment with each of these drugs matched the rate of appearance of γ—H2AX nuclear foci. These data indicate that treatment of cells with these genotoxic agents results in MK2 activation, likely as a direct result of chemotherapy-induced DNA damage.

Example 2

ATM and ATR are Required for p38MAPK/MK2 Activation Following Genotoxin-Induced DNA Damage but not in Response to UV Irradiation We analyzed the p38MAPK/MK2 activation profile in ATM-deficient and ATR-defective fibroblasts (FIG. 6). We also studied the effect of pharmacological inhibition of these kinases by addition of caffeine. Activation of the p38MAPK/MK2 complex in response to cisplatin, camptothecin or UV exposure occurred normally in ATM deficient fibroblasts, while doxorubicin treatment failed to activate either p38MAPK or MK2 in these cells. ATR-defective fibroblasts, on the other hand, failed to activate p38MAPK or MK2 following either cisplatin, doxorubicin, or camptothecin exposure. However, UV-induced p38MAPK/MK2 activation in these cells was unaffected. Similarly, treatment of U2OS cells with 20 mM caffeine, a concentration sufficient to inhibit ATM, ATR and DNA-PK, for thirty minutes prior to exposure to cisplatin and doxorubicin completely abrogated the p38MAPK/MK2 response, while the activation of these kinases by UV occurred normally under these conditions. Taken together, these data indicate that cisplatin, camptothecin, and doxorubicin require ATR for p38MAPK/MK2 activation, that doxorubicin also requires ATM activity, and that UV irradiation is capable of activating the p38MAPK/MK2 in a manner that is independent of ATM, ATR, or DNA-PK function.

Example 3

Figure 10B:
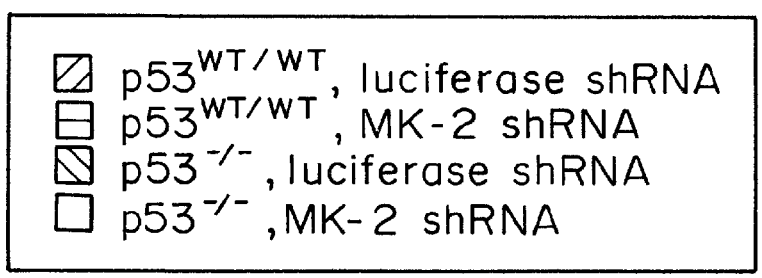
Figure 10B:
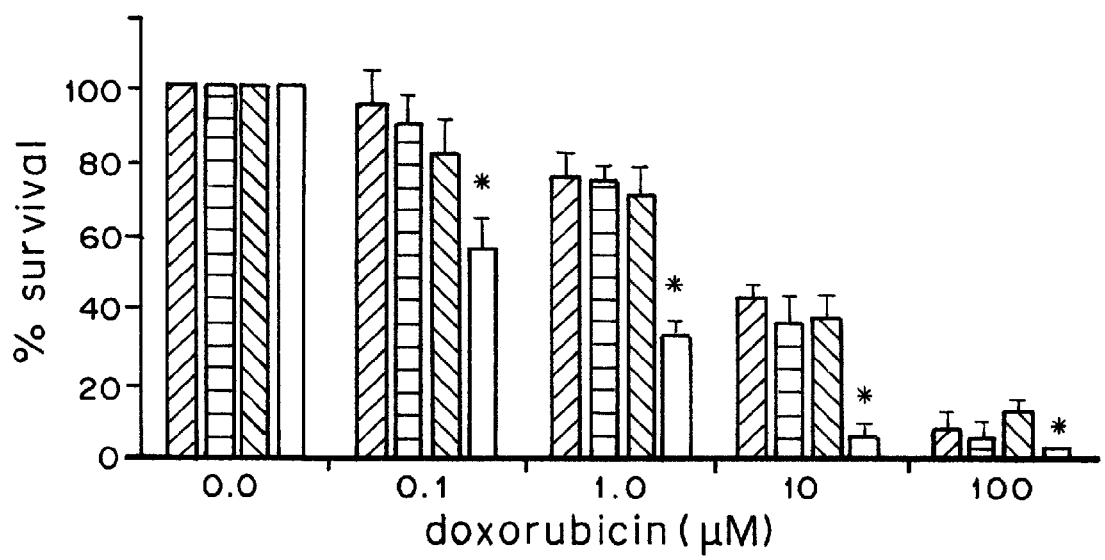

Loss of p53 Renders Cells Dependent on MK2 Signaling for Survival after Chemically-Induced DNA Damage The p53 tumor suppressor protein plays an important role in the cellular response to DNA damage by transcriptionally upregulating the Cdk inhibitor p21 to induce a $G_1$ and $G_2$ arrest. Cancer cells frequently show disruptions in the p53 pathway, eliminating this component of the DNA damage response, and leaving the cells entirely dependent on remaining checkpoint signaling pathways. To examine whether the ATR/ATMp38MAPK-MK2 pathway was required for cell survival after genotoxin-induced DNA damage in p53 wild-type and p53/MEFs, we used RNAi to deplete MK2, and examined the response of these otherwise genetically identical cells to cisplatin and doxorubicin using a colony survival assay FIGS. 10A and 10B. Cells were infected with lentiviruses delivering shRNAs against luciferase (control) or MK2 and analyzed 6 days later. Luciferase and MK2 knockdown MEFs were then exposed to increasing doses of cisplatin or doxorubicin. As seen in FIGS. 10A and 10B, there was no difference in the number of surviving colonies in the p53 wt/wt MEFs, regardless of the presence or absence of MK2, at any dose of cisplatin or doxorubicin examined. In contrast, downregulation of MK2 in p53$^{-/-}$ cells dramatically reduced the number of surviving colonies. These results demonstrate that depletion of MK2 specifically sensitizes p53-deficient cells to the anti-proliferative effects of chemotherapy-induced DNA damage. We used Western blot analysis to profile activation of the MK2 pathway and the p53 network following cisplatin and doxorubicin treatment in these four cell lines. The presence or absence of MK2 had no effect on the strong induction of p53 and p21 following exposure to cisplatin or doxorubicin in the p53 WT/WT cells. Only minimal amounts of the p53 inducer protein p19ARF were detected. Neither p53 or p21 induction was detectable in p53/MEFs in the presence or absence of MK2. However, the tumor suppressor p19ARF was strongly induced in these cells even in the absence of DNA damaging chemotherapy, likely reflecting a feedback response due to the inability of these cells to induce p53. Thus, we concluded that MK2 is not required for the normal p53/p21 induction or stabilization in response to DNA damage in wild-type primary cells, and that MK2 is unable to induce p21 expression after DNA damage in the absence of functional p53.

Example 4

Down-Regulation of MK2 Leads to Mitotic Catastrophe after DNA Damage in p537 Cells We speculated that the reduced colony formation observed in MK2-depleted p53$^{-/-}$ MEFs after DNA damaging chemotherapy might be due to mitotic catastrophe resulting from defective cell cycle checkpoints. A hallmark of mitotic catastrophe is entry of cells into mitosis despite the presence of damaged DNA, resulting in activation of the apoptotic cell death pathway. To investigate this, luciferase shRNA control and MK2 depleted p53 wild-type or null MEFs were treated with low doses of doxorubicin or cisplatin for thirty hours and immunostained with antibodies against histone H3 pSer-10 as a marker for mitotic entry, histone γ-H2AX as marker for persistent DNA damage, and cleaved caspase-3 as a marker for apoptosis. Luciferase shRNA-treated p53 wt/wt and p53$^{-/-}$ cells showed robust γ-H2AX foci after exposure to DNA damaging chemotherapy. No phospho-histone H3 or cleaved caspase-3 staining was observed in MK2-containing cells, consistent with an intact DNA damage response regardless of the presence or absence of p53. Similarly, an intact DNA damage checkpoint response was also observed in MK2 depleted cells that contained wild-type p53. In sharp contrast, however, in the MK2-deficient p53$^{-/-}$ cells, a substantial fraction of the γ-H2AX positive cells also stained positively for both phospho-histone H3 and cleaved caspase 3. Interestingly, no caspase 3 staining was observed in γ-H2AX-positive cells that did not also contain phospho-histone H3. Thus, in the absence of MK2, p53 null primary cells treated with cisplatin and doxorubicin lose one or more critical cell cycle checkpoints and undergo mitotic catastrophe.

Example 5

Figure 7D:
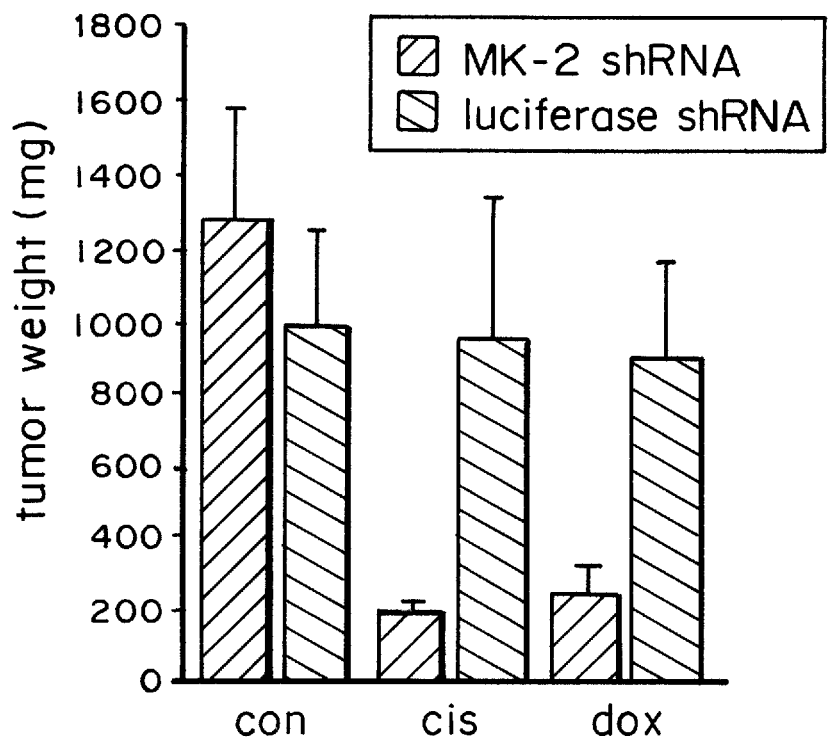

Down-Regulation of MK2 Causes Regression of Established p53$^{-/-}$ Tumors In Vivo after Low Dose Treatment with DNA Damaging Agents We investigated whether the chemo-sensitizing effect of MK2 depletion in p53 null cells in culture could also be observed when pre-existing p53 deficient tumors were treated with DNA damaging drugs in vivo. In these experiments HRas-V12 transformed p53$^{-/-}$ MEFs were stably transfected with control shRNA or MK2 shRNA expressed from a murine U6 promoter, using a lentiviral delivering system. The lentiviral transfer vector also encoded GFP under the control of a CMV promoter, allowing for fluorescent detection of tumors in situ. Tumors were induced by injection of $10^6$ cells into the flanks of nude mice. Twelve days later ~1 cm diameter tumors had formed at all injection sites, and treatment with cisplatin, doxorubicin, or vehicle was begun (FIG. 7A-7C). In the absence of treatment with DNA damaging drugs, the tumors arising from the MK2 depleted cells in the right flanks of these animals grew slightly larger than those of the luciferase shRNA control cells in the left flanks (FIGS. 7A-7D). Following treatment with cisplatin or doxorubicin, the control tumors showed either minimal reduction in size, or slow continued growth. In contrast, the MK2 depleted tumors showed a dramatic reduction in weight and diameter. Tumors depleted of MK2 shrank from 1.3 cm to 0.4 cm over fourteen days when treated with cisplatin, and from 1.4 to 0.5 cm when treated with doxorubicin. Thus, the sensitizing effect of MK2 depletion on DNA damage induced cell death in p53-deficient primary cells observed in cell culture was also maintained in vivo. These results strongly suggest that MK2 may be a useful target for the design of new cancer treatment agents.

Example 6

Figure 11:
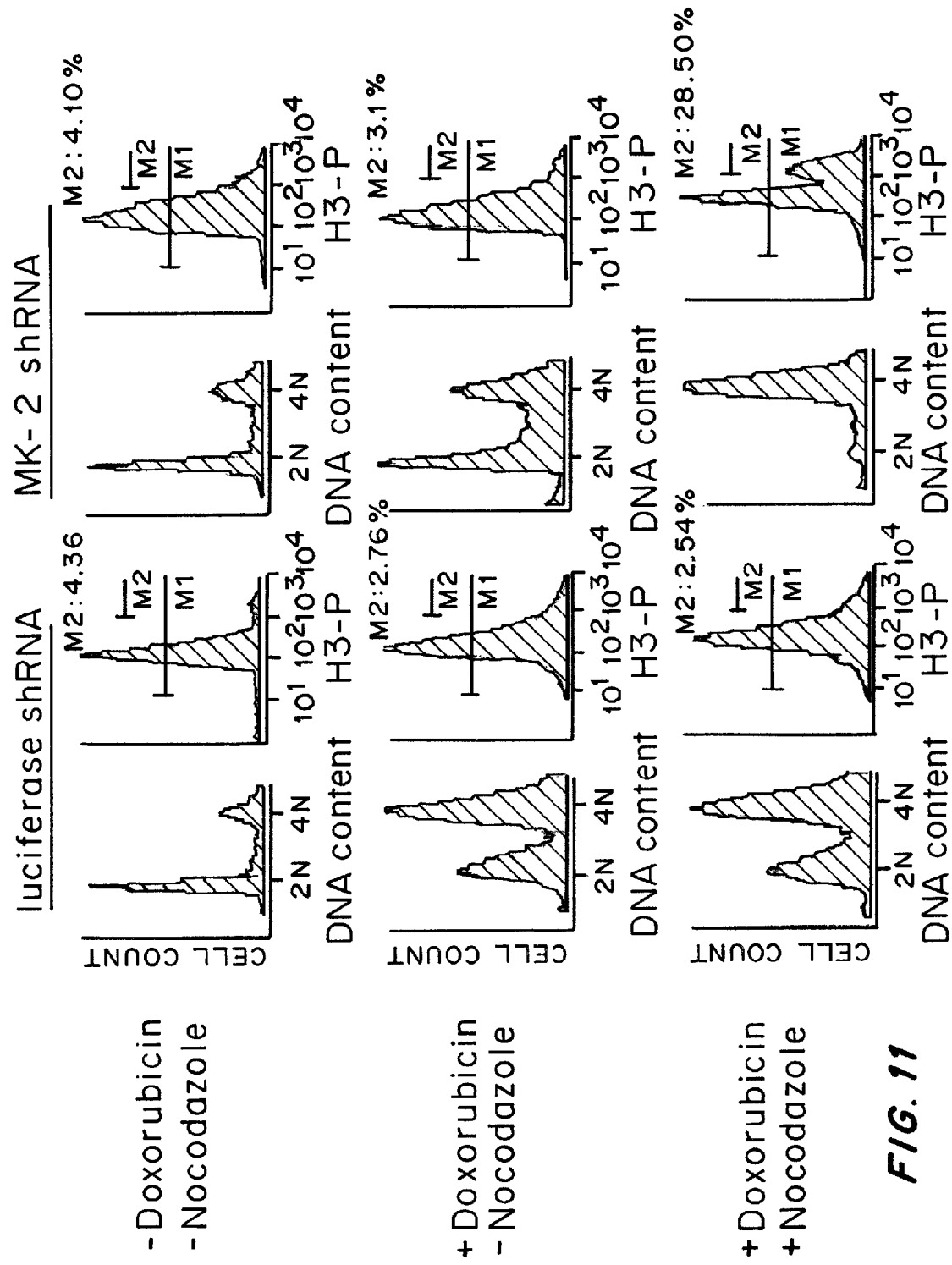
FIG. 11 shows histograms demonstrating MAPKAP Kinase 2 mediates a $G_2/M$ arrest following doxorubicin treatment. RNAi down-regulation of MK2 ablates the doxorubicin-induced $G_2/M$ checkpoint (FIG. 11). p53−/− MEFs stably expressing control luciferase shRNA (FIG. 11 left panels) or MK2 shRNA (FIG. 11 right panels) were cultured in the absence or presence of 10 μM doxorubicin and cell cycle profiles analyzed thirty hours later by FACS using PI for DNA content (blue) and phospho-histone H3 staining as an indicator of mitosis (red). In the lower set of panels, nocodazole (100 ng/ml) was added three hours following doxorubicin addition. Note that in addition to loss of the prominent $G_2/M$ checkpoint, the $G_1$ and S phase components are also eliminated in MK2-depleted cells following doxorubicin+nocodazole treatment.

MK2 is Required for the $G_2$/M Checkpoint Following Doxorubicin Treatment in p53-Deficient Cells To investigate the molecular mechanisms involved in MK2 dependent responses to DNA lesions, we examined cell cycle profiles of control and MK2 depleted p53$^{-/-}$ MEFs. Asynchronous MK2- or control knock-down p53$^{-/-}$ MEFs were mock treated or exposed to doxorubicin for thirty hour, and cell cycle distribution monitored by FACS. In one set of experiments the spindle poison nocodazole was added to the media three hours after addition of doxorubicin, to cause any cells progressing through the cell cycle to arrest in mitosis. DNA content was monitored by PI staining; phospho-histone-H3 staining was used as an indicator of mitotic entry. As shown in the left panels of FIG. 11, treatment of control knock down p53$^{-/-}$ cells with doxorubicin led to the accumulation of cells with 4N DNA content, and a lack of phospho-histone H3 staining in either the absence or presence of nocodazole, indicative of an intact $G_2$/M checkpoint. These cells expressing control shRNAs behaved identically to an untransfected control p53$^{-/-}$ cell population. In marked contrast, MK2 depleted p53$^{-/-}$ cells treated with doxorubicin displayed a cell cycle profile similar to that of untreated cells (FIG. 11, right upper and middle panels), with only a small increase in the 4N peak compared to the doxorubicin-treated luciferase shRNA controls, a slightly increased S-phase population, and the appearance of a sub-$G_1$ population indicative of apoptosis. Addition of nocodazole following doxorubicin treatment to the MK2 depleted cells caused them to accumulate in a 4N DNA containing peak, with 28.5% of the cells staining positively for phospho-histone H3 (FIG. 11, right lower panels), a value similar to that of untreated p53$^{-/-}$ cells blocked in mitosis with nocodazole. Intriguingly, MK2 depletion did not alter total Chk1 levels or reduce Chk1 activation following DNA damage. These findings demonstrate that loss of MK2 prevents p53-deficient cells from establishing a functional $G_2$/M checkpoint following doxorubicin-induced DNA damage, despite the presence of activated Chk1. Identical results were obtained using a second unrelated shRNA against to 0 MK2. Importantly, the checkpoint defect could be fully rescued in the MK2 depleted cells by expressing an shRNA-resistant form of MK2 at comparable levels to the endogenous protein.

Two Cdc25 family members, Cdc25B and C, play important roles in initiating and maintaining mitotic entry in normal cells, and are prominent targets of the $G_2$/M checkpoint. Cdc25B is believed to function by activating Cdk1/Cyclin B at the centrosome in late $G_2$ as an initiator of early mitotic events, while Cdc25C functions to further amplify Cdk1/CyclinB activity within a nuclear auto-amplification loop once mitosis has begun. In response to γ- or UV-irradiation-induced DNA damage, checkpoint kinases phosphorylate Cdc25B and C on Ser-323 and 216, respectively, to induce their binding to 14-3-3 proteins, sequestering them in the cytoplasm away from their cyclin/Cdk substrates. Cdc25B plays a particularly crucial role in initiating and maintaining normal cell cycle $G_2$/M checkpoint responses, since reactivation of Cdc25B is critical for DNA-damaged cells to re-enter the cell cycle. We therefore investigated whether MK2 signaling was required for association of Cdc25B with 14-3-3 in response to DNA damage by chemotherapeutic drugs. Both doxorubicin and camptothecin treatment, resulted in the generation of stable 14-3-3-binding sites on Cdc25B in the luciferase shRNA control cells. No 14-3-3 binding of Cdc25B, however, was detected in lysates from the MK2 depleted cells. This result is in good agreement with the cell cycle studies in panel A, which showed loss of the $G_2$/M checkpoint in MK2 depleted cells after treatment with the topoisomerase inhibitor doxorubicin. These data indicate that loss of the $G_2$/M checkpoint after DNA lesions in MAPKAP Kinase-2-depleted p53-defective cells likely arises, at least in part, from loss of Cdc25B binding to 14-3-3 proteins.

Example 7

Figure 12:
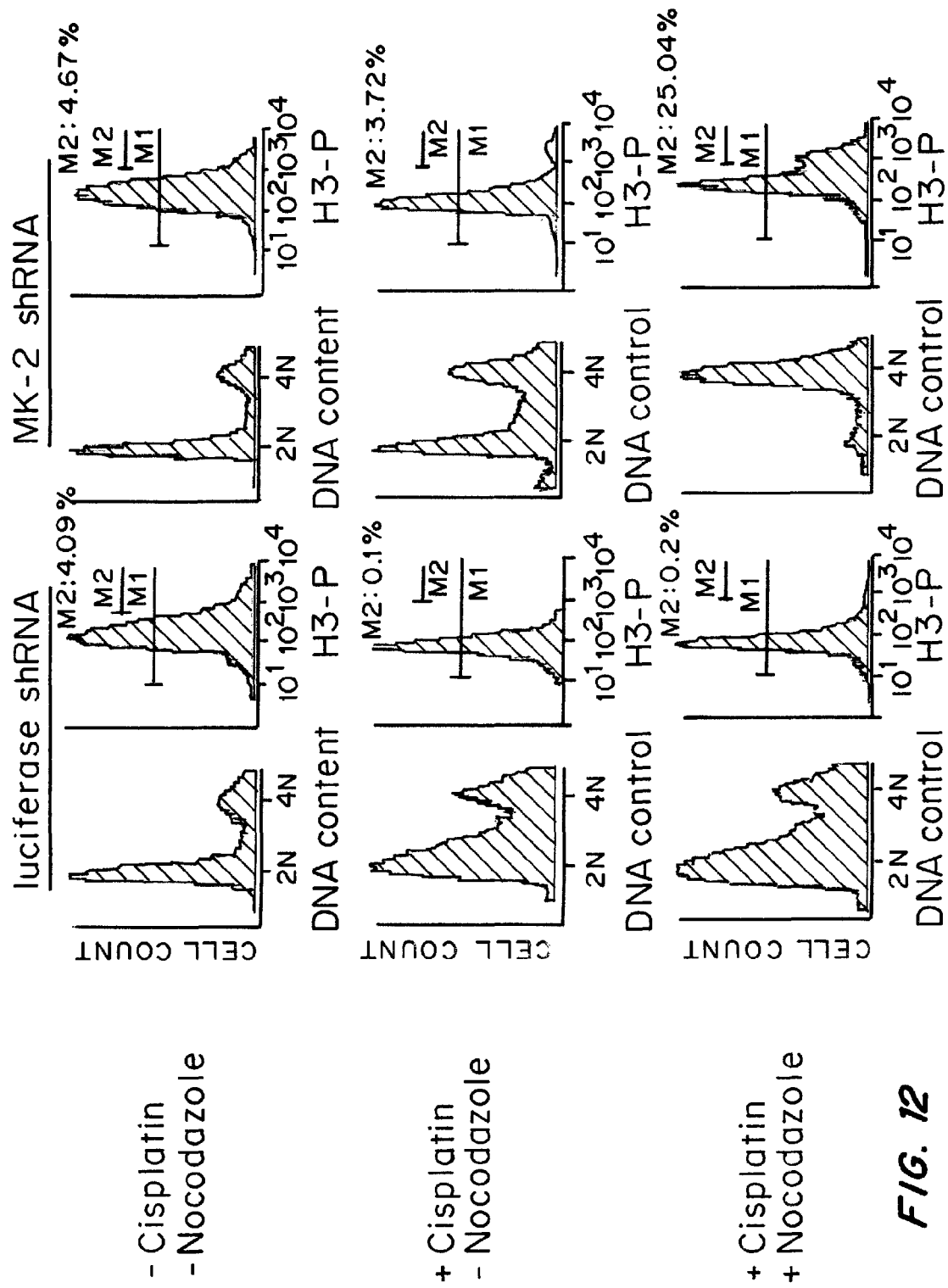
FIG. 12 shows histograms demonstrating MK2 controls the S-phase checkpoint in response to cisplatin treatment. RNAi down-regulation of MK2 ablates the cisplatin-induced S-phase checkpoint (FIG. 12). p53−/− MEFs stably expressing control luciferase shRNA (FIG. 12, left panels) or MK2shRNA (FIG. 12, right panels) were cultured in the absence or presence of 10 μM cisplatin and cell cycle profiles analyzed thirty hours later by FACS using PI for DNA content (blue) and phospho-histone H3 staining as an indicator of mitosis (red). In the lower set of panels, nocodazole (100 ng/ml) was added three hours following cisplatin addition.

MK2 is Required for S-Phase Checkpoint Arrest Following Cisplatin Treatment in p53-Deficient Cells Treatment with the DNA intra-strand cross-linker cisplatin caused p53$^{-/-}$ cells to predominantly accumulate in S phase of the cell cycle. RNA interference was used to to investigate the role of MK2 in this process. p53$^{-/-}$ control knock-down cells showed an identical accumulation in S phase after cisplatin exposure (FIG. 12, left middle panels) as that seen in untransfected p53$^{-/-}$ cells. Addition of nocodazole to the luciferase knock-down cells three hour following cisplatin treatment did not reveal the appearance of any mitotic cells over the ensuing twenty seven hours, as monitored by phospho-histone H3 staining (FIG. 12, lower left panels), indicating a functionally intact S-phase checkpoint. Depletion of MK2 prior to cisplatin exposure resulted in a dramatically different result. As seen in the right panels of FIG. 12, MK2-depleted p53$^{-/-}$ cells showed a cell cycle profile after cisplatin treatment that was similar to that of untreated cells, other than a slight increase in the total number of cells in S-phase and the appearance of a sub-$G_1$ population consistent with apoptosis. Strikingly, when nocodazole was added three hours following cisplatin addition, the MK2 depleted p53−/− cells accumulated in a 4N DNA containing peak with ~25% of the cells staining positive for phospho-histone H3. The same cell cycle defects after cisplatin exposure were observed using a second unrelated shRNA sequence against MK2, and the MK2 shRNA phenotype was completely reversed by expression of an RNAi-resistant form of MK2 at physiological levels. Similar to what was observed following doxorubicin treatment, MK2 depletion did not impair activation of Chk1 after cisplatin exposure. These data imply that MK2 is essential for the cisplatin induced S-phase arrest in p53-deficient cells, and that loss of MK2 enables these cells to override the cisplatin-induced S-phase checkpoint, despite the presence of activated Chk1, and proceed into mitosis. In contrast to the 14-3-3-mediated sequestration of Cdc25B and C involved in the $G_2$/M checkpoint response, the $G_1$ and S phase checkpoints are largely controlled by the phosphorylation-dependent degradation of another Cdc25 isoform, Cdc25A. We therefore investigated whether MK2 was required for the degradation of Cdc25A following cisplatin-induced DNA damage. Cdc25A levels were undetectable in the control luciferase knock-down cells after treatment with cisplatin. In contrast, in the MK2 depleted cells, substantial amounts of Cdc25A remain present in the lysates after cisplatin exposure, indicating that in the absence of MAPKAP Kinase-2, p53−/− MEFs cells are defective in targeting Cdc25A for degradation in response to cisplatin induced DNA damage. This impaired ability of MK2 depleted cells to degrade Cdc25A likely explains their failure to establish a sustained $G_1$/S checkpoint following cisplatin exposure. Interestingly, Cdc25A may be a direct target of MK2 in vivo, since both MK2 and Chk1 phosphorylate Cdc25A equivalently in vitro, Chk1 phosphorylation of Cdc25A in vivo has been shown to facilitate its ubiquitin-mediated proteolysis in a complex and incompletely understood manner, and MK2 and Chk1 phosphorylate the identical optimal sequence motifs when analyzed by oriented peptide library screening.

Example 8

MK2 and Chk1 are Activated Independently by DNA Damage, and are Both Potently Inhibited by UCN-01

Activation of MK2 by cisplatin, camptothecin, and doxorubicin is strikingly similar to the activation profile reported for Chk1. Similarly, the impaired S-phase and $G_2$/M checkpoints seen after these DNA damaging stimuli in MK2 knockdown cells bears some resemblance to what has been previously reported for Chk1-deficient p53-defective cells. These phenotypic similarities prompted us to further investigate whether the activation of Chk1 and MK2 was interdependent. Activation of Chk1 in response to doxorubicin and cisplatin was unimpaired in MK2 depleted cells. We therefore investigated the converse—whether the activation of MK2 after DNA damage was dependent on Chk1. U2OS cells depleted of Chk1 using siRNA were exposed to cisplatin and doxorubicin, and analyzed for activation of MK2.

Phosphorylation/activation of MK2 occurred normally after treatment with these DNA damaging agents, regardless of the presence or absence of Chk1. Thus, activation of MK2 and Chk1 after drug-induced DNA damage appears to occur independently of each other, and both kinases appear to participate in parallel DNA damage checkpoint signaling pathways that are necessary for cell survival in the absence of a strong p53 response. The staurosporine derivative 7-hydroxystaurosporin/UCN-01 has been shown to increase the cytotoxicity of chemotherapy and radiation and is currently in clinical trials. It has been demonstrated that a major target of UCN-01 is the checkpoint kinase Chk1, leading to speculation that that the increased chemo- and radiation sensitivity of cells treated with UCN-01 is a direct result of Chk1-mediated checkpoint abrogation. UCN-01 inhibits Chk1 with an $IC_{50}$ that is ~1000 fold lower than that for Chk2, and hence has been used experimentally as a Chk1 specific inhibitor. Strong circumstantial evidence, however, suggests that UCN-01 must be inhibiting other kinases involved in cell cycle control at similar concentrations as those used for Chk1 inhibition studies. For example, Chk1-depleted cells maintain phosphorylation of Ser-216, a well characterized Chk1 target site on Cdc25C, both during asynchronous growth and following γ-irradiation. Phosphorylation at this site is lost, however, when cells are treated with low doses of UCN-01 (~300 nM), indicating that UCN-01 inhibitable kinase(s) other than Chk1 participate in Cdc25C Ser-216 phosphorylation. Based on our finding that MK2 depletion results in a dramatically increased chemosensitivity of malignant cells, we asked whether MK2 might be a UCN-01 target, similar to Chk1. In vitro kinase assays were performed under identical reaction conditions with Chk1 and MK2 using the same optimal peptide substrate for both kinases with the core consensus sequence L-Q-R-Q-L-S-I, in the presence of various concentrations of UCN-01. As shown in FIG. 21A 8, UCN-01 potently inhibited both kinases, with an $IC_{50}$ value of ~35 nM for Chk1 and ~95 nM for MAPKAP Kinase-2. The $IC_{50}$ value we measured for Chk1 is in good agreement with previously published data. Importantly, the $IC_{50}$ value we measured for MK2 is significantly below the concentrations of UCN-01 that are used in "Chk1-specific" checkpoint abrogation assays, suggesting that under the conditions used in those studies, both Chk1 and MK2 were being inhibited. To examine the structural basis for UCN-01 inhibition of MK2, the structure of the MK2:UCN-01 complex was modeled using coordinates from the published MK2:staurosporine structure, and compared the results with the co-crystal structure of Chk1:UCN-01. The 7-hydroxy moiety of UCN-01 can be easily accommodated into the MK2:staurosporine structure, where its closest neighboring residues would be Val-118 (2.8 Å to Cγ2), Leu-141 (3.2 Å to Cγ1), and Thr-206 (3.6 Å to Cγ2). Lack of steric hindrance, and the overall similarity of the modeled MK2: UCN-01 structure to the Chk1:UCN-01 structure provides a structural rationale for the tight binding observed biochemically. To verify that MK2 is a direct target of UCN-01 within cells, we measured the phosphorylation of the MK2 substrate hsp-27 after heat shock, a stimulus that activates the p38MAPK/MK2 pathway. Control or MK2 shRNA expressing U2OS cells were incubated at 42° C. or 37° C. for two hours in the presence or absence of 250 nM UCN-01, and phosphorylation of hsp-27 monitored by immunoblotting. Immunoblotting shows that hsp27 is phosphorylated on Ser-82 when the control luciferase shRNA cells were placed at 42° C. This phosphorylation was completely abrogated by treatment with UCN-01. No phosphorylation was observed in MK2 knock-down cells placed at 42° C. regardless of the presence or absence of UCN-01, and no signal was observed in both the control and MK2 knock-down cells that were maintained at 37° C., with or without UCN-01 treatment. Heat shock was equally effective in promoting the phosphorylation of hsp-27 on Ser-82, and UCN-01 was equally effective in blocking Ser-82 phosphorylation in cells that were depleted of Chk1. Thus, UCN-01 inhibits MK2 in vivo, and this effect is independent of Chk1 function. This data demonstrates that UCN-01 is a direct inhibitor of MK2 within cells, and indicates that the clinical efficacy of UCN-01 in cancer treatment, particularly in p53-defective tumors, likely arises from the simultaneous inhibition of both the Chk1 and MK2 signaling pathways Example 9

Figure 13A:
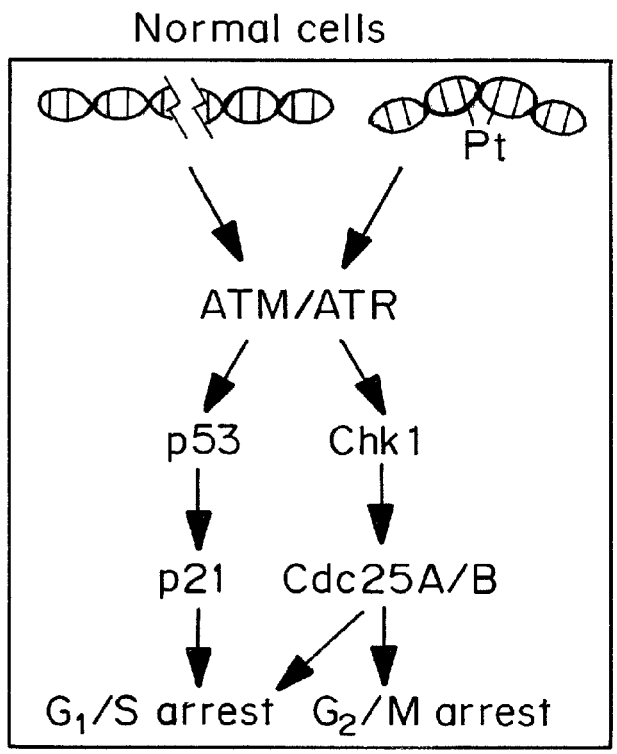
FIGS. 13A-13B are models for re-wiring of cell cycle checkpoint pathways in p53-proficient and deficient cells. Checkpoint function in p53-proficient cells is mediated primarily through a robust, sustained p53 response downstream of ATM, together with Chk1 (FIG. 13A). Although not shown explicitly in the diagram, Chk1 also directly phosphorylates p53 (Shieh et al., 2000). Under these conditions the presence of MK2 is not required for cell survival after exposure to DNA damaging agents. In p53-deficient cancer cells (FIG. 13B), checkpoint signaling following to exposure to DNA damaging agents is mediated through the combined action of both the Chk1 and the p38 MAPK/MK2 pathways. In this situation the p38MAPK/MK2 branch of checkpoint signaling becomes essential for cell survival after DNA damage. Both pathways are simultaneously inhibited by the indolocarbazole drug UCN-01.
Figure 13B:
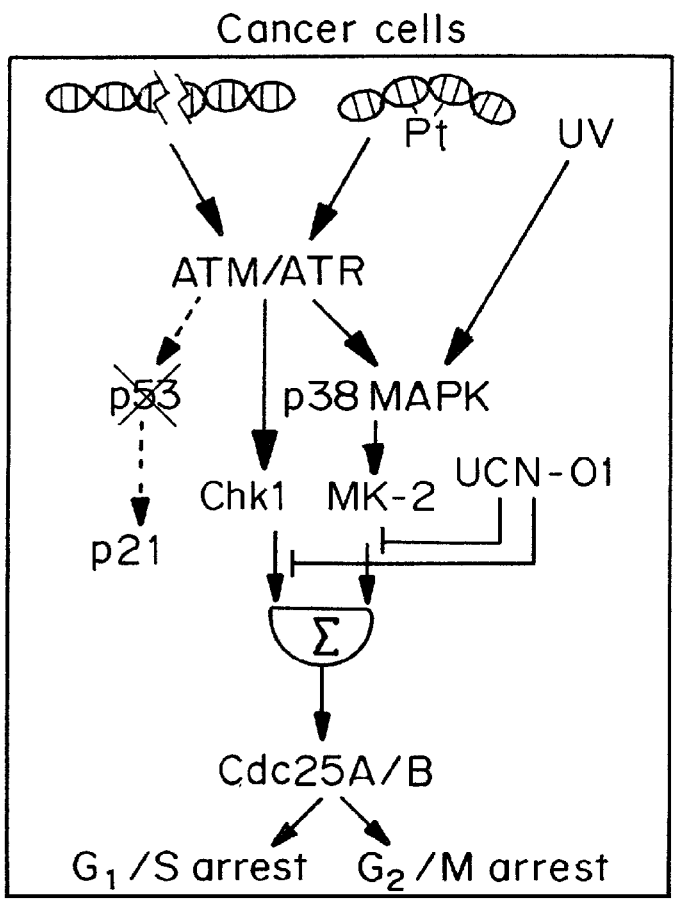

A Model for Re-Wiring of Cell Cycle Checkpoint Pathways in p53-Proficient and Deficient Cells Checkpoint function in p53-proficient cells is mediated primarily through a robust, sustained p53 response downstream of ATM, together with Chk1 (FIG. 13A). Although not shown explicitly in the diagram, Chk1 has been shown to also directly phosphorylate p53. Under these conditions the presence of MK2 is not required for cell survival after exposure to DNA damaging agents. In p53-deficient cancer cells, checkpoint signaling following exposure to DNA damaging agents is mediated through the combined action of both the Chk1 and the p38 MAPK/MK2 pathways (FIG. 13B). In this situation the p38MAPK/MK2 branch of checkpoint signaling becomes essential for cell survival after DNA damage. Both pathways are simultaneously inhibited by the indolocarbazole drug UCN-01.

Other Embodiments

All publications, patents, and patent applications mentioned in the above specification are hereby incorporated by reference. In addition, U.S. Patent Application Publication Nos. US 2005-0196808 and US 2006-0052951 are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A method of sensitizing cells to chemotherapy comprising
administering to the cells an effective amount of a MAPKAP kinase-2 polypeptide inhibitor to sensitize p53-deficient cells to a DNA damaging chemotherapeutic agent,
then administering an effective amount of a chemotherapeutic to the sensitized p53-deficient cells to kill the cells wherein the chemotherapeutic agent is administered after and within twenty-eight days of administering the MAPKAP kinase-2 polypeptide inhibitor.

2. The method of claim 1, wherein the chemotherapeutic agent is selected from the group consisting of altretamine,- amsacrine, azacitidine, bleomycin,-busulfan, capecitabine, carboplatin, carmustine, chlorambucil, 2-chlorodeoxyadenosine, cisplatin, cyclophosphamide, cytarabine, Cytoxan, dacarbazine, daunorubicin, docetaxel, doxorubicin, epirubicin, etoposide, floxuridine, fludarabine, 5-fluorouracil, gemcitabine, hexamethylmelamine, hydroxyurea,-ifosfamid, irinotecan, letrozole, lomustine, mechlorethamine, melphalen, mercaptopurine, 6-mercaptopurine, methotrexate, mitomycin, mitoxantrone, paclitaxel, pentostatin, procarbazine, raltitrexed, streptozocin, temozolomide, 6-thioguanine, topotecan, toremofine, trastuzumab, vinblastine, vincristine, vindesine, and vinorelbine.

3. The method of claim 1, further comprising administering radiation therapy simultaneously or within twenty-eight days of administering the inhibitor.

4. The method of claim 1, wherein the p53-deficient cells are cancer cells selected from the group consisting of acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor.

5. The method of claim 1, wherein the inhibitor alters a DNA damage-responsive cell cycle checkpoint of the p53-deficient cell.

6. The method of claim 5, wherein the DNA damage-responsive cell cycle checkpoint is $G_1/S$ phase arrest.

7. The method of claim 6, wherein Cdc25a degradation in the p53-deficient cells is impaired.

8. The method of claim 5, wherein the DNA damage-responsive cell cycle checkpoint is $G_2/M$ phase arrest.

9. The method of claim 8, wherein the interaction between Cdc25b and a 14-3-3 protein is reduced in comparison to a p53-deficient control cell.

10. The method of claim 1, wherein cell death is by apoptosis.

11. The method of claim 10, wherein apoptosis is at least partially dependent on caspase-3 activation.

12. The method of claim 1, wherein the MAPKAP kinase-2 polypeptide inhibitor is selected from the group consisting of a nucleic acid, a peptide and a small molecule.

13. The method of claim 1, wherein the effective amount of a chemotherapeutic to the cells to kill the cells is lower than the effective amount of the chemotherapeutic to kill cells in the absence of the MAPKAP kinase-2 polypeptide inhibitor.

14. The method of claim 1, wherein the chemotherapeutic agent is administered subsequent to administering the MAPKAP kinase-2 polypeptide inhibitor.

* * * * *

SEQUENCE LISTING

```
<160> NUMBER OF SEQ ID NOS: 50

<210> SEQ ID NO 1
<211> LENGTH: 227
<212> TYPE: PRT
<213> ORGANISM: Saccharomyces cerevisiae

<400> SEQUENCE: 1

Met Ser Ala Ser Thr Thr Ser Leu Glu Glu Tyr Gln Lys Thr Phe Leu
1               5                   10                  15

Glu Leu Gly Leu Glu Cys Lys Ala Leu Arg Phe Gly Ser Phe Lys Leu
            20                  25                  30

Asn Ser Gly Arg Gln Ser Pro Tyr Phe Phe Asn Leu Ser Leu Phe Asn
        35                  40                  45

Ser Gly Lys Leu Leu Ala Asn Leu Ala Thr Ala Tyr Ala Thr Ala Ile
    50                  55                  60

Ile Gln Ser Glu Leu Lys Phe Asp Val Ile Phe Gly Pro Ala Tyr Lys
65                  70                  75                  80

Gly Ile Pro Leu Ala Ala Ile Val Cys Val Lys Leu Ala Glu Ile Gly
                85                  90                  95

Gly Thr Lys Phe Gln Gly Ile Gln Tyr Ala Phe Asn Arg Lys Lys Val
            100                 105                 110

Lys Asp His Gly Glu Gly Gly Ile Ile Val Gly Ala Ser Leu Glu Asp
        115                 120                 125

Lys Arg Val Leu Ile Ile Asp Asp Val Met Thr Ala Gly Thr Ala Ile
    130                 135                 140

Asn Glu Ala Phe Glu Ile Ile Ser Ile Ala Gln Gly Arg Val Val Gly
145                 150                 155                 160

Cys Ile Val Ala Leu Asp Arg Gln Glu Val Ile His Glu Ser Asp Pro
                165                 170                 175

Glu Arg Thr Ser Ala Thr Gln Ser Val Ser Lys Arg Tyr Asn Val Pro
            180                 185                 190

Val Leu Ser Ile Val Ser Leu Thr Gln Val Val Gln Phe Met Gly Asn
        195                 200                 205

Arg Leu Ser Pro Glu Gln Lys Ser Ala Ile Glu Asn Tyr Arg Lys Ala
    210                 215                 220
```

Tyr Gly Ile
225

<210> SEQ ID NO 2
<211> LENGTH: 294
<212> TYPE: DNA
<213> ORGANISM: Homo sapiens

<400> SEQUENCE: 2

```
caggtgcagc tgcaggagtc gggcccagga ctggtgaagc cttcggggac cctgtccctc    60
acctgcgctg tctctggtgg ctccatcagc agtagtaact ggtggagttg ggtccgccag   120
cccccaggga aggggctgga gtggattggg gaaatctatc atagtgggag caccaactac   180
aacccgtccc tcaagagtcg agtcaccata tcagtagaca gtccaagaac cagttctcc    240 ctgaagctga gctctgtgac cgccgcggac acggccgtgt attactgtgc gaga          294
```

<210> SEQ ID NO 3
<211> LENGTH: 571
<212> TYPE: PRT
<213> ORGANISM: Saccharomyces cerevisiae

<400> SEQUENCE: 3

```
Met Ser Met Ser Ser Lys Asn Glu Asn Lys Ile Ser Val Glu Gln Arg
 1               5                  10                  15

Ile Ser Thr Asp Ile Gly Gln Ala Tyr Gln Leu Gln Gly Leu Gly Ser
             20                  25                  30

Asn Leu Arg Ser Ile Arg Ser Lys Thr Gly Ala Gly Glu Val Asn Tyr
         35                  40                  45

Ile Asp Ala Ala Lys Ser Val Asn Asp Asn Gln Leu Leu Ala Glu Ile
     50                  55                  60

Gly Tyr Lys Gln Glu Leu Lys Arg Gln Phe Ser Thr Leu Gln Val Phe
 65                  70                  75                  80

Gly Ile Ala Phe Ser Ile Met Gly Leu Leu Pro Ser Ile Ala Ser Val
                 85                  90                  95

Met Gly Gly Gly Leu Gly Gly Gly Pro Ala Thr Leu Val Trp Gly Trp
            100                 105                 110

Phe Val Ala Ala Phe Phe Ile Leu Leu Val Gly Ile Thr Met Ala Glu
        115                 120                 125

His Ala Ser Ser Ile Pro Thr Ala Gly Gly Leu Tyr Tyr Trp Thr Tyr
    130                 135                 140

Tyr Tyr Ala Pro Glu Gly Tyr Lys Glu Ile Ile Ser Phe Ile Ile Gly
145                 150                 155                 160

Cys Ser Asn Ser Leu Ala Leu Ala Ala Gly Val Cys Ser Ile Asp Tyr
                165                 170                 175

Gly Leu Ala Glu Glu Ile Ala Ala Val Thr Leu Thr Lys Asp Gly
            180                 185                 190

Asn Phe Glu Val Thr Ser Gly Lys Leu Tyr Gly Ile Phe Ala Gly Ala
        195                 200                 205

Val Val Val Met Cys Ile Cys Thr Cys Val Ala Ser Gly Ala Ile Ala
    210                 215                 220

Arg Leu Gln Thr Leu Ser Ile Phe Ala Asn Leu Phe Ile Ile Val Leu
225                 230                 235                 240

Leu Phe Ile Ala Leu Pro Ile Gly Thr Lys His Arg Met Gly Gly Phe
                245                 250                 255

Asn Asp Gly Asp Phe Ile Phe Gly Lys Tyr Glu Asn Leu Ser Asp Trp
            260                 265                 270
```

```
Asn Asn Gly Trp Gln Phe Cys Leu Ala Gly Phe Met Pro Ala Val Trp
            275                 280                 285

Thr Ile Gly Ser Phe Asp Ser Cys Val His Gln Ser Glu Glu Ala Lys
290                 295                 300

Asp Ala Lys Lys Ser Val Pro Ile Gly Ile Ser Ile Ala Val
305                 310                 315                 320

Cys Trp Ile Leu Gly Trp Leu Ile Ile Cys Leu Met Ala Cys Ile
                325                 330                 335

Asn Pro Asp Ile Asp Ser Val Leu Asp Ser Lys Tyr Gly Phe Ala Leu
                340                 345                 350

Ala Gln Ile Ile Tyr Asp Ser Leu Gly Lys Lys Trp Ala Ile Ala Phe
            355                 360                 365

Met Ser Leu Ile Ala Phe Cys Gln Phe Leu Met Gly Ala Ser Ile Thr
    370                 375                 380

Thr Ala Val Ser Arg Gln Val Trp Ala Phe Ser Arg Asp Asn Gly Leu
385                 390                 395                 400

Pro Leu Ser Lys Tyr Ile Lys Arg Val Asp Ser Lys Tyr Ser Val Pro
                405                 410                 415

Phe Phe Ala Ile Leu Ala Ala Cys Val Gly Ser Leu Ile Leu Gly Leu
                420                 425                 430

Leu Cys Leu Ile Asp Asp Ala Ala Thr Asp Ala Leu Phe Ser Leu Ala
    435                 440                 445

Val Ala Gly Asn Asn Leu Ala Trp Ser Thr Pro Thr Val Phe Arg Leu
450                 455                 460

Thr Ser Gly Arg Asp Leu Phe Arg Pro Gly Pro Phe Tyr Leu Gly Lys
465                 470                 475                 480

Ile Trp Ser Pro Ile Val Ala Trp Thr Gly Val Ala Phe Gln Leu Phe
                485                 490                 495

Ile Ile Ile Leu Val Met Phe Pro Ser Gln Gln His Gly Ile Thr Lys
                500                 505                 510

Ser Thr Met Asn Tyr Ala Cys Val Ile Gly Pro Gly Ile Trp Ile Leu
    515                 520                 525

Ala Gly Ile Tyr Tyr Lys Val Tyr Lys Lys Tyr Tyr His Gly Pro
            530                 535                 540

Ala Thr Asn Leu Ser Asp Asp Asp Tyr Thr Glu Ala Val Gly Ala Asp
545                 550                 555                 560

Val Ile Asp Thr Ile Met Ser Lys Gln Glu Pro
                565                 570

<210> SEQ ID NO 4
<211> LENGTH: 400
<212> TYPE: PRT
<213> ORGANISM: Homo sapiens

<400> SEQUENCE: 4

Met Leu Ser Asn Ser Gln Gly Gln Ser Pro Val Pro Phe Pro Ala
1               5                   10                  15

Pro Ala Pro Pro Gln Pro Thr Pro Ala Leu Pro His Pro Pro
                20                  25                  30

Ala Gln Pro Pro Pro Pro Pro Gln Gln Phe Pro Gln Phe His Val
            35                  40                  45

Lys Ser Gly Leu Gln Ile Lys Lys Asn Ala Ile Ile Asp Asp Tyr Lys
    50                  55                  60

Val Thr Ser Gln Val Leu Gly Leu Gly Ile Asn Gly Lys Val Leu Gln
```

```
            65                  70                  75                  80
        Ile Phe Asn Lys Arg Thr Gln Glu Lys Phe Ala Leu Lys Met Leu Gln
                        85                  90                  95

Asp Cys Pro Lys Ala Arg Arg Glu Val Glu Leu His Trp Arg Ala Ser
                        100                 105                 110

Gln Cys Pro His Ile Val Arg Ile Val Asp Val Tyr Glu Asn Leu Tyr
                        115                 120                 125

Ala Gly Arg Lys Cys Leu Leu Ile Val Met Glu Cys Leu Asp Gly Gly
                    130                 135                 140

Glu Leu Phe Ser Arg Ile Gln Asp Arg Gly Asp Gln Ala Phe Thr Glu
        145                 150                 155                 160

Arg Glu Ala Ser Glu Ile Met Lys Ser Ile Gly Glu Ala Ile Gln Tyr
                            165                 170                 175

Leu His Ser Ile Asn Ile Ala His Arg Asp Val Lys Pro Glu Asn Leu
                        180                 185                 190

Leu Tyr Thr Ser Lys Arg Pro Asn Ala Ile Leu Lys Leu Thr Asp Phe
                    195                 200                 205

Gly Phe Ala Lys Glu Thr Thr Ser His Asn Ser Leu Thr Thr Pro Cys
        210                 215                 220

Tyr Thr Pro Tyr Tyr Val Ala Pro Glu Val Leu Gly Pro Glu Lys Tyr
        225                 230                 235                 240

Asp Lys Ser Cys Asp Met Trp Ser Leu Gly Val Ile Met Tyr Ile Leu
                        245                 250                 255

Leu Cys Gly Tyr Pro Pro Phe Tyr Ser Asn His Gly Leu Ala Ile Ser
                    260                 265                 270

Pro Gly Met Lys Thr Arg Ile Arg Met Gly Gln Tyr Glu Phe Pro Asn
                275                 280                 285

Pro Glu Trp Ser Glu Val Ser Glu Glu Val Lys Met Leu Ile Arg Asn
            290                 295                 300

Leu Leu Lys Thr Glu Pro Thr Gln Arg Met Thr Ile Thr Glu Phe Met
        305                 310                 315                 320

Asn His Pro Trp Ile Met Gln Ser Thr Lys Val Pro Gln Thr Pro Leu
                        325                 330                 335

His Thr Ser Arg Val Leu Lys Glu Asp Lys Glu Arg Trp Glu Asp Val
                    340                 345                 350

Lys Glu Glu Met Thr Ser Ala Leu Ala Thr Met Arg Val Asp Tyr Glu
                355                 360                 365

Gln Ile Lys Ile Lys Lys Ile Glu Asp Ala Ser Asn Pro Leu Leu Leu
            370                 375                 380

Lys Arg Arg Lys Lys Ala Arg Ala Leu Glu Ala Ala Leu Ala His
        385                 390                 395                 400

<210> SEQ ID NO 5
<211> LENGTH: 10
<212> TYPE: PRT
<213> ORGANISM: Artificial Sequence
<220> FEATURE:
<223> OTHER INFORMATION: Substrate Peptide

<400> SEQUENCE: 5

Gly Arg Pro Arg Thr Thr Ser Phe Ala Glu
1               5                   10

<210> SEQ ID NO 6
<211> LENGTH: 8
<212> TYPE: PRT
```

```
<213> ORGANISM: Artificial Sequence
<220> FEATURE:
<223> OTHER INFORMATION: Substrate Peptide

<400> SEQUENCE: 6

Leu Gln Arg Gln Leu Ser Ile Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Substrate Peptide

<400> SEQUENCE: 7

Leu Tyr Arg Ser Pro Ser Met Pro Leu
1               5

<210> SEQ ID NO 8
<211> LENGTH: 10
<212> TYPE: PRT
<213> ORGANISM: Artificial Sequence
<220> FEATURE:
<223> OTHER INFORMATION: Substrate Peptide
<220> FEATURE:
<221> NAME/KEY: MISC_FEATURE
<222> LOCATION: (1)..(4)
<223> OTHER INFORMATION: X denotes all amino acids except Cys, Ser, Thr,
      and Tyr
<220> FEATURE:
<221> NAME/KEY: MISC_FEATURE
<222> LOCATION: (7)..(10)
<223> OTHER INFORMATION: X denotes all amino acids except Cys, Ser, Thr,
      and Tyr

<400> SEQUENCE: 8

Xaa Xaa Xaa Xaa Ser Pro Xaa Xaa Xaa Xaa
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Substrate Peptide

<400> SEQUENCE: 9

Gly Pro Gln Ser Pro Ile
1               5

<210> SEQ ID NO 10
<211> LENGTH: 10
<212> TYPE: PRT
<213> ORGANISM: Artificial Sequence
<220> FEATURE:
<223> OTHER INFORMATION: Substrate Peptide

<400> SEQUENCE: 10

Pro Gly Pro Gln Ser Pro Gly Ser Pro Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: p38SAPK docking motif
```

```
<400> SEQUENCE: 11

His Gln Arg Ser Arg Lys Arg Leu Ser Gln
1               5                   10

<210> SEQ ID NO 12
<211> LENGTH: 11
<212> TYPE: PRT
<213> ORGANISM: Artificial Sequence
<220> FEATURE:
<223> OTHER INFORMATION: p38SAPK docking motif

<400> SEQUENCE: 12

Val Arg Phe Leu Gln Gln Arg Arg Arg Gln Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Potential p38 SAPK docking motif

<400> SEQUENCE: 13

Pro Val Gln Asn Lys Arg Arg Arg Ser Val
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Substrate Peptide for Cdc25B
<220> FEATURE:
<221> NAME/KEY: MISC_FEATURE
<222> LOCATION: (2)..(2)
<223> OTHER INFORMATION: X can be any amino acid

<400> SEQUENCE: 14

Leu Xaa Arg Ser Pro Ser Met Pro
1               5

<210> SEQ ID NO 15
<211> LENGTH: 12
<212> TYPE: PRT
<213> ORGANISM: Artificial Sequence
<220> FEATURE:
<223> OTHER INFORMATION: Substrate peptide
<220> FEATURE:
<221> NAME/KEY: MISC_FEATURE
<222> LOCATION: (1)..(4)
<223> OTHER INFORMATION: X denotes all amino acids except Cys, Ser, Thr,
      or Tyr
<220> FEATURE:
<221> NAME/KEY: MISC_FEATURE
<222> LOCATION: (6)..(7)
<223> OTHER INFORMATION: X denotes all amino acids except Cys, Ser, Thr,
      or Tyr
<220> FEATURE:
<221> NAME/KEY: MISC_FEATURE
<222> LOCATION: (9)..(12)
<223> OTHER INFORMATION: X denotes all amino acids except Cys, Ser, Thr,
      or Tyr

<400> SEQUENCE: 15

Xaa Xaa Xaa Xaa Arg Xaa Xaa Ser Xaa Xaa Xaa Xaa
1               5                   10

<210> SEQ ID NO 16
<211> LENGTH: 7
```

```
<212> TYPE: PRT
<213> ORGANISM: Artificial Sequence
<220> FEATURE:
<223> OTHER INFORMATION: MAPKAP kinase-2 consensus motif

<400> SEQUENCE: 16

Leu Gln Arg Gln Leu Ser Ile
1               5

<210> SEQ ID NO 17
<211> LENGTH: 6
<212> TYPE: PRT
<213> ORGANISM: Artificial Sequence
<220> FEATURE:
<223> OTHER INFORMATION: MAPKAP kinase-2 phosphorylation motif
<220> FEATURE:
<221> NAME/KEY: MISC_FEATURE
<222> LOCATION: (1)..(1)
<223> OTHER INFORMATION: X can be Leu, Phe, or Ile
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be Gln, Ser, or Thr
<220> FEATURE:
<221> NAME/KEY: MISC_FEATURE
<222> LOCATION: (6)..(6)
<223> OTHER INFORMATION: X can be Ser or Thr

<400> SEQUENCE: 17

Xaa Xaa Arg Xaa Leu Xaa
1               5

<210> SEQ ID NO 18
<211> LENGTH: 6
<212> TYPE: PRT
<213> ORGANISM: Artificial Sequence
<220> FEATURE:
<223> OTHER INFORMATION: Hydrophobic motif on Cdc25
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be Ser or Thr

<400> SEQUENCE: 18

Leu Xaa Arg Xaa Xaa Xaa
1               5

<210> SEQ ID NO 19
<211> LENGTH: 16
<212> TYPE: PRT
<213> ORGANISM: Artificial Sequence
<220> FEATURE:
<223> OTHER INFORMATION: Substrate Peptide
<220> FEATURE:
<221> NAME/KEY: MISC_FEATURE
<222> LOCATION: (3)..(6)
<223> OTHER INFORMATION: X can be any amino acid except Cys, Ser, Thr,
```

```
           and Tyr
<220> FEATURE:
<221> NAME/KEY: MISC_FEATURE
<222> LOCATION: (9)..(12)
<223> OTHER INFORMATION: X can be any amino acid except Cys, Ser, Thr,
      and Tyr

<400> SEQUENCE: 19

Gly Ala Xaa Xaa Xaa Xaa Ser Pro Xaa Xaa Xaa Xaa Ala Lys Lys Lys
1               5                  10                  15

<210> SEQ ID NO 20
<211> LENGTH: 19
<212> TYPE: PRT
<213> ORGANISM: Artificial Sequence
<220> FEATURE:
<223> OTHER INFORMATION: Substrate Peptide
<220> FEATURE:
<221> NAME/KEY: MISC_FEATURE
<222> LOCATION: (3)..(6)
<223> OTHER INFORMATION: X can be any amino acid except Cys, Ser, Thr,
      and Tyr
<220> FEATURE:
<221> NAME/KEY: MISC_FEATURE
<222> LOCATION: (8)..(8)
<223> OTHER INFORMATION: X can be any amino acid except Cys, Ser, Thr,
      and Tyr
<220> FEATURE:
<221> NAME/KEY: MISC_FEATURE
<222> LOCATION: (11)..(15)
<223> OTHER INFORMATION: X can be any amino acid except Cys, Ser, Thr,
      and Tyr

<400> SEQUENCE: 20

Gly Ala Xaa Xaa Xaa Xaa Pro Xaa Ser Pro Xaa Xaa Xaa Xaa Xaa Ala
1               5                  10                  15

Lys Lys Lys

<210> SEQ ID NO 21
<211> LENGTH: 13
<212> TYPE: PRT
<213> ORGANISM: Artificial Sequence
<220> FEATURE:
<223> OTHER INFORMATION: Substrate Peptide
<220> FEATURE:
<221> NAME/KEY: MISC_FEATURE
<222> LOCATION: (3)..(4)
<223> OTHER INFORMATION: X can be any amino acid except Cys, Ser, Thr,
      and Tyr
<220> FEATURE:
<221> NAME/KEY: MISC_FEATURE
<222> LOCATION: (6)..(9)
<223> OTHER INFORMATION: X can be any amino acid except Cys, Ser, Thr,
      and Tyr

<400> SEQUENCE: 21

Gly Ala Xaa Xaa Ser Xaa Xaa Xaa Xaa Ala Lys Lys Lys
1               5                  10

<210> SEQ ID NO 22
<211> LENGTH: 14
<212> TYPE: PRT
<213> ORGANISM: Artificial Sequence
<220> FEATURE:
<223> OTHER INFORMATION: Substrate Peptide

<400> SEQUENCE: 22

Lys Lys Ala Glx Gly Pro Gln Gly Pro Gln Ser Pro Ile Glu
1               5                  10
```

```
<210> SEQ ID NO 23
<211> LENGTH: 14
<212> TYPE: PRT
<213> ORGANISM: Artificial Sequence
<220> FEATURE:
<223> OTHER INFORMATION: Substrate Peptide

<400> SEQUENCE: 23

Lys Lys Ala Glx Gly Pro Gln Ser Pro Gly Ser Pro Leu Glu
1               5                   10

<210> SEQ ID NO 24
<211> LENGTH: 55
<212> TYPE: DNA
<213> ORGANISM: Artificial Sequence
<220> FEATURE:
<223> OTHER INFORMATION: Primer for RNAi

<400> SEQUENCE: 24
tgaccaggca ttcacagaaa ttcaagagat ttctgtgaat gcctggtctt ttttc        55

<210> SEQ ID NO 25
<211> LENGTH: 55
<212> TYPE: DNA
<213> ORGANISM: Artificial Sequence
<220> FEATURE:
<223> OTHER INFORMATION: Primer for RNAi

<400> SEQUENCE: 25
ttgaccatca ccgagtttat ttcaagagaa taaactcggt gatggtcatt ttttc        55

<210> SEQ ID NO 26
<211> LENGTH: 55
<212> TYPE: DNA
<213> ORGANISM: Artificial Sequence
<220> FEATURE:
<223> OTHER INFORMATION: Primer for RNAi

<400> SEQUENCE: 26
tcgatgcgtg ttgactatga ttcaagagat catagtcaac acgcatcgtt ttttc        55

<210> SEQ ID NO 27
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: modified_base
<222> LOCATION: (20)..(21)
<223> OTHER INFORMATION: The last two Ts are deoxythymidines

<400> SEQUENCE: 27
ucccggcuau gugcaggagt t                                             21

<210> SEQ ID NO 28
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: misc_feature
<222> LOCATION: (20)..(21)
<223> OTHER INFORMATION: The last two Ts denote deoxythymidines

<400> SEQUENCE: 28
cuccugcaca uagccgggat t                                             21
```

```
<210> SEQ ID NO 29
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: misc_feature
<222> LOCATION: (20)..(21)
<223> OTHER INFORMATION: The last two Ts denote deoxythymidines

<400> SEQUENCE: 29
cgaugcgugu ugacuaugat t                                              21

<210> SEQ ID NO 30
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: misc_feature
<222> LOCATION: (20)..(21)
<223> OTHER INFORMATION: The last two Ts denote deoxythymidines

<400> SEQUENCE: 30
ucauagucaa cacgcaucgt t                                              21

<210> SEQ ID NO 31
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: misc_feature
<222> LOCATION: (17)..(17)
<223> OTHER INFORMATION: W can be an alanine, or a thymidine/uracil, and
      denotes weak interactions, 2H-bonds
<220> FEATURE:
<221> NAME/KEY: misc_feature
<222> LOCATION: (20)..(21)
<223> OTHER INFORMATION: The last two Ts are deoxythymidines

<400> SEQUENCE: 31
ugaccaucac cgaguuwaut t                                              21

<210> SEQ ID NO 32
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: misc_feature
<222> LOCATION: (20)..(21)
<223> OTHER INFORMATION: The last two Ts are deoxythymidines

<400> SEQUENCE: 32
auaaacucgg ugauggucat t                                              21

<210> SEQ ID NO 33
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: misc_feature
```

```
<222> LOCATION: (20)..(21)
<223> OTHER INFORMATION: The last two Ts are deoxythymidines

<400> SEQUENCE: 33
uggcaacagu auuucgguat t                                              21

<210> SEQ ID NO 34
<211> LENGTH: 21
<212> TYPE: DNA
<213> ORGANISM: Artificial Sequence
<220> FEATURE:
<223> OTHER INFORMATION: Primer for RNAi
<220> FEATURE:
<221> NAME/KEY: misc_feature
<222> LOCATION: (20)..(21)
<223> OTHER INFORMATION: The last two Ts are deoxythymidines

<400> SEQUENCE: 34
uaccgaaaua cuguugccat t                                              21

<210> SEQ ID NO 35
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 35
gaccaggcat tcacagaaa                                                 19

<210> SEQ ID NO 36
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 36
ttgaccactc cttgttata                                                 19

<210> SEQ ID NO 37
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 37
gaccactcct tgttataca                                                 19

<210> SEQ ID NO 38
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 38
tgaccatcac cgagtttat                                                 19

<210> SEQ ID NO 39
<211> LENGTH: 19
<212> TYPE: DNA
<213> ORGANISM: Artificial Sequence
<220> FEATURE:
<223> OTHER INFORMATION: MAPKAP kinase-2 RNAi target sequence
```

```
<400> SEQUENCE: 39
tcaccgagtt tatgaacca                                               19

<210> SEQ ID NO 40
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 40
tcaagaagaa cgccatcat                                               19

<210> SEQ ID NO 41
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 41
aagcatccga aatcatgaa                                               19

<210> SEQ ID NO 42
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 42
agtatctgca ttcaatcaa                                               19

<210> SEQ ID NO 43
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 43
ctttgaccac tccttgtta                                               19

<210> SEQ ID NO 44
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 44
tttgaccact ccttgttat                                               19

<210> SEQ ID NO 45
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 45
tacggatcgt ggatgtgta                                               19

<210> SEQ ID NO 46
<211> LENGTH: 19
```

```
<212> TYPE: DNA
<213> ORGANISM: Artificial Sequence
<220> FEATURE:
<223> OTHER INFORMATION: MAPKAP kinase-2 RNAi target sequence

<400> SEQUENCE: 46
ggacggtgga gaactcttt                                              19

<210> SEQ ID NO 47
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 47
cttgttatac accgtacta                                              19

<210> SEQ ID NO 48
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 48
gacggtggag aactcttta                                              19

<210> SEQ ID NO 49
<211> LENGTH: 19
<212> TYPE: DNA
<213> ORGANISM: Artificial Sequence
<220> FEATURE:
<223> OTHER INFORMATION: MAPKAP kinase-2 RNAi target sequence

<400> SEQUENCE: 49
ggagaactct ttagccgaa                                              19

<210> SEQ ID NO 50
<211> LENGTH: 16
<212> TYPE: PRT
<213> ORGANISM: Substrate Peptide

<400> SEQUENCE: 50

Arg Gln Ile Lys Ile Trp Phe Gln Asn Arg Arg Met Lys Trp Lys Lys
1               5                   10                  15
```